(12) United States Patent
Adar et al.

(10) Patent No.: US 12,161,612 B2
(45) Date of Patent: *Dec. 10, 2024

(54) METHODS AND COMPOSITIONS FOR REDUCING SYMPTOMS OF PARKINSON'S DISEASE

(71) Applicant: NeuroDerm, Ltd., Rehovot (IL)

(72) Inventors: Liat Adar, Ramat Gan (IL); Nelson Felix Lopes, Sermonde (PT); Laurence Salin, Bazemont (FR); Tamar Yardeni, Rehovot (IL); Nissim Sasson, Kfar Yona (IL); Sheila Oren, Herzliya (IL); Hikari Yarita, Osaka (JP); Mikio Himizu, Osaka (JP); Natalia Vostokova, Rehovot (IL)

(73) Assignee: NeuroDerm, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/636,148

(22) Filed: Apr. 15, 2024

(65) Prior Publication Data

US 2024/0342124 A1  Oct. 17, 2024

Related U.S. Application Data

(63) Continuation-in-part of application No. 18/234,232, filed on Aug. 15, 2023.

(Continued)

(51) Int. Cl.
| | |
|---|---|
| *A61K 31/195* | (2006.01) |
| *A61K 9/00* | (2006.01) |
| *A61K 31/198* | (2006.01) |
| *A61P 25/16* | (2006.01) |
| *A61P 25/20* | (2006.01) |

(52) U.S. Cl.
CPC .......... *A61K 31/195* (2013.01); *A61K 9/0019* (2013.01); *A61K 31/198* (2013.01); *A61P 25/16* (2018.01); *A61P 25/20* (2018.01)

(58) Field of Classification Search
CPC .. A61K 31/198; A61K 9/4808; A61K 9/4858; A61K 9/0053; A61K 47/183
See application file for complete search history.

(56) References Cited

U.S. PATENT DOCUMENTS

| | | |
|---|---|---|
| 3,769,424 A | 10/1973 | Bayne |
| 3,808,317 A | 4/1974 | Bigelow et al. |

(Continued)

FOREIGN PATENT DOCUMENTS

| | | |
|---|---|---|
| CA | 2143070 A1 | 8/1995 |
| CN | 101022784 A | 8/2007 |

(Continued)

OTHER PUBLICATIONS

Zhou, et al. (2010) "Design, Synthesis and Biological Evaluation of l-dopa Amide Derivatives as Potential Prodrugs for the Treatment of Parkinson's Disease," European Journal of Medical Chemistry, 45(9):4035-4042.

(Continued)

*Primary Examiner* — San Ming R Hui
(74) *Attorney, Agent, or Firm* — Goodwin Procter LLP

(57) ABSTRACT

Disclosed is a method for the treatment of a neurological or movement disorder, e.g., Parkinson's disease, in a patient in need thereof, by parenteral administration of levodopa and a dopa decarboxylase inhibitor (DDCI), such as carbidopa, benserazide or any combination thereof.

29 Claims, 13 Drawing Sheets

Increases in 'Good' ON time (ON with no or mild dyskinesia) and decreases in ON time with moderate/severe dyskinesia at Day 3 (N=19)

Related U.S. Application Data

(60) Provisional application No. 63/564,464, filed on Mar. 12, 2024, provisional application No. 63/508,634, filed on Jun. 16, 2023, provisional application No. 63/459,438, filed on Apr. 14, 2023.

(56) References Cited

U.S. PATENT DOCUMENTS

| | | |
|---|---|---|
| 3,936,495 A | 2/1976 | Sullivan, Jr. |
| 3,961,060 A | 6/1976 | Fuxe |
| 4,035,507 A | 7/1977 | Bodor et al. |
| 4,166,452 A | 9/1979 | Generales, Jr. |
| 4,241,082 A | 12/1980 | Baba et al. |
| 4,256,108 A | 3/1981 | Theeuwes |
| 4,265,874 A | 5/1981 | Bonsen et al. |
| 4,409,233 A | 10/1983 | Tsukada et al. |
| 4,642,316 A | 2/1987 | Fawzi et al. |
| 4,684,666 A | 8/1987 | Haas |
| 4,826,875 A | 5/1989 | Chiesi |
| 4,832,957 A | 5/1989 | Dempski et al. |
| 4,962,223 A | 10/1990 | Cannata et al. |
| 4,963,568 A | 10/1990 | Schoenleber et al. |
| 5,350,769 A | 9/1994 | Kasai et al. |
| 5,861,423 A | 1/1999 | Caldwell et al. |
| 5,877,176 A | 3/1999 | Gross |
| 6,153,615 A | 11/2000 | Gross |
| 6,166,083 A | 12/2000 | Barrett et al. |
| 6,245,917 B1 | 6/2001 | Bosch et al. |
| 6,274,168 B1 | 8/2001 | Addicks et al. |
| 6,348,965 B1 | 2/2002 | Palladino et al. |
| 6,500,867 B1 | 12/2002 | Virkki et al. |
| 6,620,432 B2 | 9/2003 | Addicks et al. |
| 6,716,452 B1 | 4/2004 | Piccariello et al. |
| 6,746,688 B1 | 6/2004 | Kushnir et al. |
| 6,797,732 B2 | 9/2004 | Virkki et al. |
| 6,878,529 B2 | 4/2005 | Harrow et al. |
| 6,974,591 B2 | 12/2005 | Kendrup et al. |
| 7,201,923 B1 | 4/2007 | van Lengerich |
| 7,223,776 B2 | 5/2007 | Surivet et al. |
| 7,309,719 B1 | 12/2007 | Aomatsu |
| 7,479,498 B2 | 1/2009 | Keller |
| 7,560,100 B2 | 7/2009 | Pinchasi et al. |
| 7,589,233 B2 | 9/2009 | Chandran |
| 7,709,494 B2 | 5/2010 | Defossa et al. |
| 7,863,336 B2 | 1/2011 | Yacoby-Zeevi et al. |
| 8,048,926 B2 | 11/2011 | Atlas |
| 8,058,243 B2 | 11/2011 | Tyers et al. |
| 8,173,840 B2 | 5/2012 | Chandran |
| 8,193,243 B2 | 6/2012 | Yacoby-Zeevi et al. |
| 8,207,369 B2 | 6/2012 | Stein et al. |
| 8,263,125 B2 | 9/2012 | Vaya et al. |
| 8,273,731 B2 | 9/2012 | Heldman |
| 8,815,950 B2 | 8/2014 | Remenar et al. |
| 8,921,356 B2 | 12/2014 | Heldman |
| 9,040,577 B2 | 5/2015 | Yacoby-Zeevi et al. |
| 9,040,578 B2 | 5/2015 | Yacoby-Zeevi et al. |
| 9,040,589 B2 | 5/2015 | Yacoby-Zeevi et al. |
| 9,040,590 B2 | 5/2015 | Yacoby-Zeevi et al. |
| 9,101,663 B2 | 8/2015 | Yacoby-Zeevi et al. |
| 9,381,249 B2 | 7/2016 | Yacoby-Zeevi et al. |
| 9,415,108 B2 | 8/2016 | Yacoby-Zeevi et al. |
| 9,421,267 B2 | 8/2016 | Yacoby-Zeevi et al. |
| 9,993,451 B2 | 6/2018 | Yacoby-Zeevi et al. |
| 10,022,320 B2 | 7/2018 | Yacoby-Zeevi |
| 10,258,585 B2 | 4/2019 | Yacoby-Zeevi |
| 10,624,839 B2 | 4/2020 | Yacoby-Zeevi |
| 10,813,902 B2 | 10/2020 | Yacoby-Zeevi |
| 11,213,502 B1 | 1/2022 | Birnberg et al. |
| 11,331,293 B1 | 5/2022 | Birnberg et al. |
| 11,458,115 B2 | 10/2022 | Birnberg et al. |
| 2001/0043945 A1 | 11/2001 | Addicks et al. |
| 2002/0028799 A1 | 3/2002 | Naylor et al. |
| 2002/0099013 A1 | 7/2002 | Piccariello et al. |
| 2002/0102707 A1 | 8/2002 | Harrow et al. |
| 2003/0119714 A1 | 6/2003 | Naylor et al. |
| 2003/0152628 A1 | 8/2003 | Licht et al. |
| 2004/0039033 A1 | 2/2004 | Atwal et al. |
| 2005/0038023 A1 | 2/2005 | Bebbington et al. |
| 2005/0053669 A1 | 3/2005 | Friedl et al. |
| 2005/0070608 A1 | 3/2005 | Remenar et al. |
| 2005/0163850 A1 | 7/2005 | Wong et al. |
| 2005/0163859 A1 | 7/2005 | Murthy et al. |
| 2005/0233945 A1 | 10/2005 | Brown et al. |
| 2006/0025385 A1 | 2/2006 | Atlas |
| 2006/0041014 A1 | 2/2006 | Naylor et al. |
| 2006/0088607 A1 | 4/2006 | Stefano et al. |
| 2006/0159751 A1 | 7/2006 | Gogia et al. |
| 2006/0241183 A1 | 10/2006 | Karoum |
| 2007/0191428 A1 | 8/2007 | Rao et al. |
| 2008/0051459 A1 | 2/2008 | Nyholm et al. |
| 2008/0139655 A1 | 6/2008 | Bortz et al. |
| 2008/0187590 A1 | 8/2008 | Vahervuo |
| 2008/0255235 A1 | 10/2008 | Segrell |
| 2010/0298428 A1 | 11/2010 | Yacoby-Zeevi et al. |
| 2010/0298429 A1 | 11/2010 | Yacoby-Zeevi et al. |
| 2011/0269833 A1 | 11/2011 | Yacoby-Zeevi et al. |
| 2011/0294889 A1 | 12/2011 | Segrell |
| 2012/0115823 A1 | 5/2012 | Price et al. |
| 2013/0116215 A1 | 5/2013 | Coma et al. |
| 2013/0123485 A1 | 5/2013 | Park et al. |
| 2013/0253056 A1 | 9/2013 | Nemas et al. |
| 2013/0338143 A1 | 12/2013 | Yacoby-Zeevi et al. |
| 2014/0051722 A1 | 2/2014 | Burnier et al. |
| 2014/0051755 A1 | 2/2014 | Yacoby-Zeevi et al. |
| 2014/0088192 A1 | 3/2014 | Heller et al. |
| 2014/0249228 A1 | 9/2014 | Yacoby-Zeevi et al. |
| 2014/0249229 A1 | 9/2014 | Yacoby-Zeevi et al. |
| 2014/0249230 A1 | 9/2014 | Yacoby-Zeevi et al. |
| 2014/0249231 A1 | 9/2014 | Yacoby-Zeevi et al. |
| 2015/0217046 A1 | 8/2015 | Heller et al. |
| 2015/0352212 A1 | 12/2015 | Yacoby-Zeevi et al. |
| 2016/0022573 A1 | 1/2016 | Yacoby-Zeevi |
| 2016/0106765 A1 | 4/2016 | Cardinal-David et al. |
| 2016/0151317 A1 | 6/2016 | Yacoby-Zeevi et al. |
| 2017/0157077 A1 | 6/2017 | Yacoby-Zeevi et al. |
| 2017/0157079 A1 | 6/2017 | Yacoby-Zeevi |
| 2017/0196828 A1 | 7/2017 | Yacoby-Zeevi et al. |
| 2017/0296491 A1 | 10/2017 | Yacoby-Zeevi et al. |
| 2019/0125708 A1 | 5/2019 | Yacoby-Zeevi et al. |
| 2019/0151233 A1 | 5/2019 | Yacoby-Zeevi |
| 2020/0397730 A1 | 12/2020 | Yacoby-Zeevi et al. |
| 2021/0000777 A1 | 1/2021 | Yacoby-Zeevi |
| 2021/0038505 A1 | 2/2021 | Yacoby-Zeevi |
| 2021/0077442 A1 | 3/2021 | Yacoby-Zeevi et al. |
| 2021/0093560 A1 | 4/2021 | Yacoby-Zeevi |
| 2022/0151965 A1 | 5/2022 | Birnberg et al. |

FOREIGN PATENT DOCUMENTS

| | | |
|---|---|---|
| CN | 101669925 A | 3/2010 |
| CN | 110294789 A | 10/2019 |
| DE | 2838232 A1 | 3/1979 |
| EP | 0393781 A2 | 10/1990 |
| EP | 1077692 A1 | 2/2001 |
| EP | 1462101 A1 | 9/2004 |
| EP | 2656856 A2 | 10/2013 |
| EP | 4299128 A2 | 1/2024 |
| IN | 244675 B | 12/2010 |
| IN | 251149 B | 2/2012 |
| JP | 54-50700 A | 4/1979 |
| JP | S56115749 | 9/1981 |
| WO | 1984/01501 A1 | 4/1984 |
| WO | 1996/037226 A2 | 11/1996 |
| WO | 1998/016208 A1 | 4/1998 |
| WO | 2000/054773 A1 | 9/2000 |
| WO | 2001/001984 A1 | 1/2001 |
| WO | 2004069146 A2 | 8/2004 |
| WO | 2005/099678 A1 | 10/2005 |
| WO | 2006/006929 A1 | 1/2006 |
| WO | 2006043532 A1 | 4/2006 |
| WO | 2007/138086 A1 | 12/2007 |
| WO | 2008/124330 A2 | 10/2008 |
| WO | 2010027340 A1 | 3/2010 |
| WO | 2010/055133 A1 | 5/2010 |

(56) References Cited

FOREIGN PATENT DOCUMENTS

| | | |
|---|---|---|
| WO | 2010/134074 A1 | 11/2010 |
| WO | 2012/006959 A1 | 1/2012 |
| WO | 2012/066538 A1 | 5/2012 |
| WO | 2014/141261 A1 | 9/2014 |
| WO | 2015/136538 A1 | 9/2015 |
| WO | 2017/090039 A2 | 6/2017 |
| WO | 2018/154447 A1 | 8/2018 |
| WO | 2019/038637 A1 | 2/2019 |
| WO | 2019/038638 A1 | 2/2019 |
| WO | 2019/038639 A1 | 2/2019 |
| WO | 2020075023 A2 | 4/2020 |
| WO | 2022/107125 A1 | 5/2022 |
| WO | 2023/148401 A1 | 8/2023 |

OTHER PUBLICATIONS

"Levodopa," in Encyclopedia of Drugs, p. 471 (Moscow, RLS, 2001)(2 pages; English language translation of Office Action citing reference provided as English language translation of Official Action issued in connection with Russian Patent Application No. 2011149976/15, dated Sep. 15, 2014 (6 pages).

Produodopa Summary of Product characteristics, downloaded from <https://www.hpra.ie/img/uploaded/swedocuments/Licence_PA1824-002-003_28092022110832.pdf%20>, dated Sep. 28, 2022, 16 pages.

Produodopa Package Leaflet, downloaded from https://www.hpra.ie/img/uploaded/swedocuments/b1bc0aa4-a554-4276-b7a0-27e0ed4cc2be.pdf <%20https:/www.hpra.ie/img/uploaded/swedocuments/b1bc0aa4-a554-4276-b7a0-27e0ed4cc2be.pdf%20>, 14 pages.

Solieau et al. (2022) "Safety and efficacy of continuous subcutaneous foslevodopa-foscarbidopa in patients with advanced Parkinson's disease: a randomized, double-blind, active-controlled, phase 3 trial," Lancet Neurology 21:1099-1109.

Arthur M. Felix et al., "Synthesis and antireserpine activity of peptides of L-dopa" J. Med. Chem. 17:4 422-426 (1974).

Bodor, N. et al., "Improved delivery through biological membranes. 4. Prodrugs of L-Dopa" J. Med. Chem. 20 (11) :1435-1445 (1977).

Felix AM et al., "Synthesis and antireserpine activity of peptides of L-dopa" J. Med. Chem. 17(4): 422-426 (1974).

Wang et al., "Systemic and brain bioavailabilities of D-phenylglycine-L-Dopa. a sustained dopamine-releasing prodrug" Journal of Food and Drug Analysis. Jun. I; 21(2):136-41 (2013).

Ichinose H. et al., "Increase of catecholamines in mouse brain by systemic administration of gamma-glutamyl L-3,4-dihydroxyphenylalanine" Journal of Neurochemistry. Sep; 49(3):928-32 (1987).

Shevchenko VP. et al. "Synthesis of isotopically modified derivatives of dopamine. serotonin. and doxorubicin with Boe-Pro and Boc-[2H] Pro" Doklady Akademii Nauk. Khimiya. Mar. vol. 485. No. 1. pp. 87-90 (2019). (in Russian).

CAS Registry No. 2305269-90—. CA Index Name: tyrosine. 3-methoxy-N-[2-(••methylethoxy)acetyl]—. Entered STN: Apr. 27, 2019.

Hoon M. et al. "The Design and evaluation of an L-Dopa-lazabemide prodrug for the treatment of Parkinson's disease" Molecules. Dec; 22(12):2076 (2017).

Durso R, et al. "Variable absorption of carbidopa affects both peripheral and central levodopa metabolism" The Journal of Clinical Pharmacology. Aug; 40(8):854-60 (2000).

International Search Report for International Application No. PCT/IL2022/050269, mailed Jun. 16, 2022 (6 pages).

Written Opinion of the International Search Authority for PCT/IL2022/050269 mailed Jun. 16, 2022, 14 pages.

Shaltiel-Karyo et al., "Subcutaneous Administration of Carbidopa Enhances Oral Levodopa Pharmacokinetics: A Series of Studies Conducted in Pigs, Mice, and Healthy Volunteers" Clinical Neuropharmacology, 42(4):11-116 (2019).

LeWitt et al., The Pharmacokinetics of Continuous Subcutaneous Levodopa/Carbidopa Infusion: Findings From the Nd0612 Clinical Development Program, Frontiers in Neurology, (Nov. 10, 2022) vol. 13. arn. 1036068.

Giladi et al., ND0612 (levodopa/carbidopa for subcutaneous infusion) in patients with Parkinson's disease and motor response fluctuations: A randomized, placebo-controlled phase 2 study, Parkinsonism and Related Disorders, (Oct. 2021) vol. 91, pp. 139-145.

Poewe et al., Subcutaneous Levodopa Infusion for Parkinson's Disease: 1-Year Data from the Open-Label BeyoND Study, Movement Disorders, (Nov. 2021) vol. 36, No. 11, pp. 2687-2692.

Shaltiel-Karyo et al., Subcutaneous Administration of Carbidopa Enhances Oral Levodopa Pharmacokinetics: A Series of Studies Conducted in Pigs, Mice, and Healthy Volunteers, Clinical Neuropharmacology, (Jul. 1, 2019) vol. 42, No. 4, pp. 111-116.

Ramot et al., Ninety-day Local Tolerability and Toxicity Study of ND0612, a Novel Formulation of Levodopa/Carbidopa, Administered by Subcutaneous Continuous Infusion in Minipigs, Toxicologic Pathology, (Aug. 1, 2017) vol. 45, No. 6, pp. 764-773.

Olanow et al., Continuous Subcutaneous Levodopa Delivery for Parkinson's Disease: A Randomized Study, Journal of Parkinson's disease, (2021) vol. 11, No. 1, pp. 177-186.

Albanese et al., Development of a patient journey map for people living with Parkinson's disease, Journal of Parkinson's Disease, (2023) vol. 13, Supp. Supplement 1, pp. 323; Abstract No. P43.07; 6th World Parkinson Congress, WPC 2023. Barcelona, Spain. Jul. 4, 2023-Jul. 7, 2023.

Rascol et al., Enrollment characteristics for patients entering a Phase 3 study of subcutaneous levodopa/carbidopa infusion with ND0612, Journal of Parkinson's Disease, (2023) vol. 13, Supp. Supplement 1, pp. 291-292; Abstract No. P38.06; 6th World Parkinson Congress, WPC 2023. Barcelona, Spain. Jul. 4, 2023-Jul. 7, 2023.

Olanow et al., Onset of efficacy with continuous, subcutaneous levodopa/carbidopa infusion in patients with PD experiencing motor fluctuations, Journal of Parkinson's Disease, (2023) vol. 13, Supp. Supplement 1, pp. 290; Abstract No. P38.03; 6th World Parkinson Congress, WPC 2023. Barcelona, Spain. Jul. 4, 2023-Jul. 7, 2023.

Arkadir et al., Descriptive case studies of patients in their fifth consecutive year of treatment with ND0612, European Journal of Neurology, (Jul. 2022) vol. 29, Supp. Supplement 1, pp. 616; Abstract No. EPO-373; 8th Annual Congress of the European Academy of Neurology, Vienna, Austria, Jun. 25, 2022-Jun. 28, 2022.

Birnberg et al., Pharmacokinetics-pharmacodynamics of levodopa/carbidopa following subcutaneous infusion with ND0612, European Journal of Neurology, (Jul. 2022) vol. 29, Supp. Supplement 1, pp. 608; Abstract No. EPO-363; 8th Annual Congress of the European Academy of Neurology, Vienna, Austria, Jun. 25, 2022-Jun. 28, 2022.

Birnberg et al., Population pharmacokinetic analysis of levodopa and carbidopa after subcutaneous administration with and without adjunct oral therapy, Movement Disorders, (Sep. 2020) vol. 35, No. SUPPL 1, pp. S389. Abstract No. 872. MDS International Congress. Virtual. Sep. 12, 2020-Sep. 16, 2020. 1 page.

Poewe et al., BouNDless: An active-controlled randomized, double-blind double-dummy study of continuous ND0612 infusion in patients with fluctuating Parkinson's disease, Journal of Parkinson's Disease, (2019) vol. 9, No. 1, pp. 254. Abstract No. LBP.63. 5th World Parkinson Congress, WPC 2019. Kyoto, Japan. Jun. 4, 2019-Jun. 7, 2019.

Birnberg et al., Pharmacokinetics of ND0612 administered at different infusion sites and with different cannula lengths: An open-label, randomized, cross-over study in healthy volunteers, Journal of Parkinson's Disease, (2019) vol. 9, No. 1, pp. 250. Abstract No. LBP.51. 5th World Parkinson Congress, WPC 2019. Kyoto, Japan. Jun. 4, 2019-Jun. 7, 2019.

Poewe et al., The beyond study: Design and baseline characteristics of an international, multicentre study evaluating the longterm safety of ND0612 for Parkinson's disease, European Journal of Neurology, (Jul. 2019) vol. 26, Supp. Supplement 1, pp. 154. Abstract No. EPR1071. 5th Congress of the European Academy of Neurology, EAN 2019. Oslo, Norway. Jun. 29, 2019-Jul. 2, 2019.

(56) References Cited

OTHER PUBLICATIONS

Stocchi et al., Efficacy of ND0612 for nocturnal problems and early morning Off: A blinded rater study of 2 dosing regimens, European Journal of Neurology, (Jul. 2019) vol. 26, Supp. Supplement 1, pp. 109. Abstract No. O4114. 5th Congress of the European Academy of Neurology, EAN 2019. Oslo, Norway. Jun. 29, 2019-Jul. 2, 2019.

Oren et al., Pharmacokinetic profile of ND0612L (levodopa/carbidopa for subcutaneous infusion) in patients with moderate to severe Parkinson's disease, Journal of Parkinson's Disease, (2016) vol. 6, Supp. Supplement 1, pp. 214-215. Abstract No. P35.13. 4th World Parkinson Congress, WPC 2016. Portland, OR, United States. Sep. 20, 2016-Sep. 23, 2016.

Oren et al., A randomized controlled clinical study to evaluate the efficacy and safety of subcutaneous levodopa/ carbidopa (ND0612H) in patients with advanced Parkinson's disease, Journal of Parkinson's Disease, (2016) vol. 6, Supp. Supplement 1, pp. 214. Abstract No. P35.12. Meeting Info: 4th World Parkinson Congress, WPC 2016. Portland, OR, United States. Sep. 20, 2016-Sep. 23, 2016.

Giladi et al., Stable levodopa plasma levels with ND0612 (levodopa/carbidopa for subcutaneous infusion) in Parkinson's disease (PD) patients with motor fluctuations, : Journal of Parkinson's Disease, (2016) vol. 6, Supp. Supplement 1, pp. 210. Abstract No. P35.02. 4th World Parkinson Congress, WPC 2016. Portland, OR, United States. Sep. 20, 2016-Sep. 23, 2016.

Rachmilewitz et al., ND0612—A newly developed liquid levodopa/carbidopa formulation administered continuously subcutaneously by a mini-pump—Patient use perspective, Journal of Parkinson's Disease, (2016) vol. 6, Supp. Supplement 1, pp. 170. Abstract No. P31.16. 4th World Parkinson Congress, WPC 2016. Portland, OR, United States. Sep. 20, 2016-Sep. 23, 2016.

Giladi et al., Pharmacokinetic profile of ND0612 (levodopa/carbidopa for subcutaneous infusion) in Parkinson's disease (PD) patients with motor fluctuations: Results of a phase IIa dose finding study, European Journal of Neurology, (Jun. 2015) vol. 22, Supp. SUPPL. 1, pp. 66. Abstract No. O2114.Meeting Info: 1st Congress of the European Academy of Neurology. Berlin, Germany. Jun. 20, 2015-Jun. 23, 2015.

Yacoby-Zeevi et al., Maintenance of constant steady state therapeutic plasma concentrations of levodopa following its continuous subcutaneous administration with carbidopa, European Journal of Neurology, (Sep. 2012) vol. 19, Supp. SUPPL.1, pp. 292. Abstract No. P1540. 16th Congress of the European Federation of Neurological Societies, EFNS. Stockholm, Sweden. Sep. 8, 2012-Sep. 11, 2012.

Yacoby-Zeevi et al., Markedly enhanced levodopa pharmacokinetics from continuous subcutaneous carbidopa administration, European Journal of Neurology, (Sep. 2010) vol. 17, Supp. SUPPL. 3, pp. 52. Abstract No. SC232. 14th Congress of the European Federation of Neurological Societies, EFNS. Geneva, Switzerland. Sep. 25, 2010-Sep. 28, 2010.

Adar et al., Relative bioavailability of levodopa administered as a subcutaneous infusion with ND0612 versus oral immediate-release levodopa/carbidopa tablets, Neurology, (Apr. 25, 2023) vol. 100, No. 17, Suppl. 2, pp. P2-11.004. 75th Annual Meeting of the American-Academy-of-Neurology (AAN). Boston, MA, USA. Apr. 22-27, 2023. Amer Acad Neurol. 3 pages.

Isaacson et al., Long-Term Safety of Continuous Levodopa/Carbidopa Infusion with ND0612: Results from the Ongoing BeyoND Study, Movement Disorders, (Jun. 2022) vol. 37, Supp. Supplement 1, pp. S10. Abstract No. 14. PSG 34th Annual Symposium on Etiology, Pathogenesis, and Treatment of Parkinson's Disease and Other Movement Disorders. Phoenix, AZ, United States. Jun. 2, 2022-Jun. 5, 2022.

Espay et al., BouNDless: Study Design of an Active-Controlled, Randomized, Double-Blind Double-Dummy Study of Continuous ND0612 Infusion in Patients with Parkinson's Disease and Motor Fluctuations, Movement Disorders, (Jun. 2022) vol. 37, Supp. Supplement 1, pp. S8. Abstract No. 11. Meeting Info: PSG 34th Annual Symposium on Etiology, Pathogenesis, and Treatment of Parkinson's Disease and Other Movement Disorders. Phoenix, AZ, United States. Jun. 2, 2022-Jun. 5, 2022. 1 page.

Birnberg et al., Pharmacokinetic analysis of levodopa and carbidopa following subcutaneous infusion: A population pharmacokinetics model, Neurology, (May 2021) vol. 96, No. 15 SUPPL 1. Abstract No. 2019. Meeting Info: 73rd Annual Meeting of the American Academy of Neurology, AAN 2021. Virtual. Apr. 17, 2021-Apr. 22, 2021.

Rosenfeld et al., Developing a drug-device combination for patients with Parkinson's disease during the COVID19 pandemic, Neurology, (May 2021) vol. 96, No. 15 SUPPL 1. Abstract No. 2022. Meeting Info: 73rd Annual Meeting of the American Academy of Neurology, AAN 2021. Virtual. Apr. 17, 2021-Apr. 22, 2021.

Rascol et al., BouNDless: An active-controlled, randomised, double-blind, double-dummy trial of continuous subcutaneous infusion of levodopa/carbidopa with ND0612 in patients with Parkinson's disease experiencing motor complications, European Journal of Neurology, (May 2020) vol. 27, Supp. Supplement 1, pp. 1105. Abstract No. EPO3147. Meeting Info: 6th Congress of the European Academy of Neurology. Paris, France. May 23, 2020-May 26, 2020.

Birnberg et al., Pharmacokinetics of ND0612 administered at different infusion sites and with different cannula lengths: An open-label, randomised, cross-over study in healthy volunteers, European Journal of Neurology, (May 2020) vol. 27, Supp. Supplement 1, pp. 640. Abstract No. EPO1196. 6th Congress of the European Academy of Neurology. Paris, France. May 23, 2020-May 26, 2020.

Espay et al., Efficacy of ND0612 for nocturnal problems and early morning off: A blinded rater study of 2 dosing regimens, Neurology, (Apr. 2019) vol. 92, No. 15, Supp. Supplement 1. Abstract No. P2.8-052. 71st Annual Meeting of the American Academy of Neurology, AAN 2019. Philadelphia, PA, United States. May 4, 2019-May 10, 2019.

Stocchi et al., ND0612 infusion in fluctuating Parkinson's disease: A randomised, double-blind, placebo-controlled study, European Journal of Neurology, (Jun. 2018) vol. 25, Supp. Supplement 2, pp. 515. Abstract No. EPR3066. 4th Congress of the European Academy of Neurology, EAN 2018. Lisbon, Portugal. Jun. 16, 2018-Jun. 19, 2018.

Lewitt et al., Pharmacokinetic and safety characterisation of carbidopa/levodopa subcutaneous infusion (ND0612): Phase I studies in healthy volunteers and patients with fluctuating Parkinson's disease, European Journal of Neurology, (Jun. 2018) vol. 25, Supp. Supplement 2, pp. 514. Abstract No. EPR3065. 4th Congress of the European Academy of Neurology, EAN 2018. Lisbon, Portugal. Jun. 16, 2018-Jun. 19, 2018.

Olanow et al., Efficacy and safety of subcutaneous L-dopa/carbidopa (ND0612H) infusion in fluctuating PD patients, Neurology, (Apr. 2018) vol. 90, No. 15, Supp. Supplement 1. Abstract No. S26.003. 70th Annual Meeting of the American Academy of Neurology, AAN 2018. Los Angeles, Ca, United States. Apr. 21, 2018-Apr. 27, 2018.

Kieburtz et al., The iNDiGO study: A multicenter, randomized, double-blind, placebo-controlled clinical study investigating the efficacy, tolerability, and safety of two dosing regimens of continuous subcutaneous ND0612 infusion given as adjunct treatment to oral levodopa in fluctuating PD, Neurology, (Apr. 2018) vol. 90, No. 15, Supp. Supplement 1. Abstract No. P2.044. 70th Annual Meeting of the American Academy of Neurology AAN 2018. Los Angeles, Ca, United States. Apr. 21, 2018-Apr. 27, 2018.

Adar et al., Identification of the Carbidopa Concentration in Subcutaneously Administered ND0612(Levodopa/ Carbidopa) that Provides Optimal Levodopa Bioavailability, Neurology, (Apr. 2017) vol. 88, No. 16, Supp. Supplement 1. Abstract No. P1.019. 69th American Academy of Neurology Annual Meeting, AAN 2017. Boston, MA, United States. Apr. 22, 2017-Apr. 28, 2017. 4 pages.

Adar et al., Continuous administration of subcutaneous levodopa/carbidopa (ND0612) demonstrated comparable levodopa pharmacokinetics to levodopa/carbidopa intestinal gel (LCIG), Neurology, (Apr. 2017) vol. 88, No. 16, Supp. Supplement 1. Abstract No. S4.003. 69th American Academy of Neurology Annual Meeting, AAN 2017. Boston, MA, United States. Apr. 22, 2017-Apr. 28, 2017.

(56) References Cited

OTHER PUBLICATIONS

Giladi et al., ND0612, a novel liquid formulation of levodopa/carbidopa for subcutaneous infusion in patients with Parkinson's disease achieves stable levodopa plasma levels when administered in low and high doses, Neurology, (Apr. 2017) vol. 88, No. 16, Supp. Supplement 1. Abstract No. S4.002. 69th American Academy of Neurology Annual Meeting, AAN 2017. Boston, MA, United States. Apr. 22, 2017-Apr. 28, 2017.

Nash et al., ND0612—a Newly Developed Liquid Levodopa/Carbidopa Formulation Administered Continuously Subcutaneously by a Mini-pump—Patient Use Perspective, Neurology, (Apr. 2017) vol. 88, No. 16, Supp. Supplement 1. Abstract No. P1.025. 69th American Academy of Neurology Annual Meeting, AAN 2017.

Yacoby-Zeevi et al., Continuous subcutaneous administration of carbidopa enhances levodopa pharmacokinetics: A series of studies conducted in the pig, mouse and healthy volunteers, Neurology, (Apr. 5, 2016) vol. 86, No. 16, Supp. SUPPL. 1. Abstract No. S40.002. 68th American Academy of Neurology Annual Meeting, AAN 2016. Vancouver, BC, Canada. Apr. 15, 2016-Apr. 21, 2016.

U.S. Appl. No. 12/781,357, Continuous Administration of Dopa Decarboxylase Inhibitors and Compositions for Same, filed May 17, 2010, Granted, U.S. Pat. No. 8,193,243.

U.S. Appl. No. 12/836,130, Continuous Administration of Dopa Decarboxylase Inhibitors and Compositions for Same, filed Jul. 14, 2010, Granted, U.S. Pat. No. 7,863,336.

U.S. Appl. No. 12/961,534, Continuous Administration of Dopa Decarboxylase Inhibitors and Compositions for Same, filed Dec. 7, 2010, Granted, U.S. Pat. No. 9,101,663.

U.S. Appl. No. 13/796,232, Continuous Administration of Dopa Decarboxylase Inhibitors and Compositions for Same, filed Mar. 12, 2013, Abandoned, 20130253056.

U.S. Appl. No. 14/276,211, Continuous Administration of Dopa Decarboxylase Inhibitors and Compositions for Same, filed May 13, 2014, Granted, U.S. Pat. No. 9,040,589.

U.S. Appl. No. 14/276,235, Continuous Administration of Dopa Decarboxylase Inhibitors and Compositions for Same, filed May 13, 2014, Granted, U.S. Pat. No. 9,040,590.

U.S. Appl. No. 14/789,214, Continuous Administration of Dopa Decarboxylase Inhibitors and Compositions for Same, filed Jul. 1, 2015, Granted, U.S. Pat. No. 9,993,451.

U.S. Appl. No. 15/244,326, Continuous Administration of Dopa Decarboxylase Inhibitors and Compositions for Same, filed Aug. 23, 2016, Abandoned, 20170196828.

U.S. Appl. No. 15/992,979, Continuous Administration of Dopa Decarboxylase Inhibitors and Compositions for Same, filed May 30, 2018, Abandoned, 20190125708.

U.S. Appl. No. 16/863,459, Continuous Administration of Dopa Decarboxylase Inhibitors and Compositions for Same, filed Apr. 30, 2020, Abandoned, 20210077442.

U.S. Appl. No. 13/885,518, Continuous Administration of L-Dopa, Dopa Decarboxylase Inhibitors, Catechol-O-Methyl Transferase Inhibitors and Compositions for Same, filed Oct. 29, 2013, Granted, U.S. Pat. No. 9,421,267.

U.S. Appl. No. 14/243,625, Continuous Administration of L-Dopa, Dopa Decarboxylase Inhibitors, Catechol-O-Methyl Transferase Inhibitors and Compositions for Same, filed Apr. 2, 2014, Granted, U.S. Pat. No. 9,040,577.

U.S. Appl. No. 14/243,638, Continuous Administration of L-Dopa, Dopa Decarboxylase Inhibitors, Catechol-O-Methyl Transferase Inhibitors and Compositions for Same, filed Apr. 2, 2014, Granted, U.S. Pat. No. 9,040,578.

U.S. Appl. No. 15/209,423, Continuous Administration of L-Dopa, Dopa Decarboxylase Inhibitors, Catechol-O-Methyl Transferase Inhibitors and Compositions for Same, filed Jul. 13, 2016, Abandoned, 20170157077.

U.S. Appl. No. 16/749,435, Continuous Administration of L-Dopa, Dopa Decarboxylase Inhibitors, Catechol-O-Methyl Transferase Inhibitors and Compositions for Same, filed Jan. 22, 2020, Abandoned, 20200397730.

U.S. Appl. No. 17/696,243, Continuous Administration of L-Dopa, Dopa Decarboxylase Inhibitors, Catechol-O-Methyl Transferase Inhibitors and Compositions for Same, filed Mar. 16, 2022, Pending, 20230047523.

U.S. Appl. No. 14/774,938, Method for Treatment of Parkinson's Disease, filed Sep. 11, 2015, Abandoned, 20160022573.

U.S. Appl. No. 16/876,911, Method for Treatment of Parkinson's Disease, filed May 18, 2020, Abandoned, 20210093560.

U.S. Appl. No. 17/698,189, Method for Treatment of Parkinson's Disease, filed Mar. 18, 2022, Pending, 20230047847.

U.S. Appl. No. 14/645,848, Dopa Decarboxylase Inhibitor Compositions, filed Mar. 12, 2015, Granted, U.S. Pat. No. 10,022,320.

U.S. Appl. No. 15/438,472, Dopa Decarboxylase Inhibitor Compositions, filed Feb. 21, 2017, Granted, U.S. Pat. No. 10,258,585.

U.S. Appl. No. 16/008,228, Dopa Decarboxylase Inhibitor Compositions, filed Jun. 14, 2018, Granted, U.S. Pat. No. 10,624,839.

U.S. Appl. No. 16/353,544, Dopa Decarboxylase Inhibitor Compositions, filed Mar. 14, 2019, Granted, U.S. Pat. No. 10,813,902.

U.S. Appl. No. 16/819,740, Dopa Decarboxylase Inhibitor Compositions, filed Mar. 16, 2020, Abandoned, 20210038505.

U.S. Appl. No. 17/901,078, Dopa Decarboxylase Inhibitor Compositions, filed Sep. 1, 2022, Pending, 20230240980.

U.S. Appl. No. 17/031,479, Dopa Decarboxylase Inhibitor Compositions, filed Sep. 24, 2020, Abandoned, 20210000777.

U.S. Appl. No. 17/740,698, Dopa Decarboxylase Inhibitor Compositions, filed May 10, 2020, Pending, 20230096364.

U.S. Appl. No. 15/360,165, Pharmaceutical Compositions Comprising Levodopa Amide and Uses Thereof, filed Nov. 23, 2016, Abandoned, 20170296491.

U.S. Appl. No. 17/334,554, Method for Treatment of Parkinson's Disease, filed May 28, 2021, Granted, U.S. Pat. No. 11,213,502.

U.S. Appl. No. 17/533,984, Method for Treatment of Parkinson's Disease, filed Nov. 23, 2021, Pending, 20220151965.

U.S. Appl. No. 17/567,473, Method for Treatment of Parkinson's Disease, filed Jan. 3, 2022, Granted, U.S. Pat. No. 11,331,293.

U.S. Appl. No. 17/720,777, Method for Treatment of Parkinson's Disease, filed Apr. 14, 2022, Pending, 20230064357.

U.S. Appl. No. 17/736,494, Method for Treatment of Parkinson's Disease, filed May 4, 2022, Granted, U.S. Pat. No. 11,458,115.

U.S. Appl. No. 18/092,688, Method for Treatment of Parkinson's Disease, filed Jan. 3, 2023, Pending, 20230157985.

U.S. Appl. No. 17/736,494, Methods and Compositions for Reducing Symptoms of Parkinson's Diseasep, filed Aug. 15, 2023, Pending.

"Duodopa Intestinal Gel," Electronic Medicines Compendium, XP-022724129, retrieved from https://www.medicines.org.uk/emc/medicine/20786/SPC/Duodopa+intestinal+gel/#composition on Sep. 5, 2014 (2013), 7 pages.

National Institutes of Health (2010) 'Pharmacokinetics of Levodopa/Carbidopa Infusion With and Without Oral Catechol-O-Methyl Transferase (COMT) Inhibitors (DuoCOMT),' U.S. National Library of Medicine, Clinical Trials.gov, Clinical Trials.gov Identifier: NCT 00906828, XP-002724128, retrieved from URL://http://clinicaltrials.gov/ct2/show/NCT00906828 on Sep. 5, 2014 (3 pages).

Paulekuhn, GS, et al. (2007) "Trends in Active Pharmaceutical Ingredient Salt Selection based on Analysis of the Orange Book Database," Journal of Medicinal Chemistry, American Chemical Society, 50(26):6665-6672.

Banerjee, RC, (1979) "Aminonitriles and Aminothioamides Related to Natural Amino Acids," International Journal of Peptide and Protein Res. 14(3):234-46.

Elder D., et al., (2013) "Use of Pharmaceutical Salts and Cocrystals to Address the Issue of Poor Solubility," International Journal of Pharmaceutics, 453(1):88-100.

Hilfiker et al., "Relevance of Solid-state Properties for Pharmaceutical Products" in Polymorphism: in the Pharmaceutical Industry, p. 1-19 (Ed. Hilfiker, Wiley-VCH Verlag GmbH & Co. KGaA, Weinheim, 2006).

Written Opinion of the International Searching Authority for International Application No. PCT/IB2018/056125, mailed Jan. 14, 2019 (10 pages).

International Search Report for International Application No. PCT/IB2018/056125, mailed Jan. 14, 2019 (5 pages).

(56) References Cited

OTHER PUBLICATIONS

Written Opinion of the International Searching Authority for International Application No. PCT/IB2018/056126, mailed Nov. 26, 2018 (10 pages).
International Search Report for International Application No. PCT/IB2018/056126, mailed Nov. 26, 2018 (4 pages).
Written Opinion of the International Searching Authority for International Application No. PCT/IB2018/056127, mailed Nov. 26, 2018 (7 pages).
International Search Report for International Application No. PCT/IB2018/056127, mailed Nov. 26, 2018 (4 pages).
Aldea G, et al., (2004) Abstract 15, entitled "Comparison of the speed of absorption of S(+)-ibuprofen in two pharmaceutical specialties: ibuprofen (arginate) and dexibuprofen" in Abstract Pamphlet for the XIX Congress of the Spanish Society of Clinical Pharmacology, XIX Congress of the Spanish Society of Clinical Pharmacology, Oct. 28-30, 2004, Santander, Spain (54 pages).
Levin, O.S. (2008) "Diagnosis and treatment of restless legs syndrome" Attending Physician 5(8) (retrieved Jul. 8, 2019, from the internet at <<https://www.lvrach.ru/2008/05/5154263>> (10 pages).
Technology of Dosage Forms, in Medicine, vol. 1, §10.3, p. 187-91, and §14.2, p. 223-4 (Ed. T.S. Kondrat'eva, Moscow, 1991)(7 pages; English language translation of Office Action).
"Dihydroxyphenylalanine" PubmChem CID No. 6971033, (retrieved on Jul. 8, 2019, from the internet at <<https://pubchem.ncbi.nlm.nih.gov/compound/6971033>>)(24 pages).
English language translation of Official Action issued in connection with Russian Patent Application No. 2011149976/15, dated Sep. 15, 2014 (6 pages).
CAPLUS Registry No. 34996-80-0 (1984)) retrieved from CAPLUS on May 16, 2008 (1 page).
CAPLUS Registry No. 73148-96-6 (1984), retrieved from CAPLUS database on May 16, 2008 (1 page).
CAPLUS Registry No. 120346-34-1 (1989), retrieved from CAPLUS on May 16, 2008 (2 pages).
Roche Products Limited (2016) "Madopar 50 mg/12.5 mg Dispersible Tablets, Summary of Product Characteristics" Updated Mar. 17, 2016 (9 pages).
Roche Products Limited (2016) "Madopar 100 mg/25 mg Dispersible Tablets, Summary of Product Characteristics" Updated Mar. 17, 2016 (9 pages).
Roche Products Limited (2015) "Package leaflet: Information for the patient" Updated Mar. 2015 (6 pages).
"New Zealand standardised formulation batch sheet, Carbidopa/Levodopa (Sinemet®) suspension" (2010) Last updated Dec. 2010 (1 page).
Nationwide Children's Hospital (2010) "Levodopa/Carbidopa Oral Suspension 5mg-1.25mg/mL" (1 page).
AbbVie Ltd (2017) "Duodopa intestinal gel, Summary of Product Characteristics" Updated Dec. 5, 2017 (12 pages).
Merck Sharp & Dohme Limited (2019) "Sinemet 12.5mg/50mg Tablets, Summary of Product Characteristics" Updated Feb. 1, 2019 (7 pages).
Pharminfotech (2011) "Formulation in Pharmacy Practice—eMixt: Levodopa/Carbidopa" Updated Sep. 2011 (retrieved from <http://www.pharminfotech.co.nz/maual/Formulation/mixtures/levodopa/htm> on Apr. 8, 2019)(1 page).
"Mutschler Arzneimittelwirkungen" p. 322-5 (Ernst Mutschler et al. eds., Wissenschaftliche Verlagsgesellschaft mbH, 2008)(Cited in Decision rejecting the opposition of European Patent No. 2 432 454, dated Aug. 26, 2019)(6 pages).
European Patent Office, Opposition Division "Decision rejecting the opposition of European Patent No. 2 432 454" Aug. 26, 2019 (13 pages).
S. Mondal "Basic Undergraduate Pharmacology" p. 280 (Academic Publishers, Mar. 2010) (3 pages).
Kurth et al., (1993) "Oral levodopa/carbidopa solution versus tablets in Parkinson's patients with severe fluctuations: A pilot study," Neurology 43:1036-9.
J. E. Ahlskog "Parkinson's Disease Treatment Guide for Physicians" p. 179-81 (Oxford University Press, 2009) (6 pages).
U. Moser "Arzneibuch-Kommentar" p. C18 (Wissenschaftliche Verlagsgesellschaft mbH, 1993)(Cited in Decision rejecting the opposition of European Patent No. 2 432 454, dated Aug. 26, 2019)(2 pages).
L. Braiman-Wiksman (2018) "Experimental Report, A. Stability Testing" p. 1-7.
"Mutschler Arzneimittelwirkungen: Lehrbuch der Pharmakologie und Toxikologie" p. 327 (Ernst Mutschler et al. eds., Wissenschaftliche Verlagsgesellschaft mbH, 2008)(Cited in Decision rejecting the opposition of European Patent No. 2 432 454, dated Aug. 26, 2019)(3 pages).
"The Merck Index: an Encyclopedia of Chemicals, Drugs, and Biologicals" p. xv and 784-5 (M. Windholz et al. eds., Merck & Co., Inc., 10th edition, 1983)(4 pages).
Appendices II and III, submitted to the European Patent Office on Mar. 16, 2016 in connection with European Application No. EP10725880.8, and cited in the Decision rejecting the opposition of European Patent No. 2 432 454, dated Aug. 26, 2019 (3 pages).
Nagayama, et al. (2004) "The Effect of Ascorbic Acid on the Pharmacokinetics of Levodopa in Elderly Patients with Parkinson Disease," Clin Neuropharmacol, 27(6):270-3.
Extended European Search Report (EESR) for EP 20150020, dated May 14, 2020, 11 pages.
"Pharmacokinetics of Levodopa/Carbidopa Infusion With and Without Oral Catechol-0-methyl Transferase (COMT) Inhibitors", Internet, Jan. 2010 (Jan. 2010).
Notification of the Second Office Action dated May 25, 2021 for Chinese Application No. 201910369050.X.
Notification of Office Action dated Apr. 23, 2021 for Canadian Application No. 2,942,244.
Ramot et al., "Ninety-day Local Tolerability and Toxicity Study of ND0612, a Novel Formulation of Levodopa/ Carbidopa, Administered by Subcutaneous Continuous Infusion in Minipigs" Toxicologic Pathology 2017, vol. 45(6) 764-773.
"History of Changes for Study: NCT02782481: A Clinical Study Investigating the Efficacy, Tolerability, and Safety of Continuous Subcutaneous ND0612 Infusion Given a Treatment to Oral Levodopa in Patients With Parkinson's Disease With Motor Fluctuations" NIH U.S. National Library of Medicine, (History of Changes for Study: NCT02782481 (clinicaltrials.gov) <https://clinicaltrials.gov/ct2/history/NCT02782481>, submitted Dec. 9, 2019, downloaded from ClinicalTrials.gov on Jan. 31, 2022.
International Search Report for PCT/IL2021/051355, mailed Jan. 20, 2022.
Written Opinion of the International Search Authority for PCT/IL2021/051355, mailed Jan. 20, 2022.
"Levodopa," in Encyclopedia of Drugs, p. 471 (Moscow, RLS, 2001)(2 pages; English language translation of Office Action.
Nahata, et al., (2000) "Development of Two Stable Oral Suspensions of Levodopa-Carbidopa for Children with Amblyopia," J. Pediatric Ophthal. & Strab., 37:333-337.
International Search Report for PCT/IL2015/050258, mailed Aug. 13, 2015 (3 pages).
MacEwen, et al., (1981) "Chronic Inhalation Toxicity of Hydrazine: Oncogenic Effects," Air Force Aerospace Medical Research Laboratory, pp. 1-67.
Pappert, et al., (1997) "Clinical/Scientific Notes—The Stability of Carbidopa in Solution," Movement Disorders, vol. 12, pp. 608-623.
Stocchi et al., (2005), "Intermittent vs Continuous Levodopa Administration in Patients With Advanced Parkinson Disease," Arch Neurol, vol. 62, pp. 905-910.
Ahtila S et al., (1995) 'Effect of Entacapone, a COMT Inhibitor, on the Pharmacokinetics and metabolism of Levodopa After Administration of Controlled-Release Levodopa-Carbidopa in Volunteers,' Clin Neuropharmacol, 18(1):46-57.
Ingman, K et al., (2012) 'The Effect of Different Dosing Regimens of Levodopa/Carbidopa/Entacapone on Plasma Levodopa Concentrations,' Eur J Clin Pharmacol, 68:281-289.

(56) References Cited

OTHER PUBLICATIONS

Diederich C et al., (1997), 'Effects of L-DOPA/Carbidopa Administration on the Levels of L-DOPA, Other Amino Acids and Related Compounds in the Plasma, Brain and Heart of the Rat,' Pharmacology, 55(3):109-16.
Mashkovsky, M.D., (2012) "Pharmaceuticals" 16th Edition. Moscow, New wave. 1 page. (Abstract only).
Kharkevich, D.A., (1996) "Pharmacology M., Medicine." 1 page. (Abstract only).
Office action dated Dec. 27, 2017, issued in connection with Russian Patent Application No. 2015143112 (13 pages).
Jog et al. (2008) 'Naturalistic Evaluation of Entacapone in Patients with Signs and Symptons of L-Dopa Wearing-Off,' Current Medical Research and Opinions, 24:11, 3207-3215.
Gordon, M., et al., (2007) "Intravenous Levodopa Administration in Humans Based on a Two-Compartment Kinetic Model," J. Neuroscience Methods, 159: 300-307.
Hirano, et al., (2008) "Arginine Increases the Solubility of Coumarin: Comparison with Salting-in and Salting-out Additives," J. Biochem, 144 (3): 363-369.
International Search Report for PCT/IL2010/000400, mailed Jul. 29, 2010, 4 pages.
International Search Report for PCT/IL2011/000881, mailed Apr. 3, 2012, 5 pages.
International Search Report for PCT/IL2014/050261, mailed May 30, 2014, 4 pages.
Martinez, et al., (1999) "Hypothesis: Can N-Acetylcysteine be Beneficial in Parkinson's Disease?", Life Sciences, 64 (15):1253-1257.
Mehlisch, et al., (2002) "A Controlled Comparative Study of Ibuprofen Arginate Versus Conventional Ibuprofen in the Treatment of Postoperative Dental Pain," J. Clin. Pharmacol., 42: 904-911.
Nord, M. et al., (2010) "The Effect of Peripheral Enzyme Inhibitors on Levodopa Concentrations in Blood and CSF," Movement Disorders, 25(3): 363-367.
Nutt JG, (2008), 'Pharmacokinetics and Pharmacodynamics of Levodopa,' Mov. Disord., S580-4.
Nutt, et al., (1997) "Motor Fluctuations During Continuous Levodopa Infusions in Patients with Parkinson's Disease," Movement Disorders, 12(3):285-292.
Nyholm, D. (2006) "Enteral Levodopa/Carbidopa Gel Infusion for the Treatment of Motor Fluctuations and Dyskinesias in Advanced Parkinson's Disease," Expert Review of Neurotherapeutics, 6(10): 1403-1411.
Nyholm, D., et al., (2012) "Levodopa Infusion Combined with Entacapone or Tolcapone in Parkinson Disease: a Pilot Trial," European Journal of Neurology, 19: 820-826.
Olanow, C.W. (2008) "Levopoda/Dopamine Replacement Strategies in Parkinson's Disease—Future Directions," Movement Disorders, 23:S613-S622.
Pardo, et al., (1993) "Ascorbic acid protects against levodopa-induced neurotoxicity on a catecholamine-rich human neuroblastoma cell line", Mov. Disord., 8(3):278-284. (Abstract Only).
Redenti, et al., (2001) "Cyclodextrin Complexes of Salts of Acidic Drugs. Thermodynamic Properties, Structural Features, and Pharmaceutical Applications," Journal of Pharmaceutical Sciences, 90(8): 979-986.
Steiger, M., et al., (1991) "The Clinical Efficacy of Oral Levodopa Methyl Ester Solution in Reversing Afternoon "Off" Periods in Parkinson's Disease," Clin. Neuropharmacol., 14:241-244.
Tsumoto, K., et al., (2004) "Role of Arginine in Protein Refolding, Solubilization, and Purification," Biotechnol. Prog., 20:1301-1308.
Umezawa H., et al., (1975) "Isolation of Isoflavones Inhibiting Dopa Decarboxylase From Fungi and *Streptomyces*," J Antibiot, 28(12):947-52.

Written Opinion for International Application No. PCT/IL2015/050258, mailed Aug. 13, 2015 (6 pages).
Written Opinion of the International Search Authority for PCT/IL2010/000400 mailed Jul. 29, 2010, 8 pages.
Written Opinion of the International Search Authority for PCT/IL2011/000881 mailed Apr. 3, 2012, 6 pages.
Written Opinion of the International Search Authority for PCT/IL2014/050261 mailed May 30, 2014, 5 pages.
Yacoby-Zeevi, O., et al. (2010) "Markedly Enhanced Levodopa Pharmacokinetics from Continuous Subcutaneous Carbidopa Administration," European Journal of Neurology, 17 (Suppl. 3): 52.
Roche Products (New Zealand) Limited. (2015) "Madopar Consumer Medicine Information." 1-9.
International Search Report for PCT/IL2016/051261, mailed May 29, 2017 (6 pages).
Written Opinion of the International Searching Authority for PCT/IL2016/051261, mailed May 29, 2017 (14 pages).
Food and Drug Administration (2008) "NDA 17-555/S-069: Sinemet (Carbidopa-Levodopa) Tablets," [online] Retrieved from the internet on Jun. 20, 2018, at: http://www.accessdata.fda.gov/drugsatfda_docs/label/2008/017555s069lbl.pdf (13 pages).
Kurth, MC (1997) 'Using Liquid Levodopa in the Treatment of Parkinson's Disease. A Practical Guide,' Drugs & Aging, 10 (5): 332-340.
López Lozano, JJ et al., (1995) 'Preparation of a Levodopa/Carbidopa Solution in Ascorbic Acid (Citridopa) and Chromatographic and Electrochemical Assessment of its Stability over 24 Hours,' Neurologia 10:155-158 (Abstract only).
Office Action dated Sep. 12, 2018, issued in connection with Russian Patent Application No. 2016135952 (12 pages).
Anonymous, (2002), "Levodopa: Management of Parkinson's Disease," Mov Disord, 17(Suppl 4); S23-S37.
Atlas D, (2016), "DopAmide: Novel, Water-Soluble, Slow-Release I-dihydroxyphenylalanine (l-DOPA) Precursor Moderates l-DOPA Conversion to Dopamine and Generates a Sustained Level of Dopamine at Dopaminergic Neurons," CNS Neurosci Ther, 22(6):461-7.
Chun IK et al., (2011), "Design and Evaluation of Levodopa Methyl Ester Intranasal Delivery Systems," J Parkinsons Dis, 1 (1):101-7.
Di Stefano A et al., (2009), "New Drug Delivery Strategies for Improved Parkinson's Disease Therapy," Expert Opin Drug Deliv, 6(4):389-404.
International Search Report for International Application No. PCT/IB2018/051048, mailed May 21, 2018 (3 pages).
Written Opinion of the International Searching Authority for International Application No. PCT/IB2018/051048, mailed May 21, 2018 (7 pages).
International Search Report for International Application No. PCT/IL04/00103, mailed Aug. 7, 2006 (3 pages).
Written Opinion of the International Searching Authority for International Application No. PCT/IL04/00103, mailed Aug. 7, 2006 (4 pages).
Search report for PCT/IL2024/050368, mailed Jun. 23, 2024, 3 pages.
Written Opinion for PCT/IL2024/050368, mailed Jun. 23, 2024, 9 pages.
Espay, A., et al., "Safety and efficacy of continuous subcutaneous levodopa-carbidopa infusion (ND0612) for Parkinson's disease with motor fluctuations (BouNDless): a phase 3, randomized, double-blind, double-dummy, multicentre trial", www.thelancet.com/neurology, Mar. 15, 2024.
Adar, L., et al., "Relative bioavailability of levodopa given as a subcutaneous infusion with ND0612 versus oral IR levodopa/carbidopa", European Journal of Neurology, (Jun. 2023) vol. 30, No. Suppl. 1, Sp. Iss. SI, pp. 165. 9th Congress of the European-Academy-of-Neurology. Budapest, Hungary. Jul. 1-4, 2023.

|  | Open-label run-in phase (ND0612 (n=322)) | Double-blind double-dummy phase | |
|---|---|---|---|
|  |  | Oral levodopa–carbidopa (n=131) | ND0612 (n=128) |
| Overall | | | |
| Any adverse events | 287 (89%) | 97 (74%) | 103 (80%) |
| Mild | 167/287 (58%) | 53/97 (55%) | 62/103 (60%) |
| Moderate | 108/287 (38%) | 36/97 (37%) | 36/103 (35%) |
| Severe | 12/287 (4%) | 8/97 (8%) | 5/103 (5%) |
| Drug-related adverse events | 275 (85%) | 69 (53%) | 86 (67%) |
| Serious adverse events | 6 (2%) | 5 (4%) | 7 (5%) |
| Drug-related serious adverse events | 3 (1%) | 0 | 4 (3%) |
| Adverse events leading to death | 0 | 0 | 1 (1%)* |
| Adverse events leading to discontinuation | 26 (8%) | 4 (3%) | 7 (5%) |
| Adverse events leading to discontinuation in at least two participants | | | |
| Infusion site reactions† | 19 (6%) | 0 | 3 (2%) |
| On and off occurrence | 1 (0%) | 2 (2%) | 2 (2%) |
| Fall | 0 | 0 | 2 (2%) |
| Adverse events of special interest | | | |
| Infusion-site reactions† | 266 (83%) | 56 (43%) | 73 (57%) |
| Mild | 203/266 (76%) | 48/56 (86%) | 56/73 (77%) |
| Moderate | 58/266 (22%) | 7/56 (13%) | 16/73 (22%) |
| Severe | 5/266 (2%) | 1/56 (2%) | 1/73 (1%) |
| Hypersensitivity‡ | 1 (0%) | 0 | 0 |
| Polyneuropathy‡ | 1 (0%) | 0 | 3 (2%) |
| Adverse events in ≥5% of participants | | | |
| Infusion-site nodule | 206 (64%) | 36 (27%) | 33 (26%) |
| Infusion-site haematoma | 205 (64%) | 17 (13%) | 39 (30%) |
| Infusion-site infection | 18 (6%) | 3 (2%) | 13 (10%) |
| Infusion-site erythema | 25 (8%) | 3 (2%) | 12 (9%) |
| Infusion-site pain | 55 (17%) | 9 (7%) | 11 (9%) |
| Infusion-site haemorrhage | 12 (4%) | 7 (5%) | 1 (1%) |
| Fall | 17 (5%) | 16 (12%) | 9 (7%) |
| On and off occurrence | 17 (5%) | 13 (10%) | 5 (4%) |
| Dyskinesia | 30 (9%) | 5 (4%) | 3 (2%) |
| Anxiety | 3 (1%) | 9 (7%) | 6 (5%) |
| Headache | 7 (2%) | 8 (6%) | 2 (2%) |

Data are n (%) or n/N (%). *One participant died due to a fall complicated with traumatic brain injury, which was not considered to be related to study treatment. †Grouped term including infusion-site nodule, infusion-site bruising or haematoma, infusion-site infection, infusion-site erythema, infusion-site pain, infusion-site eschar, and infusion-site swelling. ‡Adjudicated cases.

FIG. 11

METHODS AND COMPOSITIONS FOR REDUCING SYMPTOMS OF PARKINSON'S DISEASE

CROSS REFERENCE TO RELATED APPLICATIONS

This application claims the benefit and priority to U.S. Provisional Patent Application No. 63/564,464, filed Mar. 12, 2024, and is a continuation-in-part of U.S. application Ser. No. 18/234,232, filed Aug. 15, 2023, which claims the benefit of and priority to U.S. Provisional Patent Application No. 63/459,438, filed Apr. 14, 2023, and U.S. Provisional Patent Application No. 63/508,634, filed Jun. 16, 2023, the disclosure of each of which is incorporated by reference herein in its entirety.

TECHNICAL FIELD

The present invention provides a method for treatment of neurological or movement disorders such as Parkinson's disease by parenteral administration of levodopa and a dopa decarboxylase inhibitor (DDCI), such as carbidopa, benserazide, or any combination thereof.

BACKGROUND

Parkinson's disease is a degenerative condition characterized by reduced concentration of the neurotransmitter dopamine in the brain. Levodopa (L-dopa or L-3,4-dihydroxyphenylalanine) is an immediate metabolic precursor of dopamine that, unlike dopamine, is able to cross the blood-brain barrier, and is most commonly used for restoring the dopamine concentration in the brain. For the past 40 years, levodopa has remained the most effective therapy for the treatment of Parkinson's disease.

However, levodopa has a short half-life in plasma that, even under best common current standard of care, results in pulsatile dopaminergic stimulation. Long-term therapy is therefore complicated by motor fluctuations and dyskinesia that can represent a source of significant disability for certain patients. A therapeutic strategy that could ultimately deliver levodopa/dopamine to the brain in a more continuous and physiologic manner would provide the benefits of standard levodopa with reduced motor complications and is much needed by patients suffering from Parkinson's disease and other neurological or movement disorders.

SUMMARY OF THE INVENTION

Provided herein, inter alia, are methods and pharmaceutical compositions for the treatment of a neurological or movement disorder comprising parenteral administration of levodopa, or salts thereof (e.g., pharmaceutically acceptable salts thereof), and compositions comprising the same (e.g., pharmaceutically acceptable compositions, for example, liquid pharmaceutical compositions) and a dopa decarboxylase inhibitor (DDCI), or salts thereof (e.g., pharmaceutically acceptable salts thereof), and compositions comprising the same (e.g., pharmaceutically acceptable compositions, for example, liquid pharmaceutical compositions).

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof,
 wherein after 2 or 3 days of administration, the administration results in the patient having at least one of:
 an increase from baseline in daily Good ON-time,
 a reduction from baseline in daily ON-time with moderate-severe dyskinesia,
 or any combination thereof.

According to some embodiments, the pharmaceutically acceptable liquid composition comprises levodopa or a pharmaceutically acceptable salt thereof and carbidopa or a pharmaceutically acceptable salt thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa,
 wherein after 2 or 3 days of administration, the administration results in the patient having at least one of:
 an increase from baseline in daily Good ON-time,
 a reduction from baseline in daily ON-time with moderate-severe dyskinesia,
 or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa in a ratio of about 8:1 w/w,
 wherein after 2 or 3 days of administration, the administration results in the patient having at least one of:
 an increase from baseline in daily Good ON-time,
 a reduction from baseline in daily ON-time with moderate-severe dyskinesia,
 or any combination thereof.

Embodiments of the invention are directed to a method of treating a patient with Parkinson's disease, the method comprising subcutaneously administering to the patient, substantially continuously for about 24 hours/day and for about 2 or 3 days, a pharmaceutically acceptable liquid composition comprising levodopa or a pharmaceutically acceptable salt thereof and, optionally, carbidopa or a pharmaceutically acceptable salt thereof,
 wherein the administration results in the patient having at least one of:
 an increase from baseline in daily Good ON-time,
 a reduction from baseline in daily ON-time with moderate-severe dyskinesia,
 or any combination thereof.

According to some embodiments, the pharmaceutically acceptable liquid composition comprises levodopa or a pharmaceutically acceptable salt thereof and carbidopa or a pharmaceutically acceptable salt thereof.

Embodiments of the invention are directed to a method of treating a patient with Parkinson's disease, the method comprising subcutaneously administering to the patient, substantially continuously for about 24 hours/day and for about 2 or 3 days, a pharmaceutically acceptable liquid composition comprising levodopa and carbidopa,
 wherein the administration results in the patient having at least one of:
 an increase from baseline in daily Good ON-time,
 a reduction from baseline in daily ON-time with moderate-severe dyskinesia,
 or any combination thereof.

Embodiments of the invention are directed to a method of treating a patient with Parkinson's disease, the method comprising subcutaneously administering to the patient, substantially continuously for about 24 hours/day and for about 2 or 3 days, a pharmaceutically acceptable liquid composition comprising levodopa and carbidopa in a ratio of about 8:1 w/w,
wherein the administration results in the patient having at least one of:
an increase from baseline in daily Good ON-time,
a reduction from baseline in daily ON-time with moderate-severe dyskinesia,
or any combination thereof.

Embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa or a pharmaceutically acceptable salt thereof and, optionally, carbidopa or a pharmaceutically acceptable salt thereof,
wherein by the third consecutive day, the administration results in the patient having at least one of:
an increase from baseline in daily Good ON-time,
a reduction from baseline in daily ON-time with moderate-severe dyskinesia,
or any combination thereof.

According to some embodiments, the pharmaceutically acceptable liquid composition comprises levodopa or a pharmaceutically acceptable salt thereof and carbidopa or a pharmaceutically acceptable salt thereof.

Embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa and carbidopa,
wherein by the third consecutive day, the administration results in the patient having at least one of:
an increase from baseline in daily Good ON-time,
a reduction from baseline in daily ON-time with moderate-severe dyskinesia,
or any combination thereof.

Embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa and carbidopa in a ratio of about 8:1 w/w,
wherein by the third consecutive day, the administration results in the patient having at least one of:
an increase from baseline in daily Good ON-time,
a reduction from baseline in daily ON-time with moderate-severe dyskinesia,
or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof,
wherein after 2 or 3 days of administration, the administration results in the patient having at least one of:
an increase from baseline in daily Good ON-time,
a reduction from baseline in daily ON-time with moderate-severe dyskinesia,
an improvement from baseline based on a Subject Global Impression of Change (SGI-C) score,
an improvement from baseline based on a Clinical Global Impression of Change (CGI-C) score,
or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof,
wherein after 2 or 3 days of administration, the administration results in the patient having at least one of:
an increase from baseline in daily Good ON-time,
a reduction from baseline in daily ON-time with moderate-severe dyskinesia,
an improvement from baseline based on a Patient Global Impression of Improvement (PGI-I) score,
an improvement from baseline based on a Clinical Global Impression of Improvement (CGI-I) score,
or any combination thereof.

According to some embodiments, the pharmaceutically acceptable liquid composition comprises levodopa or a pharmaceutically acceptable salt thereof and carbidopa or a pharmaceutically acceptable salt thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa,
wherein after 2 or 3 days of administration, the administration results in the patient having at least one of:
an increase from baseline in daily Good ON-time,
a reduction from baseline in daily ON-time with moderate-severe dyskinesia,
an improvement from baseline based on a Subject Global Impression of Change (SGI-C) score,
an improvement from baseline based on a Clinical Global Impression of Change (CGI-C) score,
or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa,
wherein after 2 or 3 days of administration, the administration results in the patient having at least one of:
an increase from baseline in daily Good ON-time,
a reduction from baseline in daily ON-time with moderate-severe dyskinesia,
an improvement from baseline based on a Patient Global Impression of Improvement (PGI-I) score,
an improvement from baseline based on a Clinical Global Impression of Improvement (CGI-I) score,
or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa in a ratio of about 8:1 w/w, wherein after 2 or 3 days of administration, the administration results in the patient having at least one of:
an increase from baseline in daily Good ON-time,
a reduction from baseline in daily ON-time with moderate-severe dyskinesia,
an improvement from baseline based on a Subject Global Impression of Change (SGI-C) score,
an improvement from baseline based on a Clinical Global Impression of Change (CGI-C) score,
or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa in a ratio of about 8:1 w/w,
wherein after 2 or 3 days of administration, the administration results in the patient having at least one of:
an increase from baseline in daily Good ON-time,
a reduction from baseline in daily ON-time with moderate-severe dyskinesia,
an improvement from baseline based on a Patient Global Impression of Improvement (PGI-I) score,
an improvement from baseline based on a Clinical Global Impression of Improvement (CGI-I) score,
or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof,
wherein after 2 or 3 days of administration, the administration results in the patient having at least one of:
an increase from baseline in daily Good ON-time,
a reduction from baseline in daily ON-time with moderate-severe dyskinesia,
a reduction from baseline in daily OFF-time,
an increase from baseline in daily ON-time without dyskinesia,
a reduction from baseline in total daily troublesome dyskinesia,
an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
or any combination thereof.

According to some embodiments, the pharmaceutically acceptable liquid composition comprises levodopa or a pharmaceutically acceptable salt thereof and carbidopa or a pharmaceutically acceptable salt thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa,
wherein after 2 or 3 days of administration, the administration results in the patient having at least one of:
an increase from baseline in daily Good ON-time,
a reduction from baseline in daily ON-time with moderate-severe dyskinesia,
a reduction from baseline in daily OFF-time,
an increase from baseline in daily ON-time without dyskinesia,
a reduction from baseline in total daily troublesome dyskinesia,
an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
or any combination thereof.

Embodiments of the invention are directed to a method of treating a patient with Parkinson's disease, the method comprising subcutaneously administering to the patient, substantially continuously for about 24 hours/day, a pharmaceutically acceptable liquid composition comprising levodopa and carbidopa in a ratio of about 8:1 w/w,
wherein after 2 or 3 days of administration, the administration results in the patient having at least one of:
an increase from baseline in daily Good ON-time,
a reduction from baseline in daily ON-time with moderate-severe dyskinesia,
a reduction from baseline in daily OFF-time,
an increase from baseline in daily ON-time without dyskinesia,
a reduction from baseline in total daily troublesome dyskinesia,
an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
or any combination thereof.

Embodiments of the invention are directed to a method of treating a patient with Parkinson's disease, the method comprising subcutaneously administering to the patient, substantially continuously for about 24 hours/day and for about 2 to 3 days, a pharmaceutically acceptable liquid composition comprising levodopa or a pharmaceutically acceptable salt thereof and, optionally, carbidopa or a pharmaceutically acceptable salt thereof,
wherein the administration results in the patient having at least one of:
an increase from baseline in daily Good ON-time,
a reduction from baseline in daily ON-time with moderate-severe dyskinesia,
a reduction from baseline in daily OFF-time,
an increase from baseline in daily ON-time without dyskinesia,
a reduction from baseline in total daily troublesome dyskinesia,
an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
or any combination thereof.

According to some embodiments, the pharmaceutically acceptable liquid composition comprises levodopa or a pharmaceutically acceptable salt thereof and carbidopa or a pharmaceutically acceptable salt thereof.

Embodiments of the invention are directed to a method of treating a patient with Parkinson's disease, the method comprising subcutaneously administering to the patient, substantially continuously for about 24 hours/day and for about 2 to 3 days, a pharmaceutically acceptable liquid composition comprising levodopa and carbidopa,
    wherein the administration results in the patient having at least one of:
    an increase from baseline in daily Good ON-time,
    a reduction from baseline in daily ON-time with moderate-severe dyskinesia,
    a reduction from baseline in daily OFF-time,
    an increase from baseline in daily ON-time without dyskinesia,
    a reduction from baseline in total daily troublesome dyskinesia,
    an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
    or any combination thereof.

Embodiments of the invention are directed to a method of treating a patient with Parkinson's disease, the method comprising subcutaneously administering to the patient, substantially continuously for about 24 hours/day and for about 2 to 3 days, a pharmaceutically acceptable liquid composition comprising levodopa and carbidopa in a ratio of about 8:1 w/w,
    wherein the administration results in the patient having at least one of:
    an increase from baseline in daily Good ON-time,
    a reduction from baseline in daily ON-time with moderate-severe dyskinesia,
    a reduction from baseline in daily OFF-time,
    an increase from baseline in daily ON-time without dyskinesia,
    a reduction from baseline in total daily troublesome dyskinesia,
    an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
    or any combination thereof.

Embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa or a pharmaceutically acceptable salt thereof and, optionally, carbidopa or a pharmaceutically acceptable salt thereof,
    wherein by the third consecutive day the administration results in the patient having at least one of:
    an increase from baseline in daily Good ON-time,
    a reduction from baseline in daily ON-time with moderate-severe dyskinesia,
    a reduction from baseline in daily OFF-time,
    an increase from baseline in daily ON-time without dyskinesia,
    a reduction from baseline in total daily troublesome dyskinesia,
    an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
    or any combination thereof.

According to some embodiments, the pharmaceutically acceptable liquid composition comprises levodopa or a pharmaceutically acceptable salt thereof and carbidopa or a pharmaceutically acceptable salt thereof.

Embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa and carbidopa,
    wherein by the third consecutive day the administration results in the patient having at least one of:
    an increase from baseline in daily Good ON-time,
    a reduction from baseline in daily ON-time with moderate-severe dyskinesia,
    a reduction from baseline in daily OFF-time,
    an increase from baseline in daily ON-time without dyskinesia,
    a reduction from baseline in total daily troublesome dyskinesia,
    an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
    or any combination thereof.

Embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa and carbidopa in a ratio of about 8:1 w/w,
    wherein by the third consecutive day the administration results in the patient having at least one of:
    an increase from baseline in daily Good ON-time,
    a reduction from baseline in daily ON-time with moderate-severe dyskinesia,
    a reduction from baseline in daily OFF-time,
    an increase from baseline in daily ON-time without dyskinesia,
    a reduction from baseline in total daily troublesome dyskinesia,
    an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score,
    or any combination thereof.

According to some embodiments, the administration results in the patient having an increase from baseline in daily Good ON-time. According to some embodiments, the administration results in the patient having a reduction from baseline in daily ON-time with moderate-severe dyskinesia. According to some embodiments, the administration results in the patient having an improvement from baseline based on a Subject Global Impression of Change (SGI-C) score. According to some embodiments, the administration results in the patient having an improvement from baseline based on a Patient Global Impression of Improvement (PGI-I) score. According to some embodiments, the administration results in the patient having an improvement from baseline based on a Clinical Global Impression of Change (CGI-C) score. According to some embodiments, the administration results in the patient having an improvement from baseline based on a Clinical Global Impression of Improvement (CGI-I) score.

According to some embodiments, the administration results in the patient having an increase from baseline in daily Good ON-time and a reduction from baseline in daily ON-time with moderate-severe dyskinesia. According to some embodiments, the administration results in the patient having an increase from baseline in daily Good ON-time and an improvement from baseline based on a Subject Global Impression of Change (SGI-C) score. According to some embodiments, the administration results in the patient having an increase from baseline in daily Good ON-time and an improvement from baseline based on a Patient Global Impression of Improvement (PGI-I) score. According to some embodiments, the administration results in the patient having an increase from baseline in daily Good ON-time and an improvement from baseline based on a Clinical Global Impression of Change (CGI-C) score. According to some embodiments, the administration results in the patient having a reduction from baseline in daily ON-time with moderate-severe dyskinesia and an improvement from baseline based on a Subject Global Impression of Change (SGI-C) score. According to some embodiments, the administration results in the patient having a reduction from baseline in daily ON-time with moderate-severe dyskinesia and an improvement from baseline based on a Patient Global Impression of Improvement (PGI-I) score. According to some embodiments, the administration results in the patient having a reduction from baseline in daily ON-time with moderate-severe dyskinesia and an improvement from baseline based on a Clinical Global Impression of Change (CGI-C) score. According to some embodiments, the administration results in the patient having an improvement from baseline based on a Subject Global Impression of Change (SGI-C) score and an improvement from baseline based on a Clinical Global Impression of Change (CGI-C) score. According to some embodiments, the administration results in the patient having an improvement from baseline based on a Patient Global Impression of Change (PGI-C) score and an improvement from baseline based on a Clinical Global Impression of Improvement (PGI-I) score.

According to some embodiments, the administration results in the patient having an increase from baseline in daily Good ON-time, a reduction from baseline in daily ON-time with moderate-severe dyskinesia, and an improvement from baseline based on a Subject Global Impression of Change (SGI-C) score. According to some embodiments, the administration results in the patient having an increase from baseline in daily Good ON-time, a reduction from baseline in daily ON-time with moderate-severe dyskinesia, and an improvement from baseline based on a Patient Global I Impression of Improvement (PGI-I) score. According to some embodiments, the administration results in the patient having an increase from baseline in daily Good ON-time, a reduction from baseline in daily ON-time with moderate-severe dyskinesia, and an improvement from baseline based on a Clinical Global Impression of Change (CGI-C) score. According to some embodiments, the administration results in the patient having an increase from baseline in daily Good ON-time, an improvement from baseline based on a Subject Global Impression of Change (SGI-C) score, and an improvement from baseline based on a Clinical Global Impression of Change (CGI-C) score. According to some embodiments, the administration results in the patient having an increase from baseline in daily Good ON-time, an improvement from baseline based on a Patient Global Impression of Improvement (PGI-I) score, and an improvement from baseline based on a Clinical Global Impression of Improvement (CGI-I) score. According to some embodiments, the administration results in the patient having a reduction from baseline in daily ON-time with moderate-severe dyskinesia, an improvement from baseline based on a Subject Global Impression of Change (SGI-C) score, and an improvement from baseline based on a Clinical Global Impression of Change (CGI-C) score. According to some embodiments, the administration results in the patient having a reduction from baseline in daily ON-time with moderate-severe dyskinesia, an improvement from baseline based on a Patient Global Impression of Improvement (PGI-I) score, and an improvement from baseline based on a Clinical Global Impression of Improvement (CGI-I) score.

According to some embodiments, the administration results in the patient having an increase from baseline in daily Good ON-time, a reduction from baseline in daily ON-time with moderate-severe dyskinesia, an improvement from baseline based on a Subject Global Impression of Change (SGI-C) score, and an improvement from baseline based on a Clinical Global Impression of Change (CGI-C) score. According to some embodiments, the administration results in the patient having an increase from baseline in daily Good ON-time, a reduction from baseline in daily ON-time with moderate-severe dyskinesia, an improvement from baseline based on a Patient Global Impression of Improvement (PGI-I) score, and an improvement from baseline based on a Clinical Global Impression of Improvement (CGI-I) score.

According to some embodiments, the administration results in the patient having an increase from baseline in daily Good ON-time. According to some embodiments, the administration results in the patient having a reduction from baseline in daily ON-time with moderate-severe dyskinesia. According to some embodiments, the administration results in the patient having a reduction from baseline in daily OFF-time. According to some embodiments, the administration results in the patient having an increase from baseline in daily ON-time without dyskinesia. According to some embodiments, the administration results in the patient having a reduction from baseline in total daily troublesome dyskinesia. According to some embodiments, the administration results in the patient having an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score.

According to some embodiments, the administration results in the patient having an increase from baseline in daily Good ON-time and a reduction from baseline in daily ON-time with moderate-severe dyskinesia. According to some embodiments, the administration results in the patient having an increase from baseline in daily Good ON-time and a reduction from baseline in daily OFF-time. According to some embodiments, the administration results in the patient having an increase from baseline in daily Good ON-time and an increase from baseline in daily ON-time without dyskinesia. According to some embodiments, the administration results in the patient having an increase from baseline in daily Good ON-time and a reduction from baseline in total daily troublesome dyskinesia. According to some embodiments, the administration results in the patient having an increase from baseline in daily Good ON-time and an improvement from baseline in motor experiences of daily living, as assessed by the Movement Disorder Society- Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily ON-time with moderate-severe dyskinesia and a reduction from baseline in daily OFF-time. According to some embodiments, the administration results in the patient having a reduction from baseline in daily ON-time with moderate-severe dyskinesia and an increase from baseline in daily ON-time without dyskinesia. According to some embodiments, the administration results in the patient having a reduction from baseline in daily ON-time with moderate-severe dyskinesia and a reduction from baseline in total daily troublesome dyskinesia. According to some embodiments, the administration results in the patient having a reduction from baseline in daily ON-time with moderate-severe dyskinesia and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily OFF-time and an increase from baseline in daily ON-time without dyskinesia. According to some embodiments, the administration results in the patient having a reduction from baseline in daily OFF-time and a reduction from baseline in total daily troublesome dyskinesia. According to some embodiments, the administration results in the patient having a reduction from baseline in daily OFF-time and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having an increase from baseline in daily ON-time without dyskinesia and a reduction from baseline in total daily troublesome dyskinesia. According to some embodiments, the administration results in the patient having an increase from baseline in daily ON-time without dyskinesia and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in total daily troublesome dyskinesia and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score.

According to some embodiments, the administration results in the patient having an increase from baseline in daily Good ON-time, a reduction from baseline in daily ON-time with moderate-severe dyskinesia, and a reduction from baseline in daily OFF-time. According to some embodiments, the administration results in the patient having an increase from baseline in daily Good ON-time, a reduction from baseline in daily ON-time with moderate-severe dyskinesia, and an increase from baseline in daily ON-time without dyskinesia. According to some embodiments, the administration results in the patient having an increase from baseline in daily Good ON-time, a reduction from baseline in daily ON-time with moderate-severe dyskinesia, and a reduction from baseline in total daily troublesome dyskinesia. According to some embodiments, the administration results in the patient having an increase from baseline in daily Good ON-time, a reduction from baseline in daily ON-time with moderate-severe dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having an increase from baseline in daily Good ON-time, a reduction from baseline in daily OFF-time, and an increase from baseline in daily ON-time without dyskinesia. According to some embodiments, the administration results in the patient having an increase from baseline in daily Good ON-time, a reduction from baseline in daily OFF-time, and a reduction from baseline in total daily troublesome dyskinesia. According to some embodiments, the administration results in the patient having an increase from baseline in daily Good ON-time, a reduction from baseline in daily OFF-time, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having an increase from baseline in daily Good ON-time, an increase from baseline in daily ON-time without dyskinesia, and a reduction from baseline in total daily troublesome dyskinesia. According to some embodiments, the administration results in the patient having an increase from baseline in daily Good ON-time, an increase from baseline in daily ON-time without dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having an increase from baseline in daily Good ON-time, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily ON-time with moderate-severe dyskinesia, a reduction from baseline in daily OFF-time, and an increase from baseline in daily ON-time without dyskinesia. According to some embodiments, the administration results in the patient having a reduction from baseline in daily ON-time with moderate-severe dyskinesia, a reduction from baseline in daily OFF-time, and a reduction from baseline in total daily troublesome dyskinesia. According to some embodiments, the administration results in the patient having a reduction from baseline in daily ON-time with moderate-severe dyskinesia, a reduction from baseline in daily OFF-time, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily ON-time with moderate-severe dyskinesia, an increase from baseline in daily ON-time without dyskinesia, and a reduction from baseline in total daily troublesome dyskinesia. According to some embodiments, the administration results in the patient having a reduction from baseline in daily ON-time with moderate-severe dyskinesia, an increase from baseline in daily ON-time without dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily ON-time with moderate-severe dyskinesia, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily OFF-time, an increase from baseline in daily ON-time without dyskinesia, and a reduction from baseline in total daily troublesome dyskinesia. According to some embodiments, the administration results in the patient having a reduction from baseline in daily OFF-time, an increase from baseline in daily ON-time without dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily OFF-time, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having an increase from baseline in daily ON-time without dyskinesia, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score.

According to some embodiments, the administration results in the patient having an increase from baseline in daily Good ON-time, a reduction from baseline in daily ON-time with moderate-severe dyskinesia, a reduction from baseline in daily OFF-time, and an increase from baseline in daily ON-time without dyskinesia. According to some embodiments, the administration results in the patient having an increase from baseline in daily Good ON-time, a reduction from baseline in daily ON-time with moderate-severe dyskinesia, a reduction from baseline in daily OFF-time, and a reduction from baseline in total daily troublesome dyskinesia. According to some embodiments, the administration results in the patient having an increase from baseline in daily Good ON-time, a reduction from baseline in daily ON-time with moderate-severe dyskinesia, a reduction from baseline in daily OFF-time, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having an increase from baseline in daily Good ON-time, a reduction from baseline in daily OFF-time, an increase from baseline in daily ON-time without dyskinesia, and a reduction from baseline in total daily troublesome dyskinesia. According to some embodiments, the administration results in the patient having an increase from baseline in daily Good ON-time, a reduction from baseline in daily OFF-time, an increase from baseline in daily ON-time without dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having an increase from baseline in daily Good ON-time, an increase from baseline in daily ON-time without dyskinesia, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily ON-time with moderate-severe dyskinesia, a reduction from baseline in daily OFF-time, an increase from baseline in daily ON-time without dyskinesia, and a reduction from baseline in total daily troublesome dyskinesia. According to some embodiments, the administration results in the patient having a reduction from baseline in daily ON-time with moderate-severe dyskinesia, a reduction from baseline in daily OFF-time, an increase from baseline in daily ON-time without dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily ON-time with moderate-severe dyskinesia, an increase from baseline in daily ON-time without dyskinesia, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily OFF-time, an increase from baseline in daily ON-time without dyskinesia, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score.

According to some embodiments, the administration results in the patient having an increase from baseline in daily Good ON-time, a reduction from baseline in daily ON-time with moderate-severe dyskinesia, a reduction from baseline in daily OFF-time, an increase from baseline in daily ON-time without dyskinesia, and a reduction from baseline in total daily troublesome dyskinesia. According to some embodiments, the administration results in the patient having an increase from baseline in daily Good ON-time, a reduction from baseline in daily ON-time with moderate-severe dyskinesia, a reduction from baseline in daily OFF-time, an increase from baseline in daily ON-time without dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score. According to some embodiments, the administration results in the patient having a reduction from baseline in daily ON-time with moderate-severe dyskinesia, a reduction from baseline in daily OFF-time, an increase from baseline in daily ON-time without dyskinesia, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score.

According to some embodiments, the administration results in the patient having an increase from baseline in daily Good ON-time, a reduction from baseline in daily ON-time with moderate-severe dyskinesia, a reduction from baseline in daily OFF-time, an increase from baseline in daily ON-time without dyskinesia, a reduction from baseline in total daily troublesome dyskinesia, and an improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score.

Some embodiments of the invention are directed to a method of treating a patient with Parkinson's disease, the method comprising subcutaneously administering to the patient, substantially continuously for about 24 hours/day, a pharmaceutically acceptable liquid composition comprising levodopa, carbidopa, and arginine,
wherein the pharmaceutically acceptable liquid composition comprises about 60 mg/mL levodopa and 7.5 mg/mL carbidopa, and wherein the pharmaceutically acceptable liquid composition is administered to deliver about 720 mg of levodopa and about 90 mg of carbidopa to the patient over the course of about 24 hours,
wherein after 2 or 3 days of administration, the patient has at least one of:
an increase from baseline in daily Good ON-time,
a reduction from baseline in daily ON-time with moderate-severe dyskinesia,
or any combination thereof.

According to some embodiments, the increase from baseline in daily Good ON-time is an increase from baseline of at least about 0.3 to 3.5 hours in daily Good ON-time, and the reduction from baseline in daily ON-time with moderate-severe dyskinesia is a reduction from baseline of at least about 0.3 to 2.5 hours in daily ON-time with moderate-severe dyskinesia.

According to some embodiments, the method further comprises administering to the patient, before or during the subcutaneous infusion time course, at least one pharmaceutically acceptable oral composition comprising levodopa.

According to some embodiments, the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours. According to some embodiments, the low activity night rate is administered for about 6 hours or about 8 hours and the high activity day rate is administered for about 18 hours or about 16 hours, respectively. According to some embodiments, the low activity night rate is about 0.08 mL/hour. According to some embodiments, the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

Some embodiments of the invention are directed to a method of increasing Good ON-time in a patient with Parkinson's disease, the method comprising
subcutaneously administering to the patient, substantially continuously for about 24 hours/day for about 2 to 3 consecutive days, a pharmaceutically acceptable liquid composition comprising levodopa and carbidopa, in a ratio of about 8:1 w/w,
wherein by the third consecutive day the administration results in an increase from baseline of at least about 0.3 to 3.5 hours in daily Good ON-time.

According to some embodiments, the administration results in an increase from baseline of about 1.8 hours in daily Good ON-time.

According to some embodiments, the pharmaceutically acceptable liquid composition further comprises arginine. According to some embodiments, the pharmaceutically acceptable liquid composition comprises 7.5 mg/mL carbidopa and 60 mg/mL levodopa.

According to some embodiments, the pharmaceutically acceptable liquid composition is administered to deliver about 720 mg of levodopa and about 90 mg of carbidopa to the patient over the course of about 24 hours.

According to some embodiments, the method further comprises administering to the patient, before or during the subcutaneous infusion time course, at least one pharmaceutically acceptable oral composition comprising levodopa.

According to some embodiments, the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours. According to some embodiments, the low activity night rate is administered for about 6 hours and the high activity day rate is administered for about 18 hours. According to some embodiments, the low activity night rate is about 0.08 mL/hour. According to some embodiments, the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa, in a ratio of about 8:1 w/w, wherein the administration results in the patient having at least one of:
an increase in daily ON-time without troublesome dyskinesia,
a reduction in daily OFF-time,
an improvement in motor experiences of daily living, as assessed by the Movement Disorder Society-Sponsored revision of Unified Parkinson's Disease Rating Scale (UPDRS) Part II score, resulting in a reduction in the UPDRS Part II score,
an improvement based on a Patient Global Impression of Change (PGI-C) score,
an improvement based on a Clinical Global Impression of Improvement (CGI-I) score,
or any combination thereof,
wherein the improvement in the patient is measured compared to a patient treated with an immediate release oral dosage form of levodopa, and
wherein the improvement in the patient in:
daily ON-time without troublesome dyskinesia is an increase of about 1.7 hours in daily ON-time without troublesome dyskinesia,
daily OFF-time is a reduction of about 1.4 hours in daily OFF-time,
motor experiences of daily living, as assessed by the UPDRS Part II score is a decrease of about 3.0,
the Patient Global Impression of Change (PGI-C) score is an odds ratio of about 5.3, and
the Clinical Global Impression of Improvement (CGI-I) score is an odds ratio of about 7.2.

According to some embodiments, the pharmaceutically acceptable liquid composition further comprises arginine. According to some embodiments, the pharmaceutically acceptable liquid composition comprises 7.5 mg/mL carbidopa and 60 mg/mL levodopa. According to some embodiments, the pharmaceutically acceptable liquid composition is administered to deliver about 720 mg of levodopa and about 90 mg of carbidopa to the patient over the course of about 24 hours.

According to some embodiments, the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours. According to some embodiments, the low activity night rate is administered for about 6 hours or about 8 hours and the high activity day rate is administered for about 18 hours or about 16 hours, respectively, wherein the low activity night rate is about 0.08 mL/hour; and wherein the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

Some embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa and carbidopa in a ratio of about 8:1 w/w, and further comprising arginine,
wherein by the third consecutive day the administration results in the patient having at least one of:
an increase from baseline of at least about 0.3 to 3.5 in daily Good ON-time,
a reduction from baseline of at least about 0.3 to 2.5 hours in daily ON-time with moderate-severe dyskinesia,
a reduction from baseline of at least 0.1 to 2.0 in daily Off time,
an increase from baseline of at least about 0.1 to 3.5 in daily ON-time without dyskinesia,
a reduction from baseline of at least 0.1 to 3.2 in total daily troublesome dyskinesia,
a reduction from baseline of about 2 to 13 points in UPDRS Part III score,
or any combination thereof.

According to some embodiments, the pharmaceutically acceptable liquid composition is administered subcutaneously to the patient via a device comprising a control station, a reusable part and a disposable part.

According to some embodiments, the pharmaceutically acceptable liquid composition comprises 7.5 mg/mL carbidopa and 60 mg/mL levodopa. According to some embodiments, the pharmaceutically acceptable liquid composition is administered to deliver about 720 mg of levodopa and about 90 mg of carbidopa to the patient over the course of about 24 hours.

According to some embodiments, the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours. According to some embodiments, the low activity night rate is administered for about 6 hours and the high activity day rate is administered for about 18 hours. According to some embodiments, the low activity night rate is about 0.08 mL/hour and wherein the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

According to some embodiments, after about 5 hours of administration at the first flow rate, the patient is fully ON.

According to some embodiments, the patient has an improvement from baseline after two days of treatment in quality of sleep. According to some embodiments, the patient has a change from baseline after two days of treatment in quality of sleep.

Some embodiments of the invention are directed to a method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa, carbidopa, and arginine,
wherein the pharmaceutically acceptable liquid composition comprises about 60 mg/mL levodopa and 7.5 mg/mL carbidopa, and wherein the pharmaceutically acceptable liquid composition is administered to deliver about 720 mg of levodopa and about 90 mg of carbidopa to the patient over the course of about 24 hours,
wherein by the third consecutive day the administration results in the patient having at least one of:
an increase from baseline of at least about 0.3 to 3.5 in daily Good ON-time,
a reduction from baseline of at least about 0.3 to 2.5 hours in daily ON-time with moderate-severe dyskinesia,
a reduction from baseline of at least 0.1 to 2.0 in daily Off time,
an increase from baseline of at least about 0.1 to 3.5 in daily ON-time without dyskinesia,
a reduction from baseline of at least 0.1 to 3.2 in total daily troublesome dyskinesia, a reduction from baseline of about 2 to 13 points in UPDRS Part III scores, or any combination thereof.

According to some embodiments, the method further comprises administering to the patient, before or during the subcutaneous infusion time course, at least one pharmaceutically acceptable oral composition comprising levodopa.

According to some embodiments, the pharmaceutically acceptable liquid composition is administered subcutaneously to the patient via a device comprising a control station, a reusable part and a disposable part.

According to some embodiments, the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours. According to some embodiments, the low activity night rate is administered for about 6 hours or about 8 hours and the high activity day rate is administered for about 18 hours or about 16 hours, respectively. According to some embodiments, the low activity night rate is about 0.08 mL/hour and wherein the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

According to some embodiments, after about 5 hours of administration at the first flow rate, the patient is fully ON.

According to some embodiments, the patient has an improvement from baseline after two days of treatment in quality of sleep. According to some embodiments, the patient has a change from baseline after two days of treatment in quality of sleep.

Some embodiments of the invention are directed to a method of increasing Good ON-time in a patient with Parkinson's disease, the method comprising subcutaneously administering to the patient, substantially continuously for about 24 hours/day for about 2 to 3 consecutive days, a pharmaceutically acceptable liquid composition comprising levodopa and carbidopa, in a ratio of about 8:1 w/w, and further comprising arginine, wherein by the third consecutive day the administration results in an increase from baseline of at least about 0.3 to 3.5 hours in daily Good ON-time.

According to some embodiments, the administration results in an increase from baseline of about 1.8 hours in daily Good ON-time.

According to some embodiments, the pharmaceutically acceptable liquid composition is administered subcutaneously to the patient via a device comprising a control station, a reusable part and a disposable part.

According to some embodiments, the pharmaceutically acceptable liquid composition comprises 7.5 mg/mL carbidopa and 60 mg/mL levodopa. According to some embodiments, the pharmaceutically acceptable liquid composition is administered to deliver about 720 mg of levodopa and about 90 mg of carbidopa to the patient over the course of about 24 hours.

According to some embodiments, the method further comprises administering to the patient, before or during the subcutaneous infusion time course, at least one pharmaceutically acceptable oral composition comprising levodopa.

According to some embodiments, the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours. According to some embodiments, the low activity night rate is administered for about 6 hours and the high activity day rate is administered for about 18 hours. According to some embodiments, the low activity night rate is about 0.08 mL/hour. According to some embodiments, the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

According to some embodiments, after about 5 hours of administration at the first flow rate, the patient is fully ON.

According to some embodiments, the patient has an improvement from baseline after two days of treatment in quality of sleep. According to some embodiments, the patient has a change from baseline after two days of treatment in quality of sleep.

According to any of the embodiments described herein, the increase from baseline in daily Good ON-time is an increase from baseline of at least about 0.1 to 3.5 hours in daily Good ON-time.

According to some embodiments, the increase from baseline in daily Good ON-time is an increase from baseline of about 0.1 hours in daily Good ON-time. According to some embodiments, the increase from baseline in daily Good ON-time is an increase from baseline of about 0.11 hours in daily Good ON-time. According to some embodiments, the increase from baseline in daily Good ON-time is an increase from baseline of about 0.12 hours in daily Good ON-time. According to some embodiments, the increase from baseline in daily Good ON-time is an increase from baseline of about 0.13 hours in daily Good ON-time. According to some embodiments, the increase from baseline in daily Good ON-time is an increase from baseline of about 0.14 hours in daily Good ON-time. According to some embodiments, the increase from baseline in daily Good ON-time is an increase from baseline of about 0.15 hours in daily Good ON-time. According to some embodiments, the increase from baseline in daily Good ON-time is an increase from baseline of about 0.16 hours in daily Good ON-time. According to some embodiments, the increase from baseline in daily Good ON-time is an increase from baseline of about 0.17 hours in daily Good ON-time. According to some embodiments, the increase from baseline in daily Good ON-time is an increase from baseline of about 0.18 hours in daily Good ON-time. According to some embodiments, the increase from baseline in daily Good ON-time is an increase from baseline of about 0.19 hours in daily Good ON-time. According to some embodiments, the increase from baseline in daily Good ON-time is an increase from baseline of about 0.20 hours in daily Good ON-time. According to some embodiments, the increase from baseline in daily Good ON-time is an increase from baseline of about 0.22 hours in daily Good ON-time. According to some embodiments, the increase from baseline in daily Good ON-time is an increase from baseline of about 0.24 hours in daily Good ON-time. According to some embodiments, the increase from baseline in daily Good ON-time is an increase of about 0.26 hours in daily Good ON-time. According to some embodiments, the increase from baseline in daily Good ON-time is an increase of about 0.28 hours in daily Good ON-time. According to some embodiments, the increase from baseline in daily Good ON-time is an increase from baseline of about 0.3 hours in daily Good ON-time. According to some embodiments, the increase from baseline in daily Good ON-time is an increase from baseline of about 0.32 hours in daily Good ON-time. According to some embodiments, the increase from baseline in daily Good ON-time is an increase from baseline of about 0.34 hours in daily Good ON-time. According to some embodiments, the increase from baseline in daily Good ON-time is an increase from baseline of about 0.36 hours in daily Good ON-time. According to some embodiments, the increase from baseline in daily Good ON-time is an increase from baseline of about 0.38 hours in daily Good ON-time. According to some embodiments, the increase from baseline in daily Good ON-time is an increase from baseline of about 0.4 hours in daily Good ON-time. According to some embodiments, the increase from baseline in daily Good ON-time is an increase from baseline of about 0.42 hours in daily Good ON-time. According to some embodiments, the increase from baseline in daily Good ON-time is an increase from baseline of about 0.44 hours in daily Good ON-time. According to some embodiments, the increase from baseline in daily Good ON-time is an increase from baseline of about 0.46 hours in daily Good ON-time. According to some embodiments, the increase from baseline in daily Good ON-time is an increase from baseline of about 0.48 hours in daily Good ON-time. According to some embodiments, the increase from baseline in daily Good ON-time is an increase from baseline of about 0.5 hours in daily Good ON-time. According to some embodiments, the increase from baseline in daily Good ON-time is an increase from baseline of about 0.55 hours in daily Good ON-time. According to some embodiments, the increase from baseline in daily Good ON-time is an increase from baseline of about 0.6 hours in daily Good ON-time. According to some embodiments, the increase from baseline in daily Good ON-time is an increase from baseline of about 0.65 hours in daily Good ON-time. According to some embodiments, the increase from baseline in daily Good ON-time is an increase from baseline of about 0.7 hours in daily Good ON-time. According to some embodiments, the increase from baseline in daily Good ON-time is an increase from baseline of about 0.75 hours in daily Good ON-time. According to some embodiments, the increase from baseline in daily Good ON-time is an increase from baseline of about 0.8 hours in daily Good ON-time. According to some embodiments, the increase from baseline in daily Good ON-time is an increase from baseline of about 0.85 hours in daily Good ON-time. According to some embodiments, the increase from baseline in daily Good ON-time is an increase from baseline of about 0.9 hours in daily Good ON-time. According to some embodiments, the increase from baseline in daily Good ON-time is an increase from baseline of about 0.95 hours in daily Good ON-time. According to some embodiments, the increase from baseline in daily Good ON-time is an increase from baseline of about 1.0 hours in daily Good ON-time. According to some embodiments, the increase from baseline in daily Good ON-time is an increase from baseline of about 1.1 hours in daily Good ON-time. According to some embodiments, the increase from baseline in daily Good ON-time is an increase from baseline of about 1.2 hours in daily Good ON-time. According to some embodiments, the increase from baseline in daily Good ON-time is an increase from baseline of about 1.3 hours in daily Good ON-time. According to some embodiments, the increase from baseline in daily Good ON-time is an increase from baseline of about 1.4 hours in daily Good ON-time. According to some embodiments, the increase from baseline in daily Good ON-time is an increase from baseline of about 1.5 hours in daily Good ON-time. According to some embodiments, the increase from baseline in daily Good ON-time is an increase from baseline of about 1.6 hours in daily Good ON-time. According to some embodiments, the increase from baseline in daily Good ON-time is an increase from baseline of about 1.7 hours in daily Good ON-time. According to some embodiments, the increase from baseline in daily Good ON-time is an increase from baseline of about 1.8 hours in daily Good ON-time. According to some embodiments, the increase from baseline in daily Good ON-time is an increase from baseline of about 1.8 hours in daily Good ON-time. According to some embodiments, the increase from baseline in daily Good ON-time is an increase from baseline of about 1.9 hours in daily Good ON-time. According to some embodiments, the increase from baseline in daily Good ON-time is an increase from baseline of about 2.0 hours in daily Good ON-time. According to some embodiments, the increase from baseline in daily Good ON-time is an increase from baseline of about 2.1 hours in daily Good ON-time. According to some embodiments, the increase from baseline in daily Good ON-time is an increase from baseline of about 2.2 hours in daily Good ON-time. According to some embodiments, the increase from baseline in daily Good ON-time is an increase from baseline of about 2.25 hours in daily Good ON-time. According to some embodiments, the increase from baseline in daily Good ON-time is an increase from baseline of about 2.3 hours in daily Good ON-time. According to some embodiments, the increase from baseline in daily Good ON-time is an increase from baseline of about 2.4 hours in daily Good ON-time. According to some embodiments, the increase from baseline in daily Good ON-time is an increase from baseline of about 2.5 hours in daily Good ON-time. According to some embodiments, the increase from baseline in daily Good ON-time is an increase from baseline of about 2.6 hours in daily Good ON-time. According to some embodiments, the increase from baseline in daily Good ON-time is an increase from baseline of about 2.7 hours in daily Good ON-time. According to some embodiments, the increase from baseline in daily Good ON-time is an increase from baseline of about 2.75 hours in daily Good ON-time. According to some embodiments, the increase from baseline in daily Good ON-time is an increase from baseline of about 2.8 hours in daily Good ON-time. According to some embodiments, the increase from baseline in daily Good ON-time is an increase from baseline of about 2.9 hours in daily Good ON-time. According to some embodiments, the increase from baseline in daily Good ON-time is an increase from baseline of about 3.0 hours in daily Good ON-time. According to some embodiments, the increase from baseline in daily Good ON-time is an increase from baseline of about 3.1 hours in daily Good ON-time. According to some embodiments, the increase from baseline in daily Good ON-time is an increase from baseline of about 3.2 hours in daily Good ON-time. According to some embodiments, the increase from baseline in daily Good ON-time is an increase from baseline of about 3.25 hours in daily Good ON-time. According to some embodiments, the increase from baseline in daily Good ON-time is an increase from baseline of about 3.3 hours in daily Good ON-time. According to some embodiments, the increase from baseline in daily Good ON-time is an increase from baseline of about 3.4 hours in daily Good ON-time. According to some embodiments, the increase from baseline in daily Good ON-time is an increase from baseline of about 3.5 hours in daily Good ON-time.

According to any of the embodiments described herein, the reduction from baseline in daily ON-time with moderate-severe dyskinesia is a reduction from baseline of at least about 0.3 to 2.5 hours in daily ON-time with moderate-severe dyskinesia.

According to some embodiments, the reduction from baseline in daily ON-time with moderate-severe dyskinesia is a reduction from baseline of about 0.3 hours in daily ON-time. According to some embodiments, the reduction from baseline in daily ON-time with moderate-severe dyskinesia is a reduction from baseline of about 0.32 hours in daily ON-time with moderate-severe dyskinesia. According to some embodiments, the reduction from baseline in daily ON-time with moderate-severe dyskinesia is a reduction from baseline of about 0.34 hours in daily ON-time with moderate-severe dyskinesia. According to some embodiments, the reduction from baseline in daily ON-time with moderate-severe dyskinesia is a reduction from baseline of about 0.36 hours in daily ON-time with moderate-severe dyskinesia. According to some embodiments, the reduction from baseline in daily ON-time with moderate-severe dyskinesia is a reduction from baseline of about 0.38 hours in daily ON-time with moderate-severe dyskinesia. According to some embodiments, the reduction from baseline in daily ON-time with moderate-severe dyskinesia is a reduction from baseline of about 0.4 hours in daily ON-time with moderate-severe dyskinesia. According to some embodiments, the reduction from baseline in daily ON-time with moderate-severe dyskinesia is a reduction from baseline of about 0.42 hours in daily ON-time with moderate-severe dyskinesia. According to some embodiments, the reduction from baseline in daily ON-time with moderate-severe dyskinesia is a reduction from baseline of about 0.44 hours in daily ON-time with moderate-severe dyskinesia. According to some embodiments, the reduction from baseline in daily ON-time with moderate-severe dyskinesia is a reduction from baseline of about 0.46 hours in daily ON-time with moderate-severe dyskinesia. According to some embodiments, the reduction from baseline in daily ON-time with moderate-severe dyskinesia is a reduction from baseline of about 0.48 hours in daily ON-time with moderate-severe dyskinesia. According to some embodiments, the reduction from baseline in daily ON-time with moderate-severe dyskinesia is a reduction from baseline of about 0.5 hours in daily ON-time with moderate-severe dyskinesia. According to some embodiments, the reduction from baseline in daily ON-time with moderate-severe dyskinesia is a reduction from baseline of about 0.55 hours in daily ON-time with moderate-severe dyskinesia. According to some embodiments, the reduction from baseline in daily ON-time with moderate-severe dyskinesia is a reduction from baseline of about 0.6 hours in daily ON-time with moderate-severe dyskinesia. According to some embodiments, the reduction from baseline in daily ON-time with moderate-severe dyskinesia is a reduction from baseline of about 0.65 hours in daily ON-time with moderate-severe dyskinesia. According to some embodiments, the reduction from baseline in daily ON-time with moderate-severe dyskinesia is a reduction from baseline of about 0.7 hours in daily ON-time with moderate-severe dyskinesia. According to some embodiments, the reduction from baseline in daily ON-time with moderate-severe dyskinesia is a reduction from baseline of about 0.75 hours in daily ON-time with moderate-severe dyskinesia. According to some embodiments, the reduction from baseline in daily ON-time with moderate-severe dyskinesia is a reduction from baseline of about 0.8 hours in daily ON-time with moderate-severe dyskinesia. According to some embodiments, the reduction from baseline in daily ON-time with moderate-severe dyskinesia is a reduction from baseline of about 0.85 hours in daily ON-time with moderate-severe dyskinesia. According to some embodiments, the reduction from baseline in daily ON-time with moderate-severe dyskinesia is a reduction from baseline of about 0.9 hours in daily ON-time with moderate-severe dyskinesia. According to some embodiments, the reduction from baseline in daily ON-time with moderate-severe dyskinesia is a reduction from baseline of about 0.95 hours in daily ON-time with moderate-severe dyskinesia. According to some embodiments, the reduction from baseline in daily ON-time with moderate-severe dyskinesia is a reduction from baseline of about 1 hours in daily ON-time with moderate-severe dyskinesia. According to some embodiments, the reduction from baseline in daily ON-time with moderate-severe dyskinesia is a reduction from baseline of about 1.1 hours in daily ON-time with moderate-severe dyskinesia. According to some embodiments, the reduction from baseline in daily ON-time with moderate-severe dyskinesia is a reduction from baseline of about 1.2 hours in daily ON-time with moderate-severe dyskinesia. According to some embodiments, the reduction from baseline in daily ON-time with moderate-severe dyskinesia is a reduction from baseline of about 1.3 hours in daily ON-time with moderate-severe dyskinesia. According to some embodiments, the reduction from baseline in daily ON-time with moderate-severe dyskinesia is a reduction from baseline of about 1.4 hours in daily ON-time with moderate-severe dyskinesia. According to some embodiments, the reduction from baseline in daily ON-time with moderate-severe dyskinesia is a reduction from baseline of about 1.5 hours in daily ON-time with moderate-severe dyskinesia. According to some embodiments, the reduction from baseline in daily ON-time with moderate-severe dyskinesia is a reduction from baseline of about 1.6 hours in daily ON-time with moderate-severe dyskinesia. According to some embodiments, the reduction from baseline in daily ON-time with moderate-severe dyskinesia is a reduction from baseline of about 1.7 hours in daily ON-time with moderate-severe dyskinesia. According to some embodiments, the reduction from baseline in daily ON-time with moderate-severe dyskinesia is a reduction from baseline of about 1.8 hours in daily ON-time with moderate-severe dyskinesia a. According to some embodiments, the reduction from baseline in daily ON-time with moderate-severe dyskinesia is a reduction from baseline of about 1.9 hours in daily ON-time with moderate-severe dyskinesia a. According to some embodiments, the reduction from baseline in daily ON-time with moderate-severe dyskinesia is a reduction from baseline of about 2 hours in daily ON-time with moderate-severe dyskinesia. According to some embodiments, the reduction from baseline in daily ON-time with moderate-severe dyskinesia is a reduction from baseline of about 2.1 hours in daily ON-time with moderate-severe dyskinesia. According to some embodiments, the reduction from baseline in daily ON-time with moderate-severe dyskinesia is a reduction from baseline of about 2.1 hours in daily ON-time with moderate-severe dyskinesia. According to some embodiments, the reduction from baseline in daily ON-time with moderate-severe dyskinesia is a reduction from baseline of about 2.3 hours in daily ON-time with moderate-severe dyskinesia. According to some embodiments, the reduction from baseline in daily ON-time with moderate-severe dyskinesia is a reduction from baseline of about 2.4 hours in daily ON-time with moderate-severe dyskinesia. According to some embodiments, the reduction from baseline in daily ON-time with moderate-severe dyskinesia is a reduction from baseline of about 2.5 hours in daily ON-time with moderate-severe dyskinesia.

According to any of the embodiments described herein, the reduction from baseline in daily OFF-time is a reduction from baseline of about 0.1 to 2.0 hours in daily OFF-time.

According to some embodiments, the reduction from baseline in daily OFF-time is a reduction from baseline of about 0.1 hours in total daily OFF-time. According to some embodiments, the reduction from baseline in daily OFF-time is a reduction from baseline of about 0.11 hours in total daily OFF-time. According to some embodiments, the reduction from baseline in daily OFF-time is a reduction from baseline of about 0.12 hours in total daily OFF-time. According to some embodiments, the reduction from baseline in daily OFF-time is a reduction from baseline of about 0.13 hours in total daily OFF-time. According to some embodiments, the reduction from baseline in daily OFF-time is a reduction from baseline of about 0.14 hours in total daily OFF-time. According to some embodiments, the reduction from baseline in daily OFF-time is a reduction from baseline of about 0.15 hours in total daily OFF-time. According to some embodiments, the reduction from baseline in daily OFF-time is a reduction from baseline of about 0.16 hours in total daily OFF-time. According to some embodiments, the reduction from baseline in daily OFF-time is a reduction from baseline of about 0.17 hours in total daily OFF-time. According to some embodiments, the reduction from baseline in daily OFF-time is a reduction from baseline of about 0.18 hours in total daily OFF-time. According to some embodiments, the reduction from baseline in daily OFF-time is a reduction from baseline of about 0.19 hours in total daily OFF-time. According to some embodiments, the reduction from baseline in daily OFF-time is a reduction from baseline of about 0.20 hours in total daily OFF-time. According to some embodiments, the reduction from baseline in daily OFF-time is a reduction from baseline of about 0.22 hours in total daily OFF-time. According to some embodiments, the reduction from baseline in daily OFF-time is a reduction from baseline of about 0.24 hours in total daily OFF-time. According to some embodiments, the increase from baseline in daily Good ON-time is an increase of about 0.26 hours in total daily OFF-time. According to some embodiments, the increase from baseline in daily Good ON-time is an increase of about 0.28 hours in total daily OFF-time. According to some embodiments, the reduction from baseline in daily OFF-time is a reduction from baseline of about 0.3 hours in total daily OFF-time. According to some embodiments, the reduction from baseline in daily OFF-time is a reduction from baseline of about 0.32 hours in total daily OFF-time. According to some embodiments, the reduction from baseline in daily OFF-time is a reduction from baseline of about 0.34 hours in total daily OFF-time. According to some embodiments, the reduction from baseline in daily OFF-time is a reduction from baseline of about 0.36 hours in total daily OFF-time. According to some embodiments, the reduction from baseline in daily OFF-time is a reduction from baseline of about 0.38 hours in total daily OFF-time. According to some embodiments, the reduction from baseline in daily OFF-time is a reduction from baseline of about 0.4 hours in total daily OFF-time. According to some embodiments, the reduction from baseline in daily OFF-time is a reduction from baseline of about 0.42 hours in total daily OFF-time. According to some embodiments, the reduction from baseline in daily OFF-time is a reduction from baseline of about 0.44 hours in total daily OFF-time. According to some embodiments, the reduction from baseline in daily OFF-time is a reduction from baseline of about 0.46 hours in total daily OFF-time. According to some embodiments, the reduction from baseline in daily OFF-time is a reduction from baseline of about 0.48 hours in total daily OFF-time. According to some embodiments, the reduction from baseline in daily OFF-time is a reduction from baseline of about 0.5 hours in total daily OFF-time. According to some embodiments, the reduction from baseline in daily OFF-time is a reduction from baseline of about 0.55 hours in total daily OFF-time. According to some embodiments, the reduction from baseline in daily OFF-time is a reduction from baseline of about 0.6 hours in total daily OFF-time. According to some embodiments, the reduction from baseline in daily OFF-time is a reduction from baseline of about 0.65 hours in total daily OFF-time. According to some embodiments, the reduction from baseline in daily OFF-time is a reduction from baseline of about 0.7 hours in total daily OFF-time. According to some embodiments, the reduction from baseline in daily OFF-time is a reduction from baseline of about 0.75 hours in total daily OFF-time. According to some embodiments, the reduction from baseline in daily OFF-time is a reduction from baseline of about 0.8 hours in total daily OFF-time. According to some embodiments, the reduction from baseline in daily OFF-time is a reduction from baseline of about 0.85 hours in total daily OFF-time. According to some embodiments, the reduction from baseline in daily OFF-time is a reduction from baseline of about 0.9 hours in total daily OFF-time. According to some embodiments, the reduction from baseline in daily OFF-time is a reduction from baseline of about 0.95 hours in total daily OFF-time. According to some embodiments, the reduction from baseline in daily OFF-time is a reduction from baseline of about 1.0 hours in total daily OFF-time. According to some embodiments, the reduction from baseline in daily OFF-time is a reduction from baseline of about 1.1 hours in total daily OFF-time. According to some embodiments, the reduction from baseline in daily OFF-time is a reduction from baseline of about 1.2 hours in total daily OFF-time. According to some embodiments, the reduction from baseline in daily OFF-time is a reduction from baseline of about 1.3 hours in total daily OFF-time. According to some embodiments, the reduction from baseline in daily OFF-time is a reduction from baseline of about 1.4 hours in total daily OFF-time. According to some embodiments, the reduction from baseline in daily OFF-time is a reduction from baseline of about 1.5 hours in total daily OFF-time. According to some embodiments, the reduction from baseline in daily OFF-time is a reduction from baseline of about 1.6 hours in total daily OFF-time. According to some embodiments, the reduction from baseline in daily OFF-time is a reduction from baseline of about 1.7 hours in total daily OFF-time. According to some embodiments, the reduction from baseline in daily OFF-time is a reduction from baseline of about 1.8 hours in total daily OFF-time. According to some embodiments, the reduction from baseline in daily OFF-time is a reduction from baseline of about 1.8 hours in total daily OFF-time. According to some embodiments, the reduction from baseline in daily OFF-time is a reduction from baseline of about 1.9 hours in total daily OFF-time. According to some embodiments, the reduction from baseline in daily OFF-time is a reduction from baseline of about 2.0 hours in total daily OFF-time.

It is noted that daily OFF-time and total daily OFF-time are interchangeable herein, unless specifically mentioned otherwise or unless would have been understood otherwise by a person skilled in the art.

According to any of the embodiments described herein, the increase from baseline in daily ON-time without dyskinesia is an increase from baseline of at least about 0.1 to 3.5 hours in daily ON-time without dyskinesia.

According to some embodiments, the increase from baseline in daily ON-time without dyskinesia is an increase from baseline of about 0.1 hours in daily ON-time without dyskinesia. According to some embodiments, the increase from baseline in daily ON-time without dyskinesia is an increase from baseline of about 0.11 hours in daily ON-time without dyskinesia. According to some embodiments, the increase from baseline in daily ON-time without dyskinesia is an increase from baseline of about 0.12 hours in daily ON-time without dyskinesia. According to some embodiments, the increase from baseline in daily ON-time without dyskinesia is an increase from baseline of about 0.13 hours in daily ON-time without dyskinesia. According to some embodiments, the increase from baseline in daily ON-time without dyskinesia is an increase from baseline of about 0.14 hours in daily ON-time without dyskinesia. According to some embodiments, the increase from baseline in daily ON-time without dyskinesia is an increase from baseline of about 0.15 hours in daily ON-time without dyskinesia. According to some embodiments, the increase from baseline in daily ON-time without dyskinesia is an increase from baseline of about 0.16 hours in daily ON-time without dyskinesia. According to some embodiments, the increase from baseline in daily ON-time without dyskinesia is an increase from baseline of about 0.17 hours in daily ON-time without dyskinesia. According to some embodiments, the increase from baseline in daily ON-time without dyskinesia is an increase from baseline of about 0.18 hours in daily ON-time without dyskinesia. According to some embodiments, the increase from baseline in daily ON-time without dyskinesia is an increase from baseline of about 0.19 hours in daily ON-time without dyskinesia. According to some embodiments, the increase from baseline in daily ON-time without dyskinesia is an increase from baseline of about 0.20 hours in daily ON-time without dyskinesia. According to some embodiments, the increase from baseline in daily ON-time without dyskinesia is an increase from baseline of about 0.22 hours in daily ON-time without dyskinesia. According to some embodiments, the increase from baseline in daily ON-time without dyskinesia is an increase from baseline of about 0.24 hours in daily ON-time without dyskinesia. According to some embodiments, the increase from baseline in daily ON-time without dyskinesia is an increase of about 0.26 hours in daily ON-time without dyskinesia. According to some embodiments, the increase from baseline in daily ON-time without dyskinesia is an increase of about 0.28 hours in daily ON-time without dyskinesia. According to some embodiments, the increase from baseline in daily ON-time without dyskinesia is an increase from baseline of about 0.3 hours in daily ON-time without dyskinesia. According to some embodiments, the increase from baseline in daily ON-time without dyskinesia is an increase from baseline of about 0.32 hours in daily ON-time without dyskinesia. According to some embodiments, the increase from baseline in daily ON-time without dyskinesia is an increase from baseline of about 0.34 hours in daily ON-time without dyskinesia. According to some embodiments, the increase from baseline in daily ON-time without dyskinesia is an increase from baseline of about 0.36 hours in daily ON-time without dyskinesia. According to some embodiments, the increase from baseline in daily ON-time without dyskinesia is an increase from baseline of about 0.38 hours in daily ON-time without dyskinesia. According to some embodiments, the increase from baseline in daily ON-time without dyskinesia is an increase from baseline of about 0.4 hours in daily ON-time without dyskinesia. According to some embodiments, the increase from baseline in daily ON-time without dyskinesia is an increase from baseline of about 0.42 hours in daily ON-time without dyskinesia. According to some embodiments, the increase from baseline in daily ON-time without dyskinesia is an increase from baseline of about 0.44 hours in daily ON-time without dyskinesia. According to some embodiments, the increase from baseline in daily ON-time without dyskinesia is an increase from baseline of about 0.46 hours in daily ON-time without dyskinesia. According to some embodiments, the increase from baseline in daily ON-time without dyskinesia is an increase from baseline of about 0.48 hours in daily ON-time without dyskinesia. According to some embodiments, the increase from baseline in daily ON-time without dyskinesia is an increase from baseline of about 0.5 hours in daily ON-time without dyskinesia. According to some embodiments, the increase from baseline in daily ON-time without dyskinesia is an increase from baseline of about 0.55 hours in daily ON-time without dyskinesia. According to some embodiments, the increase from baseline in daily ON-time without dyskinesia is an increase from baseline of about 0.6 hours in daily ON-time without dyskinesia. According to some embodiments, the increase from baseline in daily ON-time without dyskinesia is an increase from baseline of about 0.65 hours in daily ON-time without dyskinesia. According to some embodiments, the increase from baseline in daily ON-time without dyskinesia is an increase from baseline of about 0.7 hours in daily ON-time without dyskinesia. According to some embodiments, the increase from baseline in daily ON-time without dyskinesia is an increase from baseline of about 0.75 hours in daily ON-time without dyskinesia. According to some embodiments, the increase from baseline in daily ON-time without dyskinesia is an increase from baseline of about 0.8 hours in daily ON-time without dyskinesia. According to some embodiments, the increase from baseline in daily ON-time without dyskinesia is an increase from baseline of about 0.85 hours in daily ON-time without dyskinesia. According to some embodiments, the increase from baseline in daily ON-time without dyskinesia is an increase from baseline of about 0.9 hours in daily ON-time without dyskinesia. According to some embodiments, the increase from baseline in daily ON-time without dyskinesia is an increase from baseline of about 0.95 hours in daily ON-time without dyskinesia. According to some embodiments, the increase from baseline in daily ON-time without dyskinesia is an increase from baseline of about 1.0 hours in daily ON-time without dyskinesia. According to some embodiments, the increase from baseline in daily ON-time without dyskinesia is an increase from baseline of about 1.1 hours in daily ON-time without dyskinesia. According to some embodiments, the increase from baseline in daily ON-time without dyskinesia is an increase from baseline of about 1.2 hours in daily ON-time without dyskinesia. According to some embodiments, the increase from baseline in daily ON-time without dyskinesia is an increase from baseline of about 1.3 hours in daily ON-time without dyskinesia. According to some embodiments, the increase from baseline in daily ON-time without dyskinesia is an increase from baseline of about 1.4 hours in daily ON-time without dyskinesia. According to some embodiments, the increase from baseline in daily ON-time without dyskinesia is an increase from baseline of about 1.5 hours in daily ON-time without dyskinesia. According to some embodiments, the increase from baseline in daily ON-time without dyskinesia is an increase from baseline of about 1.6 hours in daily ON-time without dyskinesia. According to some embodiments, the increase from baseline in daily ON-time without dyskinesia is an increase from baseline of about 1.7 hours in daily ON-time without dyskinesia. According to some embodiments, the increase from baseline in daily ON-time without dyskinesia is an increase from baseline of about 1.8 hours in daily ON-time without dyskinesia. According to some embodiments, the increase from baseline in daily ON-time without dyskinesia is an increase from baseline of about 1.8 hours in daily ON-time without dyskinesia. According to some embodiments, the increase from baseline in daily ON-time without dyskinesia is an increase from baseline of about 1.9 hours in daily ON-time without dyskinesia. According to some embodiments, the increase from baseline in daily ON-time without dyskinesia is an increase from baseline of about 2.0 hours in daily ON-time without dyskinesia. According to some embodiments, the increase from baseline in daily ON-time without dyskinesia is an increase from baseline of about 2.1 hours in daily ON-time without dyskinesia. According to some embodiments, the increase from baseline in daily ON-time without dyskinesia is an increase from baseline of about 2.2 hours in daily ON-time without dyskinesia. According to some embodiments, the increase from baseline in daily ON-time without dyskinesia is an increase from baseline of about 2.25 hours in daily ON-time without dyskinesia. According to some embodiments, the increase from baseline in daily ON-time without dyskinesia is an increase from baseline of about 2.3 hours in daily ON-time without dyskinesia. According to some embodiments, the increase from baseline in daily ON-time without dyskinesia is an increase from baseline of about 2.4 hours in daily ON-time without dyskinesia. According to some embodiments, the increase from baseline in daily ON-time without dyskinesia is an increase from baseline of about 2.5 hours in daily ON-time without dyskinesia. According to some embodiments, the increase from baseline in daily ON-time without dyskinesia is an increase from baseline of about 2.6 hours in daily ON-time without dyskinesia. According to some embodiments, the increase from baseline in daily ON-time without dyskinesia is an increase from baseline of about 2.7 hours in daily ON-time without dyskinesia. According to some embodiments, the increase from baseline in daily ON-time without dyskinesia is an increase from baseline of about 2.75 hours in daily ON-time without dyskinesia. According to some embodiments, the increase from baseline in daily ON-time without dyskinesia is an increase from baseline of about 2.8 hours in daily ON-time without dyskinesia. According to some embodiments, the increase from baseline in daily ON-time without dyskinesia is an increase from baseline of about 2.9 hours in daily ON-time without dyskinesia. According to some embodiments, the increase from baseline in daily ON-time without dyskinesia is an increase from baseline of about 3.0 hours in daily ON-time without dyskinesia. According to some embodiments, the increase from baseline in daily ON-time without dyskinesia is an increase from baseline of about 3.1 hours in daily ON-time without dyskinesia. According to some embodiments, the increase from baseline in daily ON-time without dyskinesia is an increase from baseline of about 3.2 hours in daily ON-time without dyskinesia. According to some embodiments, the increase from baseline in daily ON-time without dyskinesia is an increase from baseline of about 3.25 hours in daily ON-time without dyskinesia. According to some embodiments, the increase from baseline in daily ON-time without dyskinesia is an increase from baseline of about 3.3 hours in daily ON-time without dyskinesia. According to some embodiments, the increase from baseline in daily ON-time without dyskinesia is an increase from baseline of about 3.4 hours in daily ON-time without dyskinesia. According to some embodiments, the increase from baseline in daily ON-time without dyskinesia is an increase from baseline of about 3.5 hours in daily ON-time without dyskinesia.

According to any of the embodiments described herein, the reduction from baseline in total daily troublesome dyskinesia is a reduction from baseline of about 0.1 to 3.2 hours in total daily troublesome dyskinesia.

According to some embodiments described herein, the reduction from baseline in total daily troublesome dyskinesia is a reduction from baseline of about 0.1 hours in total daily troublesome dyskinesia. According to some embodiments described herein, the reduction from baseline in total daily troublesome dyskinesia is a reduction from baseline of about 0.11 hours in total daily troublesome dyskinesia. According to some embodiments described herein, the reduction from baseline in total daily troublesome dyskinesia is a reduction from baseline of about 0.12 hours in total daily troublesome dyskinesia. According to some embodiments described herein, the reduction from baseline in total daily troublesome dyskinesia is a reduction from baseline of about 0.13 hours in total daily troublesome dyskinesia. According to some embodiments described herein, the reduction from baseline in total daily troublesome dyskinesia is a reduction from baseline of about 0.14 hours in total daily troublesome dyskinesia. According to some embodiments described herein, the reduction from baseline in total daily troublesome dyskinesia is a reduction from baseline of about 0.15 hours in total daily troublesome dyskinesia. According to some embodiments described herein, the reduction from baseline in total daily troublesome dyskinesia is a reduction from baseline of about 0.16 hours in total daily troublesome dyskinesia. According to some embodiments described herein, the reduction from baseline in total daily troublesome dyskinesia is a reduction from baseline of about 0.17 hours in total daily troublesome dyskinesia. According to some embodiments described herein, the reduction from baseline in total daily troublesome dyskinesia is a reduction from baseline of about 0.18 hours in total daily troublesome dyskinesia. According to some embodiments described herein, the reduction from baseline in total daily troublesome dyskinesia is a reduction from baseline of about 0.19 hours in total daily troublesome dyskinesia. According to some embodiments described herein, the reduction from baseline in total daily troublesome dyskinesia is a reduction from baseline of about 0.20 hours in total daily troublesome dyskinesia. According to some embodiments described herein, the reduction from baseline in total daily troublesome dyskinesia is a reduction from baseline of about 0.22 hours in total daily troublesome dyskinesia. According to some embodiments described herein, the reduction from baseline in total daily troublesome dyskinesia is a reduction from baseline of about 0.24 hours in total daily troublesome dyskinesia. According to some embodiments, the increase from baseline in daily Good ON-time is an increase of about 0.26 hours in total daily troublesome dyskinesia. According to some embodiments, the increase from baseline in daily Good ON-time is an increase of about 0.28 hours in total daily troublesome dyskinesia. According to some embodiments described herein, the reduction from baseline in total daily troublesome dyskinesia is a reduction from baseline of about 0.3 hours in total daily troublesome dyskinesia. According to some embodiments described herein, the reduction from baseline in total daily troublesome dyskinesia is a reduction from baseline of about 0.32 hours in total daily troublesome dyskinesia. According to some embodiments described herein, the reduction from baseline in total daily troublesome dyskinesia is a reduction from baseline of about 0.34 hours in total daily troublesome dyskinesia. According to some embodiments described herein, the reduction from baseline in total daily troublesome dyskinesia is a reduction from baseline of about 0.36 hours in total daily troublesome dyskinesia. According to some embodiments described herein, the reduction from baseline in total daily troublesome dyskinesia is a reduction from baseline of about 0.38 hours in total daily troublesome dyskinesia. According to some embodiments described herein, the reduction from baseline in total daily troublesome dyskinesia is a reduction from baseline of about 0.4 hours in total daily troublesome dyskinesia. According to some embodiments described herein, the reduction from baseline in total daily troublesome dyskinesia is a reduction from baseline of about 0.42 hours in total daily troublesome dyskinesia. According to some embodiments described herein, the reduction from baseline in total daily troublesome dyskinesia is a reduction from baseline of about 0.44 hours in total daily troublesome dyskinesia. According to some embodiments described herein, the reduction from baseline in total daily troublesome dyskinesia is a reduction from baseline of about 0.46 hours in total daily troublesome dyskinesia. According to some embodiments described herein, the reduction from baseline in total daily troublesome dyskinesia is a reduction from baseline of about 0.48 hours in total daily troublesome dyskinesia. According to some embodiments described herein, the reduction from baseline in total daily troublesome dyskinesia is a reduction from baseline of about 0.5 hours in total daily troublesome dyskinesia. According to some embodiments described herein, the reduction from baseline in total daily troublesome dyskinesia is a reduction from baseline of about 0.55 hours in total daily troublesome dyskinesia. According to some embodiments described herein, the reduction from baseline in total daily troublesome dyskinesia is a reduction from baseline of about 0.6 hours in total daily troublesome dyskinesia. According to some embodiments described herein, the reduction from baseline in total daily troublesome dyskinesia is a reduction from baseline of about 0.65 hours in total daily troublesome dyskinesia. According to some embodiments described herein, the reduction from baseline in total daily troublesome dyskinesia is a reduction from baseline of about 0.7 hours in total daily troublesome dyskinesia. According to some embodiments described herein, the reduction from baseline in total daily troublesome dyskinesia is a reduction from baseline of about 0.75 hours in total daily troublesome dyskinesia. According to some embodiments described herein, the reduction from baseline in total daily troublesome dyskinesia is a reduction from baseline of about 0.8 hours in total daily troublesome dyskinesia. According to some embodiments described herein, the reduction from baseline in total daily troublesome dyskinesia is a reduction from baseline of about 0.85 hours in total daily troublesome dyskinesia. According to some embodiments described herein, the reduction from baseline in total daily troublesome dyskinesia is a reduction from baseline of about 0.9 hours in total daily troublesome dyskinesia. According to some embodiments described herein, the reduction from baseline in total daily troublesome dyskinesia is a reduction from baseline of about 0.95 hours in total daily troublesome dyskinesia. According to some embodiments described herein, the reduction from baseline in total daily troublesome dyskinesia is a reduction from baseline of about 1.0 hours in total daily troublesome dyskinesia. According to some embodiments described herein, the reduction from baseline in total daily troublesome dyskinesia is a reduction from baseline of about 1.1 hours in total daily troublesome dyskinesia. According to some embodiments described herein, the reduction from baseline in total daily troublesome dyskinesia is a reduction from baseline of about 1.2 hours in total daily troublesome dyskinesia. According to some embodiments described herein, the reduction from baseline in total daily troublesome dyskinesia is a reduction from baseline of about 1.3 hours in total daily troublesome dyskinesia. According to some embodiments described herein, the reduction from baseline in total daily troublesome dyskinesia is a reduction from baseline of about 1.4 hours in total daily troublesome dyskinesia. According to some embodiments described herein, the reduction from baseline in total daily troublesome dyskinesia is a reduction from baseline of about 1.5 hours in total daily troublesome dyskinesia. According to some embodiments described herein, the reduction from baseline in total daily troublesome dyskinesia is a reduction from baseline of about 1.6 hours in total daily troublesome dyskinesia. According to some embodiments described herein, the reduction from baseline in total daily troublesome dyskinesia is a reduction from baseline of about 1.7 hours in total daily troublesome dyskinesia. According to some embodiments described herein, the reduction from baseline in total daily troublesome dyskinesia is a reduction from baseline of about 1.8 hours in total daily troublesome dyskinesia. According to some embodiments described herein, the reduction from baseline in total daily troublesome dyskinesia is a reduction from baseline of about 1.8 hours in total daily troublesome dyskinesia. According to some embodiments described herein, the reduction from baseline in total daily troublesome dyskinesia is a reduction from baseline of about 1.9 hours in total daily troublesome dyskinesia. According to some embodiments described herein, the reduction from baseline in total daily troublesome dyskinesia is a reduction from baseline of about 2.0 hours in total daily troublesome dyskinesia. According to some embodiments described herein, the reduction from baseline in total daily troublesome dyskinesia is a reduction from baseline of about 2.1 hours in total daily troublesome dyskinesia. According to some embodiments described herein, the reduction from baseline in total daily troublesome dyskinesia is a reduction from baseline of about 2.2 hours in total daily troublesome dyskinesia. According to some embodiments described herein, the reduction from baseline in total daily troublesome dyskinesia is a reduction from baseline of about 2.3 hours in total daily troublesome dyskinesia. According to some embodiments described herein, the reduction from baseline in total daily troublesome dyskinesia is a reduction from baseline of about 2.4 hours in total daily troublesome dyskinesia. According to some embodiments described herein, the reduction from baseline in total daily troublesome dyskinesia is a reduction from baseline of about 2.5 hours in total daily troublesome dyskinesia. According to some embodiments described herein, the reduction from baseline in total daily troublesome dyskinesia is a reduction from baseline of about 2.6 hours in total daily troublesome dyskinesia. According to some embodiments described herein, the reduction from baseline in total daily troublesome dyskinesia is a reduction from baseline of about 2.7 hours in total daily troublesome dyskinesia. According to some embodiments described herein, the reduction from baseline in total daily troublesome dyskinesia is a reduction from baseline of about 2.8 hours in total daily troublesome dyskinesia. According to some embodiments described herein, the reduction from baseline in total daily troublesome dyskinesia is a reduction from baseline of about 2.9 hours in total daily troublesome dyskinesia. According to some embodiments described herein, the reduction from baseline in total daily troublesome dyskinesia is a reduction from baseline of about 3.0 hours in total daily troublesome dyskinesia. According to some embodiments described herein, the reduction from baseline in total daily troublesome dyskinesia is a reduction from baseline of about 3.1 hours in total daily troublesome dyskinesia. According to some embodiments described herein, the reduction from baseline in total daily troublesome dyskinesia is a reduction from baseline of about 3.2 hours in total daily troublesome dyskinesia.

According to any of the embodiments described herein, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 2 to 13 points in UPDRS Part III score.

According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 2 to 3 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 3 to 4 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 4 to 5 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 5 to 6 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 6 to 7 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 7 to 8 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 8 to 9 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 9 to 10 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 10 to 11 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 11 to 12 points in UPDRS Part III score. According to some embodiments, the improvement from baseline in motor experiences of daily living, as assessed by the Movement Disorder Society-Sponsored revision of Unified Parkinson's Disease Rating Scale Part III (UPDRS Part III) score, results in a reduction from baseline of about 12 to 13 points in UPDRS Part III score.

According to some embodiments, the increase from baseline in daily Good ON-time is sustained for at least about 1, 2, 3, 4, 5, 6, 7, 8, 9, 10, 11, 12, 15, 18, 21, 24, 27, 30, 33, or 36 months.

According to some embodiments, the reduction from baseline in daily ON-time with moderate-severe dyskinesia is sustained for at least about 1, 2, 3, 4, 5, 6, 7, 8, 9, 10, 11, 12, 15, 18, 21, 24, 27, 30, 33, or 36 months.

According to some embodiments, the reduction from baseline in daily OFF-time is sustained for at least about 1, 2, 3, 4, 5, 6, 7, 8, 9, 10, 11, 12, 15, 18, 21, 24, 27, 30, 33, or 36 months.

According to some embodiments, the increase from baseline in daily ON-time without dyskinesia is sustained for at least about 1, 2, 3, 4, 5, 6, 7, 8, 9, 10, 11, 12, 15, 18, 21, 24, 27, 30, 33, or 36 months.

According to some embodiments, the reduction from baseline in total daily troublesome dyskinesia is sustained for at least about 1, 2, 3, 4, 5, 6, 7, 8, 9, 10, 11, 12, 15, 18, 21, 24, 27, 30, 33, or 36 months.

According to some embodiments, the improvement from baseline in motor experiences of daily living, as assessed by the Movement Disorder Society-Sponsored revision of Unified Parkinson's Disease Rating Scale Part III (UPDRS Part III) score, resulting in a reduction from baseline in the UPDRS Part III score, is sustained for at least about 1, 2, 3, 4, 5, 6, 7, 8, 9, 10, 11, 12, 15, 18, 21, 24, 27, 30, 33, or 36 months.

According to some embodiments, the improvement in the Subject Global Impression of Change (SGI-C) score is sustained for at least about 1, 2, 3, 4, 5, 6, 7, 8, 9, 10, 11, 12, 15, 18, 21, 24, 27, 30, 33, or 36 months.

According to some embodiments, the improvement in the Clinical Global Impression of Change (CGI-C) score is sustained for at least about 1, 2, 3, 4, 5, 6, 7, 8, 9, 10, 11, 12, 15, 18, 21, 24, 27, 30, 33, or 36 months.

According to some embodiments, the improvement in the Patient Global Impression of Improvement (PGI-I) score is sustained for at least about 1, 2, 3, 4, 5, 6, 7, 8, 9, 10, 11, 12, 15, 18, 21, 24, 27, 30, 33, or 36 months.

According to some embodiments, the improvement in the Clinical Global Impression of Improvement (CGI-I) score is sustained for at least about 1, 2, 3, 4, 5, 6, 7, 8, 9, 10, 11, 12, 15, 18, 21, 24, 27, 30, 33, or 36 months.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof, wherein the administration results in the patient having at least one of:
a reduction in daily OFF-time,
an increase in daily ON-time without troublesome dyskinesia, an improvement in motor experiences of daily living, as assessed by the Movement Disorder Society-Sponsored revision of Unified Parkinson's Disease Rating Scale Part II (UPDRS Part II) score, an improvement based on a Patient Global Impression of Change (PGI-C) score, an improvement based on a Clinical Global Impression of Improvement (CGI-I) score, or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof, wherein the administration results in the patient having at least one of:

a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS Part II) score, an improvement based on a Patient Global Impression of Change (PGI-C) score, an improvement based on a Clinical Global Impression of Improvement (CGI-I) score, or any combination thereof.

According to some embodiments, the pharmaceutically acceptable liquid composition comprises levodopa or a pharmaceutically acceptable salt thereof and carbidopa or a pharmaceutically acceptable salt thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa, wherein the administration results in the patient having at least one of:

a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS Part II) score or Part III (UPDRS Part III) score, an improvement based on a Patient Global Impression of Change (PGI-C) score, an improvement based on a Clinical Global Impression of Improvement (CGI-I) score, or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa, wherein the administration results in the patient having at least one of:

a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS Part II) score or Part III (UPDRS Part III) score, an improvement based on a Patient Global Impression of Change (PGI-C) score, an improvement based on a Clinical Global Impression of Improvement (CGI-I) score, or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa in a ratio of about 8:1 w/w, wherein the administration results in the patient having at least one of:

a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS Part II) score or Part III (UPDRS Part III) score, an improvement based on a Patient Global Impression of Change (PGI-C) score, an improvement based on a Clinical Global Impression of Improvement (CGI-I) score, or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa in a ratio of about 8:1 w/w, wherein the administration results in the patient having at least one of:

a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS Part II) score or Part III (UPDRS Part III) score, an improvement based on a Patient Global Impression of Change (PGI-C) score, an improvement based on a Clinical Global Impression of Improvement (CGI-I) score, or any combination thereof.

In some embodiments, the administration further results in the patient having a reduction in daily troublesome dyskinesia.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof,
  wherein the administration results in the patient having at least one of:
  a reduction in daily OFF-time,
  an increase in daily ON-time without troublesome dyskinesia,
  an improvement in motor experiences of daily living, as assessed by the Movement Disorder Society-Sponsored revision of Unified Parkinson's Disease Rating Scale Part II (UPDRS Part II) score,
  an improvement based on a Patient Global Impression of Change (PGI-C) score,
  an improvement based on a Clinical Global Impression of Improvement (CGI-I) score,
  a reduction in daily troublesome dyskinesia,
  or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa or a pharmaceutically acceptable salt thereof and, optionally, carbidopa or a pharmaceutically acceptable salt thereof,
  wherein the administration results in the patient having at least one of:
  a reduction in daily OFF-time,
  an increase in daily ON-time without troublesome dyskinesia,
  an improvement in motor experiences of daily living, as assessed by the Movement Disorder Society-Sponsored revision of Unified Parkinson's Disease Rating Scale Part II (UPDRS Part II) score,
  an improvement based on a Patient Global Impression of Change (PGI-C) score,
  an improvement based on a Clinical Global Impression of Improvement (CGI-I) score,
  a reduction in daily troublesome dyskinesia,
  or any combination thereof.

According to some embodiments, the pharmaceutically acceptable liquid composition comprises levodopa or a pharmaceutically acceptable salt thereof and carbidopa or a pharmaceutically acceptable salt thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa,
  wherein the administration results in the patient having at least one of:
  a reduction in daily OFF-time,
  an increase in daily ON-time without troublesome dyskinesia,
  an improvement in motor experiences of daily living, as assessed by the Movement Disorder Society-Sponsored revision of Unified Parkinson's Disease Rating Scale Part II (UPDRS Part II) score or Part III (UPDRS Part III) score,
  an improvement based on a Patient Global Impression of Change (PGI-C) score,
  an improvement based on a Clinical Global Impression of Improvement (CGI-I) score,
  a reduction in daily troublesome dyskinesia,
  or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa,
  wherein the administration results in the patient having at least one of:
  a reduction in daily OFF-time,
  an increase in daily ON-time without troublesome dyskinesia,
  an improvement in motor experiences of daily living, as assessed by the Movement Disorder Society-Sponsored revision of Unified Parkinson's Disease Rating Scale Part II (UPDRS Part II) score or Part III (UPDRS Part III) score,
  an improvement based on a Patient Global Impression of Change (PGI-C) score,
  an improvement based on a Clinical Global Impression of Improvement (CGI-I) score,
  a reduction in daily troublesome dyskinesia,
  or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa in a ratio of about 8:1 w/w,
  wherein the administration results in the patient having at least one of:
  a reduction in daily OFF-time,
  an increase in daily ON-time without troublesome dyskinesia,
  an improvement in motor experiences of daily living, as assessed by the Movement Disorder Society-Sponsored revision of Unified Parkinson's Disease Rating Scale Part II (UPDRS Part II) score or Part III (UPDRS Part III) score,
  an improvement based on a Patient Global Impression of Change (PGI-C) score,
  an improvement based on a Clinical Global Impression of Improvement (CGI-I) score,
  a reduction in daily troublesome dyskinesia,
  or any combination thereof.

Further embodiments of the invention are directed to a method of improving at least one symptom of Parkinson's disease in a patient who is suffering from Parkinson's disease, the method comprising, subcutaneously administering to the patient, substantially continuously for about 24 hours/day, a pharmaceutically acceptable liquid composition comprising levodopa and carbidopa in a ratio of about 8:1 w/w,
  wherein the administration results in the patient having at least one of:
  a reduction in daily OFF-time,
  an increase in daily ON-time without troublesome dyskinesia,
  an improvement in motor experiences of daily living, as assessed by the Movement Disorder Society-Sponsored revision of Unified Parkinson's Disease Rating Scale Part II (UPDRS Part II) score or Part III (UPDRS Part III) score, an improvement based on a Patient Global Impression of Change (PGI-C) score, an improvement based on a Clinical Global Impression of Improvement (CGI-I) score, a reduction in daily troublesome dyskinesia, or any combination thereof.

According to some embodiments, the administration results in a reduction in daily OFF-time. According to some embodiments, the administration results in an increase in daily ON-time without troublesome dyskinesia. According to some embodiments, the administration results in an improvement in motor experiences of daily living, as assessed by the Movement Disorder Society-Sponsored revision of Unified Parkinson's Disease Rating Scale Part II (UPDRS Part II) score or Part III (UPDRS Part III) score. According to some embodiments, the administration results in an improvement based on a Patient Global Impression of Change (PGI-C) score. According to some embodiments, the administration results in an improvement based on a Clinical Global Impression of Improvement (CGI-I) score. According to some embodiments, the administration results in an improvement based on a Clinical Global Impression Change (CGI-C) score. According to some embodiments, the administration results in a reduction in daily troublesome dyskinesia.

According to some embodiments, the administration results in a reduction in daily OFF-time and an increase in daily ON-time without troublesome dyskinesia. According to some embodiments, the administration results in a reduction in daily OFF-time and an improvement in motor experiences of daily living, as assessed by the Movement Disorder Society-Sponsored revision of Unified Parkinson's Disease Rating Scale Part II (UPDRS II) score or Part III (UPDRS Part III) score. According to some embodiments, the administration results in a reduction in daily OFF-time and an improvement based on a Patient Global Impression of Change (PGI-C) score. According to some embodiments, the administration results in a reduction in daily OFF-time and an improvement based on a Clinical Global Impression Improvement (CGI-I) score. According to some embodiments, the administration results in an improvement based on a Clinical Global Impression Change (CGI-C) score. According to some embodiments, the administration results in a reduction in daily OFF-time and a reduction in daily troublesome dyskinesia. According to some embodiments, the administration results in an increase in daily ON-time without troublesome dyskinesia and motor experiences of daily living, as assessed by the Movement Disorder Society-Sponsored revision of Unified Parkinson's Disease Rating Scale Part II (UPDRS II) score or Part III (UPDRS Part III) score. According to some embodiments, the administration results in an increase in daily ON-time without troublesome dyskinesia and an improvement based on a Patient Global Impression of Change (PGI-C) score. According to some embodiments, the administration results in an increase in daily ON-time without troublesome dyskinesia and an improvement based on a Clinical Global Impression of Improvement (CGI-I) score. According to some embodiments, the administration results in an increase in daily ON-time without troublesome dyskinesia and a reduction in daily troublesome dyskinesia. According to some embodiments, the administration results in an increase in daily ON-time without troublesome dyskinesia and an improvement based on a Clinical Global Impression Change (CGI-C) score. According to some embodiments, the administration results in an improvement in motor experiences of daily living, as assessed by the Movement Disorder Society-Sponsored revision of Unified Parkinson's Disease Rating Scale Part II (UPDRS Part II) score or Part III (UPDRS Part III) score and an improvement based on a Patient Global Impression of Change (PGI-C) score. According to some embodiments, the administration results in an improvement in motor experiences of daily living, as assessed by the Movement Disorder Society-Sponsored revision of Unified Parkinson's Disease Rating Scale Part II (UPDRS Part II) score or Part III (UPDRS Part III) score and an improvement based on a Clinical Global Impression of Improvement (CGI-I) score. According to some embodiments, the administration results in an improvement in motor experiences of daily living, as assessed by the Movement Disorder Society-Sponsored revision of Unified Parkinson's Disease Rating Scale Part II (UPDRS Part II) score or Part III (UPDRS Part III) score and an improvement based on a Clinical Global Impression Change (CGI-C) score. According to some embodiments, the administration results in an improvement in motor experiences of daily living, as assessed by the Movement Disorder Society-Sponsored revision of Unified Parkinson's Disease Rating Scale Part II (UPDRS Part II) score or Part III (UPDRS Part III) score and a reduction in daily troublesome dyskinesia. According to some embodiments, the administration results in an improvement based on a Patient Global Impression of Change (PGI-C) score and an improvement based on a Clinical Global Impression of Improvement (CGI-I) score. According to some embodiments, the administration results in an improvement based on a Patient Global Impression of Change (PGI-C) score and an improvement based on a Clinical Global Impression of Change (CGI-C) score. According to some embodiments, the administration results in a Patient Global Impression of Change (PGI-C) score and a reduction in daily troublesome dyskinesia. According to some embodiments, the administration results in an improvement based on a Clinical Global Impression of Change (CGI-C) score and a reduction in daily troublesome dyskinesia. According to some embodiments, the administration results in an improvement based on a Clinical Global Impression of Improvement (CGI-I) score and a reduction in daily troublesome dyskinesia.

According to some embodiments, the administration results in a reduction in daily OFF-time, daily ON-time without troublesome dyskinesia, and an improvement in motor experiences of daily living, as assessed by the Movement Disorder Society-Sponsored revision of Unified Parkinson's Disease Rating Scale Part II (UPDRS II) score or Part III (UPDRS Part III) score. According to some embodiments, the administration results in a reduction in daily OFF-time, daily ON-time without troublesome dyskinesia, and an improvement based on a Patient Global Impression of Change (PGI-C) score. According to some embodiments, the administration results in a reduction in daily OFF-time, daily ON-time without troublesome dyskinesia, and an improvement based on a Clinical Global Impression of Improvement (CGI-I) score. According to some embodiments, the administration results in a reduction in daily OFF-time, daily ON-time without troublesome dyskinesia, and an improvement based on a Clinical Global Impression of Change (CGI-C) score. According to some embodiments, the administration results in a reduction in daily OFF-time, daily ON-time without troublesome dyskinesia, and a reduction in daily troublesome dyskinesia. According to some embodiments, the administration results in a reduction in daily OFF-time, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Patient Global Impression of Change (PGI-C) score. According to some embodiments, the administration results in a reduction in daily OFF-time, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Clinical Global Impression of Improvement (CGI-I) score. According to some embodiments, the administration results in a reduction in daily OFF-time, an improvement in motor experiences of daily living, as assessed by the Movement Disorder Society-Sponsored revision of Unified Parkinson's Disease Rating Scale Part II (UPDRS II) score or Part III (UPDRS Part III) score, and a reduction in daily troublesome dyskinesia. According to some embodiments, the administration results in a reduction in daily OFF-time, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Clinical Global Impression of Change (CGI-C) score. According to some embodiments, the administration results in a reduction in daily OFF-time, an improvement based on a Patient Global Impression of Change (PGI-C) score, and an improvement based on a Clinical Global Impression of Improvement (CGI-I) score. According to some embodiments, the administration results in a reduction in daily OFF-time, an improvement based on a Patient Global Impression of Change (PGI-C) score, and a reduction in daily troublesome dyskinesia. According to some embodiments, the administration results in a reduction in daily OFF-time, an improvement based on a Patient Global Impression of Change (PGI-C) score, and an improvement based on a Clinical Global Impression of Change (CGI-C) score. According to some embodiments, the administration results in an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Patient Global Impression of Change (PGI-C) score. According to some embodiments, the administration results in an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Clinical Global Impression of Improvement (CGI-I) score. According to some embodiments, the administration results in an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Clinical Global Impression of Change (CGI-C) score. According to some embodiments, the administration results in an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and a reduction in daily troublesome dyskinesia. According to some embodiments, the administration results in an improvement in motor experiences of daily living, as assessed by the Movement Disorder Society-Sponsored revision of Unified Parkinson's Disease Rating Scale Part II (UPDRS Part II) score or Part III (UPDRS Part III) score, an improvement based on a Patient Global Impression of Change (PGI-C) score, and an improvement based on a Clinical Global Impression of Improvement (CGI-I) score. According to some embodiments, the administration results in an improvement in motor experiences of daily living, as assessed by the Movement Disorder Society-Sponsored revision of Unified Parkinson's Disease Rating Scale Part II (UPDRS Part II) score or Part III (UPDRS Part III) score, an improvement based on a Patient Global Impression of Change (PGI-C) score, and an improvement based on a Clinical Global Impression of Change (CGI-C) score.

According to some embodiments, the administration results in a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Patient Global Impression of Change (PGI-C) score. According to some embodiments, the administration results in a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Clinical Global Impression of Improvement (CGI-I) score. According to some embodiments, the administration results in a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and a reduction in daily troublesome dyskinesia. According to some embodiments, the administration results in a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, and an improvement based on a Clinical Global Impression of Change (CGI-C) score. According to some embodiments, the administration results in a reduction in daily OFF-time, an improvement in motor experiences of daily living, as assessed by the Movement Disorder Society-Sponsored revision of Unified Parkinson's Disease Rating Scale Part II (UPDRS II) score or Part III (UPDRS Part III) score, an improvement based on a Patient Global Impression of Change (PGI-C) score, and an improvement based on a Clinical Global Impression of Improvement (CGI-I) score. According to some embodiments, the administration results in a reduction in daily OFF-time, an improvement in motor experiences of daily living, as assessed by the Movement Disorder Society-Sponsored revision of Unified Parkinson's Disease Rating Scale Part II (UPDRS II) score or Part III (UPDRS Part III) score, an improvement based on a Patient Global Impression of Change (PGI-C) score, and a reduction in daily troublesome dyskinesia. According to some embodiments, the administration results in a reduction in daily OFF-time, an improvement in motor experiences of daily living, as assessed by the Movement Disorder Society-Sponsored revision of Unified Parkinson's Disease Rating Scale Part II (UPDRS II) score or Part III (UPDRS Part III) score, an improvement based on a Patient Global Impression of Change (PGI-C) score, and an improvement based on a Clinical Global Impression of Change (CGI-C) score. According to some embodiments, the administration results in an increase in daily ON-time without troublesome dyskinesia, an improvement in motor experiences of daily living, as assessed by the Movement Disorder Society-Sponsored revision of Unified Parkinson's Disease Rating Scale Part II score, an improvement based on a Patient Global Impression of Change (PGI-C) score, and an improvement based on a Clinical Global Impression of Improvement (CGI-I) score. According to some embodiments, the administration results in an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, an improvement based on a Patient Global Impression of Change (PGI-C) score, and an improvement based on a Clinical Global Impression of Change (CGI-C) score. According to some embodiments, the administration results in an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, an improvement based on a Patient Global Impression of Change (PGI-C) score, and a reduction in daily troublesome dyskinesia.

According to some embodiments, the administration results in a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, an improvement based on a Patient Global Impression of Change (PGI-C) score, and an improvement based on a Clinical Global Impression of Improvement (CGI-I) score. According to some embodiments, the administration results in a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II score, an improvement based on a Patient Global Impression of Change (PGI-C) score, and an improvement based on a Clinical Global Impression of Change (CGI-C) score. According to some embodiments, the administration results in a reduction in daily OFF-time, an increase in daily ON-time without troublesome dyskinesia, an improvement in motor experiences of daily living, as assessed by the Movement Disorder Society-Sponsored revision of Unified Parkinson's Disease Rating Scale Part II (UPDRS II) score or Part III (UPDRS Part III) score, an improvement based on a Patient Global Impression of Change (PGI-C) score, and a reduction in daily troublesome dyskinesia.

According to any of the embodiments described above, the reduction in daily OFF-time is a reduction from baseline of at least about ≥25% in daily OFF-time.

According to some embodiments, the reduction daily OFF-time is a reduction from baseline of about ≥25% in daily OFF-time. According to some embodiments, the reduction daily OFF-time is a reduction from baseline of about ≥30% in daily OFF-time in the patient. According to some embodiments, the reduction daily OFF-time is a reduction from baseline of about ≥35% in daily OFF-time in the patient. According to some embodiments, the reduction daily OFF-time is a reduction from baseline of about ≥40% in daily OFF-time in the patient. According to some embodiments, the reduction daily OFF-time is a reduction from baseline of about ≥45% in daily OFF-time in the patient. According to some embodiments, the reduction daily OFF-time is a reduction from baseline of about ≥50% in daily OFF-time in the patient. According to some embodiments, the reduction daily OFF-time is a reduction from baseline of about ≥55% in daily OFF-time in the patient. According to some embodiments, the reduction daily OFF-time is a reduction from baseline of about ≥60% in daily OFF-time in the patient. According to some embodiments, the reduction daily OFF-time is a reduction from baseline of about ≥65% in daily OFF-time in the patient. According to some embodiments, the reduction daily OFF-time is a reduction from baseline of about ≥70% in daily OFF-time in the patient. According to some embodiments, the reduction daily OFF-time is a reduction from baseline of about ≥75% in daily OFF-time in the patient. According to some embodiments, the reduction daily OFF-time is a reduction from baseline of about ≥80% in daily OFF-time in the patient. According to some embodiments, the reduction daily OFF-time is a reduction from baseline of about ≥85% in daily OFF-time in the patient. According to some embodiments, the reduction daily OFF-time is a reduction from baseline of about ≥90% in daily OFF-time in the patient. According to some embodiments, the reduction daily OFF-time is a reduction from baseline of about ≥95% in daily OFF-time in the patient. According to some embodiments, the reduction daily OFF-time is an elimination of daily OFF-time.

According to any of the embodiments described herein, the reduction in daily OFF-time is a reduction in daily OFF-time, from baseline.

According to any of the embodiments described herein, the reduction in daily OFF-time is a reduction in daily OFF-time, in comparison to a patient treated with an immediate release oral formulation of levodopa.

According to any of the embodiments described herein, the reduction in daily OFF-time is a reduction in daily OFF-time, relative to administering an immediate release oral formulation of levodopa.

According to any of the embodiments described herein, the reduction in daily OFF-time is a reduction of at least about 0.1 to 3.5 hours in daily OFF-time. According to some embodiments, the reduction in daily OFF-time is a reduction of at least about 0.1 to 6 hours in daily OFF-time.

According to any of the embodiments described herein, the reduction in daily OFF-time is a reduction of at least about 0.1 to 3.5 hours in daily OFF-time, from baseline. According to some embodiments, the reduction in daily OFF-time is a reduction of at least about 0.1 to 6 hours in daily OFF-time, from baseline.

According to any of the embodiments described herein, the reduction in daily OFF-time is a reduction of at least about 0.1 to 3.5 hours in daily OFF-time, in comparison to a patient treated with an immediate release oral formulation of levodopa. According to any of the embodiments described herein, the reduction in daily OFF-time is a reduction of at least about 0.1 to 6 hours in daily OFF-time, in comparison to a patient treated with an immediate release oral formulation of levodopa.

According to any of the embodiments described herein, the reduction in daily OFF-time is a reduction of at least about 0.1 to 3.5 hours in daily OFF-time, relative to administering an immediate release oral formulation of levodopa. According to any of the embodiments described herein, the reduction in daily OFF-time is a reduction of at least about 0.1 to 6 hours in daily OFF-time, relative to administering an immediate release oral formulation of levodopa.

According to some embodiments, the reduction in daily OFF-time is a reduction of about 0.1 hours in daily OFF-time. According to some embodiments, the reduction in daily OFF-time is a reduction of about 0.15 hours in daily OFF-time. According to some embodiments, the reduction in daily OFF-time is a reduction of about 0.2 hours in daily OFF-time. According to some embodiments, the reduction in daily OFF-time is a reduction of about 0.25 hours in daily OFF-time. According to some embodiments, the reduction in daily OFF-time is a reduction of about 0.3 hours in daily OFF-time. According to some embodiments, the reduction in daily OFF-time is a reduction of about 0.35 hours in daily OFF-time. According to some embodiments, the reduction in daily OFF-time is a reduction of about 0.4 hours in daily OFF-time. According to some embodiments, the reduction in daily OFF-time is a reduction of about 0.45 hours in daily OFF-time. According to some embodiments, the reduction in daily OFF-time is a reduction of about 0.5 hours in daily OFF-time. According to some embodiments, the reduction in daily OFF-time is a reduction of about 0.55 hours in daily OFF-time. According to some embodiments, the reduction in daily OFF-time is a reduction of about 0.6 hours in daily OFF-time. According to some embodiments, the reduction in daily OFF-time is a reduction of about 0.65 hours in daily OFF-time. According to some embodiments, the reduction in daily OFF-time is a reduction of about 0.7 hours in daily OFF-time. According to some embodiments, the reduction in daily OFF-time is a reduction of about 0.75 hours in daily OFF-time. According to some embodiments, the reduction in daily OFF-time is a reduction of about 1 hour daily OFF-time. According to some embodiments, the reduction in daily OFF-time is a reduction of about 0.8 hours in daily OFF-time. According to some embodiments, the reduction in daily OFF-time is a reduction of about 0.85 hours in daily OFF-time. According to some embodiments, the reduction in daily OFF-time is a reduction of about 0.9 hours in daily OFF-time. According to some embodiments, the reduction in daily OFF-time is a reduction of about 0.95 hours in daily OFF-time. According to some embodiments, the reduction in daily OFF-time is a reduction of about 1 hour in daily OFF-time. According to some embodiments, the reduction in daily OFF-time is a reduction of about 1.1 hours in daily OFF-time. According to some embodiments, the reduction in daily OFF-time is a reduction of about 1.2 hours in daily OFF-time. According to some embodiments, the reduction in daily OFF-time is a reduction of about 1.3 hours in daily hours in daily OFF-time. According to some embodiments, the reduction in daily OFF-time is a reduction of about 1.4 hours in daily OFF-time. According to some embodiments, the reduction in daily OFF-time is a reduction of about 1.5 hours in daily OFF-time. According to some embodiments, the reduction in daily OFF-time is a reduction of about 1.6 hours in daily OFF-time. According to some embodiments, the reduction in daily OFF-time is a reduction of about 1.7 hours in daily OFF-time. According to some embodiments, the reduction in daily OFF-time is a reduction of about 1.8 hours in daily OFF-time. According to some embodiments, the reduction in daily OFF-time is a reduction of about 1.9 hours in daily OFF-time. According to some embodiments, the reduction in daily OFF-time is a reduction of about 2 hours in daily OFF-time. According to some embodiments, the reduction in daily OFF-time is a reduction of about 2.1 hours in daily OFF-time. According to some embodiments, the reduction in daily OFF-time is a reduction of about 2.2 hours in daily OFF-time. According to some embodiments, the reduction in daily OFF-time is a reduction of about 2.3 hours in daily OFF-time. According to some embodiments, the reduction in daily OFF-time is a reduction of about 2.4 hours in daily OFF-time. According to some embodiments, the reduction in daily OFF-time is a reduction of about 2.5 hours in daily OFF-time. According to some embodiments, the reduction in daily OFF-time is a reduction of about 2.6 hours in daily OFF-time. According to some embodiments, the reduction in daily OFF-time is a reduction of about 2.7 hours in daily OFF-time. According to some embodiments, the reduction in daily OFF-time is a reduction of about 2.8 hours in daily OFF-time. According to some embodiments, the reduction in daily OFF-time is a reduction of about 2.9 hours in daily OFF-time. According to some embodiments, the reduction in daily OFF-time is a reduction of about 3 hours in daily OFF-time. According to some embodiments, the reduction in daily OFF-time is a reduction of about 3.1 hours in daily OFF-time. According to some embodiments, the reduction in daily OFF-time is a reduction of about 3.2 hours in daily OFF-time. According to some embodiments, the reduction in daily OFF-time is a reduction of about 3.3 hours in daily OFF-time. According to some embodiments, the reduction in daily OFF-time is a reduction of about 3.4 hours in daily OFF-time. According to some embodiments, the reduction in daily OFF-time is a reduction of about 3.5 hours in daily OFF-time. According to some embodiments, the reduction in daily OFF-time is a reduction of about 3.6 hours in daily OFF-time. According to some embodiments, the reduction in daily OFF-time is a reduction of about 3.7 hours in daily OFF-time. According to some embodiments, the reduction in daily OFF-time is a reduction of about 3.8 hours in daily OFF-time. According to some embodiments, the reduction in daily OFF-time is a reduction of about 3.9 hours in daily OFF-time. According to some embodiments, the reduction in daily OFF-time is a reduction of about 4 hours in daily OFF-time. According to some embodiments, the reduction in daily OFF-time is a reduction of about 4.1 hours in daily OFF-time. According to some embodiments, the reduction in daily OFF-time is a reduction of about 4.2 hours in daily OFF-time. According to some embodiments, the reduction in daily OFF-time is a reduction of about 4.3 hours in daily OFF-time. According to some embodiments, the reduction in daily OFF-time is a reduction of about 4.4 hours in daily OFF-time. According to some embodiments, the reduction in daily OFF-time is a reduction of about 4.5 hours in daily OFF-time. According to some embodiments, the reduction in daily OFF-time is a reduction of about 4.6 hours in daily OFF-time. According to some embodiments, the reduction in daily OFF-time is a reduction of about 4.7 hours in daily OFF-time. According to some embodiments, the reduction in daily OFF-time is a reduction of about 4.8 hours in daily OFF-time. According to some embodiments, the reduction in daily OFF-time is a reduction of about 4.9 hours in daily OFF-time. According to some embodiments, the reduction in daily OFF-time is a reduction of about 5 hours in daily OFF-time. According to some embodiments, the reduction in daily OFF-time is a reduction of about 5.1 hours in daily OFF-time. According to some embodiments, the reduction in daily OFF-time is a reduction of about 5.2 hours in daily OFF-time. According to some embodiments, the reduction in daily OFF-time is a reduction of about 5.3 hours in daily OFF-time. According to some embodiments, the reduction in daily OFF-time is a reduction of about 5.4 hours in daily OFF-time. According to some embodiments, the reduction in daily OFF-time is a reduction of about 5.5 hours in daily OFF-time. According to some embodiments, the reduction in daily OFF-time is a reduction of about 5.6 hours in daily OFF-time. According to some embodiments, the reduction in daily OFF-time is a reduction of about 5.7 hours in daily OFF-time. According to some embodiments, the reduction in daily OFF-time is a reduction of about 5.8 hours in daily OFF-time. According to some embodiments, the reduction in daily OFF-time is a reduction of about 5.9 hours in daily OFF-time. According to some embodiments, the reduction in daily OFF-time is a reduction of about 6 hours in daily OFF-time.

According to some embodiments, the reduction in daily OFF-time is sustained for at least about 1, 2, 3, 4, 5, 6, 7, 8, 9, 10, 11, 12, 15, 18, 21, 24, 27, 30, 33, or 36 months.

According to any of the embodiments described herein, the increase in daily ON-time without troublesome dyskinesia is an increase in daily ON-time without troublesome dyskinesia, from baseline.

According to any of the embodiments described herein, the increase in daily ON-time without troublesome dyskinesia is an increase in daily ON-time without troublesome dyskinesia, in comparison to a patient treated with an immediate release oral formulation of levodopa.

According to any of the embodiments described herein, the increase in daily ON-time without troublesome dyskinesia is an increase in daily ON-time without troublesome dyskinesia, relative to administering an immediate release oral formulation of levodopa.

According to any of the embodiments described herein, the increase in daily ON-time without troublesome dyskinesia is an increase of at least about 0.1 to 3.5 hours in daily ON-time without troublesome dyskinesia. According to some embodiments, the increase in daily ON-time without troublesome dyskinesia is an increase of at least about 0.1 to 6 hours in daily ON-time without troublesome dyskinesia.

According to any of the embodiments described herein, the increase in daily ON-time without troublesome dyskinesia is an increase of at least about 0.1 to 3.5 hours in daily ON-time without troublesome dyskinesia, from baseline. According to some embodiments, the increase in daily ON-time without troublesome dyskinesia is an increase of at least about 0.1 to 6 hours in daily ON-time without troublesome dyskinesia, from baseline.

According to any of the embodiments described herein, the increase in daily ON-time without troublesome dyskinesia is an increase of at least about 1 to 3.5 hours in daily ON-time without troublesome dyskinesia, in comparison to a patient treated with an immediate release oral formulation of levodopa. According to any of the embodiments described herein, the increase in daily ON-time without troublesome dyskinesia is an increase of at least about 1 to 6 hours in daily ON-time without troublesome dyskinesia, in comparison to a patient treated with an immediate release oral formulation of levodopa.

According to any of the embodiments described herein, the increase in daily ON-time without troublesome dyskinesia is an increase of at least about 1 to 3.5 hours in daily ON-time without troublesome dyskinesia, relative to administering an immediate release oral formulation of levodopa. According to any of the embodiments described herein, the increase in daily ON-time without troublesome dyskinesia is an increase of at least about 1 to 6 hours in daily ON-time without troublesome dyskinesia, relative to administering an immediate release oral formulation of levodopa.

According to some embodiments, the increase in daily ON-time without troublesome dyskinesia is an increase of about 1 hour in daily ON-time without troublesome dyskinesia. According to some embodiments, the increase in daily ON-time without troublesome dyskinesia is an increase of about 1.1 hours in daily ON-time without troublesome dyskinesia. According to some embodiments, the increase in daily ON-time without troublesome dyskinesia is an increase of about 1.2 hours in daily ON-time without troublesome dyskinesia. According to some embodiments, the increase in daily ON-time without troublesome dyskinesia is an increase of about 1.3 hours in daily ON-time without troublesome dyskinesia. According to some embodiments, the improvement in the patient in daily ON-time without troublesome dyskinesia is an increase of about 1.4 hours in daily ON-time without troublesome dyskinesia. According to some embodiments, the increase in daily ON-time without troublesome dyskinesia is an increase of about 1.5 hours in daily ON-time without troublesome dyskinesia. According to some embodiments, the increase in daily ON-time without troublesome dyskinesia is an increase of about 1.6 hours in daily ON-time without troublesome dyskinesia. According to some embodiments, the increase in daily ON-time without troublesome dyskinesia is an increase of about 1.7 hours in daily ON-time without troublesome dyskinesia. According to some embodiments, the increase in daily ON-time without troublesome dyskinesia is an increase of about 1.72 hours in daily ON-time without troublesome dyskinesia. According to some embodiments, the increase in daily ON-time without troublesome dyskinesia is an increase of about 1.8 hours in daily ON-time without troublesome dyskinesia. According to some embodiments, the increase in daily ON-time without troublesome dyskinesia is an increase of about 1.9 hours in daily ON-time without troublesome dyskinesia. According to some embodiments, the increase in daily ON-time without troublesome dyskinesia is an increase of about 2 hours in daily ON-time without troublesome dyskinesia. According to some embodiments, the increase in daily ON-time without troublesome dyskinesia is an increase of about 2.1 hours in daily ON-time without troublesome dyskinesia. According to some embodiments, the increase in daily ON-time without troublesome dyskinesia is an increase of about 2.2 hours in daily ON-time without troublesome dyskinesia. According to some embodiments, the increase in daily ON-time without troublesome dyskinesia is an increase of about 2.3 hours in daily ON-time without troublesome dyskinesia. According to some embodiments, the increase in daily ON-time without troublesome dyskinesia is an increase of about 2.4 hours in daily ON-time without troublesome dyskinesia. According to some embodiments, the increase in daily ON-time without troublesome dyskinesia is an increase of about 2.5 hours in daily ON-time without troublesome dyskinesia. According to some embodiments, the increase in daily ON-time without troublesome dyskinesia is an increase of about 2.6 hours in daily ON-time without troublesome dyskinesia. According to some embodiments, the increase in daily ON-time without troublesome dyskinesia is an increase of about 2.7 hours in daily ON-time without troublesome dyskinesia. According to some embodiments, the increase in daily ON-time without troublesome dyskinesia is an increase of about 2.8 hours in daily ON-time without troublesome dyskinesia. According to some embodiments, the increase in daily ON-time without troublesome dyskinesia is an increase of about 2.9 hours in daily ON-time without troublesome dyskinesia. According to some embodiments, the increase in daily ON-time without troublesome dyskinesia is an increase of about 3 hours in daily ON-time without troublesome dyskinesia. According to some embodiments, the increase in daily ON-time without troublesome dyskinesia is an increase of about 3.1 hours in daily ON-time without troublesome dyskinesia. According to some embodiments, the increase in daily ON-time without troublesome dyskinesia is an increase of about 3.2 hours in daily ON-time without troublesome dyskinesia. According to some embodiments, the increase in daily ON-time without troublesome dyskinesia is an increase of about 3.3 hours in daily ON-time without troublesome dyskinesia. According to some embodiments, the increase in daily ON-time without troublesome dyskinesia is an increase of about 3.4 hours in daily ON-time without troublesome dyskinesia. According to some embodiments, the increase in daily ON-time without troublesome dyskinesia is an increase of about 3.5 hours in daily ON-time without troublesome dyskinesia. According to some embodiments, the increase in daily ON-time without troublesome dyskinesia is an increase of about 3.6 hours in daily ON-time without troublesome dyskinesia. According to some embodiments, the increase in daily ON-time without troublesome dyskinesia is an increase of about 3.7 hours in daily ON-time without troublesome dyskinesia. According to some embodiments, the increase in daily ON-time without troublesome dyskinesia is an increase of about 3.8 hours in daily ON-time without troublesome dyskinesia. According to some embodiments, the increase in daily ON-time without troublesome dyskinesia is an increase of about 3.9 hours in daily ON-time without troublesome dyskinesia. According to some embodiments, the increase in daily ON-time without troublesome dyskinesia is an increase of about 4 hours in daily ON-time without troublesome dyskinesia. According to some embodiments, the increase in daily ON-time without troublesome dyskinesia is an increase of about 4.1 hours in daily ON-time without troublesome dyskinesia. According to some embodiments, the increase in daily ON-time without troublesome dyskinesia is an increase of about 4.2 hours in daily ON-time without troublesome dyskinesia. According to some embodiments, the increase in daily ON-time without troublesome dyskinesia is an increase of about 4.3 hours in daily ON-time without troublesome dyskinesia. According to some embodiments, the increase in daily ON-time without troublesome dyskinesia is an increase of about 4.4 hours in daily ON-time without troublesome dyskinesia. According to some embodiments, the increase in daily ON-time without troublesome dyskinesia is an increase of about 4.5 hours in daily ON-time without troublesome dyskinesia. According to some embodiments, the increase in daily ON-time without troublesome dyskinesia is an increase of about 4.6 hours in daily ON-time without troublesome dyskinesia. According to some embodiments, the increase in daily ON-time without troublesome dyskinesia is an increase of about 4.7 hours in daily ON-time without troublesome dyskinesia. According to some embodiments, the increase in daily ON-time without troublesome dyskinesia is an increase of about 4.8 hours in daily ON-time without troublesome dyskinesia. According to some embodiments, the increase in daily ON-time without troublesome dyskinesia is an increase of about 4.9 hours in daily ON-time without troublesome dyskinesia. According to some embodiments, the increase in daily ON-time without troublesome dyskinesia is an increase of about 5 hours in daily ON-time without troublesome dyskinesia. According to some embodiments, the increase in daily ON-time without troublesome dyskinesia is an increase of about 5.1 hours in daily ON-time without troublesome dyskinesia. According to some embodiments, the increase in daily ON-time without troublesome dyskinesia is an increase of about 5.2 hours in daily ON-time without troublesome dyskinesia. According to some embodiments, the increase in daily ON-time without troublesome dyskinesia is an increase of about 5.3 hours in daily ON-time without troublesome dyskinesia. According to some embodiments, the increase in daily ON-time without troublesome dyskinesia is an increase of about 5.4 hours in daily ON-time without troublesome dyskinesia. According to some embodiments, the increase in daily ON-time without troublesome dyskinesia is an increase of about 5.5 hours in daily ON-time without troublesome dyskinesia. According to some embodiments, the increase in daily ON-time without troublesome dyskinesia is an increase of about 5.6 hours in daily ON-time without troublesome dyskinesia. According to some embodiments, the increase in daily ON-time without troublesome dyskinesia is an increase of about 5.7 hours in daily ON-time without troublesome dyskinesia. According to some embodiments, the increase in daily ON-time without troublesome dyskinesia is an increase of about 5.8 hours in daily ON-time without troublesome dyskinesia. According to some embodiments, the increase in daily ON-time without troublesome dyskinesia is an increase of about 5.9 hours in daily ON-time without troublesome dyskinesia. According to some embodiments, the increase in daily ON-time without troublesome dyskinesia is an increase of about 6 hours in daily ON-time without troublesome dyskinesia.

According to some embodiments, the increase in daily ON-time without troublesome dyskinesia is sustained for at least about 1, 2, 3, 4, 5, 6, 7, 8, 9, 10, 11, 12, 15, 18, 21, 24, 27, 30, 33, or 36 months.

According to any of the embodiments described herein, the reduction in daily troublesome dyskinesia is a reduction in daily troublesome dyskinesia, from baseline.

According to any of the embodiments described herein, the reduction in daily troublesome dyskinesia is a reduction in daily troublesome dyskinesia, in comparison to a patient treated with an immediate release oral formulation of levodopa.

According to any of the embodiments described herein, the reduction in daily troublesome dyskinesia is a reduction in daily troublesome dyskinesia, relative to administering an immediate release oral formulation of levodopa.

According to some embodiments, the reduction in daily troublesome dyskinesia is a reduction at least about 0.1 to 3.5 hours in daily troublesome dyskinesia. According to some embodiments, the reduction in daily troublesome dyskinesia is a reduction of at least about 0.1 to 6 hours in daily troublesome dyskinesia.

According to some embodiments, the reduction in daily troublesome dyskinesia is a reduction at least about 0.1 to 3.5 hours in daily troublesome dyskinesia, from baseline. According to some embodiments, the reduction in daily troublesome dyskinesia is a reduction of at least about 0.1 to 6 hours in daily troublesome dyskinesia, from baseline.

According to some embodiments, the reduction in daily troublesome dyskinesia is a reduction at least about 0.1 to 3.5 hours in daily troublesome dyskinesia, in comparison to a patient treated with an immediate release oral formulation of levodopa. According to some embodiments, the reduction in daily troublesome dyskinesia is a reduction of at least about 0.1 to 6 hours in daily troublesome dyskinesia, in comparison to a patient treated with an immediate release oral formulation of levodopa.

According to some embodiments, the reduction in daily troublesome dyskinesia is a reduction at least about 0.1 to 3.5 hours in daily troublesome dyskinesia, relative to administering an immediate release oral formulation of levodopa. According to some embodiments, the reduction in daily troublesome dyskinesia is a reduction of at least about 0.1 to 6 hours in daily troublesome dyskinesia, relative to administering an immediate release oral formulation of levodopa.

According to some embodiments, the reduction in daily troublesome dyskinesia is a reduction of about 0.1 hours in daily troublesome dyskinesia. According to some embodiments, the reduction in daily troublesome dyskinesia is a reduction of about 0.15 hours in daily troublesome dyskinesia. According to some embodiments, the reduction in daily troublesome dyskinesia is a reduction of about 0.2 hours in daily troublesome dyskinesia. According to some embodiments, the reduction in daily troublesome dyskinesia is a reduction of about 0.25 hours in daily troublesome dyskinesia. According to some embodiments, the reduction in daily troublesome dyskinesia is a reduction of about 0.3 hours in daily troublesome dyskinesia. According to some embodiments, the reduction in daily troublesome dyskinesia is a reduction of about 0.35 hours in daily troublesome dyskinesia. According to some embodiments, the reduction in daily troublesome dyskinesia is a reduction of about 0.4 hours in daily troublesome dyskinesia. According to some embodiments, the reduction in daily troublesome dyskinesia is a reduction of about 0.45 hours in daily troublesome dyskinesia. According to some embodiments, the reduction in daily troublesome dyskinesia is a reduction of about 0.5 hours in daily troublesome dyskinesia. According to some embodiments, the reduction in daily troublesome dyskinesia is a reduction of about 0.55 hours in daily troublesome dyskinesia. According to some embodiments, the reduction in daily troublesome dyskinesia is a reduction of about 0.6 hours in daily troublesome dyskinesia. According to some embodiments, the reduction in daily troublesome dyskinesia is a reduction of about 0.65 hours in daily troublesome dyskinesia. According to some embodiments, the reduction in daily troublesome dyskinesia is a reduction of about 0.7 hours in daily troublesome dyskinesia. According to some embodiments, the reduction in daily troublesome dyskinesia is a reduction of about 0.75 hours in daily troublesome dyskinesia. According to some embodiments, the reduction in daily troublesome dyskinesia is a reduction of about 1 hour daily troublesome dyskinesia. According to some embodiments, the reduction in daily troublesome dyskinesia is a reduction of about 0.8 hours in daily troublesome dyskinesia. According to some embodiments, the reduction in daily troublesome dyskinesia is a reduction of about 0.85 hours in daily troublesome dyskinesia. According to some embodiments, the reduction in daily troublesome dyskinesia is a reduction of about 0.9 hours in daily troublesome dyskinesia. According to some embodiments, the reduction in daily troublesome dyskinesia is a reduction of about 0.95 hours in daily troublesome dyskinesia. According to some embodiments, the reduction in daily troublesome dyskinesia is a reduction of about 1 hour in daily troublesome dyskinesia. According to some embodiments, the reduction in daily troublesome dyskinesia is a reduction of about 1.1 hours in daily troublesome dyskinesia. According to some embodiments, the reduction in daily troublesome dyskinesia is a reduction of about 1.2 hours in daily troublesome dyskinesia. According to some embodiments, the reduction in daily troublesome dyskinesia is a reduction of about 1.3 hours in daily hours in daily troublesome dyskinesia. According to some embodiments, the reduction in daily troublesome dyskinesia is a reduction of about 1.4 hours in daily troublesome dyskinesia. According to some embodiments, the reduction in daily troublesome dyskinesia is a reduction of about 1.5 hours in daily troublesome dyskinesia. According to some embodiments, the reduction in daily troublesome dyskinesia is a reduction of about 1.6 hours in daily troublesome dyskinesia. According to some embodiments, the reduction in daily troublesome dyskinesia is a reduction of about 1.7 hours in daily troublesome dyskinesia. According to some embodiments, the reduction in daily troublesome dyskinesia is a reduction of about 1.8 hours in daily troublesome dyskinesia. According to some embodiments, the reduction in daily troublesome dyskinesia is a reduction of about 1.9 hours in daily troublesome dyskinesia. According to some embodiments, the reduction in daily troublesome dyskinesia is a reduction of about 2 hours in daily troublesome dyskinesia. According to some embodiments, the reduction in daily troublesome dyskinesia is a reduction of about 2.1 hours in daily troublesome dyskinesia. According to some embodiments, the reduction in daily troublesome dyskinesia is a reduction of about 2.2 hours in daily troublesome dyskinesia. According to some embodiments, the reduction in daily troublesome dyskinesia is a reduction of about 2.3 hours in daily troublesome dyskinesia. According to some embodiments, the reduction in daily troublesome dyskinesia is a reduction of about 2.4 hours in daily troublesome dyskinesia. According to some embodiments, the reduction in daily troublesome dyskinesia is a reduction of about 2.5 hours in daily troublesome dyskinesia. According to some embodiments, the reduction in daily troublesome dyskinesia is a reduction of about 2.6 hours in daily troublesome dyskinesia. According to some embodiments, the reduction in daily troublesome dyskinesia is a reduction of about 2.7 hours in daily troublesome dyskinesia. According to some embodiments, the reduction in daily troublesome dyskinesia is a reduction of about 2.8 hours in daily troublesome dyskinesia. According to some embodiments, the reduction in daily troublesome dyskinesia is a reduction of about 2.9 hours in daily troublesome dyskinesia. According to some embodiments, the reduction in daily troublesome dyskinesia is a reduction of about 3 hours in daily troublesome dyskinesia. According to some embodiments, the reduction in daily troublesome dyskinesia is a reduction of about 3.1 hours in daily troublesome dyskinesia. According to some embodiments, the reduction in daily troublesome dyskinesia is a reduction of about 3.2 hours in daily troublesome dyskinesia. According to some embodiments, the reduction in daily troublesome dyskinesia is a reduction of about 3.3 hours in daily troublesome dyskinesia. According to some embodiments, the reduction in daily troublesome dyskinesia is a reduction of about 3.4 hours in daily troublesome dyskinesia. According to some embodiments, the reduction in daily troublesome dyskinesia is a reduction of about 3.5 hours in daily troublesome dyskinesia. According to some embodiments, the reduction in daily troublesome dyskinesia is a reduction of about 3.6 hours in daily troublesome dyskinesia. According to some embodiments, the reduction in daily troublesome dyskinesia is a reduction of about 3.7 hours in daily troublesome dyskinesia. According to some embodiments, the reduction in daily troublesome dyskinesia is a reduction of about 3.8 hours in daily troublesome dyskinesia. According to some embodiments, the reduction in daily troublesome dyskinesia is a reduction of about 3.9 hours in daily troublesome dyskinesia. According to some embodiments, the reduction in daily troublesome dyskinesia is a reduction of about 4 hours in daily troublesome dyskinesia. According to some embodiments, the reduction in daily troublesome dyskinesia is a reduction of about 4.1 hours in daily troublesome dyskinesia. According to some embodiments, the reduction in daily troublesome dyskinesia is a reduction of about 4.2 hours in daily troublesome dyskinesia. According to some embodiments, the reduction in daily troublesome dyskinesia is a reduction of about 4.3 hours in daily troublesome dyskinesia. According to some embodiments, the reduction in daily troublesome dyskinesia is a reduction of about 4.4 hours in daily troublesome dyskinesia. According to some embodiments, the reduction in daily troublesome dyskinesia is a reduction of about 4.5 hours in daily troublesome dyskinesia. According to some embodiments, the reduction in daily troublesome dyskinesia is a reduction of about 4.6 hours in daily troublesome dyskinesia. According to some embodiments, the reduction in daily troublesome dyskinesia is a reduction of about 4.7 hours in daily troublesome dyskinesia. According to some embodiments, the reduction in daily troublesome dyskinesia is a reduction of about 4.8 hours in daily troublesome dyskinesia. According to some embodiments, the reduction in daily troublesome dyskinesia is a reduction of about 4.9 hours in daily troublesome dyskinesia. According to some embodiments, the reduction in daily troublesome dyskinesia is a reduction of about 5 hours in daily troublesome dyskinesia. According to some embodiments, the reduction in daily troublesome dyskinesia is a reduction of about 5.1 hours in daily troublesome dyskinesia. According to some embodiments, the reduction in daily troublesome dyskinesia is a reduction of about 5.2 hours in daily troublesome dyskinesia. According to some embodiments, the reduction in daily troublesome dyskinesia is a reduction of about 5.3 hours in daily troublesome dyskinesia. According to some embodiments, the reduction in daily troublesome dyskinesia is a reduction of about 5.4 hours in daily troublesome dyskinesia. According to some embodiments, the reduction in daily troublesome dyskinesia is a reduction of about 5.5 hours in daily troublesome dyskinesia. According to some embodiments, the reduction in daily troublesome dyskinesia is a reduction of about 5.6 hours in daily troublesome dyskinesia. According to some embodiments, the reduction in daily troublesome dyskinesia is a reduction of about 5.7 hours in daily troublesome dyskinesia. According to some embodiments, the reduction in daily troublesome dyskinesia is a reduction of about 5.8 hours in daily troublesome dyskinesia. According to some embodiments, the reduction in daily troublesome dyskinesia is a reduction of about 5.9 hours in daily troublesome dyskinesia. According to some embodiments, the reduction in daily troublesome dyskinesia is a reduction of about 6 hours in daily troublesome dyskinesia.

According to any of the embodiments described herein, the improvement in motor experiences of daily living, as assessed by the Movement Disorder Society-Sponsored revision of Unified Parkinson's Disease Rating Scale Part II (UPDRS Part II) score, is a reduction in the UPDRS Part II score, from baseline.

According to any of the embodiments described herein, the improvement in motor experiences of daily living, as assessed by the Movement Disorder Society-Sponsored revision of Unified Parkinson's Disease Rating Scale Part II (UPDRS Part II) score, is a reduction in the UPDRS Part II score, in comparison to a patient treated with an immediate release oral formulation of levodopa.

According to any of the embodiments described herein, the improvement in motor experiences of daily living, as assessed by the Movement Disorder Society-Sponsored revision of Unified Parkinson's Disease Rating Scale Part II (UPDRS Part II) score, is a reduction in the UPDRS Part II score, relative to administering an immediate release oral formulation of levodopa.

According to any of the embodiments described herein, the improvement in motor experiences of daily living, as assessed by the Movement Disorder Society-Sponsored revision of Unified Parkinson's Disease Rating Scale Part II (UPDRS Part II) score, is a reduction of at least about 1.5 to about 4.5 in the UPDRS Part II score.

According to any of the embodiments described herein, the improvement in motor experiences of daily living, as assessed by the Movement Disorder Society-Sponsored revision of Unified Parkinson's Disease Rating Scale Part II (UPDRS Part II) score, is a reduction of at least about 1.5 to about 4.5 in the UPDRS Part II score, from baseline.

According to some embodiments, the improvement in motor experiences of daily living, as assessed by the Movement Disorder Society-Sponsored revision of Unified Parkinson's Disease Rating Scale Part II (UPDRS Part II) score is a reduction of at least about 1.5 to about 4.5 in the UPDRS Part II score, in comparison to a patient treated with an immediate release oral formulation of levodopa.

According to any of the embodiments described herein, the improvement in motor experiences of daily living, as assessed by the Movement Disorder Society-Sponsored revision of Unified Parkinson's Disease Rating Scale Part II (UPDRS Part II) score, is a reduction of at least about 1.5 to about 4.5 in the UPDRS Part II score, relative to administering an immediate release oral formulation of levodopa.

According to some embodiments, the improvement in motor experiences of daily living, as assessed by the Movement Disorder Society-Sponsored revision of Unified Parkinson's Disease Rating Scale Part II (UPDRS Part II) score is a reduction of about 1.5 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 1.6 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 1.7 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 1.8 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 1.9 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 2.0 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 2.2 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 2.4 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 2.6 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 2.8 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 3.0 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 3.2 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 3.4 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 3.6 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 3.8 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 4.0 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 4.2 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 4.4 in the UPDRS Part II score. According to some embodiments, the improvement in motor experiences of daily living, as assessed by the Movement Disorder Society-Sponsored revision of Unified Parkinson's Disease Rating Scale Part II (UPDRS Part II) score is a reduction of about 4.5 in the UPDRS Part II score.

According to some embodiments, the improvement in motor experiences of daily living, as assessed by the Movement Disorder Society-Sponsored revision of Unified Parkinson's Disease Rating Scale Part II (UPDRS Part II) score, is sustained for at least about 1, 2, 3, 4, 5, 6, 7, 8, 9, 10, 11, 12, 15, 18, 21, 24, 27, 30, 33, or 36 months.

According to any of the embodiments described herein, the improvement in motor experiences of daily living, as assessed by the Movement Disorder Society-Sponsored revision of Unified Parkinson's Disease Rating Scale Part III (UPDRS Part III) score is a reduction in the UPDRS Part III score, from baseline.

According to any of the embodiments described herein, the improvement in motor experiences of daily living, as assessed by the Movement Disorder Society-Sponsored revision of Unified Parkinson's Disease Rating Scale Part III (UPDRS Part III) score is a reduction in the UPDRS Part III score, in comparison to a patient treated with an immediate release oral formulation of levodopa.

According to any of the embodiments described herein, the improvement in motor experiences of daily living, as assessed by the Movement Disorder Society-Sponsored revision of Unified Parkinson's Disease Rating Scale Part III (UPDRS Part III) score is a reduction in the UPDRS Part III score, relative to administering an immediate release oral formulation of levodopa.

According to any of the embodiments described herein, the improvement in motor experiences of daily living, as assessed by the Movement Disorder Society-Sponsored revision of Unified Parkinson's Disease Rating Scale Part III (UPDRS Part III) score is a reduction of at least about 2 to about 50 in the UPDRS Part III score.

According to any of the embodiments described herein, the improvement in motor experiences of daily living, as assessed by the Movement Disorder Society-Sponsored revision of Unified Parkinson's Disease Rating Scale Part III (UPDRS Part III) score is a reduction of at least about 2 to about 50 in the UPDRS Part III score, from baseline.

According to any of the embodiments described herein, the improvement in motor experiences of daily living, as assessed by the Movement Disorder Society-Sponsored revision of Unified Parkinson's Disease Rating Scale Part III (UPDRS Part III) score is a reduction of at least about 2 to about 50 in the UPDRS Part III score, in comparison to a patient treated with an immediate release oral formulation of levodopa.

According to any of the embodiments described herein, the improvement in motor experiences of daily living, as assessed by the Movement Disorder Society-Sponsored revision of Unified Parkinson's Disease Rating Scale Part III (UPDRS Part III) score is a reduction of at least about 2 to about 50 in the UPDRS Part III score, relative to administering an immediate release oral formulation of levodopa.

According to some embodiments, the improvement in motor experiences of daily living, as assessed by the Movement Disorder Society-Sponsored revision of Unified Parkinson's Disease Rating Scale Part III (UPDRS Part III) score is a reduction of about 2 to about 3 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 3 to about 4 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 4 to about 5 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 5 to about 7.5 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 7.5 to about 10 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 10 to about 15 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 15 to about 20 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 20 to about 30 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 30 to about 40 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 40 to about 50 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 7 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 8 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 8 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 9 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 10 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 11 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 12 in the UPDRS Part III score. According to some embodiments, the improvement in motor experiences of daily living, as assessed by the Movement Disorder Society-Sponsored revision of Unified Parkinson's Disease Rating Scale Part III (UPDRS Part III) score, is a reduction of about 13 in the UPDRS Part III score.

According to some embodiments, the improvement in motor experiences of daily living, as assessed by the Movement Disorder Society-Sponsored revision of Unified Parkinson's Disease Rating Scale Part III (UPDRS Part III) score, is sustained for at least about 1, 2, 3, 4, 5, 6, 7, 8, 9, 10, 11, 12, 15, 18, 21, 24, 27, 30, 33, or 36 months.

According to some embodiments, the improvement based on the Patient Global Impression of Change (PGI-C) score is an odds ratio, from baseline.

According to some embodiments, the improvement based on the Patient Global Impression of Change (PGI-C) score is an odds ratio, in comparison to a patient treated with an immediate release oral formulation of levodopa.

According to some embodiments, the improvement based on the Patient Global Impression of Change (PGI-C) score is an odds ratio, relative to administering an immediate release oral formulation of levodopa.

According to some embodiments, the improvement based on the Patient Global Impression of Change (PGI-C) score is an odds ratio of at least about 2.4 to about 11.0.

According to some embodiments, the improvement based on the Patient Global Impression of Change (PGI-C) score is an odds ratio of at least about 2.4 to about 11.0, from baseline.

According to some embodiments, the improvement based on the Patient Global Impression of Change (PGI-C) score is an odds ratio of at least about 2.4 to about 11.0, in comparison to a patient treated with an immediate release oral formulation of levodopa.

According to some embodiments, the improvement based on the Patient Global Impression of Change (PGI-C) score is an odds ratio of at least about 2.4 to about 11.0, relative to administering an immediate release oral formulation of levodopa.

According to some embodiments, the improvement based on the Patient Global Impression of Change (PGI-C) score is an odds ratio of about 2.4. According to some embodiments, the improvement based on the Patient Global Impression of Change (PGI-C) score is an odds ratio of about 2.6. According to some embodiments, the improvement based on the Patient Global Impression of Change (PGI-C) score is an odds ratio of about 2.8. According to some embodiments, the improvement based on the Patient Global Impression of Change (PGI-C) score is an odds ratio of about 3.0. According to some embodiments, the improvement based on the Patient Global Impression of Change (PGI-C) score is an odds ratio of about 3.2. According to some embodiments, the improvement based on the Patient Global Impression of Change (PGI-C) score is an odds ratio of about 3.4. According to some embodiments, the improvement based on the Patient Global Impression of Change (PGI-C) score is an odds ratio of about 3.6. According to some embodiments, the improvement based on the Patient Global Impression of Change (PGI-C) score is an odds ratio of 3.8. According to some embodiments, the improvement based on the Patient Global Impression of Change (PGI-C) score is an odds ratio of about 4.0. According to some embodiments, the improvement based on the Patient Global Impression of Change (PGI-C) score is an odds ratio of about 4.4. According to some embodiments, the improvement based on the Patient Global Impression of Change (PGI-C) score is an odds ratio of about 4.8. According to some embodiments, the improvement based on the Patient Global Impression of Change (PGI-C) score is an odds ratio of about 5.0. According to some embodiments, the improvement based on the Patient Global Impression of Change (PGI-C) score is an odds ratio of about 5.3. According to some embodiments, the improvement based on the Patient Global Impression of Change (PGI-C) score is an odds ratio of about 5.5. According to some embodiments, the improvement based on the Patient Global Impression of Change (PGI-C) score is an odds ratio of about 6.0. According to some embodiments, the improvement based on the Patient Global Impression of Change (PGI-C) score is an odds ratio of about 6.5. According to some embodiments, the improvement based on the Patient Global Impression of Change (PGI-C) score is an odds ratio of about 7.0. According to some embodiments, the improvement based on the Patient Global Impression of Change (PGI-C) score is an odds ratio of about 7.5. According to some embodiments, the improvement based on the Patient Global Impression of Change (PGI-C) score is an odds ratio of about 8.0. According to some embodiments, the improvement based on the Patient Global Impression of Change (PGI-C) score is an odds ratio of about 8.5. According to some embodiments, the improvement based on the Patient Global Impression of Change (PGI-C) score is an odds ratio of about 9.0. According to some embodiments, the improvement based on the Patient Global Impression of Change (PGI-C) score is an odds ratio of about 9.5. According to some embodiments, the improvement based on the Patient Global Impression of Change (PGI-C) score is an odds ratio of about 10.0. According to some embodiments, the improvement based on the Patient Global Impression of Change (PGI-C) score is an odds ratio of about 10.5. According to some embodiments, the improvement based on the Patient Global Impression of Change (PGI-C) score is an odds ratio of about 11.0.

According to some embodiments, the improvement based on the Patient Global Impression of Change (PGI-C) score is sustained for at least about 1, 2, 3, 4, 5, 6, 7, 8, 9, 10, 11, 12, 15, 18, 21, 24, 27, 30, 33, or 36 months.

According to some embodiments, the improvement based on the Patient Global Impression of Improvement (PGI-I) score is an odds ratio, from baseline.

According to some embodiments, the improvement based on the Patient Global Impression of Improvement (PGI-I) score is an odds ratio, in comparison to a patient treated with an immediate release oral formulation of levodopa.

According to some embodiments, the improvement based on the Patient Global Impression of Improvement (PGI-I) score is an odds ratio, relative to administering an immediate release oral formulation of levodopa.

According to some embodiments, the improvement based on the Patient Global Impression of Improvement (PGI-I) score is an odds ratio of at least about 2.0 to about 11.0.

According to some embodiments, the improvement based on the Patient Global Impression of Improvement (PGI-I) score is an odds ratio of at least about 2.0 to about 11.0, from baseline.

According to some embodiments, the improvement based on the Patient Global Impression of Improvement (PGI-I) score is an odds ratio of at least about 2.0 to about 11.0, in comparison to a patient treated with an immediate release oral formulation of levodopa.

According to some embodiments, the improvement based on the Patient Global Impression of Improvement (PGI-I) score is an odds ratio of at least about 2.0 to about 11.0, relative to administering an immediate release oral formulation of levodopa.

According to some embodiments, the improvement based on the Patient Global Impression of Impression (PGI-I) score is an odds ratio of about 2.4. According to some embodiments, the improvement based on the Patient Global Impression of Impression (PGI-I) score is an odds ratio of about 2.6. According to some embodiments, the improvement based on the Patient Global Impression of Impression (PGI-I) score is an odds ratio of about 2.8. According to some embodiments, the improvement based on the Patient Global Impression of Impression (PGI-I) score is an odds ratio of about 3.0. According to some embodiments, the improvement based on the Patient Global Impression of Impression (PGI-I) score is an odds ratio of about 3.2. According to some embodiments, the improvement based on the Patient Global Impression of Impression (PGI-I) score is an odds ratio of about 3.4. According to some embodiments, the improvement based on the Patient Global Impression of Impression (PGI-I) score is an odds ratio of about 3.6. According to some embodiments, the improvement based on the Patient Global Impression of Impression (PGI-I) score is an odds ratio of 3.8. According to some embodiments, the improvement based on the Patient Global Impression of Impression (PGI-I) score is an odds ratio of about 4.0. According to some embodiments, the improvement based on the Patient Global Impression of Impression (PGI-I) score is an odds ratio of about 4.4. According to some embodiments, the improvement based on the Patient Global Impression of Impression (PGI-I) score is an odds ratio of about 4.8. According to some embodiments, the improvement based on the Patient Global Impression of Impression (PGI-I) score is an odds ratio of about 5.0. According to some embodiments, the improvement based on the Patient Global Impression of Impression (PGI-I) score is an odds ratio of about 5.3. According to some embodiments, the improvement based on the Patient Global Impression of Impression (PGI-I) score is an odds ratio of about 5.5. According to some embodiments, the improvement based on the Patient Global Impression of Impression (PGI-I) score is an odds ratio of about 6.0. According to some embodiments, the improvement based on the Patient Global Impression of Impression (PGI-I) score is an odds ratio of about 6.5. According to some embodiments, the improvement based on the Patient Global Impression of Impression (PGI-I) score is an odds ratio of about 7.0. According to some embodiments, the improvement based on the Patient Global Impression of Impression (PGI-I) score is an odds ratio of about 7.5. According to some embodiments, the improvement based on the Patient Global Impression of Impression (PGI-I) score is an odds ratio of about 8.0. According to some embodiments, the improvement based on the Patient Global Impression of Impression (PGI-I) score is an odds ratio of about 8.5. According to some embodiments, the improvement based on the Patient Global Impression of Impression (PGI-I) score is an odds ratio of about 9.0. According to some embodiments, the improvement based on the Patient Global Impression of Impression (PGI-I) score is an odds ratio of about 9.5. According to some embodiments, the improvement based on the Patient Global Impression of Impression (PGI-I) score is an odds ratio of about 10.0. According to some embodiments, the improvement based on the Patient Global Impression of Impression (PGI-I) score is an odds ratio of about 10.5. According to some embodiments, the improvement based on the Patient Global Impression of Impression (PGI-I) score is an odds ratio of about 11.0.

According to some embodiments, the improvement based on the Patient Global Impression of Improvement (PGI-I) score is sustained for at least about 1, 2, 3, 4, 5, 6, 7, 8, 9, 10, 11, 12, 15, 18, 21, 24, 27, 30, 33, or 36 months.

According to some embodiments, the improvement based on the Clinical Global Impression of Change (CGI-C) score is an odds ratio, from baseline.

According to some embodiments, the improvement based on the Clinical Global Impression of Change (CGI-C) score is an odds ratio, in comparison to a patient treated with an immediate release oral formulation of levodopa.

According to some embodiments, the improvement based on the Clinical Global Impression of Change (CGI-C) score is an odds ratio, relative to administering an immediate release oral formulation of levodopa.

According to some embodiments, the improvement based on the Clinical Global Impression of Change (CGI-C) score is an odds ratio of at least about 3.0 to about 15.0.

According to some embodiments, the improvement based on the Clinical Global Impression of Change (CGI-C) score is an odds ratio of at least about 3.0 to about 15.0, from baseline.

According to some embodiments, the improvement based on the Clinical Global Impression of Change (CGI-C) score is an odds ratio of at least about 3.0 to about 15.0, in comparison to a patient treated with an immediate release oral formulation of levodopa.

According to some embodiments, the improvement based on the Clinical Global Impression of Change (CGI-C) score is an odds ratio of at least about 3.0 to about 15.0, relative to administering an immediate release oral formulation of levodopa According to some embodiments, the improvement based on the Clinical Global Impression of Change (CGI-C) score is an odds ratio of at least about 3.0. According to some embodiments, the improvement based on the Clinical Global Impression of Change (CGI-C) score is an odds ratio of at least about 3.2. According to some embodiments, the improvement based on the Clinical Global Impression of Change (CGI-C) score is an odds ratio of at least about 3.4. According to some embodiments, the improvement based on the Clinical Global Impression of Change (CGI-C) score is an odds ratio of at least about 3.6. According to some embodiments, the improvement based on the Clinical Global Impression of Change (CGI-C) score is an odds ratio of at least about 3.8. According to some embodiments, the improvement based on the Clinical Global Impression of Change (CGI-C) score is an odds ratio of at least about 4.0. According to some embodiments, the improvement based on the Clinical Global Impression of Change (CGI-C) score is an odds ratio of at least about 4.4. According to some embodiments, the improvement based on the Clinical Global Impression of Change (CGI-C) score is an odds ratio of at least about 4.8. According to some embodiments, the improvement based on the Clinical Global Impression of Change (CGI-C) score is an odds ratio of at least about 5.0. According to some embodiments, the improvement based on the Clinical Global Impression of Change (CGI-C) score is an odds ratio of at least about 5.5. According to some embodiments, the improvement based on the Clinical Global Impression of Change (CGI-C) score is an odds ratio of at least about 6.0. According to some embodiments, the improvement based on the Clinical Global Impression of Change (CGI-C) score is an odds ratio of at least about 6.5. According to some embodiments, the improvement based on the Clinical Global Impression of Change (CGI-C) score is an odds ratio of at least about 7.0. According to some embodiments, the improvement based on the Clinical Global Impression of Change (CGI-C) score is an odds ratio of at least about 7.2. According to some embodiments, the improvement based on the Clinical Global Impression of Change (CGI-C) score is an odds ratio of at least about 7.5. According to some embodiments, the improvement based on the Clinical Global Impression of Change (CGI-C) score is an odds ratio of at least about 8.0. According to some embodiments, the improvement based on the Clinical Global Impression of Change (CGI-C) score is an odds ratio of at least about 8.5. According to some embodiments, the improvement based on the Clinical Global Impression of Change (CGI-C) score is an odds ratio of at least about 9.0. According to some embodiments, the improvement based on the Clinical Global Impression of Change (CGI-C) score is an odds ratio of at least about 9.5. According to some embodiments, the improvement based on the Clinical Global Impression of Change (CGI-C) score is an odds ratio of at least about 10.0. According to some embodiments, the improvement based on the Clinical Global Impression of Change (CGI-C) score is an odds ratio of at least about 10.5. According to some embodiments, the improvement based on the Clinical Global Impression of Change (CGI-C) score is an odds ratio of at least about 11.0. According to some embodiments, the improvement based on the Clinical Global Impression of Change (CGI-C) score is an odds ratio of at least about 11.5. According to some embodiments, the improvement based on the Clinical Global Impression of Change (CGI-C) score is an odds ratio of at least about 12.0. According to some embodiments, the improvement based on the Clinical Global Impression of Change (CGI-C) score is an odds ratio of at least about 12.5. According to some embodiments, the improvement based on the Clinical Global Impression of Change (CGI-C) score is an odds ratio of at least about 13.0. According to some embodiments, the improvement based on the Clinical Global Impression of Change (CGI-C) score is an odds ratio of at least about 13.5. According to some embodiments, the improvement based on the Clinical Global Impression of Change (CGI-C) score is an odds ratio of at least about 14.0. According to some embodiments, the improvement based on the Clinical Global Impression of Change (CGI-C) score is an odds ratio of at least about 14.5. According to some embodiments, the improvement based on the Clinical Global Impression of Change (CGI-C) score is an odds ratio of at least about 15.0.

According to some embodiments, the improvement based on the Clinical Global Impression of Change (CGI-C) score is sustained for at least about 1, 2, 3, 4, 5, 6, 7, 8, 9, 10, 11, 12, 15, 18, 21, 24, 27, 30, 33, or 36 months According to any of the embodiments described herein, the administration results in the patient having an improvement in quality of sleep, as assessed by the Parkinson's Disease Sleep Scale 2 (PDSS-2) score.

According to some embodiments, the improvement in quality of sleep, as assessed by the Parkinson's Disease Sleep Scale 2 (PDSS-2) score, is a reduction in the PDSS-2 score.

According to some embodiments, the improvement in quality of sleep, as assessed by the Parkinson's Disease Sleep Scale 2 (PDSS-2) score, is a reduction in the PDSS-2 score, from baseline.

According to some embodiments, the improvement in quality of sleep, as assessed by the Parkinson's Disease Sleep Scale 2 (PDSS-2) score, is a reduction in the PDSS-2 score, in comparison to a patient treated with an immediate release oral formulation of levodopa.

According to some embodiments, the improvement in quality of sleep, as assessed by the Parkinson's Disease Sleep Scale 2 (PDSS-2) score, is a reduction in the PDSS-2 score, relative to administering an immediate release oral formulation of levodopa.

According to some embodiments, the improvement in sleep, as assessed by the Parkinson's Disease Sleep Scale 2 (PDSS-2) score, is a reduction of at least about 1 to about 30 in the PDSS-2 score.

According to some embodiments, the improvement in sleep, as assessed by the Parkinson's Disease Sleep Scale 2 (PDSS-2) score, is a reduction of at least about 1 to about 30 in the PDSS-2 score, from baseline.

According to some embodiments, the improvement in sleep, as assessed by the Parkinson's Disease Sleep Scale 2 (PDSS-2) score, is a reduction of at least about 1 to about 30 in the PDSS-2 score, in comparison to a patient treated with an immediate release oral formulation of levodopa.

According to some embodiments, the improvement in sleep, as assessed by the Parkinson's Disease Sleep Scale 2 (PDSS-2) score, is a reduction of at least about 1 to about 30 in the PDSS-2 score, relative to administering an immediate release oral formulation of levodopa.

According to some embodiments, the improvement in sleep, as assessed by the Parkinson's Disease Sleep Scale 2 (PDSS-2) score, is a reduction of at least about 1 to about 30 in the PDSS-2 score.

According to some embodiments, the improvement in sleep, as assessed by the PDSS-2 scores, is a reduction of at least about 1 to about 2 in the PDSS-2 score. According to some embodiments, the improvement in sleep, as assessed by the PDSS-2 scores, is a reduction of at least about 2 to about 3 in the PDSS-2 score. According to some embodiments, the improvement in sleep, as assessed by the PDSS-2 scores, is a reduction of at least about 3 to about 4 in the PDSS-2 score. According to some embodiments, the improvement in sleep, as assessed by the PDSS-2 scores, is a reduction of at least about 4 to about 5 in the PDSS-2 score. According to some embodiments, the improvement in sleep, as assessed by the PDSS-2 scores, is a reduction of at least about 5 to about 10 in the PDSS-2 score. According to some embodiments, the improvement in sleep, as assessed by the PDSS-2 scores, is a reduction of at least about 10 to about 15 in the PDSS-2 score. According to some embodiments, the improvement in sleep, as assessed by the PDSS-2 scores, is a reduction of at least about 15 to about 20 in the PDSS-2 score. According to some embodiments, the improvement in sleep, as assessed by the PDSS-2 scores, is a reduction of at least about 20 to about 30 in the PDSS-2 score.

According to some embodiments, the improvement in sleep, as assessed by the PDSS-2 score, is sustained for at least about 1, 2, 3, 4, 5, 6, 7, 8, 9, 10, 11, 12, 15, 18, 21, 24, 27, 30, 33, or 36 months.

According to any of the embodiments described herein, the administration results in the patient having an improvement of sleep. According to some embodiments, the substantially continuous subcutaneous administration of the pharmaceutically acceptable liquid composition, as detailed herein, improves the sleep of the patient. According to some embodiments, about 10% to about 75% of patients benefit from sleep improvement in view of the substantially continuous subcutaneous administration of the pharmaceutically acceptable liquid composition, as detailed herein. According to some embodiments, about 10% to about 20% of patients benefit from sleep improvement in view of the substantially continuous subcutaneous administration of the pharmaceutically acceptable liquid composition, as detailed herein. According to some embodiments, about 20% to about 30% of patients benefit from sleep improvement in view of the substantially continuous subcutaneous administration of the pharmaceutically acceptable liquid composition, as detailed herein. According to some embodiments, about 30% to about 40% of patients benefit from sleep improvement in view of the substantially continuous subcutaneous administration of the pharmaceutically acceptable liquid composition, as detailed herein. According to some embodiments, about 40% to about 50% of patients benefit from sleep improvement in view of the substantially continuous subcutaneous administration of the pharmaceutically acceptable liquid composition, as detailed herein. According to some embodiments, about 50% to about 60% of patients benefit from sleep improvement in view of the substantially continuous subcutaneous administration of the pharmaceutically acceptable liquid composition, as detailed herein. According to some embodiments, about 60% to about 75% of patients benefit from sleep improvement in view of the substantially continuous subcutaneous administration of the pharmaceutically acceptable liquid composition, as detailed herein. According to some embodiments, about 50% of patients benefit from sleep improvement in view of the substantially continuous subcutaneous administration of the pharmaceutically acceptable liquid composition, as detailed herein.

According to some embodiments, after one day of treatment, the patient has an improvement from baseline in quality of sleep. According to some embodiments, after two days of treatment, the patient has an improvement from baseline in quality of sleep. According to some embodiments, after three days of treatment, the patient has an improvement from baseline in quality of sleep According to some embodiments, the administration results in the patient having an improvement in quality of life (QoL), as assessed by the Parkinson's Disease Questionnaire (PDQ-39) score.

According to some embodiments, the administration results in the patient having an improvement in quality of life (QoL), as assessed by the Parkinson's Disease Questionnaire (PDQ-39) score, from baseline.

According to some embodiments, the administration results in the patient having an improvement in quality of life (QoL), as assessed by the Parkinson's Disease Questionnaire (PDQ-39) score, in comparison to a patient treated with an immediate release oral formulation of levodopa.

According to some embodiments, the administration results in the patient having an improvement in quality of life (QoL), as assessed by the Parkinson's Disease Questionnaire (PDQ-39) score, relative to administering an immediate release oral formulation of levodopa.

According to some embodiments, the administration results in the patient having an improvement in quality of life (QoL), as assessed by the Parkinson's Disease Questionnaire (PDQ-39) score, is a reduction of at least about 1 to about 30 in the PDQ-39 score.

According to some embodiments, the administration results in the patient having an improvement in quality of life (QoL), as assessed by the Parkinson's Disease Questionnaire (PDQ-39) score, is a reduction of at least about 1 to about 30 in the PDQ-39 score, from baseline.

According to some embodiments, the administration results in the patient having an improvement in quality of life (QoL), as assessed by the Parkinson's Disease Questionnaire (PDQ-39) score, is a reduction of at least about 1 to about 30 in the PDQ-39 score, in comparison to a patient treated with an immediate release oral formulation of levodopa.

According to some embodiments, the administration results in the patient having an improvement in quality of life (QoL), as assessed by the Parkinson's Disease Questionnaire (PDQ-39) score, is a reduction of at least about 1 to about 30 in the PDQ-39 score, relative to administering an immediate release oral formulation of levodopa.

According to some embodiments, the improvement in QoL, as assessed by the PDQ-39 scores, is a reduction of at least about 1 to about 2 in the PDQ-39 score. According to some embodiments, the improvement in QoL, as assessed by the PDQ-39 scores, is a reduction of at least about 2 to about 3 in the PDQ-39 score. According to some embodiments, the improvement in QoL, as assessed by the PDQ-39 scores, is a reduction of at least about 3 to about 4 in the PDQ-39 score. According to some embodiments, the improvement in QoL, as assessed by the PDQ-39 scores, is a reduction of at least about 4 to about 5 in the PDQ-39 score. According to some embodiments, the improvement in QoL, as assessed by the PDQ-39 scores, is a reduction of at least about 5 to about 10 in the PDQ-39 score. According to some embodiments, the improvement in QoL, as assessed by the PDQ-39 scores, is a reduction of at least about 10 to about 15 in the PDQ-39 score. According to some embodiments, the improvement in QoL, as assessed by the PDQ-39 scores, is a reduction of at least about 15 to about 20 in the PDQ-39 score. According to some embodiments, the improvement in QoL, as assessed by the PDQ-39 scores, is a reduction of at least about 20 to about 30 in the PDQ-39 score.

According to some embodiments, the improvement in QoL, as assessed by the PDQ-39 score, is sustained for at least about 1, 2, 3, 4, 5, 6, 7, 8, 9, 10, 11, 12, 15, 18, 21, 24, 27, 30, 33, or 36 months.

Further embodiments of the invention are directed to a method of increasing Good ON-time in a patient with Parkinson's disease, the method comprising, subcutaneously administering to the patient, substantially continuously for about 24 hours/day, for about 2 or 3 days, a pharmaceutically acceptable liquid composition comprising levodopa and carbidopa,
wherein the administration results in an increase from baseline of at least about 0.3 to about 3.5 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 days, a pharmaceutically acceptable liquid composition comprising levodopa and carbidopa,
wherein the administration results in an increase from baseline of at least about 1.5 to about 6.0 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 days, a pharmaceutically acceptable liquid composition comprising levodopa and carbidopa, wherein the administration results in an increase from baseline of at least about 1.5 to about 8.5 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for about 2 or 3 days, a pharmaceutically acceptable liquid composition comprising levodopa and carbidopa in a ratio of about 8:1 w/w,
wherein the administration results in an increase from baseline of at least about 0.3 to about 3.5 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 days, a pharmaceutically acceptable liquid composition comprising levodopa and carbidopa in a ratio of about 8:1 w/w,
wherein the administration results in an increase from baseline of at least about 1.5 to about 6.0 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 days, a pharmaceutically acceptable liquid composition comprising levodopa and carbidopa in a ratio of about 8:1 w/w,
wherein the administration results in an increase from baseline of at least about 1.5 to about 8.5 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for about 2 to 3 consecutive days, a pharmaceutically acceptable liquid composition comprising levodopa and carbidopa,
wherein by the third consecutive day, the administration results in an increase from baseline of at least about 0.3 to about 3.5 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 consecutive days, a pharmaceutically acceptable liquid composition comprising levodopa and carbidopa,
wherein by the $28^{th}$ consecutive day, the administration results in an increase from baseline of at least about 1.5 to about 6.0 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 consecutive days, a pharmaceutically acceptable liquid composition comprising levodopa and carbidopa,
wherein by the $28^{th}$ consecutive day, the administration results in an increase from baseline of at least about 1.5 to about 8.5 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for about 2 to 3 consecutive days, a pharmaceutically acceptable liquid composition comprising levodopa and carbidopa in a ratio of about 8:1 w/w,
wherein by the third consecutive day, the administration results in an increase from baseline of at least about 0.3 to about 3.5 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 consecutive days, a pharmaceutically acceptable liquid composition comprising levodopa and carbidopa in a ratio of about 8:1 w/w, wherein by the 28$^{th}$ consecutive day, the administration results in an increase from baseline of at least about 1.5 to about 6.0 hours in daily Good ON-time.

Further embodiments of the invention are directed to a method of increasing Good ON-time in a patient with Parkinson's disease, the method comprising, subcutaneously administering to the patient, substantially continuously for about 24 hours/day, for at least about 28 consecutive days, a pharmaceutically acceptable liquid composition comprising levodopa and carbidopa in a ratio of about 8:1 w/w, wherein by the 28$^{th}$ consecutive day, the administration results in an increase from baseline of at least about 1.5 to about 8.5 hours in daily Good ON-time.

According to some embodiments, the increase from baseline in daily Good ON-time is an increase of at least about 0.3 to 6.0 hours in daily Good ON-time. According to some embodiments, the increase from baseline in daily Good ON-time is an increase of at least about 0.3 to 3.5 hours in daily Good ON-time. According to some embodiments, the increase from baseline in daily Good ON-time is an increase of at least about 1.5 to about 8.5 hours in daily Good ON-time. According to some embodiments, the increase from baseline in daily Good ON-time is an increase of at least about 1.5 to about 6.0 hours in daily Good ON-time.

According to some embodiments, the increase from baseline in daily Good ON-time is achieved after treatment of 21 days, 22 days, 23 days, 24 days, 25 days, 26 days, 27 days, 28 days, 29 days, 30 days, 31 days, 32 days, 33 days, 34 days, 35 days, or longer. According to some embodiments, the increase from baseline in daily Good ON-time is an increase of at least about 2.0 hours, at least about 2.1 hours, at least about 2.2 hours, at least about 2.3 hours, at least about 2.4 hours, or at least about 2.5 hour after treatment of about 1, 2, 3, 4, 5, 6, 7, 8, 9, 10, 11, 12, 18, 24, 30 or 36 months. According to some embodiments, the increase from baseline in daily Good ON-time is an increase of at least about 2.5 hours, at least about 2.6 hours, at least about 2.7 hours, at least about 2.8 hours, at least about 2.9 hours, or at least about 3 hour after treatment of about 1, 2, 3, 4, 5, 6, 7, 8, 9, 10, 11, 12, 18, 24, 30 or 36 months. According to some embodiments, the increase from baseline in daily Good ON-time is an increase of at least about 4 hours, at least about 4.1 hours, at least about 4.2 hours, at least about 4.3 hours, at least about 4.4 hours, or at least about 4.5 hour after treatment of about 1, 2, 3, 4, 5, 6, 7, 8, 9, 10, 11, 12, 18, 24, 30 or 36 months. According to some embodiments, the increase from baseline in daily Good ON-time is an increase of at least about 7.5 hours, at least about 7.6 hours, at least about 7.7 hours, at least about 7.8 hours, at least about 7.9 hours, or at least about 8 hour after treatment of about 1, 2, 3, 4, 5, 6, 7, 8, 9, 10, 11, 12, 18, 24, 30 or 36 months.

According to some embodiments, the increase from baseline in daily Good ON-time is an increase from baseline of about 0.3 hours in daily Good ON-time. According to some embodiments, the increase from baseline in daily Good ON-time is an increase from baseline of about 0.32 hours in daily Good ON-time. According to some embodiments, the increase from baseline in daily Good ON-time is an increase from baseline of about 0.34 hours in daily Good ON-time. According to some embodiments, the increase from baseline in daily Good ON-time is an increase from baseline of about 0.36 hours in daily Good ON-time. According to some embodiments, the increase from baseline in daily Good ON-time is an increase from baseline of about 0.38 hours in daily Good ON-time. According to some embodiments, the increase from baseline in daily Good ON-time is an increase from baseline of about 0.4 hours in daily Good ON-time. According to some embodiments, the increase from baseline in daily Good ON-time is an increase from baseline of about 0.42 hours in daily Good ON-time. According to some embodiments, the increase from baseline in daily Good ON-time is an increase from baseline of about 0.44 hours in daily Good ON-time. According to some embodiments, the increase from baseline in daily Good ON-time is an increase from baseline of about 0.46 hours in daily Good ON-time. According to some embodiments, the increase from baseline in daily Good ON-time is an increase from baseline of about 0.48 hours in daily Good ON-time. According to some embodiments, the increase from baseline in daily Good ON-time is an increase from baseline of about 0.5 hours in daily Good ON-time. According to some embodiments, the increase from baseline in daily Good ON-time is an increase from baseline of about 0.55 hours in daily Good ON-time. According to some embodiments, the increase from baseline in daily Good ON-time is an increase from baseline of about 0.6 hours in daily Good ON-time. According to some embodiments, the increase from baseline in daily Good ON-time is an increase from baseline of about 0.65 hours in daily Good ON-time. According to some embodiments, the increase from baseline in daily Good ON-time is an increase from baseline of about 0.7 hours in daily Good ON-time. According to some embodiments, the increase from baseline in daily Good ON-time is an increase from baseline of about 0.75 hours in daily Good ON-time. According to some embodiments, the increase from baseline in daily Good ON-time is an increase from baseline of about 0.8 hours in daily Good ON-time. According to some embodiments, the increase from baseline in daily Good ON-time is an increase from baseline of about 0.85 hours in daily Good ON-time. According to some embodiments, the increase from baseline in daily Good ON-time is an increase from baseline of about 0.9 hours in daily Good ON-time. According to some embodiments, the increase from baseline in daily Good ON-time is an increase from baseline of about 0.95 hours in daily Good ON-time. According to some embodiments, the increase from baseline in daily Good ON-time is an increase from baseline of about 1 hours in daily Good ON-time. According to some embodiments, the increase from baseline in daily Good ON-time is an increase from baseline of about 1.1 hours in daily Good ON-time. According to some embodiments, the increase from baseline in daily Good ON-time is an increase from baseline of about 1.2 hours in daily Good ON-time. According to some embodiments, the increase from baseline in daily Good ON-time is an increase from baseline of about 1.3 hours in daily Good ON-time. According to some embodiments, the increase from baseline in daily Good ON-time is an increase from baseline of about 1.4 hours in daily Good ON-time. According to some embodiments, the increase from baseline in daily Good ON-time is an increase from baseline of about 1.5 hours in daily Good ON-time. According to some embodiments, the increase from baseline in daily Good ON-time is an increase from baseline of about 1.6 hours in daily Good ON-time. According to some embodiments, the increase from baseline in daily Good ON-time is an increase from baseline of about 1.7 hours in daily Good ON-time. According to some embodiments, the increase from baseline in daily Good ON-time is an increase from baseline of about 1.8 hours in daily Good ON-time. According to some embodiments, the increase from baseline in daily Good ON-time is an increase from baseline of about 1.9 hours in daily Good ON-time.

According to some embodiments, the increase from baseline in daily Good ON-time is an increase from baseline of about 2 hours in daily Good ON-time. According to some embodiments, the increase from baseline in daily Good ON-time is an increase from baseline of about 2.1 hours in daily Good ON-time. According to some embodiments, the increase from baseline in daily Good ON-time is an increase from baseline of about 2.2 hours in daily Good ON-time. According to some embodiments, the increase from baseline in daily Good ON-time is an increase from baseline of about 2.25 hours in daily Good ON-time. According to some embodiments, the increase from baseline in daily Good ON-time is an increase from baseline of about 2.3 hours in daily Good ON-time. According to some embodiments, the increase from baseline in daily Good ON-time is an increase from baseline of about 2.4 hours in daily Good ON-time. According to some embodiments, the increase from baseline in daily Good ON-time is an increase from baseline of about 2.5 hours in daily Good ON-time. According to some embodiments, the increase from baseline in daily Good ON-time is an increase from baseline of about 2.6 hours in daily Good ON-time. According to some embodiments, the increase from baseline in daily Good ON-time is an increase from baseline of about 2.7 hours in daily Good ON-time. According to some embodiments, the increase from baseline in daily Good ON-time is an increase from baseline of about 2.75 hours in daily Good ON-time. According to some embodiments, the increase from baseline in daily Good ON-time is an increase from baseline of about 2.8 hours in daily Good ON-time. According to some embodiments, the increase from baseline in daily Good ON-time is an increase from baseline of about 2.9 hours in daily Good ON-time. According to some embodiments, the increase from baseline in daily Good ON-time is an increase from baseline of about 3.0 hours in daily Good ON-time. According to some embodiments, the increase from baseline in daily Good ON-time is an increase from baseline of about 3.1 hours in daily Good ON-time. According to some embodiments, the increase from baseline in daily Good ON-time is an increase from baseline of about 3.2 hours in daily Good ON-time. According to some embodiments, the increase from baseline in daily Good ON-time is an increase from baseline of about 3.25 hours in daily Good ON-time. According to some embodiments, the increase from baseline in daily Good ON-time is an increase from baseline of about 3.3 hours in daily Good ON-time. According to some embodiments, the increase from baseline in daily Good ON-time is an increase from baseline of about 3.4 hours in daily Good ON-time. According to some embodiments, the increase from baseline in daily Good ON-time is an increase from baseline of about 3.5 hours in daily Good ON-time. According to some embodiments, the increase from baseline in daily Good ON-time is an increase from baseline of about 3.6 hours in daily Good ON-time. According to some embodiments, the increase from baseline in daily Good ON-time is an increase from baseline of about 3.7 hours in daily Good ON-time. According to some embodiments, the increase from baseline in daily Good ON-time is an increase from baseline of about 3.8 hours in daily Good ON-time. According to some embodiments, the increase from baseline in daily Good ON-time is an increase from baseline of about 3.9 hours in daily Good ON-time. According to some embodiments, the increase from baseline in daily Good ON-time is an increase from baseline of about 4.0 hours in daily Good ON-time. According to some embodiments, the increase from baseline in daily Good ON-time is an increase from baseline of about 4.1 hours in daily Good ON-time. According to some embodiments, the increase from baseline in daily Good ON-time is an increase from baseline of about 4.2 hours in daily Good ON-time. According to some embodiments, the increase from baseline in daily Good ON-time is an increase from baseline of about 4.3 hours in daily Good ON-time. According to some embodiments, the increase from baseline in daily Good ON-time is an increase from baseline of about 4.4 hours in daily Good ON-time. According to some embodiments, the increase from baseline in daily Good ON-time is an increase from baseline of about 4.5 hours in daily Good ON-time. According to some embodiments, the increase from baseline in daily Good ON-time is an increase from baseline of about 4.6 hours in daily Good ON-time. According to some embodiments, the increase from baseline in daily Good ON-time is an increase from baseline of about 4.7 hours in daily Good ON-time. According to some embodiments, the increase from baseline in daily Good ON-time is an increase from baseline of about 4.8 hours in daily Good ON-time. According to some embodiments, the increase from baseline in daily Good ON-time is an increase from baseline of about 4.9 hours in daily Good ON-time. According to some embodiments, the increase from baseline in daily Good ON-time is an increase from baseline of about 5.0 hours in daily Good ON-time. According to some embodiments, the increase from baseline in daily Good ON-time is an increase from baseline of about 5.1 hours in daily Good ON-time. According to some embodiments, the increase from baseline in daily Good ON-time is an increase from baseline of about 5.2 hours in daily Good ON-time. According to some embodiments, the increase from baseline in daily Good ON-time is an increase from baseline of about 5.3 hours in daily Good ON-time. According to some embodiments, the increase from baseline in daily Good ON-time is an increase from baseline of about 5.4 hours in daily Good ON-time. According to some embodiments, the increase from baseline in daily Good ON-time is an increase from baseline of about 5.5 hours in daily Good ON-time. According to some embodiments, the increase from baseline in daily Good ON-time is an increase from baseline of about 5.6 hours in daily Good ON-time. According to some embodiments, the increase from baseline in daily Good ON-time is an increase from baseline of about 5.7 hours in daily Good ON-time. According to some embodiments, the increase from baseline in daily Good ON-time is an increase from baseline of about 5.8 hours in daily Good ON-time. According to some embodiments, the increase from baseline in daily Good ON-time is an increase from baseline of about 5.9 hours in daily Good ON-time. According to some embodiments, the increase from baseline in daily Good ON-time is an increase from baseline of about 6.0 hours in daily Good ON-time. According to some embodiments, the increase from baseline in daily Good ON-time is an increase from baseline of about 6.1 hours in daily Good ON-time. According to some embodiments, the increase from baseline in daily Good ON-time is an increase from baseline of about 6.2 hours in daily Good ON-time. According to some embodiments, the increase from baseline in daily Good ON-time is an increase from baseline of about 6.3 hours in daily Good ON-time. According to some embodiments, the increase from baseline in daily Good ON-time is an increase from baseline of about 6.4 hours in daily Good ON-time. According to some embodiments, the increase from baseline in daily Good ON-time is an increase from baseline of about 6.5 hours in daily Good ON-time. According to some embodiments, the increase from baseline in daily Good ON-time is an increase from baseline of about 6.6 hours in daily Good ON-time. According to some embodiments, the increase from baseline in daily Good ON-time is an increase from baseline of about 6.7 hours in daily Good ON-time. According to some embodiments, the increase from baseline in daily Good ON-time is an increase from baseline of about 6.8 hours in daily Good ON-time. According to some embodiments, the increase from baseline in daily Good ON-time is an increase from baseline of about 6.9 hours in daily Good ON-time. According to some embodiments, the increase from baseline in daily Good ON-time is an increase from baseline of about 7 hours in daily Good ON-time. According to some embodiments, the increase from baseline in daily Good ON-time is an increase from baseline of about 7.1 hours in daily Good ON-time. According to some embodiments, the increase from baseline in daily Good ON-time is an increase from baseline of about 7.2 hours in daily Good ON-time. According to some embodiments, the increase from baseline in daily Good ON-time is an increase from baseline of about 7.3 hours in daily Good ON-time. According to some embodiments, the increase from baseline in daily Good ON-time is an increase from baseline of about 7.4 hours in daily Good ON-time. According to some embodiments, the increase from baseline in daily Good ON-time is an increase from baseline of about 7.5 hours in daily Good ON-time. According to some embodiments, the increase from baseline in daily Good ON-time is an increase from baseline of about 7.6 hours in daily Good ON-time. According to some embodiments, the increase from baseline in daily Good ON-time is an increase from baseline of about 7.7 hours in daily Good ON-time. According to some embodiments, the increase from baseline in daily Good ON-time is an increase from baseline of about 7.8 hours in daily Good ON-time. According to some embodiments, the increase from baseline in daily Good ON-time is an increase from baseline of about 7.9 hours in daily Good ON-time. According to some embodiments, the increase from baseline in daily Good ON-time is an increase from baseline of about 8 hours in daily Good ON-time. According to some embodiments, the increase from baseline in daily Good ON-time is an increase from baseline of about 8.1 hours in daily Good ON-time. According to some embodiments, the increase from baseline in daily Good ON-time is an increase from baseline of about 8.2 hours in daily Good ON-time. According to some embodiments, the increase from baseline in daily Good ON-time is an increase from baseline of about 8.3 hours in daily Good ON-time. According to some embodiments, the increase from baseline in daily Good ON-time is an increase from baseline of about 8.4 hours in daily Good ON-time. According to some embodiments, the increase from baseline in daily Good ON-time is an increase from baseline of about 8.5 hours in daily Good ON-time.

According to some embodiments, the pharmaceutically acceptable liquid composition is administered for a period of more than about 1 year, more than about 2 years, more than about 3 years, more than about 4 years, more than about 5 years, more than about 6 years, more than about 7 years, more than about 8 years, more than about 9 years, or more than about 10 years.

According to some embodiments, the pharmaceutically acceptable liquid composition is administered for a period of at least about 1 year, at least about 2 years, at least about 3 years, at least about 4 years, at least about 5 years, at least about 6 years, at least about 7 years, at least about 8 years, at least about 9 years, or at least about 10 years.

According to some embodiments, the substantially continuous subcutaneous administration of the pharmaceutically acceptable liquid composition for a period of at least about 2 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 3 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 4 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 5 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 6 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 7 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 8 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 9 years results in an improvement of a treatment emergent adverse event (TEAE), compared to the administration of the pharmaceutically acceptable liquid composition for a period of about 1 year. According to some embodiments, the substantially continuous subcutaneous administration of the pharmaceutically acceptable liquid composition for a period of at least about 10 years results in an improvement of a treatment emergent adverse event (TEAE), compared to the administration of the pharmaceutically acceptable liquid composition for a period of about 1 year.

According to some embodiments, the treatment emergent adverse event (TEAE) is severe. According to some embodiments, the treatment emergent adverse event (TEAE) is serious.

According to some embodiments, the treatment emergent adverse event (TEAE) is a drug-related TEAE. According to some embodiments, the drug-related TEAE is an infusion-site reaction. According to some embodiments, the treatment emergent adverse event (TEAE) is an infusion-site reaction.

According to some embodiments, daily waking hours of the patient are normalized to about 14 hours to 18 hours. According to some embodiments, daily waking hours of the patient are normalized to about 14 hours. According to some embodiments, daily waking hours of the patient are normalized to about 15 hours. According to some embodiments, daily waking hours of the patient are normalized to about 16 hours. According to some embodiments, daily waking hours of the patient are normalized to about 17 hours. According to some embodiments, daily waking hours of the patient are normalized to about 18 hours.

According to some embodiments, the pharmaceutically acceptable liquid composition further comprises arginine.

According to some embodiments, the pharmaceutically acceptable liquid composition further comprises at least one antioxidant.

According to some embodiments, the pharmaceutically acceptable liquid composition comprises about 7.5 mg/mL carbidopa and about 60 mg/mL levodopa.

According to some embodiments, the pharmaceutically acceptable liquid composition is administered to deliver about 370 mg, about 420 mg, about 470 mg, about 520 mg, about 570 mg, about 620 mg, about 670 mg, or about 720 mg of levodopa to the patient over the course of about 24 hours. According to some embodiments, the pharmaceutically acceptable liquid composition is administered to deliver about 720 mg of levodopa and about 90 mg of carbidopa to the patient over the course of about 24 hours.

According to some embodiments, the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours.

According to some embodiments, the low activity night rate is administered for about 8 hours and the high activity day rate is administered for about 16 hours. According to some embodiments, the low activity night rate is administered for about 6 hours and the high activity day rate is administered for about 18 hours.

According to some embodiments, the low activity night rate is about 0.08 mL/hour. According to some embodiments, the low activity night rate is about 0.04 mL/hour.

According to some embodiments, the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour. According to some embodiments, the high activity day rate is about 0.32 ml/hour, about 0.295 mL/hour, about 0.275 mL/hour, about 0.25 mL/hour, about 0.225 mL/hour, about 0.205 mL/hour, about 0.18 mL/hour, or about 0.16 mL/hour.

According to some embodiments, the method further comprises administering to the patient, before or during the subcutaneous infusion time course, at least one pharmaceutically acceptable oral composition comprising levodopa.

According to some embodiments, the pharmaceutically acceptable oral composition includes one of: 50 mg levodopa, 75 mg levodopa, 95 mg levodopa, 100 mg levodopa, 125 mg levodopa, 145 mg levodopa, 150 mg levodopa, 195 mg levodopa, 200 mg levodopa, 245 mg levodopa, or 250 mg levodopa.

According to some embodiments, the pharmaceutically acceptable oral composition is a morning dose of oral levodopa.

In some embodiments, the neurological or movement disorder pertaining to the method described herein includes Parkinson's disease; secondary parkinsonism, such as drug-induced secondary parkinsonism, neuroleptic induced parkinsonism, postencephalitic parkinsonism, and vascular parkinsonism; motor fluctuations; neurodegenerative disorders; dyskinesia; reduced dopamine levels in the brain; levodopa induced dyskinesia; rapid eye movement sleep behavior disorder (RBD); dystonia; morning akinesia; tremor symptoms, such as essential tremor and drug-induced tremor; myoclonus; chorea, such as drug induced chorea; tics, such as drug induced tics and organic tics; drug induced movement disorder; drug induced akathisia; restless legs syndrome (RLS); stiff-man syndrome; benign shuddering attacks; malignant neuroleptic syndrome; Huntington's disease; Shy-Drager syndrome; brain injury induced conditions, such as carbon monoxide or manganese intoxication; or any combination thereof; for example, provided herein are methods of treating patients suffering from includes Parkinson's disease.

Generally, physicians assess the severity of Parkinson's disease patients according to objective and subjective signs and symptoms, using, e.g., various scales, and prescribe levodopa dosing administration accordingly. One of the well-known and widely used scales for diagnosing and scaling the severity of Parkinson's disease is the Unified Parkinson's Disease Rating Scale (UPDRS). Modifications of the UPDRS may also be used to classify Parkinson's disease patients (e.g., Movement Disorder Society-Sponsored revision of the UPDRS Part I (MDS-UPDRS Part I); Movement Disorder Society-Sponsored revision of the UPDRS Part II; Movement Disorder Society-Sponsored revision of the UPDRS Part III; or Movement Disorder Society-Sponsored revision of the UPDRS Part IV). Parts I and II measure the effects of non-motor and motor experiences on daily living, and both Parts I and II are patient-reported outcomes. Part III measures motor examination, and Part IV measures motor complications.

Another known method for measuring the severity of Parkinson's disease is according to the Hoehn and Yahr (H&Y) stages, which includes a scale of 5 stages, in which stages 1-2 are considered to be mild or early-stage Parkinson's disease patients, stage 3 is considered to be moderate or mid-stage Parkinson's disease patients, and stages 4-5 are considered to be advanced Parkinson's disease patients. Additional stages 0, 1.5 and 2.5 have been added to this scale, and are used broadly.

A scale for measuring change of Parkinson's disease or symptoms thereof is according to the global impression improvement scale (also known as global impression of change scale) with a score of 1 being not at all ill and a score of 7 being most severely ill. Global impression of change scores are assessed by both clinicians and subjects: Clinical Global Impression of Improvement (CGI-I) and Subject Global Impression of Improvement (SGI-I) (also known as Patient Global Impression of Change (PGI-C)). It is noted that generally in the field, the terms Subject Global Impression of Change (SGI-C), Subject Global Impression of Improvement (SGI-I), Patient Global Impression of Change (PGI-C), and Patient Global Impression of Improvement (PGI-I), are interchangeable, unless a person skilled in the art would have understood otherwise. Similarly, Clinician Global Impression of Change (CGI-C) and Clinician Global Impression of Improvement (CGI-I) are interchangeable as well, unless a person skilled in the art would have understood otherwise. Another term known in the art is Clinical Global Impression Severity (CGI-S), and may also be improved according to the methods of the invention. Any other interchangeable terms used in the art are relevant herein as well, and to be covered by this disclosure. It is noted in this respect that the definitions used in the art refer at times to "Clinical", and at times to "Clinician", or the like. These too are interchangeable in this context. For example, "Clinical Global Impression of Change (CGI-C)" is used interchangeably with "Clinician Global Impression of Change (CGI-C)." Similarly, "Clinical Global Impression of Improvement (CGI-I)" is used interchangeably with "Clinician Global Impression of Improvement (CGI-I)."

The daily levodopa dose may be defined and changed by the physician from time to time, according to, e.g., clinical findings as well as "trial and error" methods, according to the particular patient's condition, the response of that patient to the treatment, and the like. Further, the patient may be administered a different daily dose on different days, depending on signs and symptoms, wherein the range of the administered daily dose may be set by the physician, thereby allowing the patient flexibility in treatment. It is noted that physician generally refer to signs as being objective measure and to symptoms as being subjective ones.

According to some embodiments, provided herein are methods of treating advance-stage Parkinson's disease patients. According to some embodiments, provided herein are methods of treating advanced stage and/or moderate Parkinson's disease patients. According to some embodiments, provided herein are methods for treating patients with motor fluctuations. According to some embodiments, provided herein are methods for treating Parkinson's disease patients with motor fluctuations.

According to some embodiments, provided herein are methods of treating Parkinson's disease patients who require a dose of above about 300 mg levodopa/day, above about 400 mg levodopa/day, above about 500 mg levodopa/day, above about 600 mg levodopa/day, above about 700 mg levodopa/day, above about 800 mg levodopa/day, above about 900 mg levodopa/day, above about 1000 mg levodopa/day.

According to some embodiments, provided herein are methods of treating Parkinson's disease patients requiring an elevated dose of levodopa at a particular timepoint, e.g., in the morning, e.g., towards the end (about the last hour) of a low activity/night period, e.g., in the beginning (about the first hour) of a high activity/day period. For instance, according to some embodiments, there may be a certain rate for high activity/day hours and a different rate for low activity/night hours, wherein an elevated dose of levodopa may be administered towards the end of the low activity/night hours, at the end of the low activity/night hours, at the beginning of the high activity/day hours, and the like. Such an elevated dose may be provided by the administration of an oral dose of the pharmaceutically acceptable oral composition, e.g., at the times referred to above, provided concomitantly with the substantially continuous pharmaceutically acceptable liquid composition.

According to some embodiments, provided herein are methods of treating patients suffering from Parkinson's disease for a period of more than about 1 year, more than about 2 years, more than about 3 years, more than about 4 years, more than about 5 years, more than about 6 years, more than about 7 years, more than about 8 years, more than about 9 years, or more than about 10 years.

According to some embodiments, provided herein are methods of treating Parkinson's disease patients suffering from at least 1 hour, at least 1.5 hours, at least 2 hours, at least 2.5 hours, at least 3 hours, of daily OFF-time. According to some embodiments, provided herein are methods of treating Parkinson's disease patients having a modified Hoehn and Yahr Scale in "ON" state of ≤2, ≤2.5, ≤3, ≤4.

BRIEF DESCRIPTION OF THE DRAWINGS

FIG. 11 is a table describing the results from the open-label and double-blind double-dummy studies described in Example 6.

DETAILED DESCRIPTION OF THE INVENTION

Figure 1A:
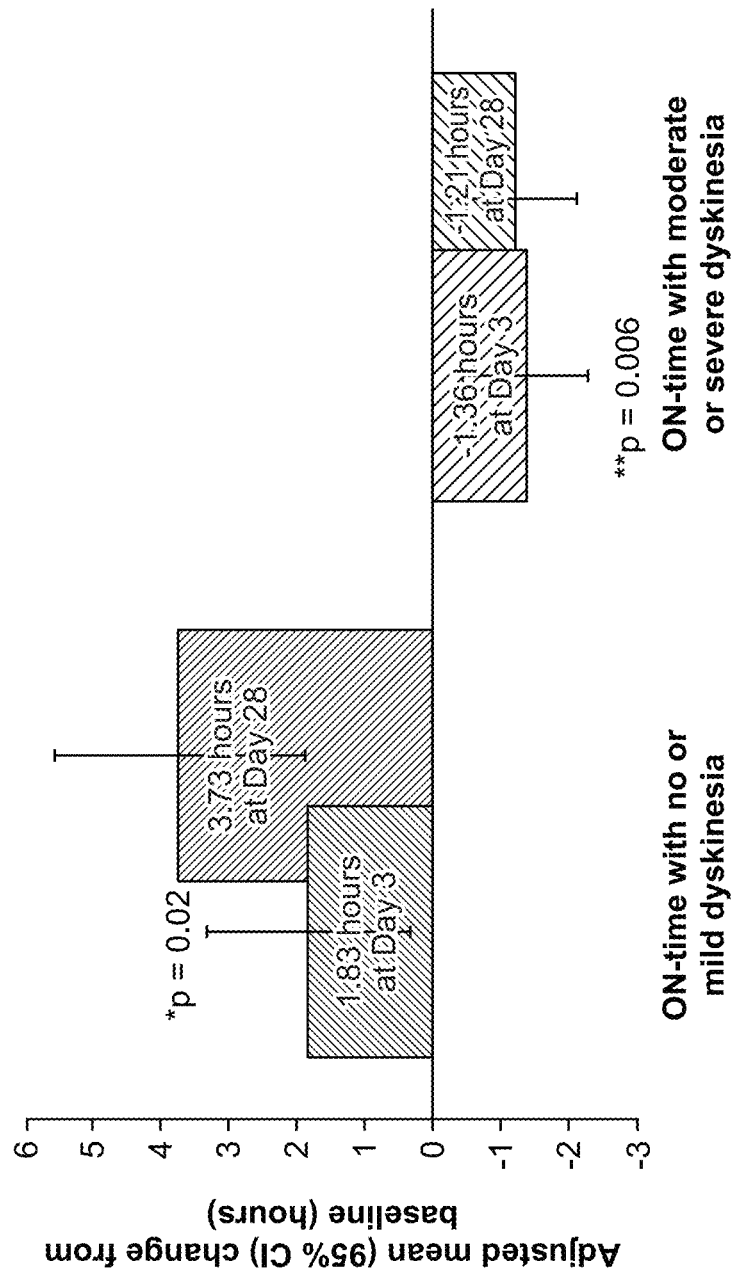
FIG. 1A is a graph showing the increase in Good ON-time and decrease in ON-time with moderate/severe dyskinesia on Days 3 and 28, as described in Example 1.

The features and other details of the disclosure will now be more particularly described. Certain terms employed in the specification, examples, and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

The term "about", as used herein, unless specifically mentioned otherwise, or unless a person skilled in the art would have understood otherwise, is considered to cover a range of ±10% of the listed value(s). It is further noted that any value provided may also be considered to cover a range of ±10% of that value, even without the use of the term "about". This includes the values in the examples section, which may vary according to the utensils and machinery used, the purity of the compounds, etc.

The term "concomitant" as used herein, unless specifically mentioned otherwise, or unless a person skilled in the art would have understood otherwise, refers to any type of combined administration of two or more active ingredients, in the same composition, as well as the administration of those active ingredients at the same time, in separate compositions, as well as administering the two or more active ingredients sequentially, consecutively, on the same day, with a predefined period of time separating the administration of the active ingredients from one another, and the like. The term "concomitant" may further be used herein to refer to any type of combined administration of two separate pharmaceutical compositions, wherein each composition may be administered in a different administration route, at different time intervals, doses, etc. For example, as detailed herein, one composition may be administered parenterally, e.g., subcutaneously, substantially continuously, while a second composition, administered concomitantly with the first, by oral administration, in a non-continuous manner. Further, the concomitant administration of two or more separate compositions may be dependent or independent from one another.

The terms "continuously" and "substantially continuously" as used herein, unless specifically mentioned otherwise, or unless a person skilled in the art would have understood otherwise, refer to a period of time during which a composition is administered over the entire period of time, with intermissions of less than about 24 hours, about 12 hours, about five hours, about three hours, about one hour, about 30 minutes, about 15 minutes, about five minutes or about one minute. The period of time during which a composition is administered may be at least about six hours, about eight hours, about 12 hours, about 15 hours, about 18 hours, about 21 hours, about 24 hours, three days, seven days, two weeks, a month, three months, six months, a year, two years, three years, five years, ten years, etc.

The term "dopa decarboxylase inhibitor" as used herein refers to an agent capable of inhibiting the peripheral metabolism of levodopa to dopamine by aromatic L-amino acid decarboxylase, such as carbidopa and benserazide.

"Individual," "patient," or "subject" are used interchangeably and include any animal, including mammals, mice, rats, other rodents, rabbits, dogs, cats, swine, cattle, sheep, horses, or non-human primates, and humans. In some embodiments, the mammal treated in the methods of the invention is a human suffering from neurodegenerative condition, such as Parkinson's disease.

The term "levodopa moiety", as used herein, unless specifically mentioned otherwise, or unless would have been understood otherwise by a person skilled in the art, includes any moiety including levodopa, including, e.g., levodopa itself, and a levodopa salt. Similarly, the term "carbidopa moiety", as used herein, unless specifically mentioned otherwise, or unless would have been understood otherwise by a person skilled in the art, includes any moiety including carbidopa, including, e.g., carbidopa itself, and a carbidopa salt.

The term "liquid" as used herein, unless specifically mentioned otherwise, or unless a person skilled in the art would have understood otherwise, refers to any type of fluid, including gels, aqueous and non-aqueous compositions, and the like.

The terms "morning dose" and "morning oral dose" as used herein, unless specifically mentioned otherwise, or unless would have been understood otherwise by a person skilled in the art, are interchangeable and refer to an oral composition (e.g., an oral dosage form) comprising levodopa, which is particularly administered in the morning hours, e.g., within 1 minute, 5 minutes, 10 minutes, 15 minutes, 20 minutes, 30 minutes, 45 minutes, 1 hour, 1.5 hours, 2 hours of the patient's waking time. According to some embodiments, the morning dose refers to an oral composition (e.g., an oral dosage form) comprising levodopa, which is administered within 1 minute, 5 minutes, 10 minutes, 15 minutes, 20 minutes, or 30 minutes of the patient's waking hours.

A neurological disorder is a disorder of the body's nervous system, and the term "movement disorder" as used herein refers to a nervous system condition that causes abnormal voluntary or involuntary movements, or slow, reduced movements. According to some embodiments, the neurological or movement disorder is Parkinson's disease; secondary parkinsonism, such as drug-induced secondary parkinsonism, neuroleptic induced parkinsonism, postencephalitic parkinsonism, and vascular parkinsonism; motor fluctuations; neurodegenerative disorders; dyskinesia; reduced dopamine levels in the brain; levodopa induced dyskinesia; rapid eye movement sleep behavior disorder (RBD); dystonia; morning akinesia; tremor symptoms, such as essential tremor and drug-induced tremor; myoclonus; chorea, such as drug induced chorea; tics, such as drug induced tics and organic tics; drug induced movement disorder; drug induced akathisia; restless legs syndrome (RLS); stiff-man syndrome; benign shuddering attacks; malignant neuroleptic syndrome; Huntington's disease; Shy-Drager syndrome; brain injury induced conditions, such as carbon monoxide or manganese intoxication; or any combination thereof. According to some embodiments, the method is directed to treating Parkinson's disease and/or motor fluctuations, including motor fluctuations stemming from Parkinson's disease, motor fluctuations in patients with Parkinson disease, and the like.

The term "OFF-time" as used herein refers to a time period when a patient experiences no response to treatment or significant symptoms (e.g., motor symptoms or non-motor symptoms) associated with Parkinson's disease. In some embodiments, OFF-time is the recurrence of Parkinson's symptoms between medication doses.

The term "ON-time" as used herein refers to a time period when a patient experiences good response to medication and few symptoms (e.g., motor symptoms or non-motor symptoms) associated with Parkinson's disease. A patient may or may not experience dyskinesia during ON-time periods.

The term "ON-time with no dyskinesia" as used herein refers to a time period when a patient experiences ON-time and has no dyskinesia (e.g., levodopa induced dyskinesia).

The term "ON-time with non-troublesome dyskinesia" as used herein refers to a time period when a patient experiences ON-time and has mild dyskinesia (e.g., mild levodopa induced dyskinesia).

The term "ON-time with troublesome dyskinesia" refers to a time period when a patient experiences ON-time and has moderate to severe dyskinesia (e.g., moderate to severe levodopa induced dyskinesia).

The term "Good ON-time" as used herein refers to the sum of ON-time with no dyskinesia plus ON-time with non-troublesome dyskinesia.

The improvement, increase, reduction, or the like, in any of the parameters referred to herein, including ON-time, OFF-time, ON-time with no dyskinesia, ON-time with non-troublesome dyskinesia, ON-time with troublesome dyskinesia, ON-time with moderate-severe dyskinesia, Good ON-time, is measured as the treatment effect of the subcutaneous formulation, administered according to the invention, in comparison to immediate release dosage forms comprising levodopa, and/or from baseline, depending on context, or as would be understood by a person skilled in the art.

The term "baseline" as used herein, is defined as the first measurement of whichever variable is referred to, as measured before the administration of the studied therapy.

The terms "Day 3" or "third day" or "third consecutive day" as used herein, are defined as the third consecutive day of the treatment, preceded by two consecutive treatment days.

The term "change from baseline" (CFB) as used herein, is defined as the change in a measured value from prior to treatment with the studied therapy to the measured time point. If the measured timepoint is a particular day of treatment, e.g., the third day, or Day 3, the measurement may be at any time during that day, unless specifically mentioned otherwise. Measurements may be in the morning, e.g., 8 AM, or a certain number of hours after the patients waking time.

The term "pharmaceutically acceptable carrier" or "pharmaceutically acceptable excipient" as used herein interchangeably refer to any and all solvents, dispersion media, coatings, isotonic and absorption delaying agents, and the like, that are compatible with pharmaceutical administration.

The terms "pharmaceutical composition" and "pharmaceutical formulation" as used herein refer to a composition or formulation comprising at least one biologically active compound, for example, levodopa or carbidopa, or a pharmaceutically acceptable salt thereof, formulated together with one or more pharmaceutically acceptable excipients.

The term "pharmaceutically acceptable salt(s)" as used herein refers to salts of acidic or basic groups that may be formed with the conjugates used in the compositions disclosed herein.

The term "physiologically acceptable pH value" and the like, as used herein, unless specifically mentioned otherwise, or unless a person skilled in the art would have understood otherwise, refers to pH values in the range of between about 4.5 to about 10. It is further noted that when pH values are provided, including in the examples, the values may be in the range of about ±0.1 and/or ±10% of the listed value(s), such that if the measured pH is 8.1, the same formulation may be prepared to provide a pH of about 8.0 or 8.2. Such differences may be due to temperature changes, various measuring devices, etc.

"Preventing" includes delaying the onset of clinical symptoms, complications, or biochemical indicia of the state, disorder, disease, or condition developing in a subject that may be afflicted with or predisposed to the state, disorder, disease, or condition but does not yet experience or display clinical or subclinical symptoms of the state, disorder, disease, or condition. "Preventing" includes prophylactically treating a state, disorder, disease, or condition in, or developing in, a subject, including prophylactically treating clinical symptoms, complications, or biochemical indicia of the state, disorder, disease, or condition in or developing in a subject.

In any of the embodiments provided herein, the change (e.g., increase, reduction, or improvement) in a value may be a significant change. The term "significant" as used herein refers to a statistically significant (e.g., p-value <0.05) change (e.g., increase, reduction, or improvement) in a value (e.g., ON-time with no dyskinesia, ON-time with non-troublesome dyskinesia, ON-time with troublesome dyskinesia, or ON-time with moderate-severe dyskinesia (e.g., daily ON-time with no dyskinesia, daily ON-time with non-troublesome dyskinesia, daily ON-time with troublesome dyskinesia, or daily ON-time with moderate-severe dyskinesia)), Good ON-time (e.g., daily Good ON-time), OFF-time (e.g., daily OFF-time), a Subject Global Impression of Change (SGI-C) score, a Clinical Global Impression of Change (CGI-C), a Patient Global Impression of Change (PGI-C) score, or a Movement Disorder Society-Sponsored revision of the Unified Parkinson's Disease Rating Scale Part II (MDS-UPDRS Part II)). In certain embodiments, the statistically significant change is a difference between an averaged value from a group of patients receiving a treatment as described herein (e.g., a 24-hour substantially continuous administration of a levodopa composition as described herein) and an averaged value from a group of patients receiving a control treatment (e.g., an oral levodopa composition).

Unless specifically mentioned otherwise or unless would have been understood otherwise by a person skilled in the art, the terms patient global impression of change (PGI-C), subject global impression of improvement (SGI-I) and patient global impression of improvement (PGI-I) are interchangeable. Similarly, clinical global impression of improvement (CGI-I) and clinical global impression of change (CGI-C) are interchangeable herein.

The terms "treat," "treatment," "treating," and the like are used herein to generally refer to obtaining a desired pharmacological and/or physiological effect. The effect may be therapeutic in terms of partially or completely curing a disease and/or adverse effect attributed to the disease. The term "treatment" as used herein covers any treatment of a disease in a mammal, particularly a human, and includes: (a) inhibiting the disease, i.e., preventing the disease from increasing in severity or scope; (b) relieving the disease, i.e., causing partial or complete amelioration of the disease; or (c) preventing relapse of the disease, i.e., preventing the disease from returning to an active state following previous successful treatment of symptoms of the disease or treatment of the disease.

The term "treatment emergent" as used herein refers to an event that occurs after administration of a dose (e.g., a first dose) of a therapy (e.g., the subcutaneous formulation, administered according to the invention). For example, a "treatment emergent adverse event" is an event that is identified upon or after a dose (e.g., a first dose) of a therapy in a clinical study. Examples of treatment emergent adverse events (TEAEs) include, but are not limited to, drug-related TEAEs (e.g., infusion-site reaction). In some embodiments, a treatment emergent adverse event (TEAE) is severe. In some embodiments, a treatment emergent adverse event (TEAE) is serious.

The term "up to" as used herein, unless specifically mentioned otherwise, or unless would have been understood otherwise by a person skilled in the art, when appearing as part of a range, is defined such that the range does not include "none", "nothing", "0". That is, if a component is an amount of up to a certain amount, e.g., 720 mg, 0 mg is not considered to be part of the range. Thus, if a composition comprises, e.g., up to 360 mg, up to 370 mg, up to 720 mg, of, e.g., levodopa, the composition must include more than 0 levodopa. Similarly, if a composition comprises, e.g., up to 45 mg, up to 46 mg, up to 90 mg, of, e.g., carbidopa, the composition must comprise more than 0 carbidopa.

Methods of Treatment

Disclosed herein are methods for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof.

Embodiments of the invention are directed to a method for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
wherein after 2 or 3 days of administration, the administration results in the patient having:
an increase from baseline in daily Good ON-time,
a reduction from baseline in daily ON-time with moderate-severe dyskinesia,
or any combination thereof.

Embodiments of the invention are directed to a method for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
wherein after 2 or 3 days of administration, the administration results in the patient having:
an increase from baseline in daily Good ON-time,
a reduction from baseline in daily ON-time with moderate-severe dyskinesia,
or any combination thereof.

Embodiments of the invention are directed to a method for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
wherein after 2 or 3 days of administration, the administration results in the patient having:
an increase from baseline in daily Good ON-time,
a reduction from baseline in daily ON-time with moderate-severe dyskinesia,
an improvement from baseline based on a Subject Global Impression of Change (SGI-C) score,
an improvement from baseline based on a Clinical Global Impression of Change (CGI-C) score,
or any combination thereof.

Embodiments of the invention are directed to a method for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
wherein after 2 or 3 days of administration, the administration results in the patient having:
an increase from baseline in daily Good ON-time,
a reduction from baseline in daily ON-time with moderate-severe dyskinesia,
an improvement from baseline based on a Patient Global Impression of Improvement (PGI-I) score,
an improvement from baseline based on a Clinical Global Impression of Improvement CGI-I) score,
or any combination thereof.

According to some embodiments, the administration results in the patient having an increase from baseline in daily Good ON-time. According to some embodiments, the administration results in the patient having a reduction from baseline in daily ON-time with troublesome dyskinesia. According to some embodiments, the administration results in the patient having an improvement from baseline based on a Subject Global Impression of Change (SGI-C) score. According to some embodiments, the administration results in the patient having an improvement from baseline based on a Patient Global Impression of Improvement (PGI-I) score. According to some embodiments, the administration results in the patient having improvement from baseline based on a Clinical Global Impression of Change (CGI-C) score. According to some embodiments, the administration results in the patient having an improvement from baseline based on a Clinical Global Impression of Improvement (CGI-I) score.

Further embodiments of the invention are directed to a method for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
wherein the administration results in an increase of at least about 0.3 to about 3.5 hours in Good ON-time in the patient over the course of about 24 hours, after treatment of at least about 2 or 3 days.

Further embodiments of the invention are directed to a method for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
wherein the administration results in an increase of at least about 1.5 to about 6 hours in Good ON-time in the patient over the course of about 24 hours, after treatment for at least about 28 days.

Further embodiments of the invention are directed to a method for treating a patient with a neurological or movement disorder, the method comprising parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
wherein the administration results in the patient having:
a reduction in daily OFF-time,
an increase in daily ON-time without troublesome dyskinesia,
an improvement in motor experiences of daily living, as assessed by the Movement Disorder Society-Sponsored revision of Unified Parkinson's Disease Rating Scale Part II (UPDRS Part II) score,
an improvement based on a Patient Global Impression of Change (PGI-C) score,
an improvement based on a Clinical Global Impression of Improvement (CGI-I) score,
or any combination thereof.

According to some embodiments, the reduction in daily OFF-time is measured compared to a patient treated with immediate release oral levodopa.

According to some embodiments, the increase in daily ON-time without troublesome dyskinesia is measured compared to a patient treated with immediate release oral levodopa.

According to some embodiments, the improvement in motor experiences of daily living, as assessed by the Movement Disorder Society-Sponsored revision of Unified Parkinson's Disease Rating Scale Part II (UPDRS Part II) score, is measured compared to a patient treated with immediate release oral levodopa.

According to some embodiments, the improvement based on a Patient Global Impression of Change (PGI-C) score is measured compared to a patient treated with immediate release oral levodopa.

According to some embodiments, the improvement based on a Clinical Global Impression of Improvement (CGI-I) score is measured compared to a patient treated with immediate release oral levodopa.

According to some embodiments, the administration results in the patient having a reduction in in daily OFF-time. According to some embodiments, the administration results in the patient having an increase in daily ON-time without troublesome dyskinesia. According to some embodiments, the administration results in the patient having an improvement in motor experiences of daily living, as assessed by the Movement Disorder Society-Sponsored revision of Unified Parkinson's Disease Rating Scale Part II score. According to some embodiments, the administration results in the patient having an improvement based on a Patient Global Impression of Change (PGI-C) score. According to some embodiments, the administration results in the patient having an improvement based on a Clinical Global Impression Improvement (CGI-I) score.

According to some embodiments, the reduction in daily OFF-time is compared to a patient treated with immediate release oral levodopa.

According to some embodiments, the increase in daily ON-time without troublesome dyskinesia is compared to a patient treated with immediate release oral levodopa.

According to some embodiments, the improvement in motor experiences of daily living, as assessed by the Movement Disorder Society-Sponsored revision of Unified Parkinson's Disease Rating Scale Part II (UPDRS Part II) score, is compared to a patient treated with immediate release oral levodopa is compared to a patient treated with immediate release oral levodopa.

According to some embodiments, the improvement based on a Patient Global Impression of Change (PGI-C) score is compared to a patient treated with immediate release oral levodopa.

According to some embodiments, the improvement based on a Clinical Global Impression of Improvement (CGI-I) score is compared to a patient treated with immediate release oral levodopa.

According to some embodiments, the reduction in daily OFF-time is relative to administering an immediate release oral dosage form of levodopa.

According to some embodiments, the increase in daily ON-time without troublesome dyskinesia is relative to administering an immediate release oral dosage form of levodopa.

According to some embodiments, the improvement in motor experiences of daily living, as assessed by the Movement Disorder Society-Sponsored revision of Unified Parkinson's Disease Rating Scale Part II (UPDRS Part II) score, is relative to administering an immediate release oral dosage form of levodopa.

According to some embodiments, improvement based on a Patient Global Impression of Change (PGI-C) score is relative to administering an immediate release oral dosage form of levodopa.

According to some embodiments, the improvement based on a Clinical Global Impression of Improvement (CGI-I) score is relative to administering an immediate release oral dosage form of levodopa. According to some embodiments, the pharmaceutically acceptable liquid composition comprises (1) levodopa, and/or a levodopa salt (2) carbidopa, and/or a carbidopa salt.

According to some embodiments, the DDCI is carbidopa, a carbidopa salt, benserazide, a benserazide salt, or any combination thereof. According to some embodiments, the DDCI is carbidopa.

In some embodiments, the pharmaceutically acceptable liquid composition comprises levodopa or a pharmaceutically acceptable salt thereof. In some embodiments, the pharmaceutically acceptable liquid composition comprises levodopa.

In some embodiments, the pharmaceutically acceptable liquid composition comprises a DDCI or a pharmaceutically acceptable salt thereof. In some embodiments, the DDCI is carbidopa.

In some embodiments, the pharmaceutically acceptable liquid composition comprises carbidopa or a pharmaceutically acceptable salt thereof. In some embodiments, the pharmaceutically acceptable liquid composition comprises carbidopa.

According to some embodiments, the pharmaceutically acceptable liquid composition comprises levodopa and carbidopa.

According to some embodiments the pharmaceutically acceptable liquid composition is administered by any parenteral administration route, e.g., subcutaneously, transdermally, intradermally, intravenously, intramuscularly, intratracheally, intranasally, intrathecally, intragastrically or intraduodenally. According to some embodiments the pharmaceutically acceptable liquid composition is administered subcutaneously. According to some embodiments, the pharmaceutically acceptable liquid composition is liquid. According to some embodiments, the pharmaceutically acceptable liquid composition is aqueous.

According to some embodiments, the pharmaceutically acceptable liquid composition is administered substantially continuously. According to some embodiments, the pharmaceutically acceptable liquid composition is administered subcutaneously via a designated pump device.

Embodiments of a designated device may be, for example, any of the device embodiments disclosed in U.S. 62/529,784, U.S. 62/576,362, U.S. 63/341,090, PCT/IB2018/054962, PCT/IL2023/050147, PCT/IL2023/050577, U.S. Ser. No. 16/027,804, U.S. Ser. No. 16/027,710, U.S. Pat. Nos. 10,463,787, 10,463,572, 10,603,430, 11,554, 210, U.S. Ser. No. 18/065,373, U.S. Pat. No. 11,779,697, U.S. Ser. No. 16/838,384, US 2020/0368448, U.S. Ser. No. 17/691,857, US 2022/0288312, U.S. Ser. No. 18/086,401, U.S. D887,577, U.S. D921,187, U.S. D921,188, U.S. D865, 665, U.S. D868,689, U.S. D921,189, U.S. D921,190, U.S. D935,478, U.S. D960,905, U.S. D960,906, U.S. D960,907, U.S. D960,908, U.S. D960,909, US D960910, U.S. D960, 911, U.S. Ser. No. 29/779,154, U.S. Ser. No. 29/779, 153, U.S. Ser. No. 29/811,491 U.S. Ser. No. 29/842,699, U.S. Ser. No. 29/842,700, U.S. Ser. No. 29/842,701, U.S. Ser. No. 29/842,702, U.S. Ser. No. 29/842,703, U.S. Ser. No. 29/842, 704, U.S. Ser. No. 29/846,963, U.S. Ser. No. 29/861,832, U.S. Ser. No. 29/655,583, U.S. Ser. No. 29/655,587, U.S. Ser. No. 29/655,589, U.S. Ser. No. 29/655,591, U.S. Ser. No. 29/655,592, U.S. Ser. No. 29/655,594, and U.S. Ser. No. 29/655,597, all of which are incorporated herein by reference in their entirety.

According to some embodiments, the dedicated device comprises a control station. According to some embodiments, the dedicated device comprises a disposable part, e.g., a medication cartridge, and a reusable part, e.g., a pump element.

According to some embodiments, the method of the invention comprises administering the pharmaceutically acceptable liquid composition at one site, two sites, or three or more sites, wherein the position of the sites may be changed at any appropriate, possibly pre-determined, intervals. Once administered via a specific site, according to some embodiments, the administration via the same site, or the vicinity of that site, may be only after a, possibly predefined, period of time. According to some embodiments, the position of any one of the sites is changed after about 12, about 24, about 36, about 48, about 60 or about 72 hours. According to some embodiments, the position of the site is changed after about 4, about 5, about 6 or about 7 days. According to some embodiments, the position of the site is changed after about two, about three or about four weeks. According to some embodiments, the position of the site is changed when required or desired, e.g., according to subjective data received from the patient and/or according to objective data received, e.g., from sensors located at, or in the vicinity of, the injection site(s).

According to some embodiments, the administrated volume and/or the administration rate is identical in all or at least two of the sites. According to other embodiments, the administration rate and/or administrated volume differ from site to site. Each site may be controlled independently or otherwise, all sites may be controlled dependently on one another.

According to some embodiments, the method of the invention comprises subcutaneously administering the pharmaceutically acceptable liquid composition of the invention over the course of about 5 to about 24 hours or more, for example, from about 5 to about 12 hours or more, from about 7 to about 10 hours or more, or for example, about 8 hours or about 24 hours.

According to some embodiments, the dose of the carbidopa moiety in the pharmaceutically acceptable liquid composition is between about 10 mg and about 25 mg per administration, between about 10 mg and about 50 mg per administration, between about 10 mg and about 75 mg per administration, between about 12 mg and about 25 mg per administration, between about 12 mg and about 50 mg per administration, between about 12 mg and about 75 mg per administration, between about 15 mg and about 25 mg per administration, between about 15 mg and about 50 mg per administration, between about 15 mg and about 75 mg per administration, between about 25 mg and about 50 mg per administration, between about 25 mg and about 75 mg per administration, between about 50 mg and about 75 mg per administration. According to some embodiments, the dose of the carbidopa moiety in the pharmaceutically acceptable liquid composition is about 90 mg, for example, administered over the course of about 5 to about 24 hours or more. According to some embodiments, the dose of the carbidopa moiety in the pharmaceutically acceptable liquid composition is between about 46 mg and about 90 mg per administration. According to some embodiments, the dose of the carbidopa moiety in the pharmaceutically acceptable liquid composition is about 90 mg, for example, administered over the course of about 24 hours. According to some embodiments, the dose of the carbidopa moiety in the pharmaceutically acceptable liquid composition is between about 46 mg to about 90 mg, for example, administered over the course of about 24 hours.

According to some embodiments, the dose of the levodopa moiety in the pharmaceutically acceptable liquid composition is between about 10 mg and about 800 mg per administration, between about 10 mg and about 25 mg per administration, between about 25 mg and about 50 mg per administration, between about 50 mg and about 75 mg per administration, between about 75 mg and about 100 mg per administration, between about 100 mg and about 150 mg per administration, between about 150 mg and about 200 mg per administration, between about 200 mg and about 250 mg per administration, between about 250 mg and about 300 mg per administration, between about 300 mg and about 350 mg per administration, between about 350 mg and about 400 mg per administration, between about 400 mg and about 450 mg per administration, between about 450 mg and about 500 mg per administration, between about 500 mg and 800 mg, between about 600 mg and about 800 mg, between about 700 mg and about 800 mg, or about 720 mg. In certain embodiments, the dose of the levodopa moiety in the pharmaceutically acceptable liquid composition is between about 370 mg to about 720 mg. In certain embodiments, the dose is administered over the course of about 5 to about 24 (e.g., about 7 to about 10, or about 8 hours, or about 24 hours) hours or more. According to some embodiments, the dose of the levodopa moiety in the pharmaceutically acceptable liquid composition is about 720 mg, for example, administered over the course of about 24 hours. According to some embodiments, the dose of the levodopa moiety in the pharmaceutically acceptable liquid composition is between about 370 mg about 720 mg, for example, administered over the course of about 24 hours. According to some embodiments, the dose of the levodopa moiety in the pharmaceutically acceptable liquid composition is between about 360 mg about 720 mg, for example, administered over the course of about 24 hours. According to some embodiments, the dose of the levodopa moiety in the pharmaceutically acceptable liquid composition is about 720 mg at the most.

In certain embodiments, the pharmaceutically acceptable liquid composition is administered in an amount to deliver from about 100 to about 200 mg of the levodopa moiety and about 12 to about 50 mg of the carbidopa moiety to the patient. In certain embodiments, the pharmaceutically acceptable liquid composition is administered in an amount to deliver from about 140 to about 170 mg of the levodopa moiety and about 16 to about 24 mg of the carbidopa moiety to the patient.

In certain embodiments, the dose is administered over the course of about 5 to about 24 (e.g., about 7 to about 10) hours or more.

In certain embodiments, the pharmaceutically acceptable liquid composition is administered in an amount to deliver from about 650 mg to about 800 mg, e.g., about 720 mg of the levodopa moiety and about 80 mg to about 100 mg, e.g., about 90 mg, the carbidopa moiety to the patient over the course of about 24 hours. According to some embodiments, the dose of the carbidopa moiety in the pharmaceutically acceptable liquid composition is between about 46 mg about 90 mg, for example, administered over the course of about 24 hours. According to some embodiments, the dose of the carbidopa moiety in the pharmaceutically acceptable liquid composition is between about 45 mg about 90 mg, for example, administered over the course of about 24 hours. According to some embodiments, the dose of the carbidopa moiety in the pharmaceutically acceptable liquid composition is about 90 mg at the most.

According to some embodiments, the pharmaceutically acceptable liquid composition comprises a levodopa moiety and a carbidopa moiety in a ratio of about 8:1 w/w. According to some embodiments, the pharmaceutically acceptable liquid composition is administered in an amount to deliver about 720 mg levodopa moiety and about 90 mg carbidopa moiety per day, about 360 mg levodopa moiety and about 45 mg carbidopa moiety per day, about 370 mg levodopa moiety and about 46 mg carbidopa moiety per day, wherein the levodopa moiety and the carbidopa moiety are in a ratio of about 8:1 w/w.

According to some embodiments, the pharmaceutically acceptable liquid composition is administered in an amount to deliver more than 0 mg and up to about 720 mg levodopa moiety and more than 0 mg and up to about 90 mg carbidopa moiety per day, wherein the ratio of levodopa moiety/ carbidopa moiety (e.g., LD/CD) administered is about 8:1 w/w. According to some embodiments, the pharmaceutically acceptable liquid composition is administered in an amount to deliver between about 8 mg to about 720 mg levodopa moiety and about 1 mg to about 90 mg carbidopa moiety per day, at a ratio of about 8:1 w/w levodopa moiety/carbidopa moiety (e.g., LD/CD). According to some embodiments, the pharmaceutically acceptable liquid composition is administered in an amount to deliver between about 360 mg to about 720 mg levodopa moiety and about 45 mg to about 90 mg carbidopa moiety per day, at a ratio of about 8:1 w/w levodopa moiety/carbidopa moiety (e.g., LD/CD). According to some embodiments, the pharmaceutically acceptable liquid composition is administered in an amount to deliver between about 370 mg to about 720 mg levodopa moiety and about 46 mg to about 90 mg carbidopa moiety per day, at a ratio of about 8:1 w/w levodopa moiety/carbidopa moiety (e.g., LD/CD). According to some embodiments, the pharmaceutically acceptable liquid composition is administered in an amount to deliver between about 370 mg to about 720 mg levodopa moiety and about 46 mg to about 90 mg carbidopa moiety per day, at a ratio of about 8:1 w/w levodopa moiety/carbidopa moiety (e.g., LD/CD).

According to some embodiments, the pharmaceutically acceptable liquid composition comprises up to about 720 mg levodopa. According to some embodiments, the pharmaceutically acceptable liquid composition comprises up to about 90 mg carbidopa. According to some embodiments, the pharmaceutically acceptable liquid composition comprises up to about 720 mg levodopa and up to about 90 mg carbidopa, wherein the levodopa and carbidopa and in a ratio of about 8:1 w/w.

According to some embodiments, the pharmaceutically acceptable liquid composition is administered in an amount to deliver about 720 mg, about 660-670 mg, about 620-630 mg, about 560-570 mg, about 510-520 mg, about 470-480 mg, about 410-420 mg, or about 370-380 mg of levodopa per day. According to some embodiments, the pharmaceutically acceptable liquid composition is administered in an amount to deliver about 90 mg, about 85-90 about 80-85 mg, about 75-80 mg, about 70-75 mg, about 65-70 mg, about 60-65, about 55-60 mg, about 50-55 mg, or about 45-50 mg of carbidopa per day. According to some embodiments, the pharmaceutically acceptable liquid composition is administered in an amount to deliver about 720 mg levodopa and about 90 mg carbidopa, about 660-670 mg levodopa and about 80-85 mg carbidopa, about 610-620 mg levodopa and about 75-80 mg carbidopa, about 560-570 mg levodopa and about 70-75 mg carbidopa, about 510-520 mg levodopa and about 60-70 mg carbidopa, about 470-480 mg levodopa and about 55-60 mg carbidopa, about 410-420 mg levodopa and about 50-55 mg carbidopa, or about 370-380 mg of levodopa and about 45-50 mg carbidopa per day, wherein the levodopa and carbidopa are administered at a ratio of about 8:1 w/w.

According to some embodiments, the pharmaceutically acceptable liquid composition comprises a levodopa moiety and a carbidopa moiety in a ratio of between about 2:1 w/w to about 40:1 w/w. According to some embodiments, the pharmaceutically acceptable liquid composition comprises a levodopa moiety and a carbidopa moiety in a ratio of between about 2:1 w/w to about 4:1 w/w. According to some embodiments, the pharmaceutically acceptable liquid composition comprises a levodopa moiety and a carbidopa moiety in a ratio of between about 4:1 w/w to about 6:1 w/w. According to some embodiments, the pharmaceutically acceptable liquid composition comprises a levodopa moiety and a carbidopa moiety in a ratio of between about 6:1 w/w to about 8:1 w/w. According to some embodiments, the pharmaceutically acceptable liquid composition comprises a levodopa moiety and a carbidopa moiety in a ratio of between about 8:1 w/w to about 10:1 w/w. According to some embodiments, the pharmaceutically acceptable liquid composition comprises a levodopa moiety and a carbidopa moiety in a ratio of between about 10:1 w/w to about 15:1 w/w. According to some embodiments, the pharmaceutically acceptable liquid composition comprises a levodopa moiety and a carbidopa moiety in a ratio of between about 15:1 w/w to about 20:1 w/w. According to some embodiments, the pharmaceutically acceptable liquid composition comprises a levodopa moiety and a carbidopa moiety in a ratio of between about 20:1 w/w to about 25:1 w/w. According to some embodiments, the pharmaceutically acceptable liquid composition comprises a levodopa moiety and a carbidopa moiety in a ratio of between about 25:1 w/w to about 30:1 w/w. According to some embodiments, the pharmaceutically acceptable liquid composition comprises a levodopa moiety and a carbidopa moiety in a ratio of between about 30:1 w/w to about 35:1 w/w. According to some embodiments, the pharmaceutically acceptable liquid composition comprises a levodopa moiety and a carbidopa moiety in a ratio of between about 35:1 w/w to about 40:1 w/w. According to some embodiments, the pharmaceutically acceptable liquid composition comprises a levodopa moiety and a carbidopa moiety in a ratio of about 20:1 w/w.

According to some embodiments, the pharmaceutically acceptable liquid composition is administered in an amount to deliver about 100 mg, about 200 mg, about 240 mg, about 480 mg, about 720 mg, about 960 mg, about 1200 mg, about 1440 mg, about 1680 mg, about 1920 mg, about 2160 mg, about 2400 mg, about 2640 mg, about 2880 mg, about 3120 mg, about 3360 mg, about 3600 mg, about 3840 mg, about 4080 mg, about 4320 mg, about 4560 mg, about 4800 mg, about 5040 mg, about 5280 mg, about 5520 mg, about 5760 mg, about 6000 mg, of a levodopa moiety over the course of about 24 hours. According to some embodiment the pharmaceutically acceptable liquid composition is administered in an amount to deliver between about 100 mg to about 6000 mg of a levodopa moiety over the course of about 24 hours. According to some embodiment the pharmaceutically acceptable liquid composition is administered in an amount to deliver between about 240 mg to about 4800 mg of a levodopa moiety over the course of about 24 hours. According to some embodiment the pharmaceutically acceptable liquid composition is administered in an amount to deliver between about 8 mg to about 1600 mg of a levodopa moiety over the course of about 24 hours. According to some embodiment the pharmaceutically acceptable liquid composition is administered in an amount to deliver between about 8 mg to about 3200 mg of a levodopa moiety over the course of about 24 hours. According to some embodiment the pharmaceutically acceptable liquid composition is administered in an amount to deliver between about 8 mg to about 3440 mg of a levodopa moiety over the course of about 24 hours.

According to some embodiments, the pharmaceutically acceptable liquid composition is administered in an amount to deliver about 5 mg, about 6 mg, about 10 mg, about 12 mg, about 24 mg, about 36 mg, about 48 mg, about 60 mg, about 72 mg, about 84 mg, about 90 mg, about 96 mg, about 108 mg, about 120 mg, about 132 mg, about 144 mg, about 156 mg, about 168 mg, about 180 mg, about 192 mg, about 204 mg, about 216 mg, about 228 mg, about 240 mg, about 252 mg, about 264 mg, about 276 mg, about 288 mg, or about 300 mg of a carbidopa moiety over the course of about 24 hours. According to some embodiments, the pharmaceutically acceptable liquid composition is administered in an amount to deliver between about 12 mg to about 240 mg of a carbidopa moiety over the course of about 24 hours. According to some embodiments, the pharmaceutically acceptable liquid composition is administered in an amount to deliver between about 1 mg to about 300 mg of a carbidopa moiety over the course of about 24 hours.

According to some embodiment the pharmaceutically acceptable liquid composition is administered in an amount to deliver between about 240 mg to about 4800 mg of a levodopa moiety and between about 12 mg to about 240 mg of a carbidopa moiety over the course of about 24 hours.

According to some embodiments, the method of the invention comprises subcutaneously administering between about 1 to about 30 mL of the pharmaceutically acceptable liquid composition of the invention over the course of 24 hours. According to some embodiments, the method of the invention comprises subcutaneously administering between about 1 to about 120 mL of the pharmaceutically acceptable liquid composition of the invention over the course of 24 hours. According to some embodiments, the method of invention comprises subcutaneously administering between about 1 mL to about 2 mL, between about 2 mL to about 3 mL, between about 3 mL to about 4 mL, between about 4 mL to about 5 mL, between about 5 mL to about 6 mL, between about 6 mL to about 7 mL, between about 7 mL to about 8 mL, between about 8 mL to about 9 mL, between about 9 mL to about 10 mL, between about 10 mL to about 11 mL, between about 11 mL to about 12 mL, between about 12 mL to about 13 mL, between about 13 mL to about 14 mL, between about 14 mL to about 15 mL between about 15 mL to about 16 mL, between about 16 mL to about 17 mL, between about 17 mL to about 18 mL, between about 18 mL to about 19 mL, between about 19 mL to about 20 mL, between about 20 mL to about 21 mL, between about 21 mL to about 22 mL, between about 22 mL to about 23 mL, between about 23 mL to about 24 mL, between about 24 mL to about 25 mL, between about 25 mL to about 26 mL, between about 26 mL to about 27 mL, between about 27 mL to about 28 mL, between about 28 mL to about 29 mL, between about 29 mL to about 30 mL, between about 30 mL to about 40 mL, between about 40 mL to about 50 mL, between about 50 mL to about 60 mL, between about 60 mL to about 70 mL, between about 70 mL to about 80 mL, between about 80 mL to about 90 mL, between about 90 mL to about 100 mL, between about 100 mL to about 110 mL, between about 110 mL to about 120 mL, of the pharmaceutically acceptable liquid composition over the course of 24 hours. According to some embodiments, the method of the invention comprises subcutaneously administering about 12 mL of the pharmaceutically acceptable liquid composition of the invention over the course of about 24 hours. According to some embodiments, the method of the invention comprises subcutaneously administering about 20 mL of the pharmaceutically acceptable liquid composition of the invention over the course of about 24 hours. According to some embodiments, the method of the invention comprises subcutaneously administering up to about 12 mL of the pharmaceutically acceptable liquid composition of the invention over the course of about 24 hours. According to some embodiments, the method of the invention comprises subcutaneously administering up to about 20 mL of the pharmaceutically acceptable liquid composition of the invention over the course of about 24 hours. According to some embodiments, the method of the invention comprises subcutaneously administering up to about 120 mL of the pharmaceutically acceptable liquid composition of the invention over the course of about 24 hours.

According to some embodiments, the pharmaceutically acceptable liquid composition is administered at a volume of between about 1 mL to about 30 mL per site per day, between about 2 mL to about 20 mL per site per day, between about 3 mL to about 10 mL per site per day, between about 5 mL to about 7 mL per site per day, or about 6 mL per site per day. According to some embodiments, the pharmaceutically acceptable liquid composition is administered at a volume of between about 1 mL to about 2.5 mL per site per day, between about 2.5 mL to about 5.0 mL per site per day, between about 5.0 mL to about 7.5 mL per site per day, between about 7.5 mL to about 10 mL per site per day, between about 10 mL to about 12.5 mL per site per day, between about 12.5 mL to about 15 mL per site per day, between about 15 mL to about 17.5 mL per site per day, between about 17.5 mL to about 20 mL per site per day, between about 20 mL to about 22.5 mL per site per day, between about 22.5 mL to about 25 mL per site per day, between about 25 mL to about 27.5 mL per site per day, between about 27.5 mL to about 30 mL per site per day. According to some embodiments, the pharmaceutically acceptable liquid composition is administered at a volume of about 6 mL per site per day.

According to some embodiments, the pharmaceutically acceptable liquid composition comprises about 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, or about 9.5 mg/mL of the carbidopa moiety. According to some embodiments, the pharmaceutically acceptable liquid composition comprises 44 mg/mL, about 48 mg/mL, about 52 mg/mL, about 56 mg/mL, about 60 mg/mL, about 64 mg/mL, about 68 mg/mL, about 72 mg/mL, or about 76 mg/mL of the levodopa moiety. According to some embodiments, the pharmaceutically acceptable liquid composition comprises about 7.5 mg/mL carbidopa and 60 mg/mL levodopa.

It is noted that the administration rate may be constant over the course of 24 hours or may change over the course of 24 hours. For instance, according to some embodiments, there may be a certain rate for high activity/day hours and a different rate for low activity/night hours. The high activity/day hours may be, e.g., about 15, about 16, about 17, about 18 or about 19 hours, while the low activity night hours may be about 9, about 8, about 7, about 6 or about 5 hours, respectively. According to some embodiments, the high activity/day rate is implemented for about 18 hours, while the low activity/night rate is implemented for about 6 hours. According to some embodiments, the high activity/day rate is implemented for about 16 hours, while the low activity/night rate is implemented for about 8 hours. According to some embodiments, the administration rate is at least partially determined by input received from the patient, a caregiver, at least one sensor and the like. According to some embodiments, the administration rate may be elevated when necessary or decreased when necessary according to a predefined pattern that may be set periodically, e.g., by a caregiver or the patient. According to other embodiments, the administration rate may be altered, e.g., elevated or decreased, in an on-line manner, for example, according input received from the patient, a caregiver, or at least one sensor, indicating that a change in administration rate is required or beneficial. For instance, if the patient wishes to rest at a certain point during the day, the rate may be decreased from day to night rate, e.g., by a command provided by the patient. In addition, a caregiver may give a command to the system in view of the patient, e.g., resting during the day. Further, a sensor may alert the system that the patient has gone to sleep (or fallen asleep) and decrease the administration rate accordingly. Sensors may also provide sleep pattern data, allowing the system to be notified in advance of the patient awaking from sleep, and in response, e.g., elevating the administration rate. The patient's monitored condition may also cause the administration rate to be altered, e.g., lapsing into an "off episode" and the like, may cause the administration rate to be raised.

The administration rate may be between about 0.01 mL/site/hour to about 1 mL/site/hour. According to some embodiments, the administration rate is between about 0.01-0.02 mL/site/hour. According to some embodiments, the administration rate is between about 0.02-0.03 mL/site/hour. According to some embodiments, the administration rate is between about 0.03-0.04 mL/site/hour. According to some embodiments, the administration rate is between about 0.04-0.05 mL/site/hour. According to some embodiments, the administration rate is between about 0.05-0.06 mL/site/hour. According to some embodiments, the administration rate is between about 0.06-0.07 mL/site/hour. According to some embodiments, the administration rate is between about 0.07-0.08 mL/site/hour. According to some embodiments, the administration rate is between about 0.08-0.09 mL/site/hour. According to some embodiments, the administration rate is between about 0.09-0.1 mL/site/hour. According to some embodiments, the administration rate is between about 0.1-0.15 mL/site/hour. According to some embodiments, the administration rate is between about 0.15-0.2 mL/site/hour. According to some embodiments, the administration rate is between about 0.2-0.25 mL/site/hour. According to some embodiments, the administration rate is between about 0.25-0.3 mL/site/hour. According to some embodiments, the administration rate is between about 0.3-0.35 mL/site/hour. According to some embodiments, the administration rate is between about 0.35-0.4 mL/site/hour. According to some embodiments, the administration rate is between about 0.4-0.45 mL/site/hour. According to some embodiments, the administration rate is between about 0.45-0.5 mL/site/hour. According to some embodiments, the administration rate is between about 0.5-0.55 mL/site/hour. According to some embodiments, the administration rate is between about 0.55-0.6 mL/site/hour. According to some embodiments, the administration rate is between about 0.6-0.65 mL/site/hour. According to some embodiments, the administration rate is between about 0.65-0.7 mL/site/hour. According to some embodiments, the administration rate is between about 0.7-0.75 mL/site/hour. According to some embodiments, the administration rate is between about 0.75-0.8 mL/site/hour. According to some embodiments, the administration rate is between about 0.8-0.85 mL/site/hour. According to some embodiments, the administration rate is between about 0.85-0.9 mL/site/hour. According to some embodiments, the administration rate is between about 0.9-0.95 mL/site/hour. According to some embodiments, the administration rate is between about 0.95-1.0 mL/site/hour.

According to some embodiments, the administration rate in the low activity/night hours is between about 0.01-0.15 mL/site/hour. According to some embodiments, the administration rate in the low activity/night hours is between about 0.01-0.02 mL/site/hour. According to some embodiments, the administration rate in the low activity/night hours is between about 0.02-0.03 mL/site/hour. According to some embodiments, the administration rate in the low activity/night hours is between about 0.03-0.04 mL/site/hour. According to some embodiments, the administration rate in the low activity/night hours is between about 0.04-0.05 mL/site/hour. According to some embodiments, the administration rate in the low activity/night hours is between about 0.05-0.06 mL/site/hour. According to some embodiments, the administration rate in the low activity/night hours is between about 0.06-0.07 mL/site/hour. According to some embodiments, the administration rate in the low activity/night hours is between about 0.07-0.08 mL/site/hour. According to some embodiments, the administration rate in the low activity/night hours is between about 0.08-0.09 mL/site/hour. According to some embodiments, the administration rate in the low activity/night hours is between about 0.09-0.1 mL/site/hour. According to some embodiments, the administration rate in the low activity/night hours is between about 0.1-0.11 mL/site/hour. According to some embodiments, the administration rate in the low activity/night hours is between about 0.11-0.12 mL/site/hour. According to some embodiments, the administration rate in the low activity/night hours is between about 0.12-0.13 mL/site/hour. According to some embodiments, the administration rate in the low activity/night hours is between about 0.13-0.14 mL/site/hour. According to some embodiments, the administration rate in the low activity/night hours is between about 0.14-0.15 mL/site/hour. According to some embodiments, the administration rate in the low activity/night hours is about 0.04 mL/site/hour. According to some embodiments, the administration rate in the low activity/night hours is about 0.08 mL/site/hour.

According to some embodiments, the administration rate in the high activity/day hours is between about 0.15-1.0 mL/site/hour. According to some embodiments, the administration rate in the high activity/day hours is between about 0.15-0.2 mL/site/hour. According to some embodiments, the administration rate in the high activity/day hours is between about 0.2-0.25 mL/site/hour. According to some embodiments, the administration rate in the high activity/day hours is between about 0.25-0.3 mL/site/hour. According to some embodiments, the administration rate in the high activity/day hours is between about 0.3-0.35 mL/site/hour. According to some embodiments, the administration rate in the high activity/day hours is between about 0.35-0.4 mL/site/hour. According to some embodiments, the administration rate in the high activity/day hours is between about 0.4-0.45 mL/site/hour. According to some embodiments, the administration rate in the high activity/day hours is between about 0.45-0.5 mL/site/hour. According to some embodiments, the administration rate in the high activity/day hours is between about 0.5-0.55 mL/site/hour. According to some embodiments, the administration rate in the high activity/day hours is between about 0.55-0.6 mL/site/hour. According to some embodiments, the administration rate in the high activity/day hours is between about 0.6-0.65 mL/site/hour. According to some embodiments, the administration rate in the high activity/day hours is between about 0.65-0.7 mL/site/hour. According to some embodiments, the administration rate in the high activity/day hours is between about 0.7-0.75 mL/site/hour. According to some embodiments, the administration rate in the high activity/day hours is between about 0.75-0.8 mL/site/hour. According to some embodiments, the administration rate in the high activity/day hours is between about 0.8-0.85 mL/site/hour. According to some embodiments, the administration rate in the high activity/day hours is between about 0.85-0.9 mL/site/hour. According to some embodiments, the administration rate in the high activity/day hours is between about 0.9-0.95 mL/site/hour. According to some embodiments, the administration rate in the high activity/day hours is between about 0.95-1.0 mL/site/hour. According to some embodiments, the administration rate in the high activity/day hours is about 0.32 mL/site/hour. According to some embodiments, the administration rate in the high activity/day hours is between about 0.32 mL/hour and about 0.64 mL/hour. According to some embodiments, the administration rate in the high activity/day hours is about 0.64 mL/hour, about 0.59 mL/hour, about 0.55 mL/hour, about 0.5 mL/hour, about 0.45 mL/hour, about 0.41 mL/hour, about 0.36 mL/hour, or about 0.32 mL/hour. According to some embodiments, the administration rate in the high activity/day hours is about 0.32 mL/site/hour, about 0.295 mL/site/hour, about 0.275 mL/site/hour, about 0.25 mL/site/hour, about 0.225 mL/site/hour, about 0.205 mL/site/hour, about 0.18 mL/site/hour, or about 0.16 mL/site/hour.

As mentioned above, while the low and high rates are referred to as night and day rates, respectively, they may be used irrespective of the time of day; rather, of the condition of the patient and the like, e.g., low activity and high activity. Further, the rate may be altered gradually, and may be set at any appropriate value, not necessarily bound to one particular high rate and one particular low rate.

According to some embodiments, the pharmaceutically acceptable liquid composition is administered over the course of about 12 to about 20 hours (e.g., about 18 hours) at a high activity rate and about 4 to about 12 hours (e.g., about 6 hours) at a low activity rate, wherein about 500 mg to about 800 mg (e.g., about 700 mg or about 691.2 mg) levodopa and about 60 mg to about 100 mg (e.g., about 80 mg or about 86.4 mg) is administered over the course of the high activity and about 20 mg to about 40 mg (e.g., about 30 mg or about 28.8 mg) levodopa and about 2 mg to about 5 mg (e.g., about 3 mg or about 3.6 mg) carbidopa is administered over the course of the low activity. According to some embodiments, the high activity rate and/or the low activity rate may be a consecutive time period in the course of 24 hours. According to other embodiments, the high activity rate and/or the low activity rate may be administered at several, non-consecutive time periods over the course of 24 hours.

It is further noted that the administrated volume and/or administration rate may be constant throughout the treatment, or may vary during different hours of the day, between different days, weeks or months of treatment, and the like. According to some embodiments, the patient is monitored, e.g., independently, by a caretaker, or electronically, e.g., by sensors, possibly found in a dedicated device, e.g., a watch-like device, patch-like sensor, the administration pump, and the like. According to such embodiments, the administration volume and/or rate are determined according to data received from such monitoring.

Some embodiments are directed to a method for administering a bolus subcutaneous injection of the pharmaceutically acceptable liquid composition of the invention. According to some embodiments, the bolus injection comprises between about 0.5 to about 2.0 mL/Kg of the pharmaceutically acceptable liquid composition. According to some embodiments, the bolus injection comprises between about 0.5 to about 0.75 ml/Kg of the pharmaceutically acceptable liquid composition. According to some embodiments, the bolus injection comprises between about 0.75 to about 1.0 ml/Kg of the pharmaceutically acceptable liquid composition. According to some embodiments, the bolus injection comprises between about 1.0 to about 1.25 ml/Kg of the pharmaceutically acceptable liquid composition. According to some embodiments, the bolus injection comprises between about 1.25 to about 1.5 ml/Kg of the pharmaceutically acceptable liquid composition. According to some embodiments, the bolus injection comprises between about 1.5 to about 1.75 mL/Kg of the pharmaceutically acceptable liquid composition. According to some embodiments, the bolus injection comprises between about 1.75 to about 2.0 ml/Kg of the pharmaceutically acceptable liquid composition. According to some embodiments, the bolus injection comprises between about 0.75 to about 1.25 mL/Kg of the pharmaceutically acceptable liquid composition. According to some embodiments, the bolus injection comprises about 1.0 mL/Kg of the pharmaceutically acceptable liquid composition.

The bolus subcutaneous injection may be administered at any time point in relation to any possible continuous subcutaneous administrations, e.g., prior to, during, or after the continuous administration. The bolus subcutaneous injection may be administered at any time point during the day. The bolus subcutaneous injection may be administered once a day, once every two, three, four five or six days, once a week, or more. The bolus subcutaneous injection may be administered when required/desired, according to feedback received from the patient, caretaker, physician, sensors, and the like, and/or according to a predefined regimen. The bolus subcutaneous injection may be administered over between about five minutes to about 40 minutes, between about five minutes to about 10 minutes, between about 10 minutes to 15 minutes, between about 15 minutes to 20 minutes, between about 20 minutes to 25 minutes, between about 25 minutes to 30 minutes, between about 30 minutes to 35 minutes, between about 35 minutes to 40 minutes.

According to some embodiments, the administered dose may be doubled, tripled or more, by using more than one pump, more than one injection site for each pump, and the like.

According to some embodiments, the pharmaceutically acceptable liquid composition is administered for a defined period of time, e.g., days, weeks, months, or years. According to some embodiments, the pharmaceutically acceptable liquid composition is administered endlessly, for the treatment of a chronic condition.

According to some embodiments, the pharmaceutically acceptable liquid composition comprises between about 1% w/v and about 40% w/v of levodopa, a levodopa salt, or any combination thereof. According to some embodiments, the pharmaceutically acceptable liquid composition comprises between about 1% w/v and about 5% w/v, between about 5% w/v and about 10% w/v, between about 10% w/v and about 15% w/v, between about 15% w/v and about 20% w/v, between about 20% w/v and about 25% w/v, between about 25% w/v and about 30% w/v, between about 30% w/v and about 35% w/v, between about 35% w/v and about 40% w/v, between about 2% w/v and about 10% w/v, between about 4% w/v and about 8% w/v, between about 5% w/v and about 7% w/v, about 6% w/v of levodopa, a levodopa salt, or any combination thereof.

According to some embodiments, the pharmaceutically acceptable liquid composition comprises between about 0.5% w/v and about 10% w/v of carbidopa, a carbidopa salt, or any combination thereof. According to some embodiments, the pharmaceutically acceptable liquid composition comprises between about 0.5% w/v and about 1% w/v, between about 1% w/v and about 1.5% w/v, between about 1.5% w/v and about 2% w/v, between about 2% w/v and about 2.5% w/v, between about 2.5% w/v and about 3% w/v, between about 3% w/v and about 3.5% w/v, between about 3.5% w/v and about 4% w/v, between about 4% w/v and about 4.5% w/v, between about 4.5% w/v and about 5% w/v, between about 5% w/v and about 5.5% w/v, between about 5.5% w/v and about 6% w/v, between about 6% w/v and about 6.5% w/v, between about 6.5% w/v and about 7% w/v, between about 7% w/v and about 7.5% w/v, between about 7.5% w/v and about 8% w/v, between about 8% w/v and about 8.5% w/v, between about 8.5% w/v and about 9% w/v, between about 9% w/v and about 9.5% w/v, between about 9.5% w/v and about 10% w/v, about 0.75% w/v of carbidopa, a carbidopa salt, or any combination thereof.

For example, provided herein is a pharmaceutically acceptable liquid composition suitable for parenteral (e.g., subcutaneous) administration, includes about 4-10% by weight levodopa, about 0.5 to about 2% by weight carbidopa, and about 10% to about 20% by weight arginine. Another exemplary pharmaceutically acceptable liquid composition provided herein includes about 6% by weight levodopa, about 0.75% by weight carbidopa, and about 10% to about 20% by weight arginine.

According to some embodiments, the pharmaceutically acceptable liquid composition comprises between about 0.05% w/v and about 2.0% w/v, between about 0.05% w/v and about 0.1% w/v, between about 0.1% w/v and about 0.2% w/v, between about 0.2% w/v and about 0.3% w/v, between about 0.3% w/v and about 0.4% w/v, between about 0.4% w/v and about 0.5% w/v, between about 0.5% w/v and about 0.6% w/v, between about 0.6% w/v and about 0.7% w/v, between about 0.7% w/v and about 0.8% w/v, between about 0.8% w/v and about 0.9% w/v, between about 0.9% w/v and about 1.0% w/v, between about 1% w/v and about 1.1% w/v, between about 1.1% w/v and about 1.2% w/v, between about 1.2% w/v and about 1.3% w/v, between about 1.3% w/v and about 1.4% w/v, between about 1.4% w/v and about 1.5% w/v, between about 1.5% w/v and about 1.6% w/v, between about 1.6% w/v and about 1.7% w/v, between about 1.7% w/v and about 1.8% w/v, between about 1.8% w/v and about 1.9% w/v, between about 1.9% w/v and about 2.0% w/v, between about 0.75% w/v and about 1.25% w/v, about 0.75% w/v, about 0.8% w/v, about 0.85% w/v, about 0.9% w/v, about 0.95% w/v, about 1.0% w/v of an antioxidant or a combination of antioxidants.

According to some embodiments, the antioxidant is selected from the group consisting of ascorbic acid or a salt thereof, a cysteine, such as N-acetyl cysteine, a bisulfite or a salt thereof, glutathione, a tyrosinase inhibitor, a bivalent cation, butylated hydroxy toluene (BHT), beta hydroxy acid (BHA) tocopherol, gentisic acid, tocopherol, tocopherol derivative, thioglycerol, and any combination thereof. According to some embodiments, the antioxidant is ascorbic acid. According to some embodiments, the antioxidant is N-acetyl cysteine (NAC). According to some embodiments, the pharmaceutically acceptable liquid composition comprises a combination of ascorbic acid and NAC. For example, provided herein is a pharmaceutically acceptable liquid composition, suitable for e.g., subcutaneous administration, that includes about 0.1% to about 10% by weight ascorbic acid or a pharmaceutically acceptable salt thereof, about 0.01% to about 1% by weight of a component selected from the group consisting of: NAC, L-cysteine and pharmaceutically acceptable salts thereof; about 2% to about 16% by weight levodopa or an ester thereof; and about 0.6% to about 2% by weight carbidopa or an ester thereof.

According to some embodiments, the pharmaceutically acceptable liquid composition comprises a base. According to some embodiments the base is selected from the group consisting of arginine, NaOH, tris(hydroxymethyl)aminomethane (TRIS), NH$_4$OH, ethylenediamine, diethylamine, ethanolamine, diethanolamine, meglumine, and any combination thereof. According to some embodiments, the base is arginine.

According to some embodiments, the pharmaceutically acceptable liquid composition comprises between about 5% w/v and about 30% w/v or a base. According to some embodiments, the pharmaceutically acceptable liquid composition comprises between about 5% w/v and about 10% w/v, between about 10% w/v and about 15% w/v, between about 15% w/v and about 20% w/v, between about 20% w/v and about 25% w/v, between about 25% w/v and about 30% w/v, between about 12.5% w/v and 17.5% w/v, or about 15% w/v, or about 15.2% w/v base.

According to some embodiments, the pharmaceutically acceptable liquid composition comprises a surfactant. According to some embodiments, the surfactant is selected from Tween-80, Tween-60, Tween-40, Tween-20, Tween-65, Tween-85, Span 20, Span 40, Span 60, Span 80, Span 85, polyoxyl 35 castor oil (Cremophor EL), polyoxyethylene-660-hydroxystearate (macrogol 660), or Poloxamer 188 (Pluronic® F-68), or any combination thereof. The pharmaceutically acceptable liquid composition of the invention may include between about 0.1 to about 3.0% w/v of a surfactant or combination of two or more surfactants. According to some embodiments, the pharmaceutically acceptable liquid composition comprises between about 0.1 to about 0.2% w/v, between about 0.2 to about 0.3% w/v, between about 0.3 to about 0.4% w/v, between about 0.4 to about 0.5% w/v, between about 0.5 to about 0.6% w/v, between about 0.6 to about 0.7% w/v, between about 0.7 to about 0.8% w/v, between about 0.8 to about 0.9% w/v, between about 0.9 to about 1.0% w/v, between about 1.0 to about 1.5% w/v, between about 1.5 to about 2.0% w/v, between about 2.0 to about 2.5% w/v, between about 2.5 to about 3.0% w/v of a surfactant or combination of two or more surfactants.

The pharmaceutically acceptable liquid composition may further comprise an additional pharmaceutically acceptable excipient, such as N-methylpyrrolidone (NMP), polyvinylpyrrolidone (PVP), propylene glycol, a preservative, a pharmaceutically acceptable vehicle, a stabilizer, a dispersing agent, a suspending agent, an amino sugar, a calcium chelator, protease inhibitors, or any combination thereof. The pharmaceutically acceptable liquid composition of the invention may comprise between about 5.0 to about 80.0% w/v or an additional pharmaceutically acceptable excipient, e.g., a solvent, such as NMP or a buffer or any other co-solvent. For example, provided here in, is a pharmaceutically acceptable liquid composition that includes about 6% by weight levodopa, about 0.75% by weight carbidopa, about 10% to about 20% by weight arginine, about 0.5% by weight of L-cysteine or NAC, and/or about 0.5% by weight ascorbic acid or a salt thereof. An exemplary pharmaceutically acceptable liquid composition may include about 6% by weight levodopa, about 0.75% by weight carbidopa, and about 14% to about 16% by weight arginine. Another exemplary pharmaceutical composition may include about 6% by weight levodopa, about 0.75% by weight carbidopa, about 14% to about 16% by weight arginine, about 0.5% ascorbic acid and about 0.5% NAC.

According to some embodiments, the pharmaceutically acceptable liquid composition of the invention comprises between about 5.0 to about 10.0% w/v, between about 10.0 to about 15.0% w/v, between about 15.0 to about 20.0% w/v, between about 20.0 to about 25.0% w/v, between about 25.0 to about 30.0% w/v, between about 30.0 to about 35.0% w/v, between about 35.0 to about 40.0% w/v, between about 40.0 to about 45.0% w/v, between about 45.0 to about 50.0% w/v, between about 50.0 to about 55.0% w/v, between about 55.0 to about 60.0% w/v, between about 60.0 to about 65.0% w/v, between about 65.0 to about 70.0% w/v, between about 70.0 to about 75.0% w/v, between about 75.0 to about 80.0% w/v of a solvent, e.g., NMP, a buffer or any other co-solvent.

According to some embodiments, the pharmaceutically acceptable liquid composition further comprises a buffer. According to some embodiments, the buffer is selected from citrate buffer, citric acid buffer, sodium acetate buffer, acetic acid buffer, tartaric acid buffer, phosphate buffer, succinic acid buffer, Tris buffer, glycine buffer, hydrochloric acid buffer, potassium hydrogen phthalate buffer, sodium buffer, sodium citrate tartrate buffer, sodium hydroxide buffer, sodium dihydrogen phosphate buffer, disodium hydrogen phosphate buffer, tromethamine (TRIS), or any combination thereof. The pharmaceutically acceptable liquid composition may comprise between about 0.1 to about 30.0% w/v of a buffer. According to some embodiments, the pharmaceutically acceptable liquid composition comprises between about 0.1 to about 1.0% w/v, between about 1.0 to about 2.0% w/v, between about 2.0 to about 3.0% w/v, between about 3.0 to about 4.0% w/v, between about 4.0 to about 5.0% w/v, between about 5.0 to about 6.0% w/v, between about 6.0 to about 7.0% w/v, between about 8.0 to about 9.0% w/v, between about 9.0 to about 10.0% w/v, between about 10.0 to about 15.0% w/v, between about 15.0 to about 20.0% w/v, between about 20.0 to about 25.0% w/v, between about 25.0 to about 30.0% w/v of a buffer.

According to some embodiments, the pharmaceutically acceptable liquid compositions further comprises an acid or a base, e.g., in order to provide a composition with a pre-defined pH. According to some embodiments, the acid is selected from HCl, HBr, methanesulfonic acid, ascorbic acid, acetic acid, citric acid, or any combination thereof. According to some embodiments, the base is selected from NaOH, Ca (OH) 2, ammonium hydroxide, arginine, magnesium hydroxide, potassium hydroxide, meglumine, tromethamine (TRIS), triethylamine, diisopropylethylamine, diazabicycloundecene or any combination thereof. The pharmaceutically acceptable liquid compositions may comprise between about 0.1 to about 30.0% w/v of a base or acid. According to some embodiments, the pharmaceutically acceptable liquid composition comprises between about 0.1 to about 1.0% w/v, between about 1.0 to about 2.0% w/v, between about 2.0 to about 3.0% w/v, between about 3.0 to about 4.0% w/v, between about 4.0 to about 5.0% w/v, between about 5.0 to about 6.0% w/v, between about 6.0 to about 7.0% w/v, between about 8.0 to about 9.0% w/v, between about 9.0 to about 10.0, between about 10.0 to about 11.0, between about 11.0 to about 12.0, between about 12.0 to about 13.0, between about 13.0 to about 14.0, between about 14.0 to about 15.0, between about 15.0 to about 16.0, between about 16.0 to about 17.0, between about 17.0 to about 18.0, between about 18.0 to about 19.0, between about 19.0 to about 20.0, between about 20.0 to about 21.0, between about 21.0 to about 22.0, between about 22.0 to about 23.0, between about 23.0 to about 24.0, between about 24.0 to about 25.0, between about 25.0 to about 26.0, between about 26.0 to about 27.0, between about 27.0 to about 28.0, between about 28.0 to about 29.0, between about 29.0 to about 30.0, of a base or acid.

The pH of the pharmaceutically acceptable liquid composition of the invention may be between about 4.5 to about 10 at about 25° C. According to some embodiments, the pH of the pharmaceutically acceptable liquid compositions is between about 4.5 to about 5 at about 25° C. According to some embodiments, the pH of the pharmaceutically acceptable liquid compositions is between about 5 to about 6 at about 25° C. According to some embodiments, the pH of the pharmaceutically acceptable liquid compositions is between about 6 to about 7 at about 25° C. According to some embodiments, the pH of the pharmaceutically acceptable liquid compositions is between about 7 to about 8 at about 25° C. According to some embodiments, the pH of the pharmaceutically acceptable liquid compositions is between about 8 to about 9 at about 25° C. According to some embodiments, the pH of the pharmaceutically acceptable liquid compositions is between about 9 to about 10 at about 25° C. According to some embodiments, the pH of the pharmaceutically acceptable liquid compositions is between about 4.5 to about 5.5 at about 25° C. According to some embodiments, the pH of the pharmaceutically acceptable liquid compositions is between about 5.5 to about 6.5 at about 25° C. According to some embodiments, the pH of the pharmaceutically acceptable liquid compositions is between about 6.5 to about 7.5 at about 25° C. According to some embodiments, the pH of the pharmaceutically acceptable liquid compositions is between about 7.5 to about 8.5 at about 25° C. According to some embodiments, the pH of the pharmaceutically acceptable liquid compositions is between about 8.5 to about 9.5 at about 25° C. According to some embodiments, the pH of the pharmaceutically acceptable liquid compositions is between about 9.5 to about 10 at about 25° C. According to some embodiments, the pH of the pharmaceutically acceptable liquid compositions is about 9.5 at about 25° C. According to some embodiments, an acid or a base is added to the pharmaceutically acceptable liquid composition in order to provide a composition with a predefined pH value. According to some embodiments, the acid is selected from HCl, HBr, methanesulfonic acid, ascorbic acid, acetic acid, citric acid, or any combination thereof. According to some embodiments, the base is selected from NaOH, arginine, an amine base, any of the bases mentioned herein, and any combination thereof.

In some embodiments, the method further comprises concomitantly administering to the patient a pharmaceutically acceptable oral composition comprising:
(a) levodopa, a levodopa salt, or any combination thereof; and
(b) a dopa decarboxylase inhibitor (DDCI), a DDCI salt, or any combination thereof.

As described herein, the present disclosure provides methods for treating a patient with a neurological or movement disorder, the method comprising:
parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
and, concomitantly, administering to the patient a pharmaceutically acceptable oral composition comprising:
(a) levodopa, a levodopa salt, or any combination thereof; and
(b) a dopa decarboxylase inhibitor (DDCI), a DDCI salt, or any combination thereof.

Disclosed herein is a method for treating a patient with a neurological or movement disorder, the method comprising:
parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
and, concomitantly, administering to the patient a pharmaceutically acceptable oral composition comprising:
(a) levodopa, a levodopa salt, or any combination thereof; and
(b) a dopa decarboxylase inhibitor (DDCI), a DDCI salt, or any combination thereof,
wherein after 2 or 3 days of administration, the patient has:
an increase from baseline in daily Good ON-time,
a reduction from baseline in ON-time with moderate-severe dyskinesia,
an improvement from baseline based on a Subject Global Impression of Change (SGI-C) score,
an improvement from baseline based on a Clinical Global Impression of Change (CGI-C) score,
or any combination thereof.

Disclosed herein is a method for treating a patient with a neurological or movement disorder, the method comprising:
parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
and, concomitantly, administering to the patient a pharmaceutically acceptable oral composition comprising:
(a) levodopa, a levodopa salt, or any combination thereof; and
(b) a dopa decarboxylase inhibitor (DDCI), a DDCI salt, or any combination thereof,
wherein after 2 or 3 days of administration, the patient has:
an increase from baseline in daily Good ON-time,
a reduction from baseline in ON-time with moderate-severe dyskinesia,
an improvement from baseline based on a Patient Global Impression of Improvement (PGI-I) score,
an improvement from baseline based on a Clinical Global Impression of Improvement CGI-I) score,
or any combination thereof.

Further disclosed herein is a method for treating a patient with a neurological or movement disorder, the method comprising:
parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
and, concomitantly, administering to the patient a pharmaceutically acceptable oral composition comprising:
(a) levodopa, a levodopa salt, or any combination thereof; and
(b) a dopa decarboxylase inhibitor (DDCI), a DDCI salt, or any combination thereof,
wherein the administration results in an increase of at least about 0.3 hours to about 3.5 hours in Good ON-time in the patient over the course of about 24 hours, after treatment for about 2 or 3 days.

Further disclosed herein is a method for treating a patient with a neurological or movement disorder, the method comprising:
parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
and, concomitantly, administering to the patient a pharmaceutically acceptable oral composition comprising:
(a) levodopa, a levodopa salt, or any combination thereof; and
(b) a dopa decarboxylase inhibitor (DDCI), a DDCI salt, or any combination thereof,
wherein the administration results in an increase of at least about 1.5 hours to about 6.0 hours in Good ON-time in the patient over the course of about 24 hours, after treatment for at least about 28 days.

Further disclosed herein is a method for treating a patient with a neurological or movement disorder, the method comprising:
parenterally administering to the patient a pharmaceutically acceptable liquid composition comprising:
(a) levodopa, a levodopa salt, or any combination thereof; and
(b) a dopa decarboxylase inhibitor (DDCI), a DDCI salt, or any combination thereof,
and, concomitantly, administering to the patient a pharmaceutically acceptable oral composition comprising:
(a) levodopa, a levodopa salt, or any combination thereof; and
(b) a dopa decarboxylase inhibitor (DDCI), a DDCI salt, or any combination thereof,
wherein the administration results in an improvement in the patient in:
daily OFF-time,
daily ON-time without troublesome dyskinesia, motor experiences of daily living, as assessed by the Movement Disorder Society-Sponsored revision of Unified Parkinson's Disease Rating Scale Part II score, a Patient Global Impression of Change (PGI-C), a Clinical Global Impression of Improvement (CGI-I), or any combination thereof.

According to some embodiments, the improvement in the patient is measured compared to a patient treated with an immediate release oral dosage form of levodopa. According to some embodiments, the improvement in the patient is relative to administering an immediate release oral dosage form of levodopa.

According to some embodiments, the concomitant administration of the pharmaceutically acceptable liquid composition and the pharmaceutically acceptable oral composition provides a synergistic effect, such that the levodopa blood levels obtained by the concomitant administration are higher than the expected additive effect when providing the pharmaceutically acceptable liquid composition and the pharmaceutically acceptable oral composition non-concomitantly. According to some embodiments, the synergism between the pharmaceutically acceptable liquid composition and the pharmaceutically acceptable oral compositions provides an elevation of between about 5% and about 50% in the levodopa blood levels, in comparison to the expected additive values. According to some embodiments, the synergism between the pharmaceutically acceptable liquid composition and pharmaceutically acceptable oral compositions provides an elevation of between about 10% and 40% in the levodopa blood levels, between about 15% and 35% in the levodopa blood levels, between about 20% and 40 in the levodopa blood levels, between about 25% and 35% in the levodopa blood levels, or about 20%, 25%, or 30% in the levodopa blood levels, in comparison to the expected additive values.

According to some embodiments, the pharmaceutically acceptable liquid composition comprises (1) levodopa, and/or a levodopa salt, and/or (2) carbidopa, and/or a carbidopa salt.

According to some embodiments, the DDCI is carbidopa, a carbidopa salt, benserazide, a benserazide salt, or any combination thereof. According to some embodiments, the DDCI is carbidopa.

In some embodiments, the pharmaceutically acceptable oral composition comprises levodopa or a pharmaceutically acceptable salt thereof. In some embodiments, the pharmaceutically acceptable oral composition comprises levodopa.

In some embodiments, the pharmaceutically acceptable oral composition comprises a DDCI or a pharmaceutically acceptable salt thereof. In some embodiments, the DDCI is carbidopa.

In some embodiments, the pharmaceutically acceptable oral composition comprises carbidopa or a pharmaceutically acceptable salt thereof. In some embodiments, the pharmaceutically acceptable oral composition comprises carbidopa.

According to some embodiments, the pharmaceutically acceptable oral composition comprises levodopa and carbidopa.

According to some embodiments, the pharmaceutically acceptable oral composition comprises levodopa and carbidopa. According to some embodiments, the pharmaceutically acceptable oral composition comprises only levodopa as the active ingredient. According to some embodiments, the pharmaceutically acceptable oral composition further comprises a catechol o-methyl transferase (COMT) inhibitor, such as entacapone or tolcapone.

The DDCI in the pharmaceutically acceptable liquid composition may be the same or different as the DDCI in the pharmaceutically acceptable oral composition.

Further, the levodopa moiety in each of the pharmaceutically acceptable liquid composition and the pharmaceutically acceptable oral compositions may be the same or different. That is, while according to some embodiments, both the pharmaceutically acceptable liquid composition and the pharmaceutically acceptable oral composition comprise levodopa, according to other embodiments the pharmaceutically acceptable liquid composition may comprise one type of levodopa moiety, e.g., a levodopa salt, while the pharmaceutically acceptable oral composition comprises a different type of levodopa moiety, e.g., levodopa. It is further noted that the concentration or amount of each moiety within the pharmaceutically acceptable liquid composition may be different than the concentration or amount of that moiety within the pharmaceutically acceptable oral composition.

According to some embodiments, the pharmaceutically acceptable oral composition is administered when desired and/or required, e.g., when symptoms from said neurological or movement disorder require such administration, or according to a predefined treatment protocol. The assessment of the timing for administering the pharmaceutically acceptable oral composition may be performed by a caretaker, a physician, the patient to whom the composition is being administered, or any combination thereof, resulting from consultation and/or joint decision making, and the like. According to some embodiments, a system supported by any type of sensors may provide data for determining the need for administering the pharmaceutically acceptable oral composition. That data may be delivered to a caretaker, a physician, the patient, or any combination thereof, via any means, such as an electronic device, e.g., a smartphone, dedicated console, tablet, email, dedicated or known application, and the like.

According to some embodiments, the pharmaceutically acceptable oral composition is administered at predefined times, predefined intervals, or both, set, e.g., according to treatment protocols or according to data received from the patient, caregiver, physician, sensors, and the like. The predetermined times and/or intervals may be reset at any time point, e.g., in view of data received from the patient, caretaker, sensors, physician assessment, and the like.

According to some embodiments, the pharmaceutically acceptable oral composition is orally administered substantially concurrently with the start of the infusion time course. According to some embodiments, the pharmaceutically acceptable oral composition is orally administered about 1, 2, 3, 4, or 5 hours after the start of the infusion time course. It is noted that the "start of the infusion time course" may be a daily time, wherein the cycle of the infusion, e.g., when new vials are introduced into the system, when a cartridge is replaced, when an infusion set is replaced, and the like.

According to some embodiments, the orally administered pharmaceutically acceptable oral composition is a morning oral dose. According to some embodiments, the morning oral dose comprises levodopa, a levodopa salt, or any combination thereof. According to some embodiments, the morning oral dose includes one of: 25 mg levodopa, 50 mg levodopa, 75 mg levodopa, 95 mg levodopa, 100 mg levodopa, 125 mg levodopa, 145 mg levodopa, 150 mg levodopa, 195 mg levodopa, 200 mg levodopa, 245 mg levodopa, or 250 mg levodopa.

According to some embodiments, the morning oral dose comprises (a) levodopa, a levodopa salt; (b) a dopa decarboxylase inhibitor (DDCI), a DDCI salt, or (c) any combination thereof.

According to some embodiments the pharmaceutically acceptable oral composition is administered up to 20 times a day. According to some embodiments, the pharmaceutically acceptable oral composition is administered about 1, 2, 3, 4, 5, 6, 7, 8, 9, 10, 11 or 12 times a day. In some embodiments, the method described herein includes administration of the pharmaceutically acceptable oral composition 1, 2, 3, 4, 5, 6, 7, 8, 9 or 10 times a day. According to some embodiments, the pharmaceutically acceptable oral composition is administered between about 3 and 7 times a day. According to some embodiments, the pharmaceutically acceptable oral composition is administered between about 4 and 6 times a day. According to some embodiments, the pharmaceutically acceptable oral composition is administered at a frequency of between about 30 minutes to about 24 hours. According to some embodiments, the pharmaceutically acceptable oral composition is administered at a frequency of between about 30 minutes to about one hour, between about one hour to two hours, between about two hours to three hours, between about three hours to about four hours, between about four hours to about five hours, between about five hours to about six hours, between about six hours to seven five hours, between about seven hours to about eight hours, between about eight hours to about nine hours, between about nine hours to about 10 hours, between about 10 hours to about 11 hours, between about 11 hours to about 12 hours, between about 12 hours to about 13 hours, between about 13 hours to about 14 hours, between about 14 hours to about 15 hours, between about 15 hours to about 16 hours, between about 16 hours to about 17 hours, between about 17 hours to about 18 hours, between about 18 hours to about 19 hours, between about 19 hours to about 20 hours, between about 20 hours to about 21 hours, between about 21 hours to about 22 hours, between about 22 hours to about 23 hours, between about 23 hours to about 24 hours.

The intervals between one administration to the next may differ as well, depending, e.g., on the patient's/caretaker's/physician's observations and assessment, on data received from any type of appropriate sensor, on a predefined treatment protocol, any combination thereof, and the like.

According to some embodiments, the administered dose of the levodopa moiety in the pharmaceutically acceptable oral composition is the same each time it is administered. According to some embodiments, the dose of the levodopa moiety in the pharmaceutically acceptable oral composition may differ between different administrations. According to some embodiments, the dose of the levodopa moiety in the pharmaceutically acceptable oral composition is between about 10 mg per day and about 3000 mg per day, between about 10 mg per day and about 50 mg per day, between about 50 mg per day and about 100 mg per day, between about 100 mg per day and about 150 mg per day, between about 150 mg per day and about 250 mg per day, between about 250 mg per day and about 350 mg per day, between about 350 mg per day and about 500 mg per day, between about 500 mg per day and about 750 mg per day, between about 750 mg per day and about 1000 mg per day, between about 1000 mg per day and about 1250 mg per day, between about 1250 mg per day and about 1500 mg per day, between about 1500 mg per day and about 1750 mg per day, between about 1750 mg per day and about 2000 mg per day, between about 2000 mg per day and about 2250 mg per day, between about 2250 mg per day and about 2500 mg per day, between about 2500 mg per day and about 2750 mg per day, or between about 2750 mg per day and about 3000 mg per day. According to some embodiments, the dose of the levodopa moiety in the pharmaceutically acceptable oral composition is between about 100 mg per day to about 1800 mg per day. According to some embodiments, the dose of the levodopa moiety in the pharmaceutically acceptable oral composition is between about 350 mg per day to about 700 mg per day.

It is noted that an administered dose is defined according to the time in which the composition is administered to the patient, and therefore, if several tablets, e.g., 4 tablets, each comprising 100 mg of levodopa are administered to the patient at practically the same time, the administered dose of the levodopa in the pharmaceutically acceptable oral composition would be considered to be 400 mg in such an instance. Further, the dose per day may consist of several administered doses, not necessarily identical to one another, e.g., a patient may be administered 100 mg at 8 am, 200 mg at 10 am, 100 mg at 3 μm and 75 mg at 7 pm, such that the dose of the levodopa moiety in the pharmaceutically acceptable oral composition would be considered to be 475 mg per day.

According to some embodiments, the dose of the levodopa moiety in the pharmaceutically acceptable oral composition is between about 10 mg and about 500 mg per administration, between about 10 mg and about 25 mg per administration, between about 25 mg and about 50 mg per administration, between about 50 mg and about 75 mg per administration, between about 75 mg and about 100 mg per administration, between about 100 mg and about 150 mg per administration, between about 150 mg and about 200 mg per administration, between about 200 mg and about 250 mg per administration, between about 250 mg and about 300 mg per administration, between about 300 mg and about 350 mg per administration, between about 350 mg and about 400 mg per administration, between about 400 mg and about 450 mg per administration, between about 450 mg and about 500 mg per administration. According to some embodiments, the dose differs between different administrations. According to other embodiments, the dose remains constant for at least two administrations, e.g., over the course of 24 hours, three days, one week, and the like.

In certain embodiments, the dose of the levodopa moiety in the pharmaceutically acceptable oral composition is about 50 mg, 75 mg, 100 mg, 125 mg, 150 mg, 200 mg, or 250 mg levodopa, e.g., in an immediate release tablet or capsule. According to some embodiments, the dose of the levodopa moiety in the pharmaceutically acceptable oral composition is about 95 mg, about 145 mg, about 195 mg, or about 245 mg levodopa, e.g., in an extended release form, e.g., a tablet or capsule.

As mentioned above, the levodopa moiety may be levodopa in the pharmaceutically acceptable oral composition is a levodopa salt. According to some embodiments, the levodopa moiety is levodopa.

According to some embodiments, the dose of the carbidopa moiety in the pharmaceutically acceptable oral composition is between about 2.5 mg and about 50 mg per administration, between about 2.5 mg and about 20 mg per administration, between about 2.5 mg and about 25 mg per administration, between about 2.5 mg and about 35 mg per administration, between about 2.5 mg and about 40 mg per administration, between about 15 mg and about 20 mg per administration, between about 15 mg and about 25 mg per administration, between about 15 mg and about 35 mg per administration, between about 15 mg and about 40 mg per administration, between about 15 mg and about 50 mg per administration, between about 20 mg and about 25 mg per administration, between about 20 mg and about 35 mg per administration, between about 20 mg and about 40 mg per administration, between about 20 mg and about 50 mg per administration, between about 25 mg and about 35 mg per administration, between about 25 mg and about 40 mg per administration, between about 25 mg and about 50 mg per administration, between about 35 mg and about 40 mg per administration, between about 35 mg and about 50 mg per administration, between about 40 mg and about 50 mg per administration. According to some embodiments, the dose of carbidopa moiety in the pharmaceutically acceptable oral composition comprises 2.5 mg, 18.57 mg, 25 mg, 31.25 mg, 37.5 mg or 50 mg carbidopa.

The pharmaceutically acceptable oral composition may be in any appropriate oral form, such as a pill, hard or soft capsule, tablet, troches, lozenges, aqueous or oily suspensions, dispersible powders or granules, emulsions, syrups or elixirs. The pharmaceutically acceptable oral composition may an immediate release form, or any type of controlled release form, such as sustained release, extended release, delayed release, prolonged release, and the like. As noted above, the pharmaceutically acceptable oral composition may comprise at least two active ingredients, e.g., levodopa and carbidopa. It is noted that each one of the active ingredients in the pharmaceutically acceptable oral composition may be formulated in a different release form, for instance, the levodopa may be in a controlled release form, while the carbidopa is in an immediate release form, or vice versa.

According to some embodiments, the pharmaceutically acceptable oral composition is administered only during high activity/waking hours, e.g., during the day, such that the administration intervals are smaller during high activity/waking hours than during other parts of the day, e.g., low activity/night hours. According to further embodiments, the doses of the pharmaceutically acceptable oral composition provided during high activity/waking hours are higher than the doses administered during other parts of the day, e.g., low activity/night hours. According to some embodiments, a dosing regimen over 24 hours is devised and may remain constant for a certain number of days, while, within the same day the regimen may be different based on wakefulness, activity, and the like. According to some embodiments, the dosing regimen may change from day to day, as well as within the same day.

In some embodiments, the method described herein includes administration of the pharmaceutically acceptable oral composition when symptoms from said neurological or movement disorder require said administration.

In some embodiments, the method described herein includes administration of the pharmaceutically acceptable oral composition at predefined times, predefined intervals, or both.

In some embodiments, the method described herein includes administration of the pharmaceutically acceptable oral composition more than once, wherein the administered dose is the same at all administrations.

In some embodiments, the method described herein includes administration of the pharmaceutically acceptable oral composition more than once, wherein the administered dose differs in at least two administrations.

In some embodiments, the method described herein includes administration of the pharmaceutically acceptable oral composition in a dose of between about 25 mg and about 400 mg levodopa or a salt thereof, in each administration.

In some embodiments, the method described herein includes as the pharmaceutically acceptable liquid composition levodopa, carbidopa and arginine or any salt thereof.

In some embodiments, the method described herein includes as the pharmaceutically acceptable liquid composition levodopa, carbidopa, arginine, or any salt thereof, and at least one antioxidant.

In some embodiments, the method described herein includes as the pharmaceutically acceptable liquid composition levodopa, carbidopa, arginine, or any salt thereof, and at least two antioxidants.

In some embodiments, the method described herein includes as the pharmaceutically acceptable liquid composition a composition that comprises levodopa, carbidopa, or any salt thereof, and a base selected from the group consisting of arginine, NaOH, tris(hydroxymethyl)aminomethane (TRIS), and any combination thereof.

In some embodiments, the method described herein includes as the pharmaceutically acceptable liquid composition a composition with a pH in the range of between about 6 to about 10, in the range of between about 8 to about 10, in the range of between about 9 to about 10, in the range of between about 9.1 to about 9.8, or about 9.5.

In some embodiments, the method described herein includes as the pharmaceutically acceptable liquid composition a composition that comprises between about 1% w/v and about 40% w/v, between about 1% w/v and about 20% w/v, between about 1% w/v and about 10% w/v, between about 2% w/v and about 8% w/v, between about 4% w/v and about 8% w/v, between about 5% w/v and about 7% w/v, or about 6% w/v of levodopa, a levodopa salt, or any combination thereof.

In some embodiments, the method described herein includes as the pharmaceutically acceptable liquid composition a composition that comprises between about 0.5% w/v and about 10% w/v, between about 0.5% w/v and about 6% w/v, between about 0.5% w/v and about 4% w/v, between about 0.5% w/v and about 2% w/v, between about 0.5% w/v and about 1% w/v, about 0.75% w/v of carbidopa, a carbidopa salt, or any combination thereof.

In some embodiments, the method described herein includes the antioxidant that is selected from the group consisting of ascorbic acid or a salt thereof, a cysteine, such as N-acetyl cysteine, a bisulfite or a salt thereof, glutathione, a tyrosinase inhibitor, a bivalent cation, butylated hydroxy toluene (BHT), beta hydroxy acid (BHA) tocopherol, gentisic acid, tocopherol, tocopherol derivative, thioglycerol, and any combination thereof.

Embodiments of the invention are further directed to a method for treatment of a neurological or movement disorder, such as Parkinson's disease, in a patient in need thereof, wherein the method comprises:
  parenterally administering a pharmaceutically acceptable liquid composition comprising:
  (a) levodopa, a levodopa salt, or any combination thereof; and
  (b) a dopa decarboxylase inhibitor (DDCI), a DDCI salt, or any combination thereof,
  and, concomitantly, administering a pharmaceutically acceptable oral composition comprising:
  (a) levodopa, a levodopa salt, or any combination thereof; and
  (b) a dopa decarboxylase inhibitor (DDCI), a DDCI salt, or any combination thereof.

Further embodiments of the invention are directed to a pharmaceutically acceptable liquid composition comprising:

(a) levodopa, a levodopa salt, or any combination thereof; and
(b) a dopa decarboxylase inhibitor (DDCI), a DDCI salt, or any combination thereof,
and, a pharmaceutically acceptable oral composition comprising:
(a) levodopa, a levodopa salt, or any combination thereof; and
(b) a dopa decarboxylase inhibitor (DDCI), a DDCI salt, or any combination thereof,
for use as a combination in the treatment of a neurological or movement disorder, for example, Parkinson's disease, wherein the pharmaceutically acceptable liquid composition is formulated as a parenteral composition and the pharmaceutically acceptable oral composition is formulated as an oral composition.

Further embodiments of the invention are directed to a pharmaceutically acceptable liquid composition comprising:
(a) levodopa, a levodopa salt, or any combination thereof; and
(b) a dopa decarboxylase inhibitor (DDCI), a DDCI salt, or any combination thereof,
a pharmaceutically acceptable oral composition comprising:
(a) levodopa, a levodopa salt, or any combination thereof; and
(b) a dopa decarboxylase inhibitor (DDCI), a DDCI salt, or any combination thereof, and instructions for the concomitant administration of the pharmaceutically acceptable liquid composition and the pharmaceutically acceptable oral composition for the treatment of a neurological or movement disorder, such as Parkinson's disease.

Further embodiments of the invention are directed to a pharmaceutically acceptable liquid composition comprising:
(a) levodopa, a levodopa salt, or any combination thereof; and
(b) a dopa decarboxylase inhibitor (DDCI), a DDCI salt, or any combination thereof,
a pharmaceutically acceptable oral composition comprising:
(a) levodopa, a levodopa salt, or any combination thereof; and
(b) a dopa decarboxylase inhibitor (DDCI), a DDCI salt, or any combination thereof,
and instructions for the concomitant administration of the pharmaceutically acceptable liquid composition and a pharmaceutically acceptable oral composition for the treatment of a neurological or movement disorder, such as Parkinson's disease, wherein the pharmaceutically acceptable oral composition is provided separately.

Further embodiments of the invention are directed to a method of treating Parkinson's disease in a patient in need thereof, wherein the patient was previously administered a previous form of levodopa other than immediate release carbidopa-levodopa tablets in a ratio of 1:4, and wherein the method comprises:
converting the patient from the previous form of levodopa to oral immediate release levodopa-carbidopa 100/25 mg tablets;
subcutaneously administering to the patient, over a subcutaneous infusion time course of at least about 24 hours or more, a pharmaceutically acceptable liquid composition comprising levodopa; and
administering to the patient, before or during the subcutaneous infusion time course, at least one pharmaceutically acceptable oral composition comprising levodopa.

Further embodiments of the invention are directed to a method of treating Parkinson's disease in a patient in need thereof, wherein the patient was previously administered a previous form of levodopa other than immediate release carbidopa-levodopa tablets in a ratio of 1:4, and wherein the method comprises:
converting the patient from the previous form of levodopa to an oral immediate release levodopa-carbidopa form;
after said conversion, subcutaneously administering to the patient, over a subcutaneous infusion time course of at least about 24 hours or more, a pharmaceutically acceptable liquid composition comprising levodopa; and
administering to the patient, before or during the subcutaneous infusion time course, at least one pharmaceutically acceptable oral composition comprising levodopa.

Further embodiments of the invention are directed to a method of treating Parkinson's disease in a patient in need thereof, wherein the patient was previously administered a previous form of levodopa other than immediate release carbidopa-levodopa tablets in a ratio of 1:4, and wherein the method comprises:
converting the patient from the previous form of levodopa to an oral immediate release levodopa form, thus administering an amount of oral immediate release levodopa to said patient;
following said conversion, subcutaneously administering to the patient, over a subcutaneous infusion time course of at least about 24 hours or more, a pharmaceutically acceptable liquid composition comprising a subcutaneous amount of levodopa, wherein if the amount of oral immediate release form of levodopa is higher than the subcutaneous amount of levodopa, the amount of oral immediate release form of levodopa is reduced by about the amount of the subcutaneous amount of levodopa and the patient is administered a remaining amount of oral immediate release levodopa; and
if the amount of oral immediate release form of levodopa is lower than the subcutaneous amount of levodopa, the patient is not administered the oral immediate release form of levodopa except for a morning dose of oral immediate release levodopa, administered before or during the subcutaneous infusion time course.

Further embodiments of the invention are directed to a method of treating Parkinson's disease in a patient in need thereof, wherein the patient was previously administered a previous form of levodopa other than immediate release carbidopa-levodopa tablets in a ratio of 1:4, and wherein the method comprises:
converting the patient from the previous form of levodopa to an oral immediate release levodopa form, thus administering an initial daily amount of oral immediate release levodopa to said patient;
following said conversion, subcutaneously administering to the patient, over a subcutaneous infusion time course of at least about 24 hours or more, a pharmaceutically acceptable liquid composition in an amount to deliver about 720 mg of levodopa to the patient over the course of at least about 24 hours, wherein if the initial daily amount of oral immediate release form of levodopa is higher than about 700 mg, the amount oral immediate release form of levodopa is reduced by about 700 mg and the patients is administered with a remaining amount of oral immediate release levodopa, equal to the initial daily amount of oral immediate release levodopa minus 700 mg; and if the initial daily amount of amount of oral immediate release form of levodopa is lower than about 700 mg, the patient is administered only with a morning dose of oral immediate release levodopa, administered before or during the subcutaneous infusion time course.

In certain embodiments of the methods described herein, the concomitant administration of the pharmaceutically acceptable liquid composition (parenteral, e.g., subcutaneous administration) and the pharmaceutically acceptable oral composition (e.g., oral tablet) to the patient results in a higher area under the curve (AUC) for levodopa from time 0 to the end of the parenteral, e.g., subcutaneous, infusion as compared to the combined AUC for levodopa in the patient when the pharmaceutically acceptable liquid composition and the pharmaceutically acceptable oral composition are not concomitantly administered, wherein the total amount of levodopa administered is the same, whether administered concomitantly or non-concomitantly.

Unless explicitly stated, the method embodiments described herein are not constrained to a particular order or sequence. Additionally, some of the described method embodiments or elements thereof can occur or be performed simultaneously, at the same point in time, or concurrently.

It is appreciated that certain features of the invention may also be provided in combination in a single embodiment. Conversely, various elements of the invention that are, for brevity, described in the context of a single embodiment, may also be provided separately or in any suitable subcombination or as suitable in any other described embodiment of the invention. Further, certain features described in the context of various embodiments are not to be considered essential features of those embodiments, unless the embodiment is inoperative without those elements.

Various embodiments and aspects of the present invention as delineated hereinabove and as claimed in the claims section below may be supported by the following examples; however, they are not to be limited by the examples.

EXAMPLES

Example 1—Onset of Efficacy with Continuous, Subcutaneous Levodopa/Carbidopa Infusion in Patients with PD Experiencing Motor Fluctuations Objectives: This study evaluated the onset of efficacy for continuous 24-hour subcutaneous infusion of liquid levodopa/carbidopa (LD/CD) with ND0612, a liquid formulation of LD/CD, comprising 60 mg/ml LD and 7.5 mg/ml CD.

Background: Primary results from a previous study demonstrated that 28 days of treatment with 24-hour ND0612 infusion reduced OFF-time by 2.8 [−4.6, −0.9] hours (P<0.0004), increased ON-time with no/mild dyskinesia (Good ON-time) by 3.7 hours, [95% CI: 1.9, 5.6] hours (p<0.001), and reduced ON-time with moderate/severe dyskinesia by 1.2 [−2.1, −0.3] hours (p≤0.01) in patients with PD experiencing motor fluctuations.

Methods: Described herein is data from a secondary analysis of patients treated with the 24-hour ND0612 infusion regimen (N=19). Patients received the infusion at a rate of 0.64 mL/hour from 4 AM to 10 PM and 0.08 mL/hour between 10 PM and 4 AM to a total LD/CD dose of 720/90 mg. Motor status was determined by a blinded-rater at 30-minute intervals for 8 hours. Patients also assessed the time to full ON each morning in a diary. The first post-baseline efficacy evaluations were performed at Day 3. Day 3 is the third consecutive day of the treatment, preceded by two consecutive treatment days. Unless specifically mentioned otherwise, the baseline evaluations were performed on Day 1 of the treatment, prior to initiation of the treatment and the Day 3 evaluations were performed during Day 3, possibly at 8 am, after 4 hours of high rate, and possibly at another time point during Day 3. The "change from baseline" relating to any Day 3 data is the difference between the Day 3 measurement and the baseline measurement on Day 1, wherein at least 48 hours of treatment have been concluded.

Model Results: At Day 3, patients treated with 24-hour ND0612 infusion for two consecutive days showed a significant increase in the adjusted mean change from baseline in Good ON-time* (+1.83 [95% CI: 0.30, 3.35] hours, p=0.02), and a significant reduction in the adjusted mean change from baseline in ON-time with moderate-severe dyskinesia* (−1.36 [95% CI: −2.29, −0.42] hours, p=0.006) (FIG. 1A).

Figure 1B:
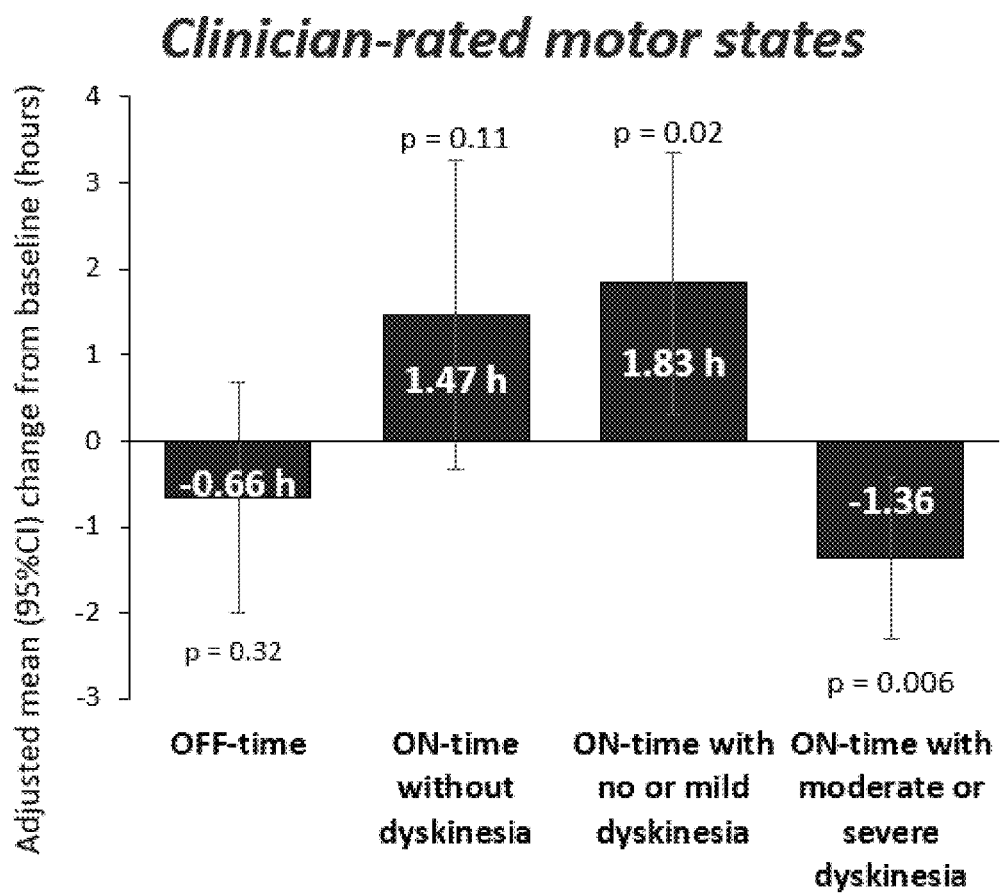
FIG. 1B is a graph showing changes from baseline in OFF-time (reduction), ON-time without dyskinesia (increase), Good ON-time or ON-time with no or with mild dyskinesia (increase), and ON-time with moderate or severe dyskinesia (reduction), as described in Example 1.

At Day 3, patients treated with 24-hour ND0612 infusion for two consecutive days further showed a reduction in the adjusted mean change from baseline in OFF-time* (−0.66 [95% CI: −1.98, 0.67] hours, p=0.319) as well as an increase in the adjusted mean change from baseline ON-time without dyskinesia* (+1.47 [95% CI: −0.32, 3.27] hours, p=0.105) (FIG. 1B). *The values provided were calculated according to the following model. The Mixed Model for Repeated Measures included the observed change from baseline to Day 3 and Day 28 in total daily "ON" time or "OFF" time as dependent variable. The model included randomized treatment regimen, the scheduled study day, the interaction between the randomized treatment regimen and scheduled study day, and region as fixed factors, and the "ON" time/ "OFF" time at baseline (Day 1) as a covariate. An unstructured covariance structure was assumed and the denominator degrees of freedom were computed using the Kenward-Roger method.

Figure 1C:
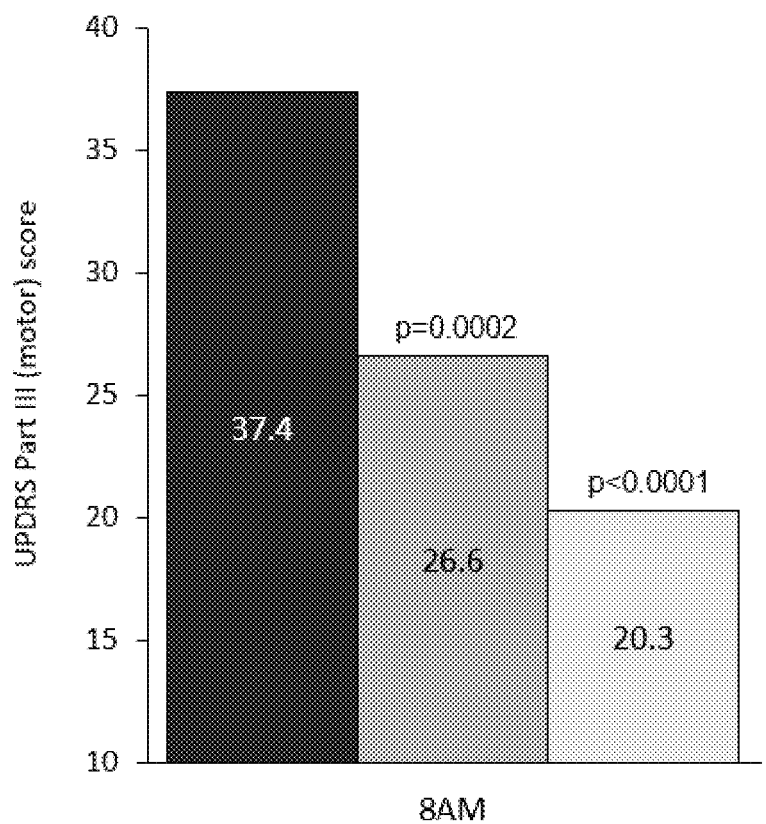
FIG. 1C is a graph showing the improved UPDRS Part III scores as described in Example 1.

Results based on raw data (descriptive statistics): At Day 3, patients treated with 24-hour ND0612 infusion for two consecutive days showed a decrease in both Off time and troublesome dyskinesia, as well as an increase in Good ON time. The UPDRS Part III scores improved significantly as well (FIG. 1C), as did the quality of sleep of 50% of the patients. See table below:

TABLE 1

| | Baseline (Day 1, pre-dose) Mean (SD)/ Median | Day 3 Mean (SD)/ Median | Change from baseline (Day 3 vs Day 1) Mean (SD)/Median |
|---|---|---|---|
| OFF time (h) | 5.55 (2.065)/5.00 | 4.94 (3.587)/5.00 | −0.61 (3.104)/−2.00 |
| Good ON-time (h) | 9.24 (3.255)/9.00 | 10.59 (4.146)/ 10.67 | 1.35 (3.355)/2.67 |
| Troublesome dyskinesia (h) | 1.21 (2.820)/0.00 | 0.47 (2.065)/0.00 | −0.74 (2.330)/0.00 |
| UPDRS Part III Scores (earliest morning values) | 37.4 (14.48)/39.0 | 26.6 (13.46)/27.0 | −10.7 (16.93)/ −13.00 |
| Quality of night sleep | | | 50% of patients shows improvement |

N = 19 (MITT set, observed cases), ON/OFF diary normalized by 16 h waking time

Figure 2:
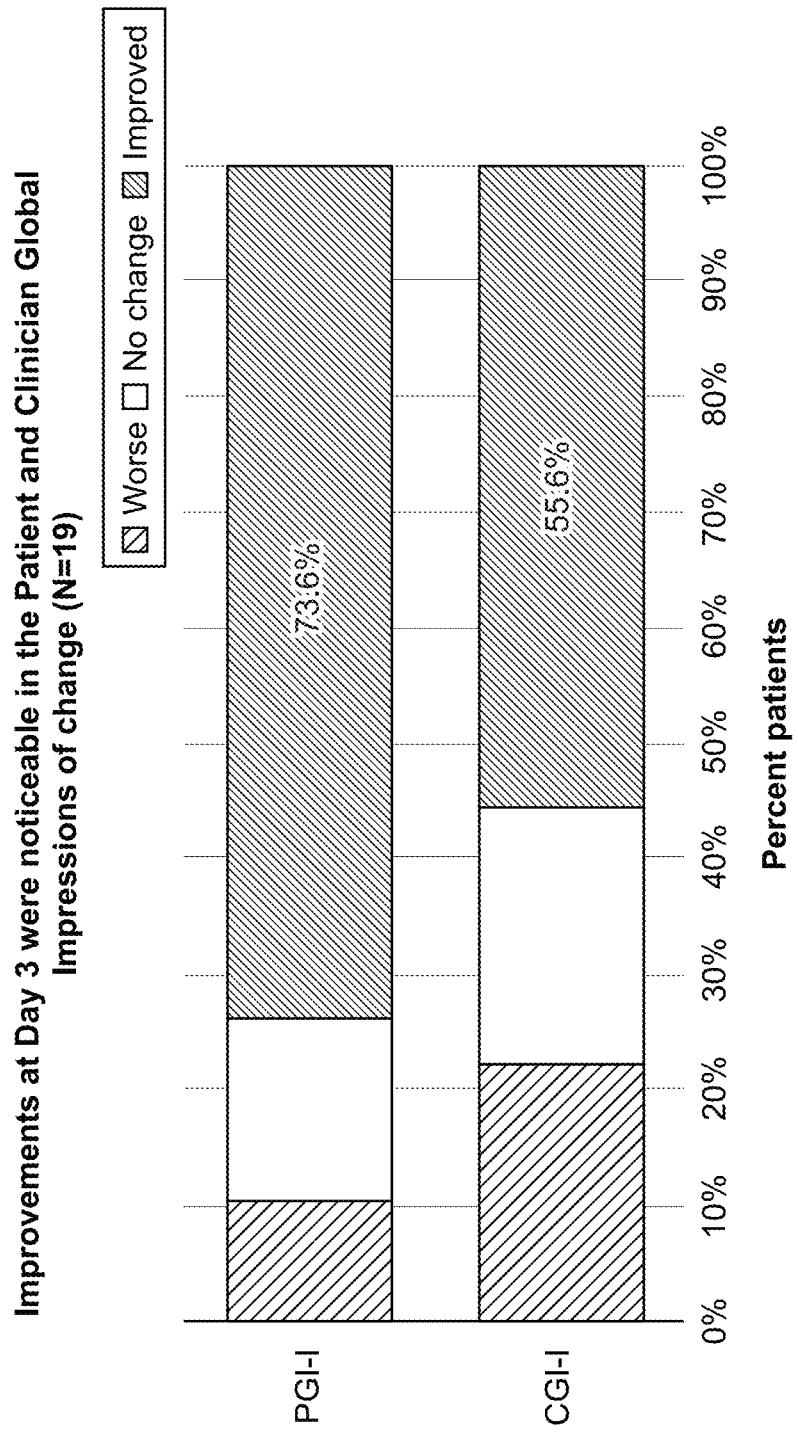
FIG. 2 is a graph showing the improvements in Patient Global Impressions of Change and Clinician Global Impressions of Change as described in Example 1.
Figure 3:
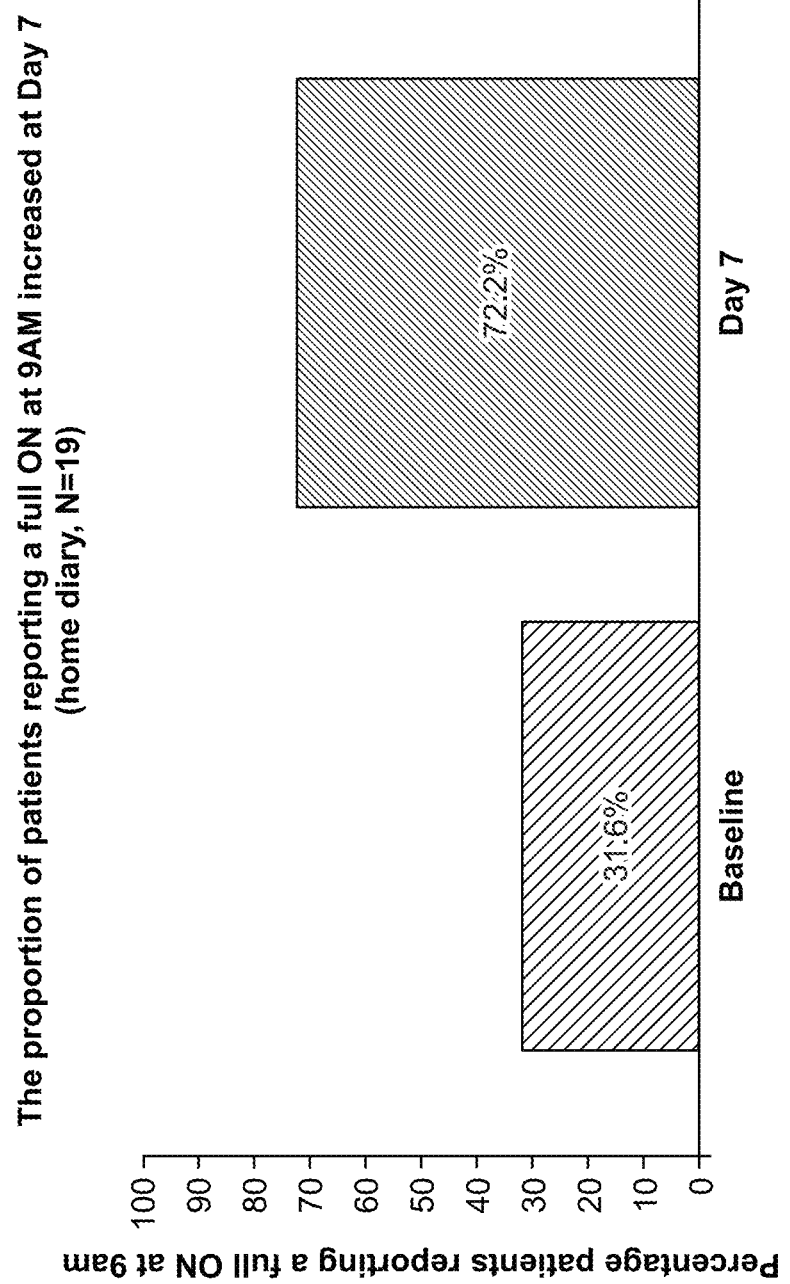
FIG. 3 is a graph showing the proportion of patients reporting full ON at 9 AM at Day 7 as described in Example 1.

Improvements at Day 3 were also noticeable in the Patient and Clinician Global Impressions of change: PGI and CGI improvements were reported for 73.7% and 52.6% of patients, respectively (FIG. 2). By the end of the first week of treatment, the proportion of patients who reported achieving a full ON at 9 AM increased from 31.6% at baseline to 72.2% (FIG. 3).

Conclusions: Results of this analysis demonstrate that patients experience statistically significant and clinically relevant improvements with 24-hour subcutaneous infusion with ND0612 at Day 3 after treatment initiation that improved further to Day 28 (primary endpoint).

Example 2—Safety and Efficacy of Continuous Subcutaneous Levodopa/Carbidopa Infusion for Parkinson's Disease: Reduction in OFF-Time for Patients with Parkinson's Disease Experiencing Motor Fluctuations Objectives: This study evaluated the efficacy of 24-hour continuous, subcutaneous infusion of liquid levodopa/carbidopa with ND0612 in reducing OFF-time in people with Parkinson's disease (PwP) experiencing motor fluctuations.

Background: A previous study demonstrated that one year treatment with ND0612 infusion is safe and well-tolerated. Adjusted mean daily Good ON-time (i.e., the sum of ON-time without dyskinesia+ON-time with non-troublesome dyskinesia) increased from baseline by 2.3 hours at month 3 and was maintained for at least 12 months.

Methods: This open-label study of ND0612 treatment was conducted in PD patients (n=214) aged ≥30 years with Hoehn & Yahr score of ≤3 during ON experiencing ≥2 hours daily OFF-time despite receiving ≥4 levodopa doses per day and ≥other PD medication. Patients received a 16-hour/day or 24-hour-day subcutaneous infusion of LD/CD for a total daily LD/CD dose of 720/90 mg.

In this analysis of daily OFF-time (patient home diaries), a responder was conservatively defined as a patient who achieved ≥50% reduction from baseline in adjusted mean daily OFF-time.

Results: Using the last observation carried forward, 44.0% patients were classified as treatment responders, and this level of response was maintained over the 12 months of follow-up. Moreover, 63.5% of patients achieved a >25% reduction in OFF-time from baseline and 26.9% of patients achieved a >75% reduction in OFF-time. Additionally, in 12.8% of patients, the OFF-time was completely eliminated. Using only observed cases (i.e., not LOCF), the percentage of ND0612 treatment responders increased from 44.0% at Month 1 (N=150) to 53.3% at Month 6 (N=107), and 56.7% at Month 12 (N=90).

Extension study: Of the 214 patients who entered this study, 114 patients entered in the extension study. Baseline demographic and disease characteristics of the 114 patients who entered the extension study are shown in the table below.

TABLE 2

| Baseline characteristics | N = 114 |
|---|---|
| Age (years), mean ± SD | 63.6 ± 8.9 |
| <65 years, n (%) | 61 (53.5%) |
| ≥65 years, n (%) | 53 (46.5%) |
| Sex (Female/Male), n (%) | 36 (31.6%)/78 (68.4%) |
| Modified Hoehn & Yahr, n (%) | |
| ≤2 | 57 (50.0%) |
| 2.5 | 27 (23.7%) |

TABLE 2-continued

| Baseline characteristics | N = 114 |
|---|---|
| 3 | 30 (26.3%) |
| OFF time (hours), mean ± SD | 5.6 ± 2.9 |
| UPDRS motor score, mean ± SD | 26.1 ± 12.8 |
| Time since PD diagnosis (years), mean ± SD | 8.7 ± 4.3 |
| Time since fluctuations (years), mean ± SD | 4.7 ± 4.0 |
| Prior total daily oral levodopa dose (mg), mean ± SD | 1021 ± 585 |
| ≤720 mg, n (%) | 36 (31.6%) |
| >720 mg, n (%) | 78 (68.4%) |
| Number of prior oral levodopa doses per day, n (%) | |
| 4-5 doses per day | 63 (55.3%) |
| 6-13 doses per day | 36 (31.6%) |
| Other | 14 (12.3%) |
| Concomitant medications, n (%) | |
| COMT inhibitors | 23 (20.2%) |
| MAO-B inhibitors | 47 (41.2%) |
| Dopamine agonists | 55 (48.2%) |
| Amantadine | 28 (24.6%) |

At baseline, most patients still had a Hoehn and Yahr score less than 2 to 2.5 but the mean time since fluctuations began was 4.7 years. Patients came into the study already on levodopa and at least one adjunct medication. About a third of patients came in on less than the 720 mg of levodopa that ND0612 provides, while ⅔ came in on higher doses. The baseline medication data show that patients who stayed on treatment past one year came into the trial with a broad range of baseline severities.

94 patients completed 2 years of treatment. 76 patients completed 3 years of treatment. While infusion skin reactions emerge in most patients, they generally get very used to them and they were only a cause of discontinuation in 4 patients in the third year. Adverse events are summarized in the table below.

TABLE 3

| | 1st year (N = 114) | 3nd Year (N = 112)* | 3rd Year (N = 94) |
|---|---|---|---|
| Any TEAE (treatment emergent adverse event) | 93.0% | 71.2% | 77.7% |
| Drug-related TEAEs | 73.7% | 36.6% | 39.4% |
| Severe TEAEs | 16.7% | 12.6% | 10.6% |
| Serious TEAEs | 15.8% | 13.5% | 19.1% |
| Infusion-site reaction | 60.5% | 26.1% | 27.7% |
| Dyskinesia | 3.5% | 0 | 1.1% |

*N = 114 in first year versus N = 112 in second year: 2 patients completed 1 year but not 365 days, so they were not included in the second year data set.

Figure 4:
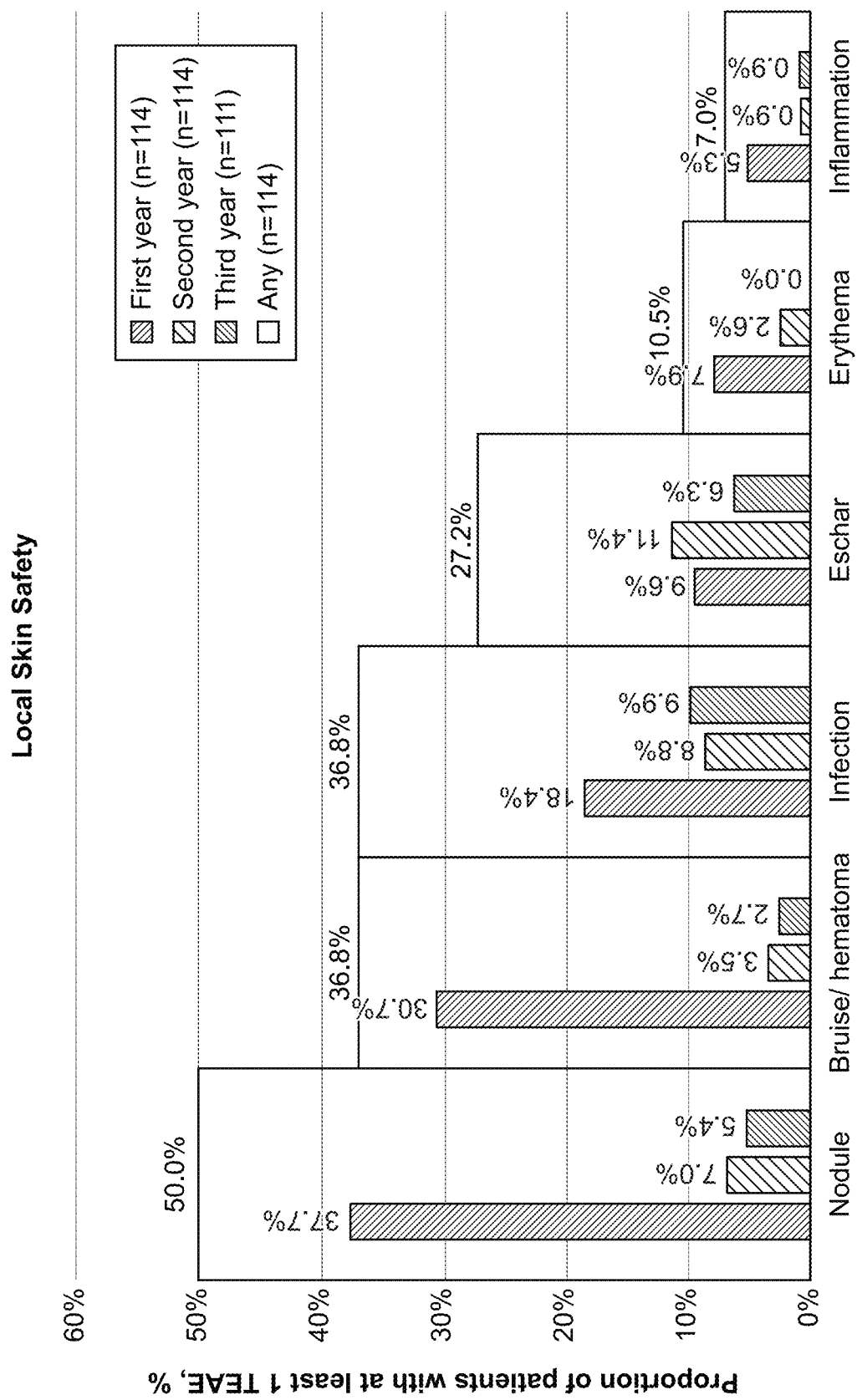
FIG. 4 is a graph showing the drug related TEAEs reported in the first three years of the continuous subcutaneous levodopa/carbidopa infusion for Parkinson's disease described in Example 2.

The favorable safety profile seen at one year continued through the study. Drug related TEAEs mainly reflected infusion site reactions, and these tended to be reported as an adverse event less often over time (FIG. 4). Otherwise, the systemic safety was as expected for a levodopa product. Of note, dyskinesia was rarely reported as an TEAE.

Figure 5:
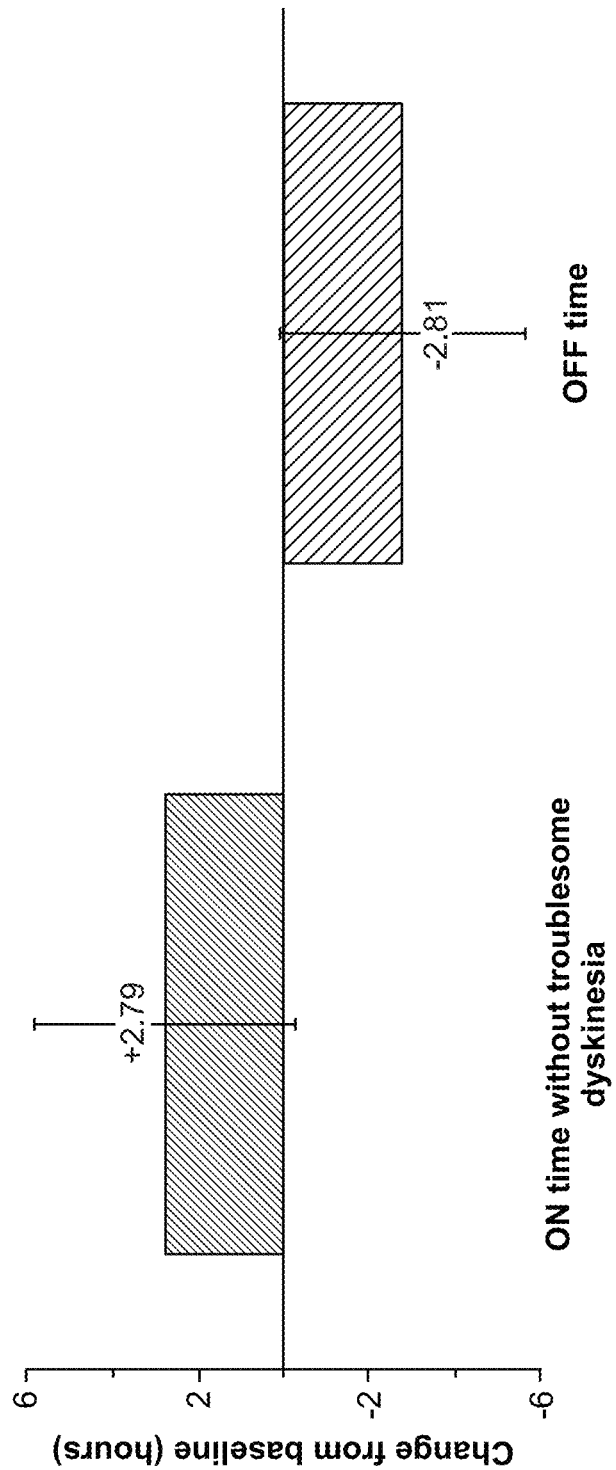
FIG. 5 is a graph showing the increase in ON-time without troublesome dyskinesia and the reduction in OFF-time observed at month 36 of the continuous subcutaneous levodopa/carbidopa infusion for Parkinson's disease described in Example 2. Waking hours were normalized to 16 hours.

Improvements in ON-time and OFF-time remained clinically relevant at 3 years and were generally similar to that already reported at 1 year, showing a good maintenance of efficacy as one would expect with levodopa (FIG. 5).

Conclusions: This open-label study provides support for the 12-month and 36-month efficacy of treatment with ND0612 in reducing OFF-time in patients with PD experiencing motor fluctuations.

ND0612 treatment shows a favorable safety profile and is well tolerated over the longer term in patients with PD experiencing motor fluctuations. The systemic safety profile of ND0612 is that typical to known oral LD/CD. Infusion site reactions are common, mostly mild, and infrequently lead to discontinuation. Of the patients continuing in the OLE (open label extension), ISRs (infusion site reactions) led to discontinuation in 4 patients (3.5%) over 3 years. Patients achieved clinically relevant increases in ON-time without troublesome dyskinesia as well as reduction in OFF-time.

Example 3—Safety and Efficacy of Continuous Subcutaneous Levodopa/Carbidopa Infusion for Parkinson's Disease: Case Study Case studies: This example describes four case studies from the trial described in Example 2 above.

Case 1:

Patient: Patient is male, aged 67.9 years old with BMI 32.5, 12 years since PD diagnosis; H&Y Stage 3; motor fluctuations with no dyskinesia for 7 years; levodopa (ER) daily dose 800 mg in 4 doses; amantadine 300 mg/day and selegiline 5 mg/day.

ND0612 treatment: 4.5 years of treatment with ND0612, at a daily dose of 720 mg/90 mg, levodopa/carbidopa, provided together with adjunct oral extended release (ER) levodopa (625 mg daily).

Safety and tolerability: Over 4.5 years, there were nodules of moderate intensity ongoing since the first months of ND0612 initiation; mild/moderate infusion site reactions (eschars, erosions, edema, erythema); 3 events of infection (cellulitis/abscess), all resolved without treatment discontinuation (1 abscess reported as serious); moderate constipation and vitamin B6 deficiency.

Results: For this patient, the baseline of Good ON-time was 10.2 hours and the baseline daily OFF-time was 5.8 hours. After 36 months of treatment, the Good ON-time increased by 2.2 hours, and the daily OFF-time decreased by 2.2 hours. It is noted that the motor status was normalized to 16 waking hours.

Case 2:

Patient: Patient is female, aged 63.9 years old with BMI 23.4, 11 years since PD diagnosis; H&Y Stage 2; motor fluctuations and dyskinesia for 3 years; levodopa (ER) daily dose 2200 mg in 5 doses; amantadine 200 mg/day.

ND0612 treatment: 4.5 years of treatment with ND0612, at a daily dose of 720 mg/90 mg, levodopa/carbidopa, provided together with adjunct oral extended release (ER) levodopa (780 mg daily) as well as amantadine (200 mg/day).

Safety and tolerability: Over 4.5 years, there were mild to moderate infusion site reactions (nodules, hematomas, excoriation, eschar); 5 events of infection (cellulitis/abscess) all resolved with oral antibiotics; no systemic AE reported.

Results: For this patient, the baseline of Good ON-time was 13.3 hours and the baseline daily OFF-time was 2.7 hours. After 36 months of treatment, the Good ON-time increased by 2.7 hours, and the daily OFF-time was eliminated. It is noted that the motor status was normalized to 16 waking hours.

Case 3:

Patient: Patient is female, aged 65.8 years old with BMI 22.8, H&Y Stage 2.5; motor fluctuations for 5 years; dyskinesia for 4 years; levodopa (ER) daily dose 900 mg in 5 doses; ropinirole 4 mg/day.

ND0612 treatment: 4.7 years of treatment with ND0612, at a daily dose of 720 mg/90 mg, levodopa/carbidopa, provided together with adjunct oral extended release (ER) levodopa (350 mg daily).

Safety and tolerability: Over 4.7 years, there were moderate bruising and mild pain at infusion sites that resolved over time; moderate nodules, one which has persisted for about 19 months; no systemic AE reported.

Results: For this patient, the baseline of Good ON-time was 5.4 hours and the baseline daily OFF-time was 8.5 hours. After 36 months of treatment, the Good ON-time increased by 7.7 hours, and the daily OFF-time decreased by 5.5 hours. This patient also had baseline 2 hours of ON-time with troublesome dyskinesia, and at the month 36 visit, she had no ON-time with troublesome dyskinesia. It is noted that the motor status was normalized to 16 waking hours.

Case 4:

Patient: Patient is male, aged 60.7 years old with BMI 22.9; H&Y Stage 2.5; motor fluctuations for 1 year; levodopa (ER) daily dose 750 mg in 5 doses; rasagiline 1 mg/day.

ND0612 treatment: 4.25 years of treatment with ND0612, at a daily dose of 720 mg/90 mg, levodopa/carbidopa, provided together with adjunct oral extended release (ER) levodopa (1000 mg daily).

Safety and tolerability: Over 4.25 years, there were mild nodules and moderate erythema at infusion site; 1 event of mild infection at infusion site, which resolved; mild urticaria reaction which resolved without any corrective treatment and without interruption of study drug.

Results: For this patient, the baseline of Good ON-time was 7.6 hours and the baseline daily OFF-time was 8.3 h. After 36 months of treatment, the Good ON-time increased by 4.1 hours, and the daily OFF-time decreased by 4.6 hours. It is noted that the motor status was normalized to 16 waking hours.

Example 4—Efficacy of Continuous, Subcutaneous Levodopa/Carbidopa Infusion (ND0612) on Motor Signs of PD and Experiences of Daily Living Objective: Evaluate the effect of investigational ND0612 on motor signs of PD and motor experiences of daily living (m-EDL), as assessed using the MDS-UPDRS.

Background: BouNDless study demonstrated superiority of ND0612 over immediate-release levodopa/carbidopa (IR-LD/CD) in reducing motor fluctuations and improving m-EDL (MDS-UPDRS Part II).

Design/Methods: MDS-UPDRS Part II and Part III (at OFF-state) subscores were assessed in the BouNDless study at ND0612 initiation (i.e., in the run-in phase) and at double-blind period Weeks 8 and 12. Presented here is a descriptive analyses of changes from ND0612 initiation to each double-blind visit. Additionally, a post hoc analysis was performed with grouped symptom-related items (from Parts II and III) for tremor, rigidity, bradykinesia, postural instability gait disorder (PIGD), speech and oral health, and self-care using a Mixed Model for Repeated Measures. P values are displayed nominally with no adjustment.

Results: Treatment differences (ND0612 vs IR-LD/CD) in Part II subscores favoring ND0612 over IR-LD/CD were observed at both Week 8 (mean [95% CI] difference: −2.4 [−3.5, −1.3]) and Week 12 (−3.1 [−4.3, −1.8]). Similarly, treatment differences in Part III subscores were −4.2 [−6.7, −1.7] at Week 8 and −2.4 [−5.2, 0.4] at Week 12. Differences favoring ND0612 vs IR-LD/CD were observed for PIGD (−0.26 vs 0.02, p=0.0012), speech and oral health (−0.11 vs 0.05, p=0.0140), tremor (−0.15 vs −0.05, p=0.0992), and self-care (−0.08 vs 0.09, p=0.0528). No relevant differences were observed for rigidity and bradykinesia.

Conclusions: In addition to reducing motor fluctuations, our results support the clinical benefit of ND0612 24-hour continuous subcutaneous therapy across different symptom domains of MDS-UPDRS II and III.

Example 5-Dose Proportionality

Example 5a

Dose proportionality of levodopa (LD) and carbidopa (CD) administered subcutaneously was demonstrated in a clinical trial (ND0612-001, a single dose, single-center, randomized, double-blind, placebo controlled, dose escalation study in healthy male subjects).

Subjects were administered with a composition comprising LD (6% w/w)/CD (1.4% w/w) by way of a 24 hour continuous infusion at varying infusion rates:
Group 1:80 μl/h
Group 2:120 μl/h
Group 3:160 μl/h
Group 4:200 μl/h
Group 5:240 μl/h Several PK parameters were derived for both LD and CD in the dose proportionality assessment, including AUC (hr*ng/ml), $C_{max}$ (ng/ml), $C_{15}$ (ng/ml), and $C_{24}$ (ng/mL).

Figure 8:
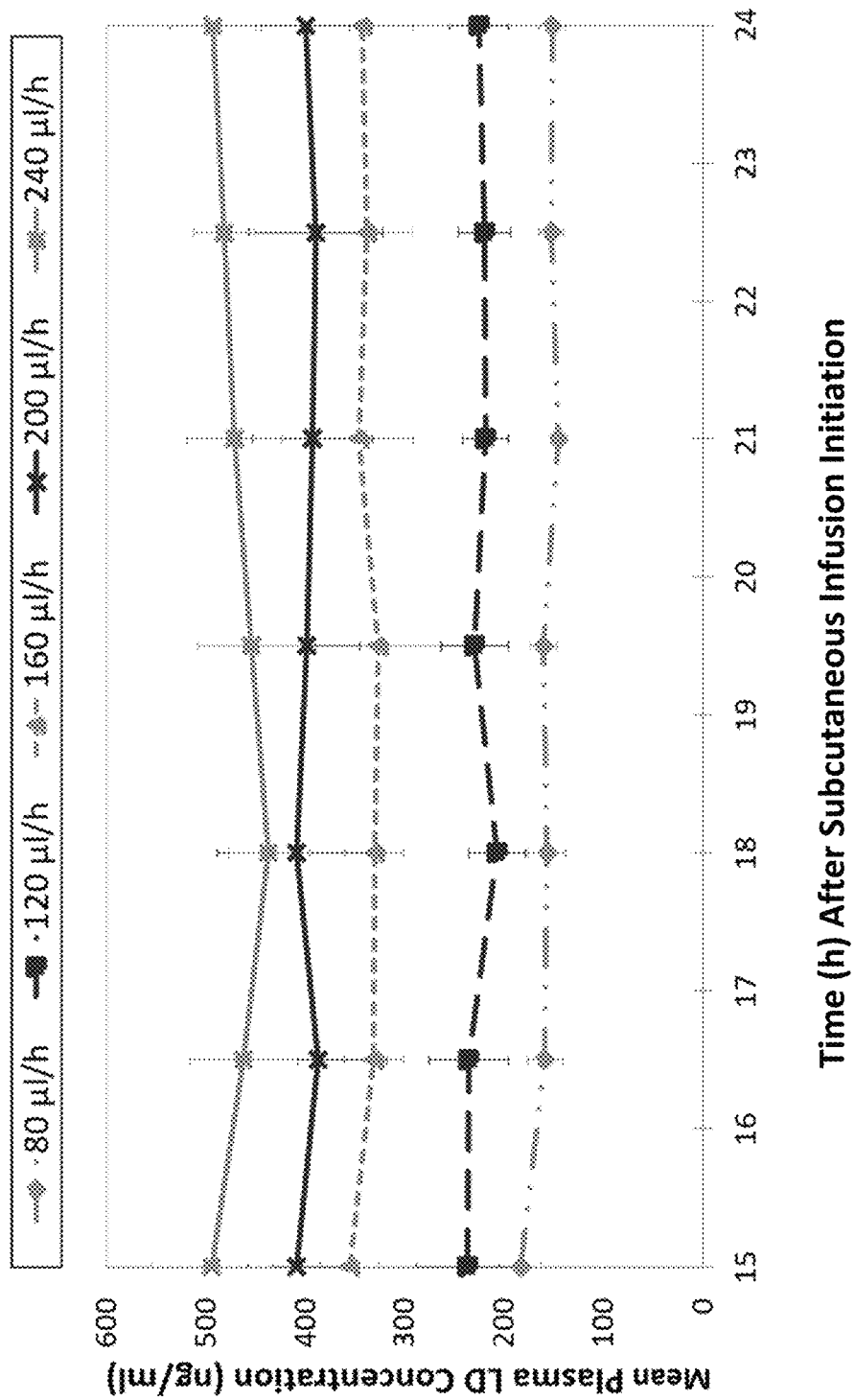
FIG. 8 provides a graph showing the mean plasma levodopa concentration of five tested groups vs the time in hours after subcutaneous infusion initiation.

All analyses performed for all PK parameters studied demonstrated dose proportionality for both LD and CD. Reference is made to FIG. 8, which presents the mean plasma levodopa concentration of the five tested groups .vs. the time (in hours) after subcutaneous infusion initiation. As clearly shown in FIG. 8, the levodopa plasma levels are dependent on the administered dose of levodopa and are proportional to one another. Similar results were obtained for carbidopa.

Example 5b

Figure 9:
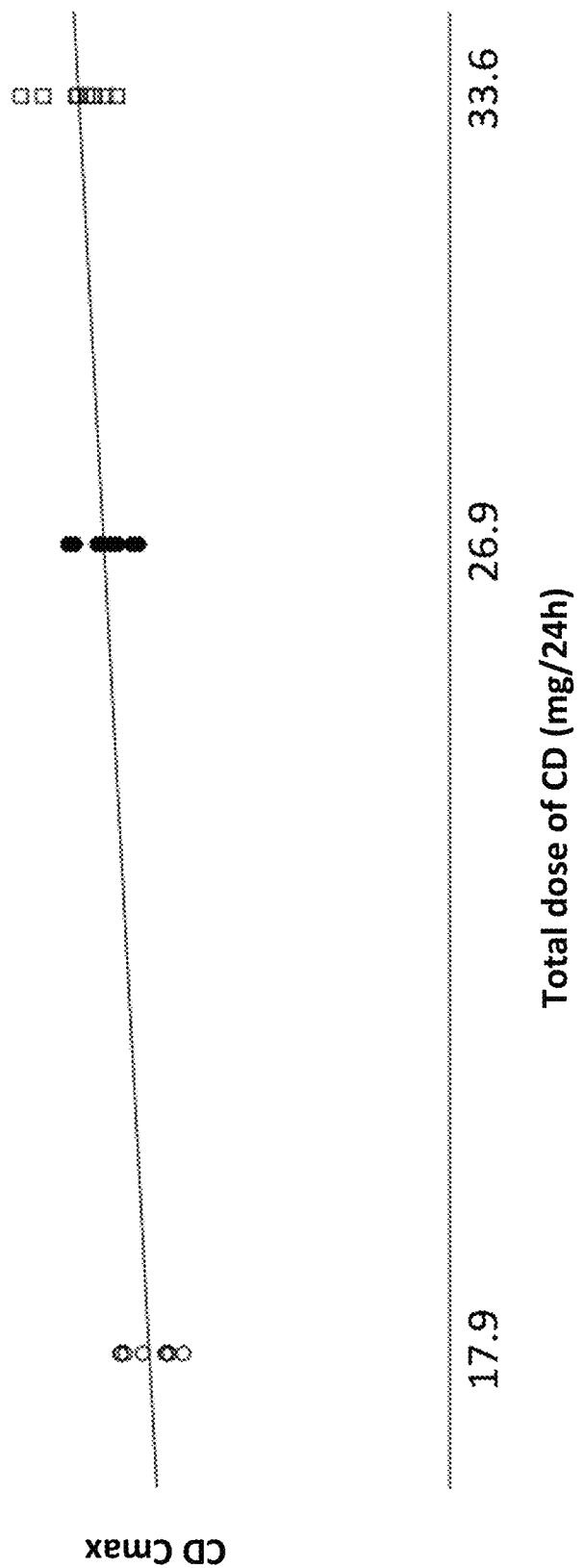
FIG. 9 provides a graph showing $C_{max}$ carbidopa values obtained from the subcutaneous administration of three different administered carbidopa concentrations.

In a separate clinical trial (ND0612-005a and ND0612-005b, open label design studies), the plasma carbidopa levels were tested in view of the subcutaneous administration of several carbidopa doses. Three formulations, comprising 60 mg/ml levodopa and (a) 7.5 mg/ml; (b) 6 mg/ml; or 4 mg/ml of carbidopa, were administered to three groups of subjects over the course of 24 hours, providing a total of 17.9 mg/24 h carbidopa to each subject in the first group, 26.9 mg/24 h carbidopa to each subject in the second group and 33.6 mg/24 h carbidopa to each subject in the third group. The obtained carbidopa Cmax values showed clear dose proportionality (see FIG. 9).

Example 6—Continuous Subcutaneous Levodopa-Carbidopa Infusion (ND0612) Compared with Oral Immediate-Release Levodopa-Carbidopa in Treating Parkinson's Disease with Motor Fluctuations. A Phase 3 Randomised, Double-Blind, Double-Dummy Trial (BouNDless)

This was a randomised, double-blind, double-dummy, active-controlled study conducted at 117 academic and community neurology sites across the USA, Europe, and Israel. Patients with PD who experienced ≥2.5 h/day of OFF-time underwent an open-label, run-in phase (up to 12 weeks) during which their optimal oral IR-LD/CD regimen and then their optimal ND0612 (with supplemental oral levodopa/carbidopa) regimen were established. Participants were then randomised (1:1 stratified by region using a permuted block schedule) to 12 weeks of double-blind, double-dummy treatment with either their optimised ND0612 or oral levodopa/carbidopa regimens. The primary efficacy endpoint was the change from randomisation to end of the double-blind phase in total daily ON-time without troublesome dyskinesia.

Figure 6:
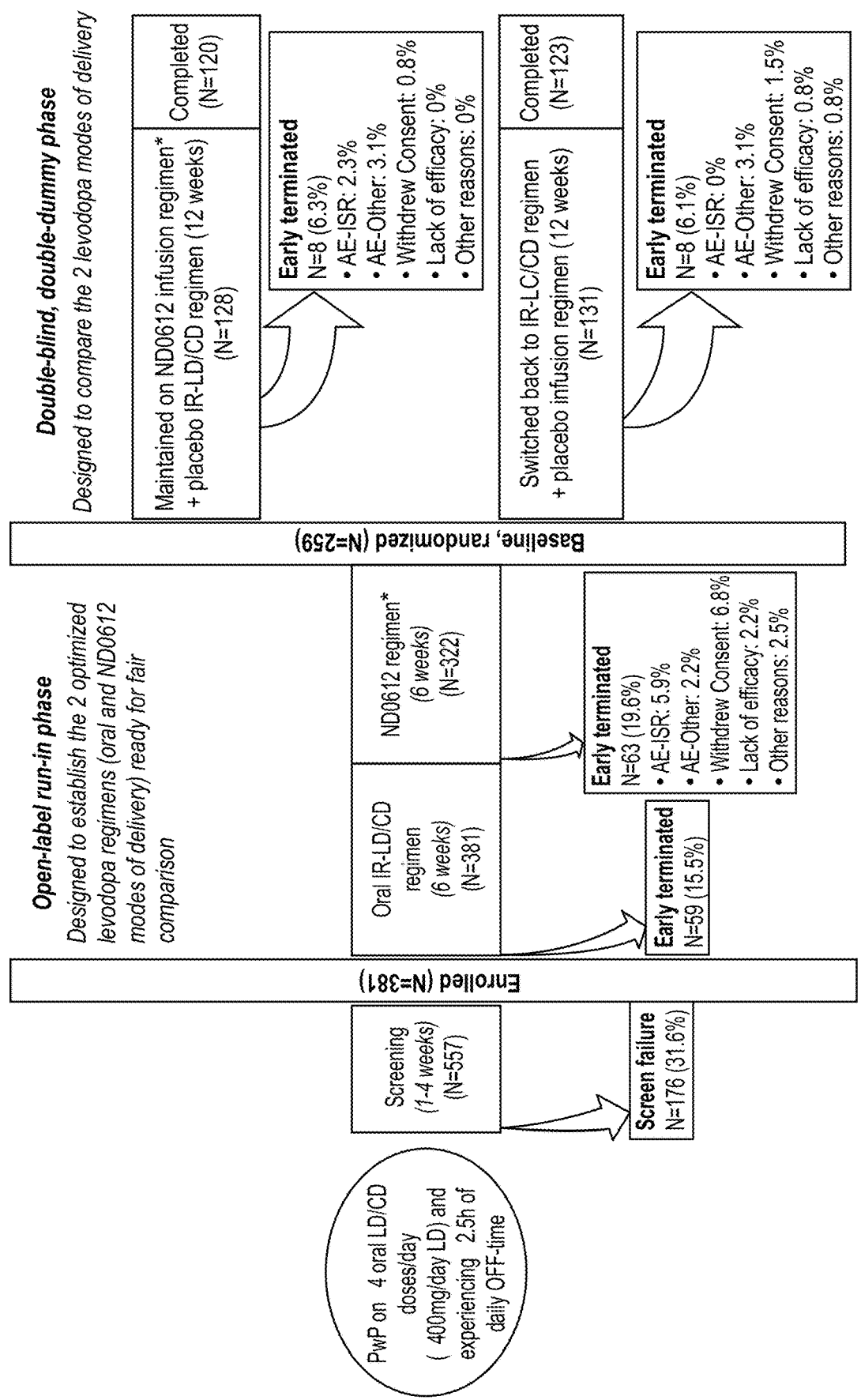
FIG. 6 provides a flow chart describing the patient flow through the active-controlled study with an open-label run-in and a randomized double-blind, double-dummy comparative phase.

Design/Methods: A phase 3, double-blind, double-dummy, active (IR-LD/CD) controlled, multicentre pivotal trial of ND0612 was conducted at 117 academic and community neurology sites in 16 countries across the USA, Europe, and Israel. The study included a screening period (1-4 weeks), an open-label run-in phase (8-12 weeks) to establish the optimised clinical status and experimental treatment regimens for fair comparison (initially 4-6 weeks to optimise IR-LD/CD dosing followed by 4-6 weeks to optimise ND0612), and a randomised, double-blind, double-dummy, active-controlled phase (12 weeks) (FIG. 6). At the end of the double-blind phase, participants could choose to continue treatment with ND0612 in an optional open-label extension study (results to be reported separately).

Eligible participants were males and females (as identified by medical records) aged 30 years or older with a diagnosis of Parkinson's disease (Hoehn and Yahr Stage ≤3 in ON state). Participants were required to be on at least 4 daily doses of oral levodopa/decarboxylase therapy or 3 daily doses of extended-release LD/CD capsules (Rytary®), with a total daily levodopa equivalent dose of at least 400 mg. Participants underwent training on a self-completed home diary, capturing their response to medications every 30 minutes. Participants were eligible if they experienced a mean average OFF-time of ≥2.5 h/day over 3 consecutive days (≥2 h each day) that could not be further improved by adjusting antiparkinsonian medications (as determined by the treating physician). Eligibility was confirmed at the end of the screening period by an independent Enrolment Committee, who operated under a pre-specified charter. Key exclusion criteria were atypical or acquired parkinsonism, acute psychosis or troublesome hallucinations in the prior 6 months, previous surgical treatment for PD, use of apomorphine or inhaled levodopa, severe disabling dyskinesia, or any unstable medical, surgical, or psychiatric condition or laboratory abnormalities which could represent a safety risk or prevent full study participation.

Randomisation and Masking: Randomisation was performed at the start of the double-blind, double-dummy phase (termed baseline/randomisation visit). Participants who completed the open-label run-in phase were randomly assigned by the interactive web response system (Suvoda LLC) in a 1:1 ratio to receive their optimised ND0612 or IR-LD/CD regimen achieved during the run-in phase. Randomisation was stratified by region using a permutated block schedule.

To ensure treatment allocation remained masked during the double-blind phase, a double-dummy approach was employed in which participants randomised to ND0612 also received oral placebo for their IR-LD/CD treatment regimen (i.e., patients received the same number of capsules at the same times of day), and participants randomised to IR-LD/CD also received a placebo infusion for their ND0612 treatment regimen. ND0612 and matching placebo solutions were supplied in identical vials and packaging. The active IR-LD/CD capsules (supplied as encapsulated tablets 100/25 mg) were also identical in packaging and of similar appearance to their placebo counterparts. Study sites had three distinct personnel with non-overlapping roles: an efficacy rater, a safety assessor, and a designated member of staff to perform drug accountability procedures and manage potential situations of unintentional unblinding. Scheduling efforts were made such that participants did not meet each other, and participants were advised at the beginning of each study visit not to discuss any adverse reactions with the efficacy rater.

Procedures: The open-label run-in phase comprised two parts. Enrolled patients initially underwent an oral IR-LD/CD optimisation period (4-6 weeks to include at least 2 weeks of stable dosing) where the participants' current oral levodopa formulations, including COMT inhibitors, were converted to equivalent doses 16 of supplied IR-LD/CD (100-mg increments) and adjusted until the dose was optimised (investigator's judgment). Use of any other levodopa formulations or COMT inhibitors was then prohibited until the end of the double-blind phase. Other antiparkinsonian medications were kept stable during the entire study. Once the appropriate IR-LD/CD regimen was identified and eligibility was reconfirmed, participants entered an open-label ND0612 optimisation period (4-6 weeks, including ≥2 weeks of stable dosing), during which treatment was initiated with ND0612 (replacing up to 700 mg of oral IR-LD/CD) and complemented as needed with oral IR-LD/CD (including at least a morning dose). The pump system was pre-programmed to deliver fixed night-time and flexible daytime rates of 6 h and 18 h, respectively. The night rate was fixed at 0.08 mL/h providing approximately 30-mg levodopa for the 6-h period. The flexible day rate could be adjusted by the investigator to a maximal rate of 0.64 mL/h, providing approximately 690-mg levodopa over 18 h, for a total of up to 720 mg/day. If patients required less than the 720 mg of levodopa from ND0612, the daytime pump flow rate was reduced until optimisation.

Participants who completed the open-label run-in phase were then randomised either to maintain their optimised ND0612 regimen (i.e., ND0612 plus complementary IR-LD/CD) with the addition of placebo IR-LD/CD or switched back to their optimised IR-LD/CD plus placebo for the ND0612 regimen for a further 12 weeks of double-blind, double-dummy treatment. Throughout the trial, ND0612 and matching placebo infusion were self-administered via 2 subcutaneous sites (up to 6 mL per site over 24 h) connected to a single ambulatory pump system. The infusion sets and syringes were changed every day at the same time and participants and their care partners were trained in their homes on the proper operation of the pump system, as well as the importance of maintaining good skin hygiene.

Endpoints: The primary efficacy endpoint was the change from baseline/randomisation to the end of the double-blind phase in average hours of daily ON-time without troublesome dyskinesia (sum of ON-time without dyskinesia and ON-time with non-troublesome dyskinesia) as assessed by a patient home diary over 3 consecutive days before the visits. Nine secondary efficacy endpoints were prespecified in hierarchical order: (1) daily normalised OFF-time as assessed by the home diary over 3 consecutive days (key secondary endpoint); (2) Motor Experiences of Daily Living as assessed by the Movement Disorder Society-Unified PD Rating Scale (MDS-UPDRS) part II score; (3) Patient Global Impression of Change (PGIC); (4) Clinical Global Impression of Improvement (CGI-I); (5) motor symptoms as assessed by the MDS-UPDRS part III score (during OFF state); (6) daily normalised ON-time without dyskinesia; (7) proportion of OFF-time responders (response defined as ≥50% reduction in OFF-time; (8) PD Questionnaire-39 (PDQ-39) summary index scores; and (9) PD Sleep Scale-2 (PDSS-2) total score. Changes in patient diary and rating scale scores were assessed between randomisation and end of the double-blind phase, while the frame of reference for PGIC, CGI-I, and responder rates was from the start of open-label ND0612 treatment to the end of the double-blind phase. Daily ON and OFF-times were normalised to a typical waking day (16 h) to account for different sleep patterns across participants. In addition, the changes in diary motor states from the time of study enrolment to end of the open-label and double-blind phases were analyzed as exploratory endpoints.

Safety and tolerability were assessed by the incidence of adverse events (AEs), changes in vital signs, clinical laboratory parameters, electrocardiograms, the Columbia-Suicide Severity Rating Scale (C-SSRS), the Questionnaire for Impulsive-Compulsive Disorders in PD-Rating Scale (QUIP-RS), and the Epworth sleepiness scale (ESS). AEs of special interest were predefined as infusion site reactions (ISRs), hypersensitivity, and polyneuropathy; a blinded independent adjudication process was implemented for AEs of hypersensitivity and polyneuropathy. Investigators received training on the identification, management, and reporting of ISRs, including assessments of pain (visual analogue scale [VAS]), as well as patient and clinician assessment of local skin reaction burden. All ISRs were reported irrespective of severity or burden.

An independent data safety monitoring committee (comprised of a neurologist, a dermatologist, and a statistician, all not otherwise involved in the trial) reviewed safety data every six months. At the end of the study, participants completed a blinding questionnaire which asked what treatment they believed they were on during the double-blind, double-dummy period and why.

Results: 557 participants were screened and 381 were enrolled (FIG. 6). Of these, 259 completed the open-label run-in phase and were randomly allocated in the double-blind, double-dummy phase, and 243 completed the study. The primary reasons for drop-out in the open-label run-in phase were withdrawal of consent (7.9% during oral IR-LD/CD optimisation and 6.8% during ND0612 optimisation) followed by AEs (4.2% during oral IR-LD/CD optimisation and 8.1% during ND0612 optimisation). During the double-blind phase, discontinuation rates were similar for the two treatment arms (ND0612 6.3% vs IR-LD/CD 6-1%). The table below shows the key demographic and clinical characteristics of the ITT set at screening and enrolment. Mean (SD) total daily levodopa doses increased from 1079 (487) mg at enrolment to 1237 (447) mg at randomisation for the ND0612 arm (including 534 mg from adjunct oral levodopa), and from 981 (450) mg at enrolment to 1065 (409) mg at randomisation in the IR-LD/CD arm.

TABLE 4

Participant characteristics

| | Oral IR-LD/CD (N = 131) | ND0612 (N = 128) |
|---|---|---|
| Assessed at screening | | |
| Age (years) | 63.5 (8.5) | 63.5 (9.5) |
| Sex | | |
| Female | 51 (39%) | 43 (34%) |
| Male | 80 (61%) | 85 (66%) |
| BMI (kg/m2) | 26.3 (4.6) | 26.6 (4.3) |
| Time since diagnosis of Parkinson's disease (years) | 9.9 (4.7) | 9.3 (3.8) |
| Time since onset of motor fluctuation (years) | 4.9 (3.7) | 4.1 (2.9) |

TABLE 4-continued

Participant characteristics

| | Oral IR-LD/CD (N = 131) | ND0612 (N = 128) |
|---|---|---|
| Assessed at enrolment | | |
| ON-time without troublesome dyskinesia (h)* | 9.4 (1.9) | 9.4 (1.7) |
| Assessed at screening | | |
| OFF-time (h)* | 6.1 (1.9) | 6.1 (1.6) |
| Levodopa dose (mg); mean (SD) | 981 (450) | 1079 (487) |
| [range]** | [380-3325] | [400-3188] |
| Proportion of patients receiving | | |
| Dopamine agonists | 87 (66%) | 77 (60%) |
| MAO-B inhibitors | 60 (46%) | 63 (49%) |
| COMT inhibitors | 46 (35%) | 45 (35%) |
| Anticholinergics | 2 (2%) | 4 (3%) |
| Amantadine | 53 (40%) | 37 (29%) |
| Other antiparkinsonian medication | 1 (1%) | 2 (2%) |

Data are mean (SD) unless otherwise stated.
*Data normalised to 16 h,
**levodopa dose including COMT.
BMI = body mass index,
COMT = Catechol-O-methyl transferase,
MAO-B = Monoamine Oxidase type B.

Figure 7:
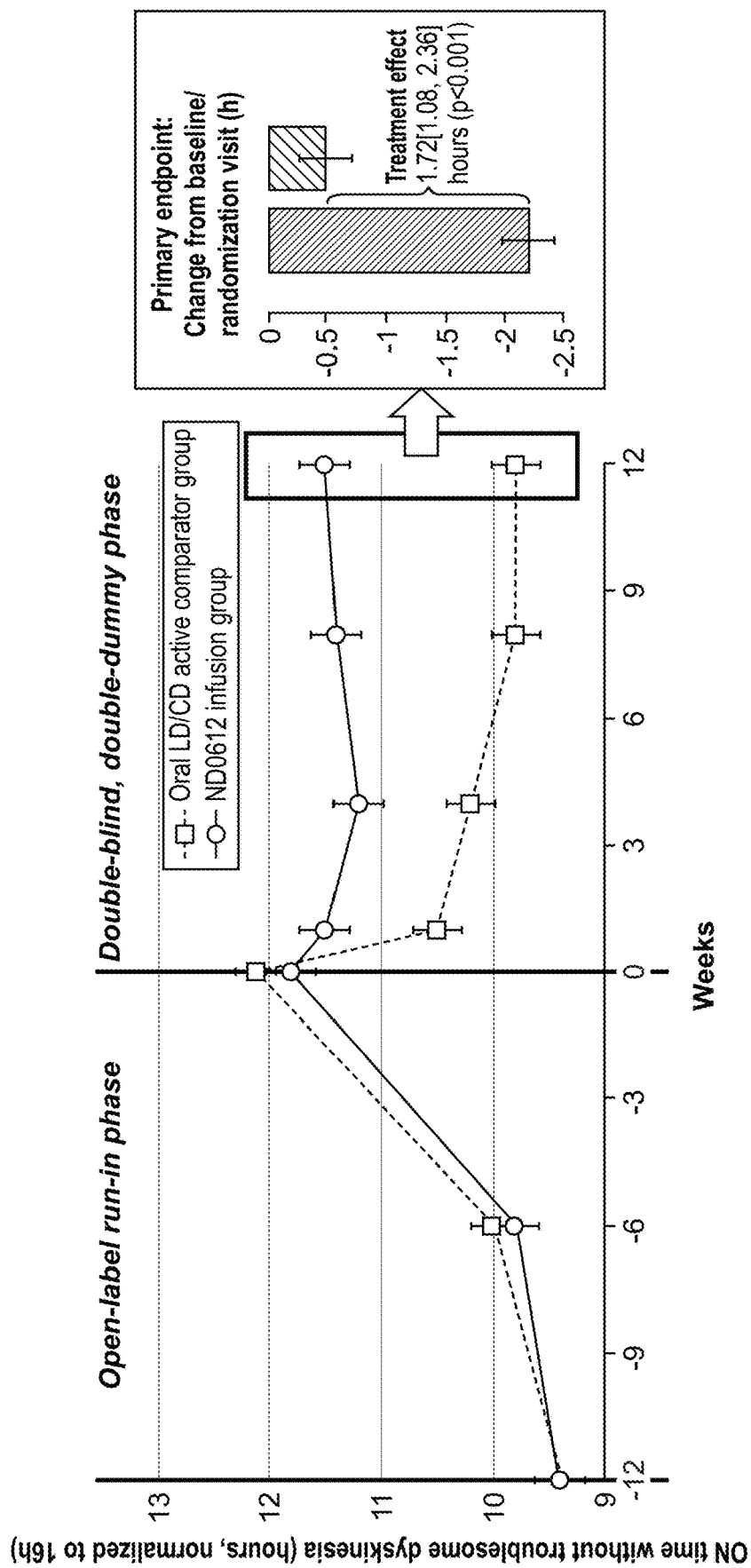
FIG. 7 is a graph showing that treatment with ND0612 provided an additional 1.72 h of ON-time without troublesome dyskinesia compared to immediate release levodopa/carbidopa (IR-LD/CD; p<0.0001).

In the ND0612 open-label run-in phase, mean normalised ON-time without troublesome dyskinesia increased while receiving open-label ND0612 from 9.4 h (both arms) at enrolment to 11.8 h at randomisation in the ND0612 arm and 12.1 h in the IR-LD/CD arm. During the 12 weeks of double-blind treatment, the gain in ON-time without troublesome dyskinesia was maintained in the ND0612 arm (11.47 h at study endpoint) and decreased in the IR-LD/CD arm (9.75 h at study endpoint). Thus, the trial met its primary efficacy endpoint with ND0612, providing an additional 1.72 h [95% CI: 1.08 to 2.36 h] of ON-time without troublesome dyskinesia at Week 12 compared to IR-LD/CD ($p<0.0001$) (table below; FIG. 7).

TABLE 5

Summary of primary and secondary efficacy findings

| | Oral IR-LD/CD (N = 131) | ND0612 (N = 128) | Treatment difference | p value |
|---|---|---|---|---|
| ON-time without troublesome dyskinesia*, h/day | −2.20 (0.23) [−2.65 to −1.74] | −0.48 (0.23) [−0.94 to −0.02] | 1.72 (0.33) [1.08 to 2.36] | <0.0001 |
| OFF-time*, h/day | 1.90 (0.22) [1.48 to 2.32] | 0.50 (0.22) [0.07 to 0.92] | −1.40 (0.30) [−1.99 to −0.80] | <0.0001 |
| MDS-UPDRS part II score | 2.75 (0.45) [1.87 to 3.62] | −0.30 (0.45) [−1.18 to 0.58] | −3.05 (0.63) [−4.28 to −1.81] | <0.0001 |
| Proportion of participants with PGI-C improvement** | 0.31 (0.05) [0.21 to 0.42] | 0.70 (0.05) [0.59 to 0.79] | Odds ratio 5.31 (0.35) [2.67 to 10.58] | <0.0001 |
| Proportion of participants with CGI-I improvement** | 0.31 (0.05) [0.22 to 0.43] | 0.77 (0.05) [0.66 to 0.85] | Odds ratio 7.23 (0.36) [3.57 to 14.64] | <0.0001 |
| MDS-UPDRS part III score | 3.39 (1.00) [1.43 to 5.36] | 0.98 (1.02) [−1.02 to 2.98] | −2.42 (1.42) [−5.20 to 0.37] | 0.089 |
| ON-time without dyskinesia*, h/day | −2.53 (0.25) [−3.03 to −2.04] | −0.41 (0.26) [−0.91 to 0.09] | 2.12 (0.36) [1.42 to 2.82] | — |
| Proportion of participants with ≥50% reduction in OFF-time** | 0.10 (0.03) [0.05 to 0.17] | 0.29 (0.06) [0.19 to 0.41] | Odds ratio 3.63 (0.43) [1.56 to 8.44] | — |
| PDQ-39 summary index score | 4.29 (0.77) [2.79 to 5.79] | 1.60 (0.78) [0.07 to 3.13] | −2.69 (1.09) [−4.83 to −0.55] | — |
| PDSS-2 total score | 1.47 (0.70) [0.10 to 2.84] | 0.05 (0.71) [−1.34 to 1.44] | −1.42 (0.99) [−3.35 to 0.52] | — |

Data are LS mean (SE) [95% confidence intervals] change from baseline to study endpoint (week 12 of double-blind, double-dummy phase) unless otherwise stated. Treatment difference is the difference between least squares mean changes (SE); odds ratios are presented as ND0612 vs IR-LD/CD.
*Diary data are normalised to 16 h,
**Based on categorical data of change from start of open-label treatment with ND0612 to study endpoint.
MDS-UPDRS = Movement Disorder Society-Unified Parkinson's Disease Rating Scale,
PDSS-2 = Parkinson's Disease Sleep Scale-2,
PDQ-39 = 39-item Parkinson's Disease Questionnaire.
IR-LD/CD: n = 122 for PGIC, n = 119 for CGI-C and 126 for off time responders;
ND0612: n = 121 for PGIC and CGI-C and n = 126 for off time responders.

Figure 10:
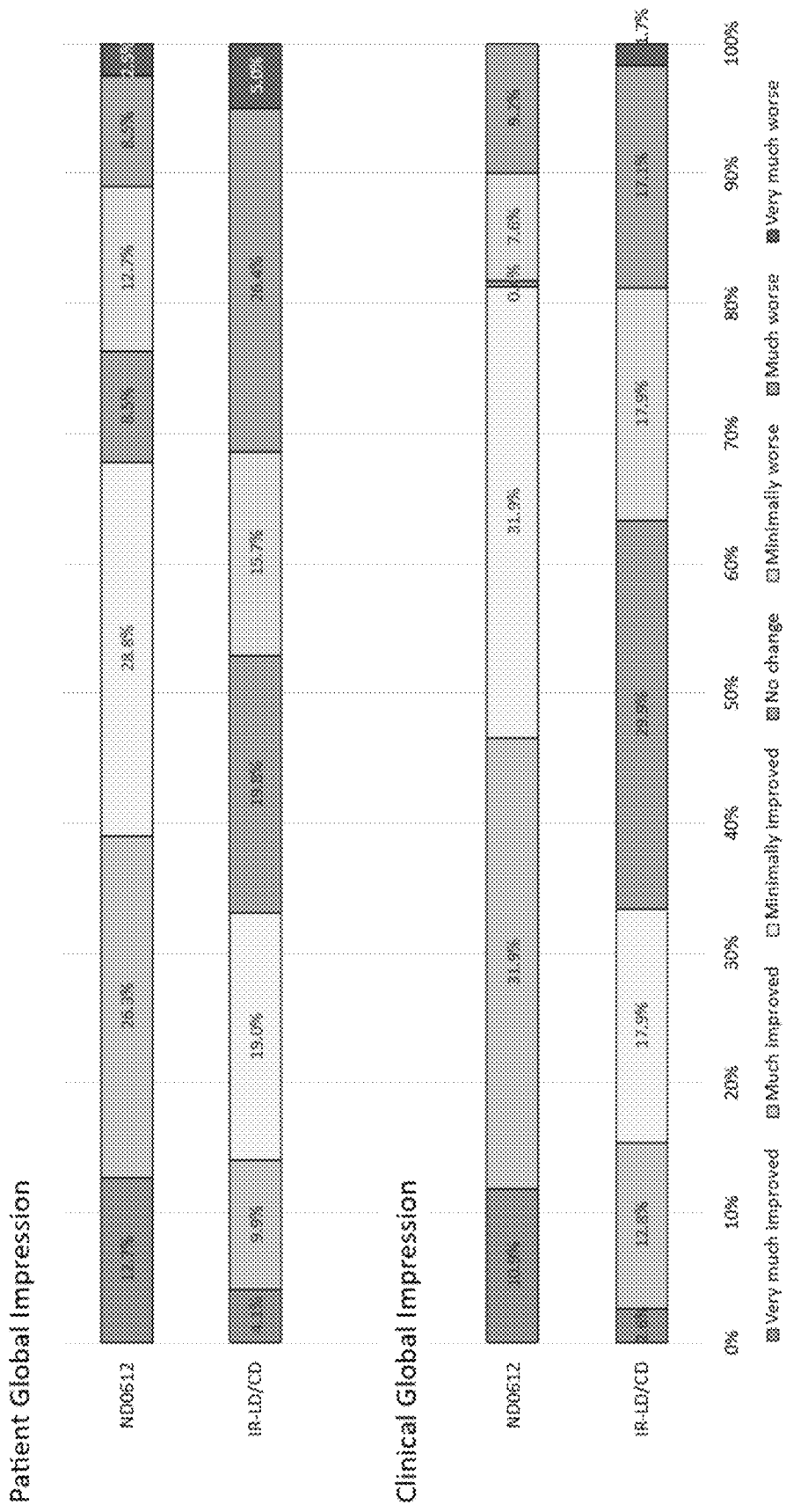
FIG. 10 provides a graph showing the PGI-C and CGI-I assessments of ND0612 versus IR-LD/CD.

Significant treatment differences vs IR-LD/CD were also seen in the first four hierarchical secondary endpoints (Table 4). The key secondary endpoint, reduction in normalised daily OFF-time, showed a treatment difference of −1.4 h [95% CI: −1.99 to −0.80] in favour of ND0612 vs IR-LD/CD (p<0-0001). ND0612 infusion also significantly improved MDS-UPDRS Part II scores compared to IR-LD/CD (−3.05 [95% CI: −4.28 to −1.81] points, p<0.0001). Results of the PGI-C and CGI-I assessments at week 12 were aligned, with significantly higher proportions of both participants and clinicians (FIG. 10) recording an improvement with ND0612 vs IR-LD/CD (both p<0.0001). Change in MDS-UPDRS part III score (during OFF) showed a numerical difference in favour of ND0612 but did not reach significance. While formal hierarchical testing was terminated at this comparison, analysis of normalised ON-time without dyskinesia, proportion of OFF responders, and PDQ-39 scores favoured ND0612 vs IR-LD/CD (Table 4) with nominal p values <0.05; there was no difference between treatment arms in PDSS-2 scores. In addition, analysis of diary motor states from enrolment to end of the double-blind phase indicated that reductions in OFF-time and in ON-time with dyskinesia (either troublesome or non-troublesome) were observed together with increases in ON without any dyskinesia with ND0612 but not with the IR-LD/CD regimen.

One participant died due to COVID-19 infection during open-label IR-LD/CD optimisation. During open-label ND0612 optimisation, 287 (89%) participants reported AEs, of which most (n=167, 58%) were rated as mild by the treating investigator (FIG. 11).

Six participants (2%) experienced serious AEs, of which three had serious AEs assessed as related to study treatment (nausea and visual hallucination; infusion site cellulitis; and infusion site abscess). Two hundred sixty-six (83%) participants reported ISRs, of which most were rated as mild (76%) or moderate (22%) events, and five (2%) participants experienced events rated as severe.

During the double-blind, double-dummy phase, AEs were reported by 103 (81%) participants in the ND0612 arm and 97 (74%) in the IR-LD/CD arm (FIG. 11). The incidence of serious adverse events was similar between the treatment arms. Serious AEs in four of the seven ND0612-treated participants were related to study treatment (infusion site abscess and infusion site ulcer; infusion site cellulitis [2 participants]; paraesthesia and peripheral sensorimotor neuropathy). One participant in the ND0612 arm died during the double-blind phase due to an AE assessed as not related to study treatment (fall leading to traumatic brain injury).

The rate of discontinuation due to AEs was highest in the open-label ND0612 phase (8.1%, n=26), with the most common reasons being infusion site nodule (4%), infusion site pain (3%), and infusion site haematoma (3%). During the double-blind phase, AEs led to discontinuation in seven (6%) participants in the ND0612 arm (including three due to ISRs) and four (3%) in the IR-LD/CD arm. Across the study, a total of 15 participants treated with ND0612 and one treated with placebo infusion (infusion site abscess) were referred to a dermatologist. Four (1.2%) participants had polyneuropathy AEs adjudicated to ND0612. Severe/serious polyneuropathy events were reported in only one participant and no participant required discontinuation of treatment due to polyneuropathy. One participant had a non-serious event of hypersensitivity during open-label ND0612 treatment, which resolved with antihistamine treatment and ND0612 discontinuation.

No clinically meaningful changes were observed for laboratory results, vital signs, or electrocardiogram for either treatment arm. Positive responses indicative of suicidal ideation or behaviour on C-SSRS were reported with a low and similar incidence across treatment arms (6 [5%] in the ND0612 arm and 6 [5%] participants in the IR-LD/CD arm). There was no evidence of impulse control disorders based on QUIP-RS data; one participant reported the appearance of compulsive shopping with ND0612 (resolved without treatment modification). Rates of daytime sleepiness as assessed by ESS remained low across the study and comparable between treatment arms, and mean scores never crossed the threshold of 10 points for relevant sleepiness. Similarly, the incidence of somnolence reported as an AE in the double-blind phase was 0 in the ND0612 arm and 2 (1.5%) in the IR-LD/CD arm.

Overall, a higher percentage of patients in the IR-LD/CD arm ($^{85}/_{131}$, 65%) correctly guessed their treatment allocation than those in the ND0612 arm ($^{63}/_{128}$, 49%), with the most common reason for guessing correctly being related to efficacy (IR-LD/CD, $^{49}/_{85}$ [58%] and ND0612, $^{53}/_{63}$ [84%]). One participant in the ND0612 arm and none in the IR-LD/CD arm correctly guessed their treatment allocation due to safety.

Conclusion: There were 381 participants enrolled, of whom 259 were randomised in the double-blind phase (ND0612 n=128, IR-LD/CD n=131), and 243 completed the study. At the end of the 12-week double-blind phase, treatment with optimised ND0612 provided an additional 1.72 h [95% CI: 1.08, 2.36] of ON-time without troublesome dyskinesia compared to IR-LD/CD (p<0.0001). Significant treatment differences favouring ND0612 were also found in the hierarchical secondary endpoints of daily OFF-time (−1.4 h [−1.99, −0.80], Movement Disorders Society-Unified Parkinson's Disease Rating Scale part II scores (−3.05 [−4.28, −1.81]), Patients Global Impression of Change (Odds Ratio [OR]: 5.31 [2.67, 10.58]), and Clinical Global Impression of Improvement (OR: 7.23 [3.57, 14.64]). The most reported adverse events were infusion site reactions (82.6% during open-label ND0612 optimisation and 57.0% for ND0612 vs. 42.7% for oral IR-LD/CD during the double-blind phase), most of which were mild.

Example 7—Quality of Life with 24-Hour Subcutaneous Levodopa/Carbidopa Infusion (ND0612): PDQ-39 Results from a Phase 3 Randomized, Active-Controlled Study Objective: Evaluate quality of life (QoL) data from the Phase 3 randomized, active-controlled BouNDless study.

Background: Pivotal data from the BouNDless study showed that treatment with investigational ND0612 provided patients with Parkinson's disease (PD) and motor fluctuations an additional 1.72 h [95% CI: 1.08 h, 2.36 h] of ON-time without troublesome dyskinesia compared with IR-LD/CD (p<0.0001).

Design/Methods: Patients with PD on ≥4 oral LD/CD doses/day (≥400 mg/day LD) and experiencing ≥2.5 h of daily OFF-time underwent 4-6 weeks of open-label IR-LD/CD dose adjustment followed by 4-6 weeks of open-label ND0612 conversion (+IR-LD/CD). Patients were then randomized (1:1) to 12-week double-blind treatment with either their optimized regimen of ND0612 or IR-LD/CD. Change from the start of open-label ND0612 conversion to end of double-blind treatment in QoL was assessed using the PD Questionnaire-39 (PDQ-39) and analyzed using ANCOVA following multiple imputation.

Results: At the end of the double-blind phase, the adjusted mean [95% CI] change in PDQ-39 index scores showed improvements with ND0612 treatment (−2.1 [−3.7, −0.6]) compared to no change in the IR-LD/CD group (+0.6 [−0.9, 2.1]), resulting in a treatment difference of −2.7 [−4.8, −0.6] (nominal p=0.014). PDQ-39 domain analyses favored ND0612 treatment in most domains; mean changes (ND0612 vs IR-LD/CD) were: mobility (−0.2 vs +2.4), bodily discomfort (−4.3 vs −2.3), cognition (−0.9 vs −0.3), activities of daily living (−0.6 vs −0.1), stigma (−2.6 vs −2.4), social support (0.4 vs 0.7), communication (2.3 vs −0.4), and emotional well-being (0.6 vs −1.3).

Note—the data in Example 7 is from before the first dose of ND0612 (V7, exploratory analysis from the start of the ND0612 open label conversion to the end of the DBDD period), while the data in Example 6 is from randomization (V13) to the end of the DBDD period. Accordingly, while the treatment difference is the same in both examples (−2.7), the results differ.

Conclusions: ND0612 improved quality-of-life as measured by PDQ-39 compared to IR-LD/CD, further supporting the clinical meaningfulness of the observed reduction in motor fluctuations from a PD patient perspective.

Example 8—Long-Term Efficacy of 24-Hour Subcutaneous Levodopa/Carbidopa Infusion (ND0612) for Motor Fluctuations in Parkinson's Disease: The BouNDless Open-Label Extension Objective: Describe 1-year efficacy outcomes from the ongoing open-label extension (OLE) phase of the BouNDless study of subcutaneous levodopa/carbidopa infusion (ND0612) for fluctuating PD patients.

Background: It has been previously reported that open-label treatment with ND0612 was associated with a sustained ≥2-hour increase in daily ON-time without troublesome dyskinesia (Good ON) and a reduction in OFF-time versus baseline. The double-blind phase of the BouNDless study demonstrated that treatment with investigational ND0612 provided patients an additional 1.72 h of Good ON-time compared with immediate-release levodopa/carbidopa (IR-LD/CD) (p<0.0001). Methods: Patients who completed the double-blind phase of the BouNDless study were eligible to enter the ongoing OLE phase (up to 54 months). Patients received ND0612 and all anti-PD medications (including ND0612) were adjusted according to individual response. This analysis was performed at 6 months and 1 year post enrollment of the last patient who entered the OLE. Changes in OFF-time, ON-time without dyskinesia, ON-time with non-troublesome dyskinesia, and ON-time with troublesome dyskinesia, measured from ND0612 initiation in the run-in phase of the pivotal study to Months 6 and 12 of the OLE phase, were normalized to 16 h and analyzed without imputation. Changes in ON-time with troublesome dyskinesia were analyzed for the subgroup of patients who had ≥1 h troublesome dyskinesia at treatment onset.

Results: Of 232 participants who entered the OLE phase (n=113 previously randomized to ND0612, n=119 previously randomized to IR-LD/CD), 167 (72%) completed 1 year of ND0612 treatment in the OLE phase. By Month 6, patients had a mean±SE change of −2.2±0.2 h in OFF-time and an +2.4±0.2 h in Good ON-time (+2.7±0.2 h in ON-time without dyskinesia and −0.3±0.2 in ON-time with non-troublesome dyskinesia). Efficacy benefits were sustained at Month 12 with a change of −2.1±0.2 h in OFF-time and +2.2±0.2 h in Good ON-time (+2.3±0.3 h in ON-time without dyskinesia and −0.2±0.2 h in ON-time with non-troublesome dyskinesia). Patients who had ≥1 h of ON-time with troublesome dyskinesia at ND0612 initiation (n=45) showed a change of −1.2±0.3 h at Month 6 and −1.5±0.3 h at Month 12.

Conclusions: Results corroborate previously published data on the long-term efficacy of ND0612 for PD patients experiencing motor fluctuations.

Example 9—Impact of 24-Hour Subcutaneous Levodopa/Carbidopa Infusion (ND0612) on Motor State Transitions Throughout the Day Objective: Evaluate the effect of investigational ND0612 infusion on the daily number of, duration of, and transitions between PD motor states, as assessed by home diaries.

Background: Primary efficacy analysis (ON-time without troublesome dyskinesia) demonstrated superiority of ND0612 over immediate-release levodopa/carbidopa (IR-LD/CD), with a significant difference of 1.72 h (p<0.0001).

Design/Methods: Post hoc analysis of diary data from the BouNDless study. The number and duration of episodes spent in the OFF state, ON without dyskinesia, ON with non-troublesome dyskinesia, and ON with troublesome dyskinesia (collected on the last day prior to each visit) were analyzed descriptively. Episodes were defined as time spent in a PD-diary state before transitioning to any other state. The total number of transitions between any motor state were analyzed by baseline-adjusted Poisson Regression.

Results: Motor state characteristics were balanced between ND0612 and IR-LD/CD groups prior to ND0612 initiation (i.e., in the run-in phase). At the end of the double-blind phase, patients in the ND0612 vs IR-LD/CD group experienced an average of 2.4 vs 3.3 OFF episodes per day, with a total daily OFF-duration of 3.8 h vs 5.2 h. Participants (ND0612 vs IR-LD/CD) experienced 2.7 vs 3.1 episodes of ON without dyskinesia (total duration of 9.4 h vs 7.4 h); 1.2 vs 1.4 episodes of ON with non-troublesome dyskinesia (total duration of 2.2 h vs 2.7 h); and 0.3 vs 0.5 episodes of ON with troublesome dyskinesia (total duration of 0.4 h vs 0.7 h). The mean number of daily transitions between motor states was lower with ND0612 compared to IR-LD/CD treatment (5.7 vs 7.3, p<0.0001).

Conclusions: Treatment with ND0612, versus IR-LD/CD, led to more stable motor control, as demonstrated by fewer daily transitions between motor states, and by more time in the ON state without any dyskinesia.

Example 10—Dopaminergic Adverse Events with 24-Hour Subcutaneous Infusion of ND0612

Objective: Characterize dopaminergic treatment-emergent adverse events (TEAEs) reported with 24 h ND0612 treatment in clinical studies.

Background: Dopaminergic adverse events are commonly reported across the spectrum of available dopaminergic therapies for PD. ND0612 is an investigational, continuous 24 h subcutaneous infusion of levodopa/carbidopa (max daily dose 720/90 mg) in development for the management of PD motor fluctuations.

Methods: An integrated safety analysis of dopaminergic TEAEs reported in PD patients treated with a 24 h regimen of ND0612 and supplemental immediate-release levodopa/carbidopa, from two phase 2 and one phase 3 study was conducted. Selected dopaminergic TEAEs of interest to this population included dizziness, nausea, vomiting, dyskinesia, hallucinations (grouped term), impulse control disorders (ICDs, grouped term), orthostatic hypotension, sleep disturbances, and somnolence. The exposure-adjusted incidence rate (EAIR) was calculated as the total number of patients who experienced a TEAE divided by the total time patients were at risk for the event (person-years).

Results: A total of 419 patients (528.8 person-years, median exposure to ND0612 of 346 days [up to 6.6 years]) were included in the analysis. The most common dopaminergic TEAE (% patients; EAIR) was dyskinesia (13.1%; 0.114). Other dopaminergic TEAEs were reported in less than 5% of patients: dizziness (4.3%; 0.035), hallucinations (3.8%; 0.031), orthostatic hypotension (3.6%; 0.029), nausea (2.9%; 0.023), somnolence (1.4%; 0.011), unspecified sleep disorder (1.2%; 0.010), and ICD (1.2%; 0.010). Vomiting, nightmares, REM sleep behavior disorders were reported in ≤3 patients each (≤0.7%; 0.006).

Conclusions: The 24 h continuous subcutaneous administration of ND0612 demonstrated overall tolerability and a low incidence of dopaminergic adverse events.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about". It should be noted that where particular values are described in the description and claims, unless otherwise stated, the term "about" means that an acceptable error range, e.g., up to 5% or 10%, for the particular value should be assumed.

INCORPORATION BY REFERENCE

The entire contents of all patents, published patent applications, websites, and other references cited herein are hereby expressly incorporated herein in their entireties by reference.

The invention claimed is:

1. A method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa and carbidopa in a ratio of about 8:1 w/w, and further comprising arginine,
wherein by the third consecutive day the administration results in the patient having at least one of:
an increase from baseline of at least about 0.3 to 3.5 hours in daily Good ON-time,
a reduction from baseline of at least about 0.3 to 2.5 hours in daily ON-time with moderate-severe dyskinesia,
a reduction from baseline of at least 0.1 to 2.0 hours in daily OFF-time,
an increase from baseline of at least about 0.1 to 3.5 hours in daily ON-time without dyskinesia,
a reduction from baseline of at least 0.1 to 3.2 hours in total daily troublesome dyskinesia,
an improvement from baseline in motor experiences of daily living, as assessed by the Movement Disorder Society-Sponsored revision of Unified Parkinson's Disease Rating Scale Part III (UPDRS Part III) score, resulting in a reduction from baseline of about 2 to 13 points in the UPDRS Part III score,
or any combination thereof.

2. The method of claim 1, wherein the pharmaceutically acceptable liquid composition is administered subcutaneously to the patient via a device comprising a control station, a reusable part and a disposable part.

3. The method of claim 1, wherein the pharmaceutically acceptable liquid composition comprises 7.5 mg/mL carbidopa and 60 mg/mL levodopa.

4. The method of claim 1, wherein the pharmaceutically acceptable liquid composition is administered to deliver about 720 mg of levodopa and about 90 mg of carbidopa to the patient over the course of about 24 hours.

5. The method of claim 1, wherein the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours.

6. The method of claim 5, wherein the low activity night rate is administered for about 6 hours and the high activity day rate is administered for about 18 hours.

7. The method of claim 5, wherein the low activity night rate is about 0.08 mL/hour and wherein the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

8. The method of claim 5, wherein after about 5 hours of administration at the first flow rate, the patient is fully ON.

9. The method of claim 1, wherein the patient has an improvement from baseline after two days of treatment in quality of sleep.

10. A method of treating a patient with Parkinson's disease, the method comprising subcutaneously administering to the patient, substantially continuously for about 24 hours/day and for about 2 to 3 consecutive days, a pharmaceutically acceptable liquid composition comprising levodopa, carbidopa, and arginine,
wherein the pharmaceutically acceptable liquid composition comprises about 60 mg/ml levodopa and 7.5 mg/mL carbidopa, and wherein the pharmaceutically acceptable liquid composition is administered to deliver about 720 mg of levodopa and about 90 mg of carbidopa to the patient over the course of about 24 hours,
wherein by the third consecutive day the administration results in the patient having at least one of:
an increase from baseline of at least about 0.3 to 3.5 hours in daily Good ON-time,
a reduction from baseline of at least about 0.3 to 2.5 hours in daily ON-time with moderate-severe dyskinesia,
a reduction from baseline of at least 0.1 to 2.0 hours in daily Off time,
an increase from baseline of at least about 0.1 to 3.5 hours in daily ON-time without dyskinesia,
a reduction from baseline of at least 0.1 to 3.2 hours in total daily troublesome dyskinesia,
a reduction from baseline of about 2 to 13 points in UPDRS Part III scores,
or any combination thereof.

11. The method of claim 10, wherein the method further comprises administering to the patient, before or during the subcutaneous infusion time course, at least one pharmaceutically acceptable oral composition comprising levodopa.

12. The method of claim 10, wherein the pharmaceutically acceptable liquid composition is administered subcutaneously to the patient via a device comprising a control station, a reusable part and a disposable part.

13. The method of claim 10, wherein the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours.

14. The method of claim 10, wherein the low activity night rate is administered for about 6 hours or about 8 hours and the high activity day rate is administered for about 18 hours or about 16 hours, respectively.

15. The method of claim 14, wherein the low activity night rate is about 0.08 mL/hour and wherein the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

16. The method of claim 14, wherein after about 5 hours of administration at the first flow rate, the patient is fully ON.

17. The method of claim 10, wherein the patient has an improvement from baseline after two days of treatment in quality of sleep.

18. A method of increasing Good ON-time in a patient with Parkinson's disease, the method comprising
subcutaneously administering to the patient, substantially continuously for about 24 hours/day for about 2 to 3 consecutive days, a pharmaceutically acceptable liquid composition comprising levodopa and carbidopa, in a ratio of about 8:1 w/w, and further comprising arginine, wherein by the third consecutive day the administration results in an increase from baseline of at least about 0.3 to 3.5 hours in daily Good ON-time.

19. The method of claim 18, wherein the administration results in an increase from baseline of about 1.8 hours in daily Good ON-time.

20. The method of claim 18, wherein the pharmaceutically acceptable liquid composition is administered subcutaneously to the patient via a device comprising a control station, a reusable part and a disposable part.

21. The method of claim 18, wherein the pharmaceutically acceptable liquid composition comprises 7.5 mg/mL carbidopa and 60 mg/mL levodopa.

22. The method of claim 18, wherein the pharmaceutically acceptable liquid composition is administered to deliver about 720 mg of levodopa and about 90 mg of carbidopa to the patient over the course of about 24 hours.

23. The method of claim 18, wherein the method further comprises administering to the patient, before or during the subcutaneous infusion time course, at least one pharmaceutically acceptable oral composition comprising levodopa.

24. The method of claim 18, wherein the pharmaceutically acceptable liquid composition is administered subcutaneously to the patient at a first flow rate and a second flow rate over the course of 24 hours, wherein a first flow rate is a high activity rate for day hours and the second flow rate is a low activity rate for night hours.

25. The method of claim 24, wherein the low activity night rate is administered for about 6 hours and the high activity day rate is administered for about 18 hours.

26. The method of claim 24, wherein the low activity night rate is about 0.08 mL/hour.

27. The method of claim 24, wherein the high activity day rate is about 0.64 mL/hour, about 0.59 mL/hour, about 0.55 mL/hour, about 0.50 mL/hour, about 0.45 mL/hour, about 0.41 mL/hour, about 0.36 mL/hour, or about 0.32 mL/hour.

28. The method of claim 24, wherein after about 5 hours of administration at the first flow rate, the patient is fully ON.

29. The method of claim 18, wherein after two days of treatment, the patient has an improvement from baseline in quality of sleep.

* * * * *